United States Patent
Bovijn et al.

(10) Patent No.: US 11,891,607 B2
(45) Date of Patent: Feb. 6, 2024

(54) METHODS OF TREATING DECREASED BONE MINERAL DENSITY WITH CLUSTER OF DIFFERENTIATION 109 (CD109) INHIBITORS

(71) Applicants: Regeneron Pharmaceuticals, Inc., Tarrytown, NY (US); The Royal Institution for the Advancement of Learning / McGill University, Montreal (CA)

(72) Inventors: Jonas Bovijn, Tarrytown, NY (US); Olukayode Sosina, Tarrytown, NY (US); Sirui Zhou, Montreal (CA); Luca Andrea Lotta, Tarrytown, NY (US); Aris Baras, Tarrytown, NY (US); John Brent Richards, Montreal (CA)

(73) Assignees: Regeneron Pharmaceuticals, Inc., Tarrytown, NY (US); The Royal Institution For the Advancement of Learning/McGill University, Montreal (CA)

( * ) Notice: Subject to any disclaimer, the term of this patent is extended or adjusted under 35 U.S.C. 154(b) by 0 days.

(21) Appl. No.: 17/816,084

(22) Filed: Jul. 29, 2022

(65) Prior Publication Data
US 2023/0055912 A1    Feb. 23, 2023

Related U.S. Application Data

(60) Provisional application No. 63/230,707, filed on Aug. 7, 2021.

(51) Int. Cl.
| | | |
|---|---|---|
| *C12N 15/113* | (2010.01) | |
| *C07K 16/28* | (2006.01) | |
| *C12Q 1/6883* | (2018.01) | |
| *A61K 31/4535* | (2006.01) | |
| *A61K 31/565* | (2006.01) | |
| *A61K 31/57* | (2006.01) | |
| *A61K 31/663* | (2006.01) | |
| *A61K 31/675* | (2006.01) | |
| *A61K 38/23* | (2006.01) | |
| *A61K 38/29* | (2006.01) | |

(52) U.S. Cl.
CPC ...... *C12N 15/1138* (2013.01); *A61K 31/4535* (2013.01); *A61K 31/565* (2013.01); *A61K 31/57* (2013.01); *A61K 31/663* (2013.01); *A61K 31/675* (2013.01); *A61K 38/23* (2013.01); *A61K 38/29* (2013.01); *C07K 16/2875* (2013.01); *C12Q 1/6883* (2013.01); *C12N 2310/11* (2013.01); *C12N 2310/14* (2013.01); *C12N 2310/531* (2013.01); *C12N 2320/30* (2013.01); *C12Q 2600/156* (2013.01)

(58) Field of Classification Search
None
See application file for complete search history.

(56) References Cited

PUBLICATIONS

Song et al., "CD109 regulates the inflammatory response and is required for the pathogenesis of rheumatoid arthritis", Annals of the Rheumatic Disease, 2019, 78(12), pp. 1632-1641.
Mundy, "Osteopenia", Disease-A-Month, 1987, 33(10), pp. 537-600.
Wang et al., "CD109 plays a role in osteoclastogensis", PLOS ONE, 2013, 8(4), pp e61213.
International Search Report and Written Opinion dated Nov. 10, 2022 for International Patent Application No. PCT/US2022/074307.
Morris et al., "An atlas of genetic influences on osteoporosis in humans and mice", Nature Genet, 2019, 51, pp. 258-266.

*Primary Examiner* — Sean McGarry
(74) *Attorney, Agent, or Firm* — Armstrong Teasdale LLP

(57) ABSTRACT

The present disclosure provides methods of treating a subject having decreased bone mineral density or at risk of developing decreased bone mineral density, and methods of identifying subjects having an increased risk of developing decreased bone mineral density.

18 Claims, No Drawings
Specification includes a Sequence Listing.

SEQUENCE LISTING

```
Sequence total quantity: 58
SEQ ID NO: 1            moltype = DNA  length = 132532
FEATURE                 Location/Qualifiers
source                  1..132532
                        mol_type = genomic DNA
                        organism = Homo sapiens
SEQUENCE: 1
atagttgcta tgaatttctc ctcacaagga tgggcctgtt tactcaccct gggcatcgtt   60
ggtagagcgc tagtgtaaac agcctgagga acccggtggg ccggggaagt gggcgcgctc   120
tgttctccgc ggccagctgg gacgccgggc caggtgggc cgcctgcgtt tagcaactgc    180
tttctcaccc cctggatttg cgatgtttgc cacagcagcg agaagcgcca ttgtaatggg   240
gatgggaggg gtggagcctc caagtcctgt ctcaatttag atctctcact ctgctgttag   300
gcgcgcccat ttcagattac taaactcgaa ttaagaggga aaaaaaatca gggaggaggt   360
ggcaagccac accccacggt gcccgcgaac ttccccggca gcggactgta gcccaggcag   420
acgccgtcga gatgcagggc ccaccgctcc tgaccgccgc ccacctcctc tgcgtgtgca   480
ccgccgcgct ggccgtggct cccgggtagg aacgtgggcg cgcgggggc gcgcgggcgc   540
gcgggcctgg gccgctctgc ggctctgggc cagggcttcg ggaggtggc ggctgctgtg    600
cagcagcggg tgggaaatgc cctcgcggct gcagtcccca gcctggtact ggcctggagg   660
```

```
tttgaccata tgtagcttca gcgtggctct ccatgggaca gttaacttt c tccactcatg  720
aagttgttta agcgtctccc cggccataac aactttctga agagagtcat tttattttta  780
gtccacattg cctctgcctt ttgcttctca acttttgct cccagattgc gattcttctc  840
tcaaagacat gatatatttt ttctaaccaa gatgtctcaa ccttagcatt gccaaagtgt  900
ggcggagggg actgatgtat gggttcaggg gcagacatta taggaagaaa acaacagcac  960
ccaataatgg caagccccat tcattcctaa agatttctgt agttgagccc taaccccta g 1020
ttatagcaga gaaagtgctg ctttagtgac ttcttttatg attcgctata cctggaatt t 1080
tcaccagttg tagtttattt tcaaatggta tatttcaatc aatggtattg gttaaataat 1140
ttttaccct cgttgggcag ctactcaagg ataaaggttt gaataagaaa caggcaaaat 1200
cttagttaaa aaataacaac aacaacaaga aaataatcac gctgggataa ggtcctctgt 1260
aaaggagaag cttagagact tttgctttgc caataactcc attatgcccc ggtgcaagcc 1320
atttacatca tggttccttc tgtgcggttc gtggtttata aatgtgaaat aataacacag 1380
gccttcctct agtagtgatg catgaattac tgcattaaaa ttgattttatg ggaattattg 1440
ttgtttcagt agcatttcaa ttcagttgcc aaatagagca gtgggcaatg ttaacggaaa 1500
caactgcaat tggcgcagta tggagtgcct atcgcactag gaaatctgag ggtcacaaaa 1560
gaaaggagat gtgaggataa gaaactttgt ttttcccttg ttgggaactc tttaggcctc 1620
ggtttctggt gacagcccca gggatcatca ggcccggagg aaatgtgact attggggtgg 1680
agcttctgga acactgccct tcacaggtga ctgtgaaggc ggagctgctc aagacagcat 1740
caaacctcac tgtctctgtc ctggaagcag aaggagtctt tgaaaaaggt aagataaaca 1800
gcataaagtc ttacccttct gcagtaataa ctggaatatg ttaataaggt catgtgttag 1860
gtagtatagc agagaaaccc caaatttgca gtatcttacc taatatactt ttaattctca 1920
ctcatgtaaa gtcctagatg gtgttcctgg atgctcttcc aagtgcagat tcagagaccc 1980
agtttccttc cattttgtgg ctccattatc atcacttggc tcccaagact gcaggggaag 2040
atcatgcagt ttcttcatgg gagaagggga agaggatggg aagagcatat ggaaggtttt 2100
tatgggatag gcctagaaat agcttacatc actactgctc atattcacag gcaagggagg 2160
ctgggaagtg taggctaatg tgtgcccag aagaggaaat gggctagtct ctaacacaaa 2220
accatattta ttgagtgcaa agtatttact agaataggcc tgtaggaagg aaaggaaaag 2280
ctacacaata gttaaaatcc agtttatgg aatatttctt aagttttaaa gtaacaagag 2340
aaaaaagaa aatagtgtga aagtgggagc catttgtagc agaaccaagt ttggttcttg 2400
tttcaagttt gggttctgac gggcccaag attaaattgg gccaatgaat gtcttctttt 2460
tcagtgctaa gggaaaaata atttttgggag gaagaggtaa atacttaaat acttaaaaca 2520
tttttcatta aaatgaactt ttattgcatt ttttttcttt tttagattct tataattatt 2580
tttagagaca agctctcacc atgttgccca ggctggtctc gaactcctaa gttcaagtga 2640
tccacccacc ttggcctccc aaagtgctgg gattacagtc ctaagctact gctcctggcc 2700
gagacataca ttttttataat gttaagagtt atttaaaaaa aaaaatttaa ggcacgtaat 2760
gaagggtggt tggtattcat tacataagtg tttattctct acaagcgtag agaaatgaac 2820
accatcatga aatgaaataa agtaaagtt ttatctgcat ctgtggttct ttccccactg 2880
gaagttcact gggtaggtat atttggaata ggagtcagga agagatggtg tgtgtagggg 2940
caagtcactt ttgtccctca tagaagcaat gtcagggaag tggaggtctt tatttccctg 3000
gaggggaagt ataggttagc ccttaagatc tgagtttgaa tcctggtact actttgctac 3060
tagttgtatg atcttaggta ggttacttaa ctgctttgag ccacagtttc cttgtctata 3120
aaatggaaat aatgaaactg atttcccagg gcagttataa agttaaaatc tgtatatagt 3180
acctcttagg catgcaataa acaacaattg ctaatattat ttgtgtaata atactgcaga 3240
agaggatgca gaaagtccat ttccttttta catgggggca gacttcaact ttcgttattg 3300
gactatcatt tctgaaaatg aatgaccct gatcttatga tagtcgctaa agaaaatatt 3360
gaaatattaa atcacaggac ataatactta aggtagttcc acattcatta tttattcatt 3420
aagaatttat gagtgggaag agggagggta ttaaaaaacc acctattggg taccacactt 3480
atcacctgga tgatgaaata acatgtacac taaagcccta tgacaggcat tttacctata 3540
taacaaacct gcacgtgtat ccctgaaact aaaataaaag ttaaaaaaaa aagaatttat 3600
aatattggct ccactagtgt ggcagttttc ctgcaatgca gagatccaga atatatatgg 3660
atgttttga taaatatttg agctttgctt ggacatttac atactctaat tctagaattt 3720
cacctgttag gtcttttctg tgatctctgt tatcagtctc tcttttttttt tgcaacaaat 3780
agtacctaca ttggggtgca tgtgttgtg cttggtttt cagcttatt cttagatctt 3840
ctttttggag aaggggttcct tgtatgccca taggaaagtt caagtactca agactggggc 3900
gggcaaagct gtcctgggag cagaatggat ctgtgggaag gaaggaggga aaacgctgct 3960
tcttttcatgg gctgtttttg actctattga catagagttt cattggaaat gccattgcta 4020
ggagcactct cctgtttcaa aggagaatgt tactgtatta tcagaggctg ggagttattg 4080
ttctcagagc agatgcttcc tgtaatgtga ggacttgagg atcaagacac ttctccctgc 4140
ttgtcttcac atccttttgct ttatctggct tctccagttg taacaatatg tagataaacc 4200
aggacttcta aatcagggggt ctggatcttc aagtatccgag atgtggattc atgtttttgtt 4260
ttttctccat cacataaaca ccaaacacca acaaataaat accttttatt tttaagggac 4320
agagtctcac tctgttgccc aggccagagt gcagtggtga aatcatagct cactgcaact 4380
tggaattctt gggctcaagt gatcctgctg tctcagcctc ctgaatcagc tgggactaca 4440
ggcaagtgcc agcatgctag gtttaaaatt tttttttttt ttgtagagat ggggtcttgc 4500
tatgttgccc agactggtct tgaactcctg ggctcaagcg atcttcctgc ctcagcctcc 4560
cgaagtgctg ggattatggg tatgagcctg attgttcat tttcctatga gccaccccca 4620
gccccccaac agaaggttgg ttttaataaa gatttatctt ctagtaaagt tgggtaaggc 4680
agtagactgt gtcttagtag cttatttcca gcagttttag atttcttaga aatcctcagg 4740
ataggaggt gttttaccca aaccacaata gatttctggc tcaatttgtg ttggaaatag 4800
taataactaa attgttcaaa tggagaatgt atttaataaa ggtgaaaaag tatggcattt 4860
cttcagggaa gagttcattt gttttgtttga cagatatggg ggagatttta tttacattc 4920
cacttttatg gccaggagtg taggttatat tactgttatt cattaaaaa tacattaatt 4980
ctacatttat tggggattga ttgtagtttt tttttttttt tttttttttt tttttgagac 5040
acagtctcac tctgtcaccc aggctggagt gcagtggtgc gatctcggct cactgcaaca 5100
tctgcctccc tggttcaagc gattctcctg cctcagcctt ccgagtaact gggactacag 5160
gcatgtgcca ccatgcctgg ctaatttttt gtatttttag tagagacgag tttcactgtt 5220
gttagccagg ttggtcttga actcctgacc tcgtgacctg cctgcctcgg cctcccaaag 5280
tgctaggatt ataggcgtga gccaccgtgc ccagcgatta tgggctttt tttttttttt 5340
ggtgaataat agacctttag aaaaagtatt tctgctacac tttgcagagt tctgggaagg 5400
```

```
tgtatcaatg cctttctagt agtgagattc aaaagattgc ttgtcactgt taccactgtc   5460
actgcctcta ccactatcag catcattgcc atcagctcca tagtgattag aactatgttc   5520
ctaatcttat cttcctttgc ataaagagtt agttaaataa acataactgg caaaacgtag   5580
taaaagttca gcaggtaata attaccagag gaaagaagat ggcacagcta ttggcattta   5640
aaatcaagtc agattactgt tttgggtgga gagtgagtcc gtcccctttgt ctcttcccat   5700
atttttttc  tctttcctta ctgtgaaagg agttccttgc caaatcaaga aaaaagaaat   5760
taagaacatt ttgagaactg tcctctcatc tgttaaggca tataaaataa tttaattttc   5820
gtgatgtcct tgaaaccata atttctgttt tattttccct tctcttgcta caatttgaca   5880
ttttcatttg taaactttca gtagttttcc tgaacaagag tcacttcaag taataaagaa   5940
tataaccttt ctccctcatt aatgaattca tcatcattag tttcatgtaa acctgattta   6000
agaaaaaatg ctagaggctg agtgcagtgg ctcacaaccg taatcccaga gcttgggagg   6060
ctgaggtggg aggattgctt gagcccagga gtttgagacc agcctggaca acacagtgaa   6120
attctatctc aaaaacaaaa acaaaagaac ccttaaaacc aaaaactccc aaaaacctaa   6180
actgaaaatg cctactgaaa ttttgggaac tctgcatggg cgtctccagg tgagtgcctg   6240
ctggtttggg ggcaccattt tttaaatgct gccaatccta cttccatctt cccattgagt   6300
tactggggtg gaatgtgctc tataaatgtg tctgtaactc gcttttttctt tttgccctaa   6360
aatcctggag agttaatgga gtgttaacct tttttttaaag attttttaaa aaatctattt   6420
tttcctttgt tgtctttctc acattgacta tgatatattt tattttccat cttggctcag   6480
taagggtggg aaattttttaa aaattgagat attagctgaa aaacttaaaa aatcatccaa   6540
tttggtttga atggtttcct ggtggaaaca aagctcctga acatgcattt catgcctcgt   6600
agataaaaat cagtcccatg gtctttatga aagtagatta attagtgtag tgtgtgggca   6660
gatctcccag agcaggtttt cacaggcagc tttgccaaca taactcagtc tgaacctgca   6720
gttatgttag aattatttttt aaagggtgta ggcttttcat tcacacatcg tctttgttct   6780
tgtgtgtgat gtatattaac aggtaggtgg tacctgagaa taaaggacca cagcataatc   6840
acgatgtgcc tgggctctgg agcctggcta cctgggcaca ggtgctggcc attccactta   6900
gtggttgtgt ggctgtgggc agtcatgatc tcactaggct tcagtttcat catctgaaaa   6960
atagtggttt ctgccttata caattatatg gatattgtga ggattaaatg aggtaacata   7020
ttcaaggcac ttaacacaaa ggaattattc aagaaaatgg tagctattgt tactagaaga   7080
gagtagcaac agtttatgtc aaaggcaatt attaatcacc tattgtgaca atcttgaacc   7140
gggaactcta taaaagacac atccctagga gggattgga aagggattta catattaaat   7200
atccagtttc ctcatagtgc caaggacttt atgcactata tttaatttta acaacttgat   7260
gaagtagata ctcttgtctt cattttggag gtgaggaaat tgaggcaaag agagaagaat   7320
tagtttttct gagttaaccc agttagtaaa tggtgaagcc tgaatttgaa gttagttgta   7380
tctgaggtcc agagaccata aggttttcta ttgctgggaa gagagtgaag tatttttatt   7440
tccttgattt tgggatattg atgcaatgtt gcagttgtct tccactaaaa tcattttcac   7500
atttgcttgc agtagataga cctggatcta atgaaatcta atttgaatcg aaagaattac   7560
aaaatgaaat gccagctctc ctcttaattt actttcagcc tcatagagtt ttggagctgg   7620
aggggacctc aaagataagc aaattcaata gcctaatata tggctgggag actgaggtga   7680
ggcatgggat ctggggattt tccaaggtc aaatcactta ttggtggcag agctggaaac   7740
agattgcagt ttcccaaatt tgcagtccag tgctatttcc agtatactct acgaaagttt   7800
cctaacatat ggagagctga gcttaagacc taagatatat ttacaaatgc tgattcttct   7860
gatatggaag aaaataaggc taactaagga gtttaaaaat gcttacttgc atactgtgaa   7920
agtttcttat tttagctcaa ggtggagttg ctctttatgc actatttgtt ctgtataagg   7980
ggtgggggct gggttagaag cttcatagac ctttttaaaa ctaaattctg ttgctttgtt   8040
tctcagagtc caaattgtat ttattaaaaa ggctgattca tggcctccct caagacatgg   8100
gtaagaatca agaatctcag ctgggtgtgg tggctcacgc ctataatccc agcactttgg   8160
gaagccaagg taggtggatc acttgaggcc agaagttcga gaccagcctg gccaacatgg   8220
tgaaaccccg tctctaccaa aaacacaaaa attagccagg tgtggtggtg ggcgcctata   8280
gtcccagtta cttgggaggc tgaggcagga gaatcgcttg aacccaggag gcagaggctg   8340
cagtgagatt gtaccagtgc actccagcct gggtgacaga gcaagactcc atctcaaaaa   8400
aaaaaaaaaa aagagaatct aacctttatg ttccaccatg accacaggtg attcttagtc   8460
acattagaat gagaacaact gcccttgggt atctcacaaa ttgtactcga ccaaatactg   8520
gaaagctcga gggtgagtag catgcccctg caagcctgtg atgattcatg gcggcggagg   8580
gaaggctcct cgtggacttt catgtttgct tttaagcaac cctcaaccct aagcgctggt   8640
gttcattttc agccgcagag aaacatgact tgggggtttga ttgtgaatca acgattgggt   8700
gaagttaaaa gtgaacacac tgattctttta aactccaagt taaacatgtg ctgctcctct   8760
tctagcactg gatgagtcac tgtcctagtg actcactgaa ggattgtggt ggaaatagaa   8820
aacagatccc ataagaattt gggctgggtt actgttgatc ctttatgtcc tgtgaagagg   8880
gcttttataat gctgaaacta gttgtttccc cacagacatt tcttctcatt aatgtattat   8940
ttattgatta tttgctgtat gtgaaacatg aatgaatggg gagtggggaa taagagaaag   9000
gaaggcactg gaggacattc agaggtccca aagggataat ataatattaa aagtgcagaa   9060
ggctagagga gttttattt tttgtataaa aaatacaatg cggtttgtaa atagtgcttc   9120
ttgtatgtga gcctgtgcct ggtactatta tcttttactt ccagagctat acagatgtcc   9180
attcataaat gtcccaccct tgctgacata tttggccttt ggaggggaaca gttacttcac   9240
gtactagaga cgggaagggt gtgccggagg aaagagctgc tggctggtgt ggcagttatg   9300
aaaaggagat aggggttttgt gtatatattt tctaaaagaa tgtttcattc tgctttggat   9360
atgagtttgg ggagacatcc aggtggagat gtccagcaga tagttttgaa attgcagctg   9420
gggagagaga tttaggcatt attttcatag aggcagacaa tattttgaag tcctggaaat   9480
acataagatg cacaagagag acagagctca tggaaagaac aagtcttttg agagaagctt   9540
ggaaagagga aaataagtta atgaaggaa aaagaccaga cacagtggct catgcctgta   9600
atcccagcaa cttgggaggc tgaggtgagc agatcgcttg agtcaagag tttgaaatca   9660
gcctggacaa catattggaa cctcatctct actaaaaata aaaaaaggt agctggacgt   9720
ggtgacatgt gcttgtagtc ccagctactc aggaggctca ggcaggagga tttcttgagc   9780
tacagttata gtgccgttgt actctagcct gggtaacaaa gcatgcctct gtctcaagaa   9840
aaagaaaaga aaagaaaaga aagaaaaga ataagaataga caacgagcaa tcagagaagg   9900
gtaaattgaa aatgtctcag aagccaaggg aagaagaagt tccaagaagg aaggttttaat   9960
agttaataat caattctctc aggtcagaga agaggaggac agaggaaaga acattggtga   10020
cgcttaagta aatggcttta agttgaatgt tggaagcaaa agcaaatttg agggaataaa   10080
tggatggtga aaaatataat caaaatttat tcttccccaga agtttggtag ttgaaaggag   10140
```

```
agaggtggac ggtctctcaa aaggcacatt agaaaggtga aagtggttaa ggcaaaggag   10200
agggtggata attcctgggt tagaagtggt gagatcagta ttggggcaga ggcaagtgga   10260
ttatccttaa aaaaccctca tactttcttc tttgaagaaa gaaagaaata gaagagaatc   10320
attaaggaaa gaaatatttt gaggtatgaa attgagatga agaataaaat tgaaatacag   10380
ttttaggaaa acttatttac cgacttgtaa attgcacaga tctggccacc actttatagg   10440
aaatgggggt aaaagttaaa agtagtggca gaccagaatg agaaacacag gactggagat   10500
cttcctggt ggtgccctaa actgggtcac cgctggattg taggaaatta gaatacaggg   10560
gcaggaagtc atatttgtat ctgggagagc taacacaggg aggagagaga agaggaaagg   10620
gctgtttacg atgaagatat gcctcagttg aagctcgaga ggactgggtg gagttcttta   10680
attactgcca tggttgtcag tgaatttgta attcactctt agtgtgggcc aagatgacca   10740
aggtgcaatg ataaaacttg tctaggagga ttaaagtgga tcttggtctt gctctatctc   10800
tttcactctt cacttacctc ggagaattct atgaggagac tttcttccgt tgcaaggctc   10860
agggtgaaat tggtcaaaga tttggtggag ggggtagcag taggtaggta gatgacaggt   10920
ctataggttg ttagttctga agaaacgatt cataaattaa aatccgaaaa ccagactggt   10980
aaagagcttg gaaataaatg aagaggaaaa ttttttaaaga acacctagta gctcccttt   11040
ggcagggctg tgttaggaat ttacatttat gaaaatatag ctggcagaaa tgatttagta   11100
ttacaaactt aagtttcact gcaatatatg ttaaagctcc tcaggaatat agataagaca   11160
gggaatttat tattctgagc aattcaaatt tattcagcac caaattgcct atggcacaat   11220
gctgggtgac ataaatattt ggtgaccaca tgaggttcct gtgcctgtgc tcttcgcagg   11280
gaagcagagt aggcttcatt tgatgtgtcc tcccacgttg attatagagg cttgttcggg   11340
tgccgtgttg acagtttcaa agtcaagcgt gggtttactg gactagagaa ctggatgaat   11400
tgtctgtgtc tgccatggcc atgggagttg gggagttgtg tatgaatgct gcgaaggatt   11460
ctgtagccca tccataaact ttatttatgg atcagttgaa gaggaatggt ctaagaggaa   11520
cggttatcta cgtagctaca taggggcttg aggtagtaac aacatggata agagagaaca   11580
gacgaaagag tgggtgtatc caaatagtaa atgagagtgg agtaagctac agaggaggaa   11640
caaggaggga agggatatga ggttatgttt gcactactgt tttggaagga ataagctgggt   11700
ctgtcctgca ctgtttggga ggcacagtgg gttagaatgg gtgctcagga accacactga   11760
aattgaaccc tagcatcacc taatagtagt acccacctcg tagcattgtt gagaggatta   11820
aatgagataa tacttaagag ctgtatcatc caatatggta gctactaacc acatgtggtt   11880
tttgagcact tgaaatgtgg ctcatacaaa ttgagatgtg ccaggagtat aaaatacata   11940
atggattttg aatacttagt tccaagaaat gcaataaaac ttatgatttt aaaataatga   12000
tttcatgttc aatgttaata ttttggacat attgagttaa ataaaatatg ttattaaaag   12060
taatgtcacc caatttttc tttttttggc acataaaaga cacctaattt aataaatatt   12120
agttattatt ttctctttta ttatgcagtt aagaactttg atttaaaatt gttatcttta   12180
tatatatata tatatatata tatatatata tatatatata tatatttatt atactttatg   12240
tcctagggta catgtgcaca acatgcaggt tgttacata tgtatacatg tgccatgttg   12300
gtgtgctgca cccattaacg cgtcacttac attaggtgta tctcctaata ctatcccttc   12360
cccttcccc catcccacga caggcccgg tgtgtgatgt tcccgtcct gtgtccaagt   12420
gttctcattg ttcaattccc acctatgagt gagaacatgc ggtgtttggt tttttgtcct   12480
tgcgatagtt tgctgagaat gatggtttcc agcttcatcc atgtccctac aaaggacatg   12540
aactcatcat ttttttatggc tgcattgtat tccatggtgt atatgtgcca caattttctta   12600
atccagtctg ttgttgttgg acatttgggt tggttccaag tctttgctat tgtgaataat   12660
gcctcaataa acatacgtgt gcatgtgtct ttatagcagc atgatttata gtcctttggg   12720
tatatacccca gtaatgggat ggctgggtca aatggtattt ctagttatag atccctgagg   12780
aatcaccacc ctgtcttcca caatggttga actagtttac agtcccacca acagtgtaaa   12840
agtgttccta tttctccaca tcctctccag tacctgttgt ttcctgactt tttaatgatc   12900
gccattctaa ctggtgtgag atggtatctc attgtggttt tgatttgcat ttctctgatg   12960
gccagtgatg atgagcattt ttccatgtgt tttttggctg cacaaatgtc ttcttttgag   13020
aagtgtgtgt tcatatcctt tgcccacttg ttgatgggt tgtttgtttt ttttcttgta   13080
aatttgttg acttctttgt agattctgga tattagcccc ttgtcagatg agtaggttgc   13140
aaaaatgttc tcccattctg taggctgcct gttcactcg atggtagttt cttttgctg   13200
gcagaagctc tttagtttaa ttagatccca tttgtcaatt ttggcttttg ttgctattgc   13260
ttttggtgtt ttagacatga agtccttccc catgcctgtg tcctgaatgg tattgcctag   13320
gttttcttct agggttttta tggttttagg tctaacattt aagtctttaa tccatcttga   13380
attaattttt gtataaggtg taaggaaggg atccagttc agctttctac atatggctag   13440
ccagttttcc cagcaccatt tattaaatag ggaatccttc ccccattct tgtttgtgtc   13500
aggtttgtca aagatcagat agttgtagat gtgtggcatt atttctgagg gctctattgt   13560
gttccattgg tctatatctc tgttttggta ccagtaccat gctgtttggg ttactgtagc   13620
ctcgtagtat agtttgaagt caggtagcat gatgcctcca gctttgttct tttggcttag   13680
gattgacttg gcaatgtgag tgttttttg gttccgtatg aactttaaag tagttttttc   13740
cagttctgtg aagaaagtca ttggtagctt gatggggatg gcattgaatc tataaattac   13800
cttgggcagt atggccattt tcctgatacc aaagcctggc agagacacaa caaaaaaaga   13860
gaattttagg ccaatatccc tgatgaacat cgatgcaaaa atcttcaata aaataccggc   13920
aaaccaaatc cagcagcaca tcaaaaagct tatccaccat gatcaagtgg gcttcatccc   13980
tgggatgcaa ggctggttca acatatgaaa atcaataaac gtaatccagc atataaacag   14040
aaccaaagac aaaaaccaca tgattatctc aacagatgca gaaaaggcct ttgacaaaat   14100
tcaacagcgc ttcatgctaa aaactctcaa taaattaggt attgatggga catatctaaa   14160
aataataaga gctattcatg acaaacccac agccaatatc atactgaatg ggcaaaaact   14220
ggaagcattc cctttgaaaa ctggcacaag acagggatgt cctctctcac cactcctatt   14280
caacatagtg ttggaggttc tggctagggc aatcaggcag gagaaagaaa taaaggtat   14340
tcaattagga aaagaggaag tcaaattgtc cctgtttgta gatgacatga ttgtatatct   14400
agaaaacccc attgtctcag cccaaaatct ccttaagctg ataagcaact tcagcaaagt   14460
ctcaggatac aaaatcaatg tgcaaaaatc accagcattc ttatacacca ataacagaca   14520
aacagagagc caaatcatga gtgaactccc attcacaatt gcttcaaaga gaataaaata   14580
cctaggaatc caacttacaa gggatgtgaa ggacctcttc aaggagaact acaaaccact   14640
gctcaacgaa ataaaggagg acacaaacaa atggaagaac attccatgct catgggtagg   14700
aagaatcaat atcttgaaaa tggccatact gcccaatttt ctctattttt ttttagtgc   14760
acatctttaa aacatttatc acaatgcttg gtacatagaa gacaccgagg gaatgttaac   14820
tatgttgtac ctggtgtttc tcagtatcag atattaatac tgatgcctga ccacaagcct   14880
```

```
gtggcatgag tccaagtctc cctgctgatg actcattttg gcttaggtag atcttcaccc    14940
ttatcctta  tcccttgagg aagaagaaaa tctccctaaa gagagccaca ggggtcggca    15000
aaatttctgt aaagggccag atgttaagca tgtaggtttt gccaaccttc aggtctttat    15060
tacagctgct caactctgcc tttatagctc ggaagcagct gtagacggtt cataaacaaa    15120
agagcatggt tgtgtaccag cagaacttta tttatggatg ctgaaatttt gagttcatat    15180
aattttact  tatcatgaaa tattcttctt cttttgatat tcccccagc tatttagaaa     15240
tgcaaaccca ttcttagttc atgaactgta caaaaaacag gcgtgggcca gactggatct    15300
gtaggctgtg gattgctgac cctgccatta aaaatgccct gtacatttag cagccaagaa    15360
ccttgcttga ctctgggttt ttcatttgta cttaacctaa catttgcttt atagtgtacc    15420
attttattta ttttacttt  agtaggtttg tgtttgacct gcttttttt  ttactcaatg    15480
tttgtgttta acctgctttt tttagacaa  tggaacaaaa ctttgtttat gaaactcaaa    15540
tttattaaga tatttgtaag caaagggaaa taagagagaa aaatataaaa ggagtatgta    15600
agggaccaaa ggagattttt tgtttggttt tgttctgctc agaatacttg tgtttttctgt   15660
gtagactgaa tttacccaat agttttttg ccttaaagtg acattaaact gtgaagcaga     15720
aacattgtat tttaaaatc gtactttaag tttttttttt tttttttgag acggagtctc     15780
gctctgtcgc ccaggctgga gtgcagtggc gggatctcgg ctcactgcaa gctccgcctc    15840
ccgggttcac gccattctcc tgcctcagcc tcccaagtag ctgggactac aggcgcccgc    15900
cactacgccc ggctaatttt ttttagtaga gacgggggttt caccgtttta               15960
gccgggatgg tctcgatctc ttgacctcgt gatccgcccg cctcggcctc ccaaagtgct    16020
gggattacag gcgtgagcca ccgcgcccgg cctaagtttt taaaatattt tattttttata   16080
gatttagggg gtacatgtgc agttttctta catggatatt tgggtagtg gtggagtctg     16140
ggcttttagt ataaacatca gccaaatagt gtatgttgta ttcattaagt catttcttat    16200
cccttacctc cctgccatat gaatctccaa tgtctattat ttcactctct aaaaaatatt    16260
gtattttata caaaaaattag ccgggtatgg tggcgcatgc ctctaatccc agctactggg    16320
gggctgaggc aggaggattg cttgaacctg gaaagcggag gttgtagtga ccgagatca     16380
tgccactgca ctccagcctg ggcaacgaag cgagactccg tctcaaaaaa aaaaaaattg    16440
tattttaaag ttttgttttc catgaattttg tggggaaaa acccttattt cttaccttat    16500
ctgttgatca aagaaactgc tgaagaatga ggaaaaaaat ttagtaactt gataaagaga    16560
tcaaaattttt cagctaaaaa agtgataata aatttattat tgcataagac tgagtagcaa   16620
aaggctgcca aaaaaattta agcagcaaac actaagtcag gcatatatat atatctagtg   16680
gaaaatccac ttttttttt  atagagagta tttctgtacc tagttggatt tccggttaca    16740
cactactcct tcccttcaat gattttccaa agttatttgg tgaggacaga tgtcagaaga    16800
ggcagcatat aatggtatta cagagtatgt ttaaaaagtt aaggaaaggt tagttttgt     16860
gtatgcttat tacacaattt aaaaatagct ttgactctat ttgtaaatca aatggccagt    16920
tctcaggctg tgccaaatgc gaagccttca aacaaggttt cttctgagtt gcttaagcag    16980
ccctgggaag gagaaagcat ctgaaagggt tttcagattg attgtctctg gttatacaca    17040
gaaatgattg gagttttata aagttatcta taaaacact aagaagaacc ttacataaca     17100
gagtgtgtct ttagttagtg atttaaaaga gtgccatact gggtttcaag aggtggtgac    17160
catttcccgt gtctgaatgg agcctcgcca aaagggagaa aaatgttcac aacagtttgc    17220
aaatactatc tatttaattc tcaacctagc aacagcagag aaagagatta ttattcctct    17280
ctcatctatg ctgcccccac tctcctcccc gctgccccg  atttttatgtt ttggttgtgt    17340
aaattattgc taaatgaata gaactttcaa ataagtccta tgctaggact tcataagtgc    17400
ctaggaaatt ccaagctgta tttgtaaatt taaagggaag atcagcagaa aaaaatgtca    17460
agtacttaaa atcgactttt tattaaggac gcatgagacc agtgagtagg ccttagattg    17520
gatgtgtcca catatcctct gagtcgctcc ctggatccag caagaaatag gggtgggtgg    17580
gacatctttg tccctacacc atagcgttgg ggaagagtct ttgtattttg tattttatt    17640
ttttttttaa tagagatggg gtcacacgat gttgcccagg ctggtcttga actccttgcc    17700
tcaagggatc cttctgcctc agccctccca aagtgctggt attataggcg tgagctgcca    17760
cacctggcct gggtaggact tctgtttcta gctctgtatc tttcttgcat ctgtgaacag    17820
ataaggtcat gtgtctgagc agtaggaccc aggcatgcag ttgaactgct cgtccaactt    17880
ctctctggtg agagaattcc tcaaagattt gacttcattc agagctgcat taaaaacaaa    17940
agacaaaaca aaaaacactt ctactatgaa atgagatttc ctgcacttca aatctgttta    18000
gcttgttttg aagtgccaga atgctggcc  tccaattagt caatctccga gagcctcatt    18060
tggattgtag actcccaact gtttttttac tttctccttg ctgatgtcat tggataaaaa    18120
taaattacca ccccctcccc gtcgttcttc atctttgtaa atttgctgcc ggtgggtggt    18180
agctggtatc agaccagggc aggaaggaag cacattgctt cctccagtta tggagctagc    18240
ataatagtca accccctgatg atttatctta atacaatgaa aaataagtaa ctctcaataa    18300
tggagggtgc tggtttgttg gggcgaagct cactgcagtt tgtttctatt ttattccaat    18360
gtgggacatt gtggtggatg ctgtgttta  gggcccagat cgctctttag ggatgaagga    18420
cttttcccg  aaagtgcta  ggagtgttgt gcccgactgc cttcagagcc agttgtctct    18480
gatgatcgta tcagctagag aattgccttg cccatggtgg cctccctcct ggggatggcc    18540
tgtattatgt gactgattga cgtgggtat  gaaggtctgg ccctttcgcc ccagttcagg    18600
acaactctca ctggccctga ctgcttctga gctgccctgg tggatgcctc tttggagcct    18660
gcattgcagc cccactgctc tctcccctag tgcagtttcc cccttccct  tctgcaggtg    18720
ctgatccacc gaatactcct tagtaaacct cctgcattgt aattaccgtc tcagagttgg    18780
ctactgtttta actttccttt gaagaggaat gtttcagatc ttgaatcaa  cttcaaacat    18840
gtcaaaactg tgtagtgtga agaattgaca tgagttggga aagtctttcg tttttatatc    18900
cttttcagag ttcttgtatg acacaaaata ttttagagtt agctccgcta ctgcagtgct    18960
tggagtataa ctctaagttt cttctaagag aaacttcatg gaagaagaat ccacaggttt    19020
tggtgagtga taaacttaga gttgaggaga aaaagagtt  caagatgatt gagattttga    19080
acatccatga ttgaggaagt ggtgatagca acatatacaa acaggctata caggcagtgg    19140
aacttttact ataatcaaag atatgtataa tgaaaacaat ggtgaggcac aaggctggt     19200
ccagtggctc acgcctgtaa tcccagcact tgggaggct  gaggcgggca gatcacttga    19260
ggtcaggagt tcgagaccaa cctgtcctct ctaaaaatac                           19320
aaaaaattag ccagctgtga tggtgcttgc ctgtagtccc agctacatgg aggctgagg     19380
catgagaatc tcttgaaccc gggaggtgga ggttgcagtg agctgagatc gtgccactgc    19440
actccagcct gggtgacaga gcaagactct gtctcaaaaa caaacaaaaa accagtgatg    19500
aggcacggtg actcacatct gtaatcctag ggcttggga  agtcaaggtg gaggatcac     19560
tcgagcctag gagtttgaga gcagcctggg caacataatg agcccccatt tctacaaaaa    19620
```

```
agtaaaaaaa attagccagg catggtggcc tgtgcttgta gtcctagtta ctggggaggc    19680
tgaggcagga agatcgcttg agtccaggag tttggggtgg cagtgagcta tgattgcacc    19740
actgtactcc agcctgggtg acagagtgag accctgtctc caaaaaaaaa aaaaaaaaag    19800
gtatgtataa taaaaccaac tatacaactg attcttttt taattttaa ttgttgtgga     19860
tacatagaag atgtatatat ttacagggta catgagatac tttgaaacag gcatgcaatg    19920
tcaacaacca catcatagta actggggtat ccgttccctc aagcatttgt cctttgtgtt    19980
acaaacaatc cagttatact attttagtta tttaaaaatg tacaatcaaa ttgttattga    20040
ctacagtcct cctgttgtgc tatcaaatac taggtcttat tcattttct aactattttt    20100
tgtgcccatt aaccatctcc acttgctccc taaccctttca ctactctccc tagcctctgt    20160
taaccatcct tctacactct tatctccatt attagttaaa ttgttttaat ttttagctac    20220
cacaaataag tgagaacatg caaagtttgt ctttctgtgt ttgggttatt tcacttaaca    20280
taatgacctt cagttccatc catgttgttg caaatgacag gatctcattc attttttatgg    20340
ctgagtagta cttaattgtg tacatgtacc acattttctt tatccattca tttgttgatg    20400
gacacttagg ttgcttccaa atcttagcta ttatgaacag tggtgtaaca aacatgggag    20460
tgcagatagc tctttgatat actgatttcc tttctttgg gtatatactc agcagtggga     20520
ttgctagatt gtatggtagc tctatttta gttttatgag gaacctccaa actgttctcc     20580
atagtggttg tgctaatttt catttccatc aacagtgtat gaggggttccc tttcctccac    20640
atcctcatca gcatttgtta ctgcctgtct tttggataaa agccatttta actggggcga    20700
gatgatatct cattgtagtt ttgatttgca tttctctaat gatcaatggt gttgagaggg    20760
ccttttcata tacctgtttg ccatttgtat gtcttctttc gagaaatgtc tattcagatc    20820
gttttcccat ttttaattgg attattagat ttttcctgt agagttattt gagttcctta    20880
tgtgttttgg ttattaatcc cttgtgagat gagtagttac aaagattttc tctcattctg    20940
agttgtatct tcattttgtt gattgtttcc tttattgcgc agaagctttt taacttgacg    21000
tgatcccatt tgtcgatttt tgctttggtt gcctgtgctt gtgggatatt gctcaagaaa    21060
tctttgccca gttcagtgtc ctggagagtc cctccaaagt tttctttag tagtttcaca    21120
gttttaggtt ttaggtttaa gtcttaatc cattttgatt tgattttagt gtatggtgag    21180
agacagggtc tagtttcatt cttctgcata tgtacatcca gatttcctag caccattat     21240
tgaagagact atcttttcct caatatatgt tcttggcacc tttgtcaaaa atgagttcac    21300
tgtaggtgta tggatttgtt tctggcttct ctattgtgtt ccattggtcg tgtgtctgtt    21360
tttatgccaa tatcatactg tttttggttac tatagctctg tagcataatt tgaagtcagg    21420
taatgtgatt cctccttttt ttttttcttt ctcagtatgg ctttggctat tctgggtctt    21480
tggtggttcc ataaaaattt taggattttt tttctatttc tgtgaagaat gccattggta    21540
ttttgataga gattgcatta aatctataga ttgcttagg cagcatggac attttaacaa    21600
tattgataat ttcaatccgt gaacatgaaa tatcttttca tttttttggt gtcatcttca    21660
atttttttca tcagtgtttt atacttttca ttgtacagat tttcacttc tttgatcaag    21720
ttaatgcctg ggtatttaac tttatttgct gctattgtaa atgggattac ttcttgatt     21780
tcttttcag attgttcact gctggcatat agaaattcta ctgattcttt tttttttttt    21840
ttttttttt tttgagatgg agtctcgctc tgtcacccag gctggagtgc agtggcgcaa    21900
tctcggctca ctgcaaactc cgcctcccgg gttcaggcga ttctcctact tcagacttcc    21960
aagtagctgg gactcaggc gcctgcaacc acgcccggct aatttttgt atttttagta      22020
gagacgggt ttcaccgtgt taaccaggac ggtctcgatc tcctgacctc gtgatccgcc     22080
cacctcggcc tcccaaagtg ctgggattac aggcgtgagc caccgcgcct ggcttctact    22140
gattcttgta tgttgatttt gtatcctgca actagactga gtttatcagt tctaatcgtg    22200
tttggtggc atctttaggt ttttccaaat ataagatcat attggctggg cgtggtgact    22260
catgcctgta atcccagcac tttgggaggt ggaggaggc cagatcactt gagcctggga    22320
gtctgagacc agcctgggca acataggag acctgtgtc tatttatctt taaaaagtaa     22380
attaattaaa aatattatat catctgcgaa caaaaataat ttgacttctt cctttccaat    22440
ttgcctgccc ttcatttctt tctcttgtct gattgcccta gctaggactt ccagtactat    22500
gttgagtaac agtggtgaaa gtgggcattc ttgtcgtctt cctgatctta gaggaaaggc    22560
tttcagtttt tcccccattta gtatcatact agctgtggg ctgtcatata tggcttttt     22620
tgttggagg tgtgttcctt ctatatgcag tttttttgag ggtttttatc atgaagaggt    22680
gctgaatttt atcaaatttt tttaaattat caattgaaat gatcatgtag tttttgccct    22740
tcattctgtt gatatgatgt atcacattga ttgatgtgca tacaactttt ttttttttta    22800
tattcagagt cagtgcagag cagtggttta gagctcaggc ccatgagtca ggtggttagg    22860
gtcagaagct tggcccact acttttttgtc tgtgtgacct tgggaaagtc atttcacatg    22920
tctatgtctc agtgttctca tttgtaaaat aagggtaata atacttaata gtattgttgt    22980
gagctttaaa ctcaatgtat gtaatgcttt agaacactct gtaagtggta tgtactatta    23040
ttattattttt attcatataa ctaaaaatt gtattctgtc tgatctgttg gttgtttcat    23100
tgttgctaaa cacaaattta agtcttctat ccccgtgacc agttctgtcc aatacaagta    23160
taagtcaact acataagtta ttggcaattt tctagtagcc gcactaaaaa agaaagagaa    23220
acaggtgaaa ttaattgtaa taatatattt tatttaaccc aataatttac aagtattatt    23280
agttcagcat ttaatcacta taaaattatt gacatgacat tttacatttt tttggttgta    23340
agtctcagaa atatggggtg tattttacac ttgctgctta tttcagtggc tcaatagcca    23400
catgtattta gaggctcctg tatgtgactg agcagcttta aagagttgct agttaatctt    23460
gctcatttct gaagtgttcc agtcaactgt tgctgtgaaa taagccgccc ccagatttag    23520
tagattaaaa caacaatggt ttattattt tcacaattct catttagcct atacatgcta    23580
gattgatgat tattgccatt attttgtga tagttgtgaa ttccatgata gttttgaat     23640
tccacgattc cttctacatt tattagttgg aattctgtgg taaggaataa ctctttcttc    23700
tctttcactc agtcatatat ttaattgtac atcagcatga actcatagat tcttgttgta    23760
ttcagtaggt tgtaacccat tatttatttt attattcaag tgatctgacc ataatatttt    23820
aaattaagaa aacaccctct ccacacatgc tcaggtacct gatgagatca gaacaaattc    23880
tgctacatgg atggtattct caattccatc ccccaacacc cccgtattgc aatgtttaaa    23940
tgtttcagcc caaatatttc acagggtctg cttgcagagc cccatgcttc tcttcaacaa    24000
atgtttttac aggacaaaat ttgtcagta aattgtctct atttatgtt cctttgaaag      24060
ttttaccaag tttacttgct gaaatatcct agggcttttc aatttcactt caattcagta    24120
tagaatataa taagtctttc ccattaaaag taagcttaat gaacagaagt tcttcctac    24180
aaggtaagat actcccaaag tataactggt gtatatccaa agatatgaaa tcagtatgtt    24240
gaagagatag ctgcacccc acatccactg cagcattatt cccaatatct aagatatgga    24300
atcgatgtca gtgtccatca atggataaat ggataaagaa agtgtggtat atatacgtaa    24360
```

```
tggaacacta ttcagccatt ttttttaaca aaaaaaatgt aaaaagaagg aggtcttgtc 24420
attttcagtg acatggatga acttggagga cattatgtta agtgaaataa gccaagcaca 24480
gaaaaacaaa tattgcatga tctcacttat atgtggaagg taaaaaaaga tgaactcata 24540
gaaacaaagg gtaaaatggc agttaccaga agtgaaagga atggggagat gttggtcaat 24600
agacacaaaa tttcagttat acgggaggaa taatttcaag agatctagtg tacagcatgg 24660
tgactatggt taatatcaac atattgtata cttaaaaatt gcttagagta gattttaatt 24720
gttcctttcc acaagtagtt atgtgaggta aggcacatgt taaatagtgt ggtttagcca 24780
ttccataagt tatacctcat tccataaggt atacatctat catctatatg tcgcatacca 24840
taaatatatt caattattac ttgtcaatta aaaaaagaat aaaacattttt cagagttaat 24900
ttatgtgcac attaaaccca tcctagaata atattttgct aaccaaaaaa agatccagga 24960
caaatgctaa atcaggatgc tggaataaca gcgtcaactg ggataatcct ggtgaggcct 25020
catcttgtcc aaagaccccc ttttgattgg gccaggcctc ctggctactg ctgtctttct 25080
ggctgtggtc tttgctcacc cagctctttg gtttggtaga ctcaggttga tctccactgc 25140
tttgcatttg ctgctctttt gcctgtaaca ttgtacccct ccttgctcat atggctaatt 25200
tctccatatc ctacaacctt agacactggc atcgttttct ctaggtgcct tcccttcatc 25260
cctccaatgt gctccttgtc ctacctgtac tatgtatatc tgttccacga tacttccttc 25320
ttcacctttt tgaaacacca tgttcaatat cctgttattt aagagtcttg ctcttttgctt 25380
cctatgataa cagttattag aggaactgat ctgtgctagg tggtaagtga tggtgatgaa 25440
ttacttatct gttcctgaaa acatacttgt atttcatgga ggcccactgg ggtggtagtc 25500
ttcaaagtga gtgtgcacac gtctaagagt atatgagacc atttataagg atggaagtag 25560
aaaatgtagt aattttttatt tcttttttttt ttttttttga gacagtatct ccctctgtag 25620
cccaggctgg agtgcagtgg cacgatcttg gctcgctgca agctctgcct cctgggttca 25680
caccattctc ctgcctcagc ctcccgagta gctaggacta caggcgcctg ccaccacacc 25740
cggctaattt ttggtatttt tagtagagat ggggtttcac catgttagcc aggatggtct 25800
caatctcctg acctcatgat ccaccgcct cggcctccca aagtgctggg attacaggca 25860
tgagccaccc acgcccggcc agtaattttt atttctatta ttttattaag caaagctaag 25920
aagttaaagt gtttctcttt ttcttttat tgatttattt atttattttt gagacagagt 25980
cttgctctgt tgcccaggct gtagtgcagt gatgtgatct cagctcactg caacctccac 26040
ctcctggggtt caagcaatcc tccttcctca gcttccaag tagctgggac tacaggcgtg 26100
ccactatgcc tggctaattt ttgtagtttt tagtgggagt ggggttttgc catgttggcc 26160
aggctggtct ctaactcctg acttcaggtg ttctgtctgc ctcagtctcc caaagtgctg 26220
ggattatagg tgtgagccac tgtgcctggc tataaagttt ttctaatgtt taatattttg 26280
gttgagaaaa tacatgtata taattttata aatctaattt gacattggta aggtatacta 26340
agtattttta ttgatggagt actctatcat aaaaatttga agactacgtc tatagggcca 26400
tatgacatcc tcaatggaaa actcttcaag cttttttgaca ctataatagc taacatattt 26460
caagtgtttt ctatgtgtca cgcactgttc tatatgcttt acaggtatca acatacgtat 26520
tccttataac cacctcatga gattgatatg attattagca tcctcatctt atggatgaaa 26580
aaaattgagc tagagaatca ggtaatttgt tcaaggacag ggccagtaca tatcaaattc 26640
ttgatgtggt ctgattccag atgctgctag cttaacccct gctgtgtact gtgctgtgct 26700
ctggtgcctc tgctctcaca tgatagaccc atttggcttc ctggaggaga gggaccacat 26760
ctgtcttgca cattgtgcta gttttttacgg ggcctattat ttccttctct ctctttaaaa 26820
tcatcttttg ctccattttta tttcccaagg gcctgccatc ttcgatagga acttggaca 26880
agttctcttt tatttttaac atgaaaccat ttttcccctt gaaataaatg gatctgatga 26940
gaaattggca tgagtttaat tagcagtcct atgtatagaa acttacacg aaaaaagtct 27000
gcatcacccc agtactcacg agtcagttat gagtcccagc tcacccctga catgactaat 27060
gccttccttt cttcctttat cacgagggta tgaggacaag aaataaacct cagactactt 27120
ctgtcagcg tgtgaagtgt cccgcaagca cgtataacct taaaatagca acaagggcag 27180
cagcaacaac gacaacaaaa atgataatgg caaagagaag cagaacctaa tgttttttgg 27240
gtttgcccac tgatacccctt ttaatcctga ttttttaattg tttggcacaa agatatgtaa 27300
taatttcttg ggtcttctgg gcatttaaat gtcatttttgg tttcaccaaa tgtatttatg 27360
attccaccta cacatgtaag agtattggga gagttttgaa aggtttgtat tctatcatca 27420
tattcaaatt gtgctaactc tgttttcttt cctgtttttcc ttgtaggctc ttttaagaca 27480
cttactcttc catcagtaag tatccattta aaaaatttgg tttcagaaat atattgtatc 27540
agtgaactaa ataaattaat attttattgg attttatgtc aattcacaca tttcacgttt 27600
catgtaagtt tggcttgagt ttagttcagc cttcagatta tttatgaata atattatttc 27660
aaggagattg attatgaggc tcttcaaact cttggcagag attttcctct tgtaaaatag 27720
aagacttcac tgaaggaaac tggcctggac tattagcaca gaaatctgga ctggtcataa 27780
aaaggaacga gaccatgtcc tttgcaggaa catggatgga gctggaggcc attatcttta 27840
gcaaactaaa ataggaacag aaaactaaac accacatgtt ctcacttata agtgggagct 27900
gaatgatgag aacacatgga cacatagagg ggaacaacac acactggggc ctactggagg 27960
gtagagggag ggaggaggga gaggagcagg aaaaatagct aatggggtct aggtttagca 28020
actgggtgat gaaataatct gtgcgacaac ccccatgaca caagtttacc tatgtaacaa 28080
acctgcactt gtacccctga acttaaaata aaagttaaaa aaaaacaagg catctgggct 28140
ggtttgctcc tgcttctgtc gtaatgagcc ttctagtgtg aactctgct cctcagtttc 28200
cttgtgcttg aaaagagcag tgccatgctg agacatacta gaacttgagg caaaaggaaa 28260
aatcagtaat attgaccctg tctttgttta aaacttcgac ttctttgttt ataatttttt 28320
gcattaattt tgatattta aaatattgta ttaaatatt atttttcttga ttgctaaatt 28380
ttttggtacc cccttaaatt ttgcacctta gacaagtgcc tcactcacct caccatagcc 28440
ctggccttgg aaaagagaat gaagatacca tctttatctc acagcatgtc ctggagtgaa 28500
atgagatgtg gaagtgttgt agcacttgct atagaaatgg aaaggagtta ttattttgtt 28560
gagagattca taaaacctta ttattaaatg tttgtggatg aatcttccta tagctttgat 28620
ttggaagttt atactttcat tactatgctt tgttttgggg ctttacatgc ttaatgtaca 28680
gtatagtaaa ccacagcatc caacatcagg tgcagtttga tatatgtact tttctgagaa 28740
cagaggacta atgacttagg ccctgacaca ctgtatacct gattagtatc agcattacct 28800
cataagccag gttcgctcat taccttaaat ttttttttttt tttttttga gacaggtctt 28860
ggtctgttgc ccgggctgga gttcagtggc acaatcatgg ctcactgcag cctcaatctc 28920
ccaggttcaa gcaatcttct cacctcagcc tcccgactac tggcatgtgc caccatgcct 28980
ggctgatttt ttatttttttg tagaaacagg tttccctatg ttgcccaggc ttgtctcaaa 29040
ctcctgggcc caagcatccc tcctgccttg gtcccccaaa gtgctgggat tacaggagtg 29100
```

```
aaccaccatg cctggcccac ttagtacctt ttgaaagtta cttgtcaagt acattcagaa  29160
accacattta tttgggggg ttcatagaga atattatact ctcaaacaat actttataaa  29220
aattacttag tatgctatat ctattctgtt tgttacatat tatatttgta ctttctttcc  29280
taagaaatat actgctgcta ataatagaaa gtggaagaaa aaaggcataa gcaggcagaa  29340
gtgggggaaa aaaaccctgc aatctttgtg gcaataaaac attagattgc attaaaataa  29400
cctaaaacat tagatactgg ccccagtgcc tgggcgcaga actttgttga aagggtattc  29460
cagtggtaag atgaaaataa atcctgtgtc gtatatttgc cctatagcag aaggagggtg  29520
gggtttaagc tcaggaatca cagcctaaag cacaataatt gtctggtttc ctcaaaggag  29580
tttgcagttt cacataccgg aagtgtagaa aggctgaaag gagaaggcgg ggcaagggca  29640
tgagagtttc tttcaatgat actagtataa actgtacgtg tctgagctaa tattaactag  29700
aaatttgtct actacacttc ttttttttt ttttttttt tgagacagag tttctctctt  29760
gttgcccagg ctggagagca gtggcgcgat ctcggctcac tgcaacctcc gtttcccgga  29820
ttcaagagat tctcctgcct cagcctcccg agtagctggg attacaggca tgcccaccca  29880
tgcccagcta attttttttt gtattttag tagggacaga gtttcgccat gttggtctgg  29940
ctggtcttga acttccaacc tcaagtaatc cgcctgcctc ggcctcccaa agtcctggga  30000
ttacaggcgc aagccactgc gcccagccta ctatacttct tttaagtctt aagtatatga  30060
aatactaact ctgacatcca gtatttgtct ttaatattat gtcatttcaa ttgtatataa  30120
atatagctat tatctattga aagctttatt agagattata ttttggagtg tatctctttt  30180
tagtaaagca cagtatgaaa gacttagaaa taaagtgtat ggacaaattt gataatgctt  30240
gacaaaaaaa gaaggctctg cattttaatg agttttcaat taaagcagaa ccaactttct  30300
ttttcccag tgaaacata cctgtgaata gaaccacctt ttaaagtgca cttgcattct  30360
gacacttgta agtgtaatat tttaaattat ttttcaggtc tttatggctt ttagtgtaa  30420
aatataaata tttcaagaat gtgttaacac aaatgtgttt tttatttctg atttactcat  30480
tgtacttcaa gacactaaaa taccccaa tatgaagtaa ataaaaaaca taaattgaga  30540
caatataaat attgttttgt acacaatatg gcagaaaaac ttcttttgtt ctctttgtca  30600
aatgaaggag tggttttatt tgattagaaa tgtttttaaa gtgtaagtat aattactaat  30660
atattttaa tggaaactat catcttagat ttctcaattt tattttgaaa aattgtctcc  30720
gttatgtttg gtaactggca ttattcctga agtatatgag gataaatact attgtgttgt  30780
ctcagttttcc ttacagcagt gaatcttca gagaaggtga aatggcttta gacagcccag  30840
attagaataa gtaatcctta tttattgtct agcaagaata tttttgaatg tgcttacctt  30900
atgtatccta ggcagagagc tatcatctcc tcagagagtt tgcatttatg tatacacgaa  30960
atagatgtgc ctaagtgaga gtcaacatag ccaatccaga ggctgattga tattctgttg  31020
gtcaaagctt tgggatattg tcaattccca gactcttgtc ctgctttcag acagcctctc  31080
actgtgggaa ctgcaccttc ctccagccct gtgcctgtca gtcaaggagt ccaaaatctc  31140
tgtgggtaaa taattgactc ctgtttaaga gccatgaag tcacttatca aggaacagct  31200
ttttttcccc cttcccccca ccaatttcgg gaacctttt cagtaactgt ggccccaaga  31260
cggcagaagg caatttacca gtaaagatgc aggagcttct gttacctcat agtgtccact  31320
ctgctgtggg caggttataa cccactccag atctggcaca gagagagaaa cttttataaa  31380
aattgcttaa agtcaataat ctttcttca gtctcattat gcgcccccat tgttaaccat  31440
ggagcaccga ggtctgcatt gacaccacaa gactctggag caccacccag agtacgtggt  31500
gacacccga gacatgtggt gatgcccat gcttcataca ggcacccagg tctaatgatt  31560
caccaaggcc catattgtca tctctgggtg gcttgccctg ggactaacac tgagtctttg  31620
aggatcccaa attacctaaa tttatatat ggcaaggtgg ggttttttaac gggaaaagt  31680
taaaaagca aattagttaa ggtaacccaa aggaacagga agatagtcag taatgtttcc  31740
cctgagtcag tgtcagctcc ctgaaggagg atagagtagg aggtagaata aaatgttttc  31800
gggcatattt gcatttattt taattctctg acccttagg ctgcttgtgg ttaataggct  31860
tctttagctc taggcctctg tgtcattaat ttgacatcag tcttcaatct agcatctgtt  31920
ctggggcctc tgtgccacta aaaatgataa acatatcaaa tcaggaagag caatcccatc  31980
aaatatattt ttaaacatga aatatttaga aatcgatgcc atttataagc atataatatt  32040
ctggttcctg gtgtatatat tttcttgttt atagtattag gaaatctgat tcaaagagtc  32100
tgaggactga agtatcactt gagaaaatag aatttaagat tgcaagttcc aggctagact  32160
ctgctctacc agggcacagg tctttggttc atgttgtatc ccaagtacct agggcgtcct  32220
ggtacacaaa gggtgctcaa taaatacttc tttaggctgg gcgcagtggc tcacatgtat  32280
aatcccatca ctttgggagg ccgaggtggg tggatcactt gagttcagga attcgaaacc  32340
agcctggcca acatggtaaa accttttctc tactaaaaat acaaaaatta gctaggcatg  32400
gtggcgcaca cctgtagtcc cagctacttg ggaggctgag gcaggagaat cgcttgaacc  32460
caagaggtgg ggttgagatt gggccactgc actccagcct gggcaacaga gcaagagttc  32520
gtctcaaaac aaaacaaaac aaaacaaaac acttcttat tgaataaaag caaaaattga  32580
caccagaagt cattttgaagg tgacatactg attgttttc ctaacatttt attattaact  32640
tttcaaatat acaaaaaact tgaaaatgtt tcataatgaa cactcctata cttgccactt  32700
agggtctacc attaacattt tactatactt gctctatcat acatctatcc atctacccat  32760
cttttctatcc atccattagt tcatcttatt tttaaatgta tttccaagta aattgcagac  32820
atcaatactc ttctccctaa atattgctgc tgaccatttt attgttgaca gtggtttctt  32880
gcactttctt catattctta accacattga tagcattctg atgtctgcta ttattggaaa  32940
atcccctttg agctatctgt agacaaaact tattttgcaaa aatgagtcag gatatagttt  33000
cgggacctca gttttaatat gaaaatcaac taaaagtcaa gcatgctagt tatctattgc  33060
taagtaactc taaaactttg cttcaaacaa taataaaatta aactttttatt acttctcaca  33120
gtctttgtgg gtgaagaatt gggaacaata tggttgggca tttctgattt ggagtctcac  33180
gaggttgcaa tcaagatatc agctagggct gcagtcatct gaaggcttca tcagggctaa  33240
cacattctgt gaggcagctc attcactagg ctgacacgtg gttgttggtg gttggtggga  33300
ggccctggtt cctcccaatg tgggcctctc cacagacttc tttagtgtcc ttaccacacc  33360
actctggctt cctccagagt gagtgatcca agcgagaaag agagacaaca gggaagaagg  33420
tattcttttt ctgacatagc ctaattctag gatttggaag gaaatcacta agtctgggga  33480
attaggcttc acctttttgaa gggactaaag tcagagaatt tttaaaatt  33540
accacatcaa agtgtgtgtg tgtgtgtgtg tgtgtagtgt gtgtgtctga aatgattta  33600
ataagaatat ccacctgagg gattgttgtg aattaaaatg atatagtgca ggtaaactgc  33660
tcagtatggc tctggtctgc taatgctaga aggtaggact tctattgtta ttattattat  33720
tattattatt attattatta ttattattat tttgagacaa attctcgctc tgttgcccag  33780
gctggagtgc agtggcacga tctcggctca ctgcaacctc catgttcaag cgattctcct  33840
```

```
gcctcagcct cccggagtag ctgggactac aggcgcatgc caccacacct gggtgatttt   33900
tgtagtttta gtagagatgg ggtttcacca tgttggccag gctggtctca aactcctgac   33960
ctcaggtgat ctgcctgcct tggtctccca aagtgctggg attacaggtg tgagttaacg   34020
tgcctgggaa ggatttctgt tattaatagt agtagtagaa gtagcagcat catcatccct   34080
accaagacta tgcacatat gcgcaagatc cattaggaga atgcatctca gaaaacaggt    34140
tgagagaata tagcaagaaa caaattttgt gcagaagagc ctttcatcag ctgactgcct   34200
caaatagggt gagcgtggaa aagaaggttg aaggatgtta gatattctga cctgcaataa   34260
ctgttaggga ggatgaattt gcacttggaa taggaaatgg caaggtgact cctgctgagg   34320
gagagcagtg ggctatgtgt cccccattcc aggagccctg tgatgtaact ggagagcaaa   34380
ctgcaggaag ttaaaagagg gaaaacaaat taactctgat gcctgggagg ggcaaatttt   34440
caacatcgca gttacttttg ataatactgt gtatttactt ttttttattct aacttgcaat   34500
taaaacattt ttgaggtaaa ataatgagac cttgatgtgt gatctctttt tcccccccagc   34560
tacctctgaa cagtgcagat gagatttatg agctacgtgt aaccgacgt acccaggatg    34620
agatttttatt ctctaatagt acccgcttat catttgagac caagaaata tctgtcttca   34680
ttcaaacaga caaggcctta tacaagccaa agcaagaagt gaagtttcgc attgttacac   34740
tcttctcaga ttttaagcct tacaaaacct ctttaaacat tctcattaag gtaagtgcca   34800
gacagaaatg aagcaaggaa ttctagccat cttactaaac ccctctggga agttctgctt   34860
tgtgttactga cactggaata ttttagaatt caactaagat aagcttccct cccaacatgg   34920
aactcctcta ataggaaaga aggtggtgca tgcactgggt taagagctca gcctctagag   34980
tcaacctgct tgagttccag gcctgggtc ttcattgatt tatacagttg tcaaacattt    35040
attaaacttc tgtgttccag gcacagcgat agggcagtga acagaagaga ttaagtccct   35100
gctgacactg agtttatttt tcagtgggta gtaggagaca gacataataa ataaacatac   35160
aaatatatat ttataaaggg acagatatgt atgtatttgt gtgtgtgtat gagagagaaa   35220
aagggagtga gagacagaga gtttgtgttt gctattttct ttctttcttt tttttttttg   35280
agatggagtt tcactcttgt tgcccaggct ggagtgcaat ggcacgatct ggctcactg    35340
caacctccgc ctccttggtt caagcgatcc tcctgcctca gcctcctggg tagctgggat   35400
tataggcatg tgccaccacg tctgcctaaa tttgaatttt tagtagagac ggggttttcac   35460
catgttggtc aggctgacct cgtgatccac ccacctcagc ctcccaaaga tgctgggatt   35520
ataggcgtga gccactgcgc ccagcatgtt tgttgctttc tctagggttg tctgggaaga   35580
ctgatttgag cagagagcca aaggcagtaa aagaaaataa gcccatacag agggggaagc   35640
acatggaaag gccctgaggg ggagcttgtt tggcgcattg gaggaacaac aagctggcag   35700
tgtgctggag ccccgggcg aggggacagg tgctaggaca tgaggtccta tacaagtagg    35760
tgggttaggg tggggctcat gcagggcctt attggccatg ataggggactt tgaaacttat   35820
gctaagtgaa gtgagaattc actggagaat tctgagtcag agcttgatgt aatctaactt   35880
aacatcttaa aaggatcact gtcagctcta agaagaatag atgctagatg ctagctgtgt   35940
gatcctgggt aaatttatta accttctaga acctcagttt ccttatctag aaaatatgta   36000
ataataaac ctcaaaaggt ttttatgagg cttaagtgag ataattcaag taaaccattt    36060
agaactgtgt ctggcacata gtacatgctc actaaacgtt agccattatt attattttag   36120
gaacccttt tgaaaggtag tagttttgtc tctgctgctt aatactctga tgatttgggg    36180
gcactgtggt tagcacactg agtgcttcc tgtgagaatc aagttgaaga caactgagat    36240
ccagctgggc ctggttttct gtatttaaac ggagaagaac actggacatt tgatcattac   36300
ttggaaatag ggtgactaac atcccagtct gcctgggatg cctctgattt taaaactgaa   36360
aagtcctgtg tcctgggaac ctccttagtc tcaggacatt ggttactcca gatattctaa   36420
tgaataacat agtgtggaag gtaaagtagg cctttttagtt tggtatcttc ctattcttag   36480
tttatttgtt gttataaatt aaaacaacaa acccaatca aataaacatg tatacattta    36540
actttgagcc aagatatatt tgtagccagt atcacatttg ttgccatggt gttcaatgca   36600
tattgcttga attgaactag cattatttca gagtttgcct ttggtatgta atggaatgtt   36660
tataaagcag gttgacatag tgaatagtat ttctaaattc atgtcacccc cctgagcaga   36720
gttgaactga ctccattcat accatctttt atcatttatc cacatatatg gagagcttac   36780
tgtatgtcag aaaggatgtg tacaatagat ggttaataa atgtctggct atctctgggt   36840
gtttacattc aatgcttcct tctactgcag gcaaataaaa gttagcactg cataaattgc   36900
ctgttctaga catcaaccca gaactaaccc tgctggttct ggataattag tctgtgcatt   36960
ttcatagttc tgcctgtcta ctctgctcta gtatcttcct ttgaatcttt gatttgcaga   37020
ttctttgggc tcttctgtgc agtttgggac ttagcagacc acgtttggct ttctggaaag   37080
ggctcagaga gactttcctc ttattagctc tggtactgat atgactctct tggccagggg   37140
aggggagttt aaaactaaaat tctacctgga acccaaagtg ttttggaact atgagtgagg   37200
ggtggccatg ctcctgtctc tgtacctggg aagtgatgct caaatgtgga cttaggtcta   37260
gctgccttcc tccttgtaac ttgcagaggc caggtgggag cagtaatgtg aactctttca   37320
gctgaaaaca gacatttggg ccaggtttac aagtctatga tattttctac atcttttcagt  37380
gtggaataat tggtgtcttg gcaaaacttt tcagaacaaa ttgggactta gcctgaactg   37440
gagccctga ctgagacagt tgtactcctt ggcacagcac cacctgcagg ctgatgtgga    37500
gaagtgcacc tgagagttaa cggggcccat cttgcccagc tagaaatggc tgcaggatgt   37560
agctaagata ctgactgtca cagcaccttc agggtgttca ttgttgttct tggggactgc   37620
aggccatctt tgggtgttat tcattttgca tgccccaata tgctcttc tcaggaggga    37680
aaggagcttc gaggcctttt ggcagtagaa aaaacataac ctatgtctcc cacgcttctg   37740
gcctcctcta gccaatttgg cctgacacaa tggaattgag tgcctctgac actgcgatgg   37800
cagctggcat ggctggcttc tgctctgacc tctccatcca gaagttgttg gtgctagtac   37860
gggtgaatga tcttgtaggg gaacaggtgt tattggcttg ggggtatatc ctgttattgt   37920
gccctgacac tcagttttgg agcagtggtg gctaactcag aagctgaccg ctggccaggt   37980
gaagaagcta ccttatttga gtgatttgaa ttctctaatt ctacaggctg acagacatg    38040
ttattcacac ataatccaga aatagtcctc acagacatat tctccagcca gggagcttac   38100
tgcttgagac aatcaggtac tgtgtgctgt gttgaggcat ctcagagatc cagagcgatc   38160
taaaggtgac tcgaagggca tgtggggcca ctattccagg atctctggcc tgcagctttt   38220
ctggtctgtga cggggtatt gctcatactg tacatgctg tgtcgtagca gcagatggcc    38280
gcatgcaaat gctgggctcc gctgtgacat caccatgctt ggctggttca aatcctgatg   38340
tgtcttgtag acttctggtg tttctgcatt ctctccctct gccttattgg taacagttag   38400
acctaggtcc aagacaggct tgggaaagca gaggaattat tcattctcc cccaaccctc    38460
cagatccccc aggtacaaag ccatcaatga ggtcagttca gacttcattg tccaggagaa   38520
atgtatgccc tcactaccat aatgttttcag tagaatatgg acattccatt ttcctacact   38580
```

```
tcaggtaaca ccaagaatta ttgttattat tattttttatc tttgtcagac tgacagaaga    38640
aacacaatat tgttttcatt tgtatttcct taattactag acagcatata tttattggct    38700
atttgtattt cttcctttgt tcctgagcct ttgaacttca tagccctccc atgcgtcatg    38760
ctgtggcagg cacagtaggg ccaactgccc attacaatgc ctggcccagg agtttaccaa    38820
ggatacagtg acctgcttgt tcttgacttg cttttggtct ctggttttca caattggttt    38880
ctggcttatt agactgcttt ctgcacagtt ctcagcattg tacttacccc taactgtcat    38940
atctccactc tgggagagag gtttcttctg ttctaataac tggccccact cactacttct    39000
aggcaaagtt tagaggataa gtctaaggga aaatattcaa cccctgctct cagtcacagt    39060
ctagttggga ataataaaat atagattttt ggcaaaataa aatatgtaaa ataaacatat    39120
tttactgcct ttaacaaaaa tatgtattca agagagataa actccagata tactagggac    39180
tttccaggaa gaagtcacct ctgcctattg gaggcatgta taggaggcaa gaaactgaaa    39240
ctgatttcac cagtggacaa ggaagggagg gatttccatg cagcagttgc agagacctac    39300
atgcatgggc ttttgggaa taaactgcaa acaaatccgt atgtttggag gaagatgagc    39360
ctagaaatgt agatggagta gtattagtaa gggccttgta aactaggcaa aggagtgtag    39420
acttcctgta ggcaaacaaa agccatgggg acctagtggt ctagtataat catcatatac    39480
tataattagg gactataaaa agtgtatagc cactgctttt tatatgccag ggactgtgcc    39540
aagtatttca accactgtaa ctcattctca gatttgcgtt tcagatggat cacactgttg    39600
gcagtgggga agatgtattg tagagggcaa gactagaggg ggaagattag ttgcattagt    39660
tagaaaatag gacatggtgg ctggatgtga ggatggaaag aaggagacaa attagagata    39720
tattaaccta acaaagttaa aatgtcagga aatgtgagag aggaatctag gatgactgct    39780
ggaatggctt ggataaatgt tgcatgaagg gattgttgtt tgggaggtta taggaagaat    39840
gaagtgtttt ccatgtatat ccgtgattaa acatctctct aatatgcttt tgttgagtta    39900
aaaggcagac atgagtttgg attctgaatt tcatcatgca ctggtgctgt aatattgagt    39960
catgccagtc acttgaatgc gtacctccct ctccaggcat cagttttctc aactataaag    40020
tgaggataac catgtcctaa aggagaattg taatgattag agataaggca gagtgcctga    40080
cacatattgg gcctttaata aatggggcct gttatctcta cagttaaatt ttcttttaac    40140
actactacca ccaccgccgc caccaggggt ttggtgacga acatgttgta gtgtttcatg    40200
tagaaggaaa taggtgccta ggaattaaaa ggtggagcag aatcaagatg aacttgggag    40260
aaatatgaga aaagaataaa cttgattgg tcttctttag aaatatagag cctacgtttt    40320
ccaaaatgtt catgcagcat tcatccaagc cattccagca gtcatcctag attcctctct    40380
cacatttcca gacctttaa ctttgttagg ttaatatatc tctaatgtgt ctccttcttt    40440
ccatcctcac atcctgccat ccagccatat ttgtgccgta ttttggagta aagttctgga    40500
cctgggtggg aatgctgcaa ggcattattc ctaacctgat aggatacaca tgcacatggg    40560
cagcctctac atacttacat gtctggtttt cattttagga ccccaaatca aatttgatcc    40620
aacagtggtt gtcacaacaa agtgatcttg gagtcatttc caaaacttttt cagctatctt    40680
cccatccaat acttggtgac tggtctattc aagttcaagt gaatgtgagt ataaatatat    40740
tttttggggg gaatgttaaa gtgatttaat taggtcaggt gggggaaaat ctccaaagtc    40800
atttatacaa tgaagagaaa aaaattaatg tgaacattta gacaatttaa acggtttatt    40860
tttaatttat gatgttttatc aagggtttat ttagctttca ttctaacata ttagaatttt    40920
cataactgtt gtcttttttct atgatatgat gtttaaaggt taaaacattt tgacatttta    40980
gtacacaatg tttacttatt tgtttcatgc attattttaa aactaagtaa tgaacacata    41040
gctattattt ggcaaatttt atgccttaga ataatgactc ctaatgagtg attagattaa    41100
cctacttttta tctttgttttt aagaaacagt gacttaaata gctacaccga ctgctattcc    41160
ccaatccttt ttccctagct tctacaccta ttgcctttac ttgctgccaa cttgtatagc    41220
tctgaaatct aaatgagggg cattaaatgg catataaatc taaatggggg gcattcattg    41280
gaatgaatga gacataaaca caatgggatg gaaacaattt taaaaagcaa tgagacttaa    41340
ctgttttatg tgatataaat tggtcattta gtatataaca tgtaaacctt tatatttttc    41400
tatatttatg tgcatataa acatataaga tataatcaac tttttctgta tctaaagggg    41460
aagatatgta atatgaaatg catgaaattg tagcttattc taagcattgt tgctgagcct    41520
tgagtaggtg ggactcgtgt gtgaattgac ctgtatgaat gagaacagtg ctggaggcac    41580
aatgactct caatatttgc ttcatggcca ccctgcttct ttatgggtgt ttgtatgatg    41640
tgtttaccaa tattattctt tttaaggtag cagaagctct accgaatgaa tgtatgatgt    41700
ggttttaaag aacatttgag gcaatattat gaaagggct catactgtta gagaacaatg    41760
taatgcataa ccattaaagt catggacaat tttcagtgag gtctttgctt atttccttac    41820
ttataacagt gtaataataa ccactgttat aaatggcagc ctagagcagg atgtgatgag    41880
ttctagggga agtggaattc tttatatctg agcttgtaga gaaagtggaa agagtaggca    41940
tttgtgaaac ttagaaaata gggaaaaatt tgtgtgggag tagggaaaat ggaagagaac    42000
gttatgtgtc tggggatttg ggagaagttg atgttactgg agcatgtgga gaatgatggc    42060
ggtgtagatt aggaagcacg ttgtgagttt aaagtagttt gaatattatt ttcagtttccc    42120
acttaaattc ttaagaatca cttttttttgg tccatccatc catcgatcct tctatccacc    42180
cacccaccca ccaacccagt atgtgttaag gactttatgg ctgtgatgaa tacaaagaag    42240
gtaaacatat gacctccatt ttcaaaggtc attgtcatgg tgacatgaac aatatgataa    42300
aaattaaatg acataagggg gacagacaaa cacagggcag tgcaatagca gaggaattgt    42360
aaggtgttca gtccagcttg gtgataaaga gggtttattg ttagcacaag cactgatgtt    42420
ttggggccag ctgctccttc tgtctcccat ggtctgctct gttctccttt cactcttctg    42480
ccaacctttg aggtgttctt cagttcttct gattccatta gcttagctaa ataaccatca    42540
tgcccagaat cttttaaagca agcctctgca caggtggctg gcagcctgtg ggtgggccgc    42600
cctgggtcaa ggtgtccatt tttggtccat tcagatgcca cctatgcaca atgaccagca    42660
agagcagttt tagctggata acaggcgctg agggattaat ttgtttcattg aatggtggac    42720
agaataagta ccagaagaga gggggataga atagcagagg gagactttgc agaagatgtg    42780
agattatact ttgaaagatt tataggattt atcatgttgt ggtttgtgga cttggcttgt    42840
catattgctt ttatagaaaa caaatgctct taaggaaatt taggtgctta aaaaatgaaa    42900
agcatttgca ggatctggcc cttgcccaac ttttcagtct tgtaaagtgc cgcccttcct    42960
cttgaactct ttaagaagga catcttatgt cccttaagtt tcttaaactc accgatctgt    43020
ctcattctag agcctttcat catgctgttc cctctgctga gaatgttttt tcttccttat    43080
tctcgctact tgcttttaac ctgcagccat tctctaaagt ggcctggctg ttccagacat    43140
tcccatagta ctgtgtgctt cccttaattc attcatctca cttttaatta gtggtccatg    43200
atagacagta gcctttgtaa agctggtgac cttctgtcct tgctcacctc tctattcctg    43260
ggaccaagtt cagtgctttt gcatgtaagt agaaaagcagt attttcttaa aacgaatgtg    43320
```

```
tgaaaactat atagcaataa tttgtcttga accaaatgca attttcccct ttgtatattc  43380
tataaagcat ctttatcttt ttgaagacaa gtatactgat caggtacttg tcatttgagg  43440
tatgttaatt tgaggcattc agctaagaaa aaataagccc cttaaaaaaa agagccctt   43500
tagaaccacc aggggtcagt ataaccaagg aaatgttatg agaagcaact gtggccttgg  43560
tctctggctt ttgttttcct ttgactactg cgcagcatta aaggactgta tatttcttgt  43620
tattaaaccc cttttctttt agtagtgaat aataacatag aggaaatgta tttattattt  43680
aaatagccca ccattagaga ctatatttt  acttttcggt ggcagtcacc attctcaata  43740
taaaactcag ggaaggaaaa tatttattt  caagaaagta ttggctgggc gtggtggctc   43800
acacctgtaa tcccagcact tgggaagcc  gaggcgggcg gatcacgagg tcaggagac    43860
gagaccatct tggctaatac agtgaaaccc cgtctctact aaaaatacga aaaattagct   43920
gggtgtggtg gcgggcgcct gtagtcccag ctactcggga ggctgaggca ggagaatggc   43980
gtgaacctgg gaggcggagc ttgcagtgag ccaagatcat gccaccgctc tccagcctgg   44040
gcgacagagt gatactctgg ctaaaaaaaa aggaagtatt tttaaattt  tttaatttgt   44100
aagagacagg gttgtcgtct gtcactcagg ctagagtgaa gtggcacaat catgttcac    44160
tgcagcctcg aactcctggg ctcaagtgat cctcctgcct cagcctcctg agtagcaggg   44220
actacaggta tgtgccacta cgcctgccta gttaaaaaat ttttttttcc ttttcataga   44280
gacagggtct tgttatgttg cccaggctga tcttgagctc ctggactcaa gcaatccttc   44340
tgccttggcc tcacaaagtg ctgggattac atgtgtgagc catcatacac agccttggg    44400
agagttttga aattccattt tgtctgtaga aaaaatatgg aatgatatga gtattcccac   44460
tgatggacaa tctctttaag aattaccgga gttatcagag ctttgatttg taatgactat   44520
acaggtaatc agaagtggt  attcttcagt taccctttgt cctaggtcag gaaaggatc    44580
ctttaagtaa aacatacttg acggctcctt ggcatttctc cacttgtatt aataacatgt   44640
ttgtttgtag agtaagagtg aataagtcct ttatgatacc gtgttaacct ttctggatta   44700
atctaaattg tttgccctt  aagtattgta ttgcttttca ccttcaaggt tttttatgat   44760
agtaatggtg agtaattatt ttggtctagt atgatttcta gttttctttt ctttctttct   44820
tttttttttt tttcgagaca gagtctcgct ctttgccca  ggccgtgttg tgatctcggc   44880
tcactgaaac ctccacatcc caggttcaag cgattctcct gcctcagcct cctgagtagc   44940
tgggattaca ggcatgcacc accatgccca gctaatttt  gtattttag  tagagacggt   45000
ttcatcatgt tggccagggt ggtcttgaac tccagacctc aagtgatgca ccctactcgg   45060
cctcccaaag tgctgggatt acaggcatga gccactgtgc ctggccaaga aaggaaacaa   45120
atgttttggg ggattagtta agtgatttgc ccaatgtccc acaacttacc aaactaggat   45180
tagaactcag gccttttgac accaaatcca aggttctctc tacccctgcca ccttggtttt   45240
ccatcttatg ttttatctct gtcattgttc agcatatgat ggtgggacat cataagttct   45300
caatatatac atagactttt tttttttttta caatgctagt ttaatcaaat tgcaaagaaa   45360
ctcttgatga ttataatgtt taagacctct taaaatcagt aaagtttagt aagagccctg   45420
gctctttttg tgctacttat acgtgtgctt aattgacaca catattctag tgtgaatagt   45480
tctttgctac tttggggatt gtacttcttc tcttgagaat gtgaccaagt cttctacttc   45540
tgccatactt tgattgccct gctctttttc atcatttctt tgtctagagc accaagccct   45600
cctctcagag ggcagaggta tattttagct gtaacatctt ttcataagg tgtgttttat    45660
agggccgtta tactttaggt acattataag ttgagtgtgg gaatatgttc tgatttaata   45720
attgacttga aaatacacct taggaagata atgtgttta  aaagttagac attccttat    45780
tttcatttct ttgcaatata gttctctagg taccttatct ctaggtatgt tatctcttga   45840
ttggtgttga cagttttctc aaataattgc acatggtttt tttgttttgt tttgttttgt   45900
tttttgagaa agagtctcac tctgttgacc agtctggagt gcagtgtgca atctcagctc   45960
attgcaacct ccacctccca ggttgaagtg attttcctgc ctcagcctcc tgagtagctg   46020
ggattacagg tgtgcaccat catgttcagc taatttttgt atttttagta gagatggggt   46080
ttcaccatgt tggtcaggct gggctcgaac tcctgacctc aggtgattca cttgccttgg   46140
gtttccaaag tgctaggatt acaggcatga gccactgtgc ctggcctgca aatggttttt   46200
ccctccattt tttatttct  gtagtaaaat acacataacg taaaatttgc cattgtaacc   46260
atttttaagt gtacagttca gtggtattaa gtacattaat attgttgtgc attcatcacc   46320
accatccatc tctgtaactc ttttcatctt gcaaaactga aaatctacac ctattaaaca   46380
ataactctcc attccctccc accccccagc ccctggcagc cactgtacat tctatctctg   46440
tggtgttgat tagtcttata tcagcagaat catacaggat ctcttttga  gactggcttt   46500
tttctcttag cataatgtta ttatggctca cccatgttgt agcatatatc agaattttct   46560
tctttttaaa ggctgaataa tattccattg tgtgaatata ccacatttgg ttgcgaatgt   46620
ttttgcatct atgatttaaa aattatattc gaggttatta gaaggtgatt ttagggggttc  46680
tttaaaagaa aggctaatgt tggtgtctga gaaccaggct tctgggagcc aggaggcatc   46740
tggccagagc agtgcagcct gcagcccaga gctccaggtc tttgcgtgac ccacgcactg   46800
gtgctcatgt tcctccaaga gcccgaaaga agagcctgag tcactgagag attcctggtc   46860
atttgatgac ggcagccctg tgctgtcttt cctcattgtc agatggaagt ctcttcttct   46920
ttctagagtg gcttaggcat ttgagtttac cataatggcc acctgaggct gcagctggtt   46980
ctgaaacatc agtgtgccac agaatcaatg gactgggagc ttgtttaaag atgcatagtc   47040
caggtcccac cccccagatca caatttacta attttggcat gggagctagg agtttgaatt   47100
ttaaataagc actcaaggaa attctactag ttttttgaac acattttga  gaagtgctca   47160
taaatgcccg cagctaggca tctttagaat ccatctttc  cattgagagg cagtgttggg   47220
cagtgttggg cagtcaacaa ggtatggaac tggggacagg ccatctgatt tattctttga   47280
attcctcagc agtgctactt tctgctattt actttacctt tttaggtaat cagctcagta   47340
gagctcccca gcaccttaga cattactaagt cagaatttct gggacaatgt atatccttta   47400
caacgcttc  tctgatgctt cagatgcaca gccagcttgg gaaccactga acttgataat   47460
catcttttct atctgtcact aactacaatt tcgtaaccgt tgtctcaatc ttaagccatt   47520
gttagaggtg gggaacaaga aatagcaagc agaaaactca acagggttaa ggcttgaagt   47580
cactcttctg gagccctgta taatgaaacg ggttatcaaa ttattatgta actcagaagc   47640
aatctgcatt gagttatttc tttgcatcta acagttatat ctagttttctc ttgagttact   47700
tgttttttct agattaggtg aggggttgcca acaccttact gttttttata acctttcagg   47760
atattcctta ttttttttctgg acttgttgtc cagcctctgc ctgggtcagc ttgctgcttc   47820
tgttaagtat ctctgagcc  gttttcttt  tgcaaagag  cacatctttg tttgacagt    47880
tcttgtccct aaagcactct accaggagca tctgcttaac ccgcctggct tgtgacgaca   47940
acttaacaga aagcatggag caaaactttg acaggtcaga aaacagtggc attctctctg   48000
aaatgtggtt gtggcttcca aaatactttc actagtcttt gcttataaga agaatgcttt   48060
```

-continued

```
gtttgggaag gatctcaaac tcttacttcc ttgttcagtg agaaaggag  ggaggagatg   48120
gttttagaat attgatttct tagagcatta tctggcagag ctcagcactt tctcctccat   48180
tcttccaaag gccccgataa acacctctag aatagcattt attaatcagt gtagcgttat   48240
tttcgttttt taaaaactgt ggtaagatat atatgtaaaa tttaccattt taacaattta   48300
aaagttaagt agcatcaggt gcattcacat tgtggtgaca ccatctgcca ccatccatct   48360
ccagaaccta ttattatctt cagatatttta aaaaaatgtc tgcctcattt cttaaactgt   48420
gaactccttg aagacaggaa ttctatttta ttaatttttca tatttgttct gtctaatata   48480
atatctgacc tgttatggga actcattcat gcttgtggga tgaaagaatg agtgaataga   48540
gcttcttcta gatgattgct gttattatcc tttgtgatgt tctttgactt ctagtctcac   48600
tctgctatat catcttgcaa cttagtagaa atatctttgt atatttttcat tttgagaata   48660
tatatggttg ctgtatttga tgaacctgtg agctaatgga aaacaggact tttggattaa   48720
tgccctggac tttctcattt tgaaaattaa aaaaaatctc aggcaagagc tgaatattct   48780
agtttgttat aaagtctaaa atagacttat aattttggtg ccatattatt cttgtgtctt   48840
tattcagcca tttgatctgc tagtgccagt cctttgcagt tgtgcatttt aatttctagg   48900
ccccatatgc aaattttcat gaggagttct ttgttttgtt cttctctac  agaagccacc   48960
ctaggaggac ccctcctttc aaatgtgtct tctgtacccc tctctgaaga gacatgtttt   49020
tggcatcagt tagaaaactt tggggccaga cttaggatg ttgtgttcat caatgaaatg    49080
gagggtctga gtatgtagca tcatcagtac ataggatagg gactcagtgc tatagatgat   49140
cttagaggtc gcctagatcc atctcccac  tttatggagg aagaatctga gataagtgac   49200
gtgacctggt taggctcaca cagtgtgttg tgggagggtc aggactagca actagtttac   49260
tcatactttc agttctgtaa aattaaatta tttaatatgt gcagcaattg ctgttttatt   49320
tatttattta tttttgagac agagtcttgc tctgtcaccc aggctggagt gcagtggtgc   49380
tgtctcagct tactgcaact tctgcctccc aggttcaagt gattcctctg ccttagcctc   49440
ctgagtagct gggatttaca ggcatgtgcc accatgggcc tggctaattt ttgtattttt   49500
agtagagaca gggtttcacc atgttggcca ggctggtctt gaactcttga cctcaggtga   49560
tccgcccgcc ctggcctccc aaagtgctgg gattacaggc atgagtcatc atgcctgcc   49620
agcaattgct gttttaatat ggcctccttt taaggttgaa tttagatgtc aacagggctt   49680
gctgtatgca ttggtggaga agatacctac ttcttttata tgacttgtgg atgccacggg   49740
atcaccttgt ttgcacgttg gattgttccc aacgtgtccc agattctgac cacagcagcc   49800
atgtgtttag attgaagatt tgagtccagc atgtaggtta cttggttcat ctatttaata   49860
tccattaata tactattaag gattaggctg ctgtcacctc acagcctcta taaccttggt   49920
catatgaggc ttacaaagat taatttttg  ttgtttgttt ttgagacaga gtctcgctgt   49980
gtcacccagg ctggagtgca gtggcacaat cttggcttac tgtaacctcc gcctcccagg   50040
ttcaagcgat tcacctgcct cagcctcccg agtaactggg attacaggca tccaccacca   50100
cgcctgccta aatttttgta ttttagtag  agacaaggtt tgccacatt  ggccaggctg   50160
gtcttgaact tctgacctca agtgatccgc ctgcctctgc cttccaaagg gctgggatta   50220
taggcataag ccactgtgct cagccaagaa gattaatttt aaaaataact gtttaccttt   50280
aggtagattc acagaaaagtt gcgaagatag cacaaagcgg ccctatatta tcttaacgca   50340
gtgcacccag tggttatatc ttatgttatt atagtacaat ataaaaagca agaatttgac   50400
gtttgtgtgg tatgtgtgta tggttctgta tgatgcttta ttttcagtgg catagaggga   50460
gttttggaaa atgataactc actgggctct gaccagtggt ggcagccctg ggtgaggggg   50520
aagggggcac tgaaatgagt accaagtccc tgggtggagt gaggaaaggg agaaagagca   50580
agaaatggag ttattttccc tcaaggataa cttccctatt cagtacaaac ctgtagctat   50640
gctgctgctt ttgctcccttt gcttgagata ggtgcccaag aaaggtggtc atgttacatg   50700
tctttaaaaa ccatagttcc ttctactttg agtaggaaca gagaggggta aatgggtgat   50760
ttttgtttat tgtttgtttt taaagagaat atgtttctag ttagtacttt ttttttttca   50820
acaccaagga aacaagtttg tccttgtac  tgcataatgt atttgtactg cagatggtaa   50880
cactgtttta ggagtatgaa tgtgcttgtg atccctggat acctggccac tattctgcta   50940
actgaaggct tgtatggtct atgtcttggt cattggttag atccattatt cccaagtcct   51000
gtcactatga gtgactgtca ggtatagacc agcttcagtt cttcaggtgt ttagttccag   51060
cctgataag  aaccagaata tttgtaatcc tttctaatga gagaagggat ccaggaacaa   51120
aactgtctcc tggggaggtt ctgattcctc cctcctcaca ctcagtagat tatcttcctt   51180
tccacttcac agagaacaca gtcatcagat gggaatttct ttcacttttt ctgccagatt   51240
tgcatgtgtt gcctgtgccc atctcatgct tattctcttc tttttagagg aaaggtccta   51300
ttcttcacat ctaagaccaa tatcccgatt tctgccttgc cttctttctt cctctacttt   51360
gtcagaaaac ttgcagtgtt gacagtctct ttcttctcag tcttcaaact ggatctcttt   51420
ctgtcttaga tcttttttata aaatctaata tgtttaattc tttctcattg aaaaaacaaa   51480
aaatatagag aagtactgta ctttaactct acttcctctt cagtgacttc acattccat    51540
tctagccagt cttctaaaaa aaaatgtctg atctctctgc ctccattttc ccaactcact   51600
ccagtttgac tgagatttct ttctactttgt ttggattctt cttcttggtc acttttcgtca   51660
tttactctct attacatatt ggcacattgc aagtttggtt ttaagttct ttcatttctc    51720
actctaggga agttcacccg aaggcatggt tcagtttttcc atctatacac caatgactct   51780
caaattggcc tctctgagag aacctatacc tctgagttct agaccctttaa aactatctac   51840
ctttaaaact atcaacatct gtatttggat gtttcaaagc acccccaaact cttcatgtcc   51900
agtatcattc ttaacaatct ttccccacca cacctggctc ctctgcagca tttcctacct   51960
tatttaattc tctatccatt cggctgtgca ggctggtaac cttagagttc ttgacacctc   52020
atgctgcctg accacccata ttcaggcctt catcaattcc cacagctttt tcccttaaat   52080
aaatatattt cttttttt   tcctaccctg agacagagtc ttgctctgtc   52140
acccaggcaa tctcagctca ctgcaacctc cacctcccga gttcaagtga tcttcctgcc   52200
tccatctccc gagtagctgg gagtacaggc gtgtgccacc atgcccggct aatttttgta   52260
ttttttgtag agatggggtt tcaccatgtt gcccaggctg gtctctaact ccttagctca   52320
agtgatctgc ctgcctcaac cttaaatata tttcaaatcc acctactctt ctatttccac   52380
ctctccctcc tttgtccaag ccactattat attgttccta gatattacag tgtctcttaa   52440
tctctctgca tttggttttt ttccccttttg caaccaatta ctcacacagc agtaaaaata   52500
atctcaacat tagctggatc atgttattcc ccagcttaaa actgtccaaa gactttccac   52560
tggcctcaga acaaaattca gatgtttttac catggcctac acagggtctt acctgatctg   52620
actctgttttt tccatctcta tctccagatt tcataactct ctgtaaatgt taattcacag   52680
cttttatcat aaatttgtaat acatactcac atatgtggtt atttgataaa tatccttctt   52740
tccactagat cagaaggtcc atgcggggtt gtattccat  tacacctgcc actcaggcgc   52800
```

```
aatgaatatc tcttgaagga atggatgaat gaatgcattt gttgtgtttg ggcctcagcc   52860
ctggtaattc tgattcagta gctctggggt aggaactgga cacctctatt tattaaaccc   52920
accacagctg attctgatgc tgagtttggg ttgaacccca tagagaaata tgttgcaact   52980
acagtttaga ccacaggtgt ttagactcta aacaggaaag ggaaggaaag gatgatgtaa   53040
atgttaataa acattttctc tcattttgca aaccctattg actctgtcat tcctctaagt   53100
aggacagtgt acatcagctg acactttttac aggatgatat ttccattgtg atttcttttt   53160
tattttttaag ctctcccaat tttatggtaa aaataaaaga ggggaaaaat agggtattac   53220
atgattgcta ttacgtaggc aataggttta ggcatagtca ggttagtagg gatcggaata   53280
aagctaaaaa tatgaagctt ttgtgttgta tgcgagggtg ggaagaaaca ccagtcagta   53340
cacatctaaa ggtgacaaga cacagacctg gctttcaagg agcttacaat cagaaaagct   53400
tcgtgtaaca aatgcaaaga gcattagatt aggagtccta agacctgggt actgtgctct   53460
agttaagtga tggtgggcat ggcatttcag ctgtgggtct ccgtttcctc agctgtaaaa   53520
taaggggttt ggatcaaggg attttttaagg atcttcacaa ctttacaagt ccaagatagg   53580
gctggagggg actgtaggat ttggatggga agtggtgggc tctgagctgg ctgacaggge   53640
tgtggggctg ggagcaggca ctggctggca tggagggctt gtagagagta gtagttgaag   53700
agaaggtgg ggaagtttgt gggccgagct gtggaggata ttggctatca ggctgaaatt   53760
ttgtatttca ttttgtagac aacaggcagc tctaaaaact tttgtgtatt ttactttgaa   53820
tttcaatcag tgatgcaaat ttcaatatag gacttctgag gacaaaggaa acaaaatgtg   53880
tgtgaatggg tctctcaaat tataaaagtt ataggatcat accttcataa ttttcctctg   53940
gttataaaag taatgcatga gtaaggtaaa aacatccaaa catgatagtg tagaaagtat   54000
gacacccttta tggtaaactt ccaaacaaac aaaaatcatc agtatgtgtt gtcttcttat   54060
tgcttttagta gaaagtttct atgtaaaagt atgacatgat taaagttgta ttttaggaag   54120
atcactttgg tggcagcatg tagggtgatt agagggagag aaactaaagt ccaggagact   54180
accaggggggt tagtattatt gtttaacaaa tatacgaata ccttcaatgt tagcttataa   54240
tcgaatacct tcagtgttag taagttcaaa ggtaatgggg gactgcggta agagagcaga   54300
aaaaattaaa gaggaatgga tgaattcaag agacacttaa aggcagaatc attaggatta   54360
gtgactggat ttcgattgga gcagagaaga aagaggagca aaaggtacct gggaatttca   54420
agttgggtct ttgggagaat cacccatatc agttctaggg aagttaggga tggaagctca   54480
gtttgggtga gtgggtatgag ctagatgtat ttggactgag ccatcagaaa tcacatttag   54540
gagcaaagca gagaagccat ccaaagcaat agagaaagaa cagccagttt tgggaagaga   54600
aaagcaagca agttcaggca cagagcagag ggcaagagat tcagagagag tggctttcca   54660
ggtgctgcag aggcctcaaa gggagtgagg cctgagaaag gtgacaggcg gttagaggaa   54720
agcaacctgg cataccgagc atcttctggg gtcagtgaaa tgggagaggc agaatcgaga   54780
tttcaagagc aataaagcgc ataaatagct atacataaca tagctatgta atgtagggta   54840
atgtatataa tagtctacaa cttctgttcc taagaaggag agaattaata tgattatctg   54900
gtggaggcag cagcaatata atttcattta tgttatggta ttcctattct tacttaacat   54960
attcatgccc agttatttat gtgtaactgt gaggttgaac atttattact tgacaggtga   55020
agtaaaaaag cacattattt ttgtgccatt ttgtcctgtt ctttgggacg aattcttccc   55080
tactccttgg ataaaatgta gggaaaatc catcattttt atggttactc tttggtaaca   55140
aaaggtcctg tcatgttcgg ttactttcat atacacagtc tacattcagt aattaatatg   55200
tccagtctaa taaaataaaa tgctcccttc tccagctcgg gtcttctttg gtctggatgc   55260
ctgcctccaa ctcactaggc tgcctttgac tcctccagac tgaattgggt ggaggaaaga   55320
gaagtgaggg gtaacaaaat tctcatctga tgtataaggg tagtcatgt gaacttgcta   55380
atatttgtcc tgcaaaaatg tcaatttaat atggttcaat gtaatactgt tgtcatctgc   55440
atgagacctg tctgggctaa gacggcattt aaaactacat ttttcctttt tagaactcct   55500
ttctgtattc ctaggaggac ccttaagatt gtggggaggg ctttcatcca aagtaccctg   55560
gatgcttttg aatctgtctc ctccaaatgg cagctcataa ctccatcttt agctgctggg   55620
catctagatc acacacctca gcttccctct tctgagggct tgccttattc ctactaaggc   55680
tgttttgatc aggatagaaa acagttccat gctgacttgc tcttttggca tatctagttg   55740
agggaaaatg ctcatgcttt ctctgatcct gaacattcag gagatgcaga ccactcctag   55800
catagcacac tcttagctcc actgccagca caaatattat acccttttaga gtttttcaggt   55860
gtgtcaacag cctgctcact gacagcttga ggatgctccc agggacacat acctagttgt   55920
ctgcattgtc tatggaagcc cgtttcccta ggcttgaaat gagggccaag caactctacc   55980
tgatgcccca gggtgggggtg agtgccactc ctagctcatc gaaagctctc tcctgaaatt   56040
ccctttctagt tttattttta tcttgacctt tccaccttgt tgatgggtta agagttacaa   56100
aaccagttt tggaaacctc ctttacaggt cctgcatcct tcacctgtgg aaggtggaca   56160
tagttgacat ctattgtctt gggggctaaa cgcaaaactg agtctgaaat agttcccttt   56220
taacctcccg ttatgtgcag atttaacaaa ttcagtgcct ttcttaaagt aaaaggtaca   56280
tccagacact ggagagtagt gctaaaacaa actattaggg aattgaaatg accataaaag   56340
aacataatga acaaacagaa ataatccaac cagcaccttaa gttttgattc tggcattgct   56400
ttttactcca gaagcaagag ttgaaagaaa ctgacctgca tttttaaaata tattttttaa   56460
tggtcatgta atatgctata tttcttcaaa tctgttaaaa atagaaactc aagagttgga   56520
tggcatcatg gttagggaag aaaaattctg taactggaat agatggttgt agtaattcac   56580
atgtctcaat ttgtattcta gtcataacat acttcttaaa agggtggtaa aaatatggtg   56640
ttttctctttt cccacttcat ttgtctaatt tctgtaacat acaccctcac aatgaattat   56700
tgactcaggg acaagaggta gagaaattac agaggttgct aagaataccct gctgactctt   56760
attttctact tctgctttag aagttgttta gaaaatctaa tcaaggccgt cttacatcca   56820
gtagaaacag agagttttcta ctggatgtgc tttggagcag gtttttaagg agacatgag ttatgcttct   56880
cccatggaag agtgaccata ttggggaaag aagagctcag gagacattag gagagcttcc   56940
cttgcctggg gaggtgtttg cttaaaagac atgctgccca agtatttaag ccttcaggtt   57000
agggtctttt ttccagttgt tggcagagtg aatgagcatg aactgtattt gatgaactac   57060
agttaacaca aatactcatt tgaagcagaa taaaattatt ttgaaagtga aggaaaattg   57120
tttcataaga gaaacttgta cttcctacga aaagactgtg ttttttttgct ccatgttttt   57180
agtaaagttt agtcaaattt agtttagttc acctagaacg aacactgaac aatttgaaa   57240
tacatttttat tccttttttt aaactagagg ttagcaaacc ctgcagaaaa aaccaaatgt   57300
agcctgacac ctgttttttgt gaataaagat ttattggaac atagtcgtgc tcgtttgttt   57360
acaaattgtg tctggctaca tttgcattgc aacagcattg ttaagtagtt gggacagaga   57420
ccatatggcc tgcaaagcct aaaatatttta ctatcccact ctttacagga aagtttgca   57480
gatccctgtt ctagattaat gaaagtactc agtatcagtg ttttttgtggt tatatatggc   57540
```

```
ataaatggct attaattctc tgaattatta ttaattttaa atatttcagt atcttttgta   57600
cttgattata tatctcatta aaataattga attaattctg aaaattggta tggtctgttt   57660
gcctaatgga caatacactg gacattacaa aactaatttc tgcttttcaa atcccttgga   57720
cagtaaaata atttatttct tgatttgcat tttaccacat atgagcacct tgggaagaca   57780
ttgtgtagta gaaagcatac tgtcagcacc cacttccaaa atgtttttca gatttattgg   57840
aacaatttaa aatgtcagtg aaaagaagta cttttcttcc tttgtgttct tcattttctt   57900
atgatggctg gatgcattca ctccttgggg cattcatgtt ccttcctaa agggcagagt   57960
taaggttact ctgtgggtca tttgcctctt cagggttgtt tgatccttct caagagaaga   58020
ttattttaat gtattgcagg agatgctgcc tgataactga ggctgatctg ttgagcactg   58080
taggaaccag actgggggaca agaattgact catttattca tttatactta tgtttattca   58140
acaaacgttg aaggcatgct ttactaggtt ctgtgctctc aaggatttca tagtctctta   58200
caggagatga acacaaagca aatgattatc atatactgtg ttaggcaaga tgattgagtt   58260
atagtcagga tattataga gagaaggggc atctaatcca ccatggggag agggcaataa   58320
agaaaagcta tttgaaaagag gctaaaatcca gatcaataaa tccaggacat tctgtcagaa   58380
attcagatgg agatgtctgg caggtggatt tgagtctcaa tctgggatag agataaggat   58440
ttaggtgtct ttattctagg aatggcagtt aaaaccctga gagctgatga gagcctgaag   58500
agtgggaaga gggctcagca tgggaaaggc caacatttaa ggatcagaaa gagatgcata   58560
aaggaaacaa ggaagggtc aagagaataa ttaggaatac caagagaaca aaagacaatg   58620
gtgtttagag actgagtgag gggaaggaga cggtcaatgg aaagatgaa aatccaggat   58680
tgatcaggga ctggcaatgt aggaggcaga ggggagatgg aattcatttc aaatattcta   58740
atgtaaacta cttatgtgtt aaacaaatga tgacctaaaa cttagtttca ggctgttgtt   58800
taaagtaggc tcaaataagt aagttgattt cctatatttg taaaagctaa taattttttat   58860
ttaatcaaac acacatttat tgagcactta ttttgtacta ggtgctataa caggttggca   58920
ccctaaggga taaactatgc gggatataaa aatgatcaaa aagtgaagta gtaaatttta   58980
agctaagccc tggaaaatgg ggagggatgg aagtacatat aagtcaagaa taggcaagag   59040
ttagagcaaa aacacagtgc atgaaacccc aggacactgt cagtcttgaa ttattgttct   59100
tgactatgtc tgtctccacc actagactct ctaatgctga ggactgtgat ttatagagcc   59160
tcacatggtg ttttgcatgt tgtatttact caattaatgt ttgctatatg aatgaaactt   59220
gagaaacaga aacatcataa ttgttactta ttccatagtc ttgtctgtgc tggcctcagt   59280
aataaagcaa aaactaactt aaagactagc attcttatgt tcattagtaa aacaggtaat   59340
agataaaatta ccttcttgat ttgacttttg agaatgacgt gttagaactt ataaatgaat   59400
caaatacgtg taatttataa tgttactata tgatatgaaa acaatttgag atagaagtca   59460
taaatatgaa gtttcttaag actttgatca aaacaacaaa atttctttga gattttcttt   59520
ttttaaaact tttattttc aacaacagct aaccaaagat gggacttct ttacatgaca   59580
atgttgaagc caattgatac acaatttatt tgttagcgtg ttagtggttc tatttgtttt   59640
atattttgaa gtgaactatg gccttctttt aggactgaaa aataacttcg tggtgtacag   59700
atatttaga ttaaccaagg gtacttgtta acaaagcta ttattttata gctgcatctc   59760
cgtgtttgat ttgataaatt tgggaattaa atttacaatg caaatttcat tagtggaatt   59820
acatagccaa tttggagagg ttctatttaa tgtgctacct tgatttagaa tgagcgattt   59880
agaaatatga agagttgact gggcatggtg tctcatgcct gtaatcctag gactttggga   59940
ggctgaggtg tgattgcttg agctcaggag tttgagacca gcctgggcaa catggcaaaa   60000
tcctgttcta cttaaaaaaa aaaaaaatta gctgggcata gtgacttgcc cctgtggtcc   60060
cagctagttg gtgggctgag gcaggagaat cgcttgactc caggaggttg aggcttcagt   60120
gagctgtgtt tgtgccacta tactccagcc tgggtgacaa agtgagaccc tgtctgaaaa   60180
aacaaaaaca aaaacaaaag caacaaaaaa aggagaaata tgaagagtta gataaatgat   60240
acgataatag cccacgtttt cttgttgatt gtggaaaagg aaataattaa cagtatctat   60300
tataaccaca taggatgtat tgatttaaga attacagtag aaaataattc aaggaattgg   60360
aaaagtgagg catgttgttc tatgaagatt ttgcatcctt aattatttat aagtatttga   60420
gttatgtgta acttcatttt ctccattaat ttttgataat gatatccaaa acaaatctgc   60480
agttatttgt tagtttgacc tgtgttatct ttgcttcata aattcctcaa ttatctagtt   60540
taatctagtt cttatttcac aaatgatgga agtcagatta agcagtttgt tttaaatgaat   60600
cgcaatgaat tatagagata ggtcaccatt ttatgctaac ggggttggcaa gaaaaattca   60660
tgaaatttta caggcttcat gttgcagttg tctacaaata cacttccata aatgaaaata   60720
aacaagtttg ttcattgcat cattataaat gtaatttaaa aattaatttt ctaaattgtt   60780
ttatgcaagt aagtaagcaa gcaaaataaa taagaactca tatactttcc tgtcttttt   60840
ttctcccctg cccaatagga ccagacatac tatcaatcat ttcaggtttc agaatatggt   60900
aagagttcct caatctattt tggaagaaaa aaacatttgt tactttcagc agagattaga   60960
gaaatttta agagatgtat tatttgaagt aaaaatctca atggagttaa aattctggtg   61020
tttttaaag gcctaaccat atttttttc ctttgtaaaa attctaaaat ctcattatac   61080
agaaaaaagt agaaaaaaat cacctatagt tgcattgtgc tagtcttttt cttatccaca   61140
acatgatttt tctattttc tactttgttg tgataaaaaa atatttaaag tgttgcactt   61200
aaaaatactt aacaaattct cttccatatt tttcatttga ttgacattgg taaagatggt   61260
ctgtttctca ggtaaatcct cttcttgcag gtgccatact tacaatatct gttagaaacc   61320
catagataaa acagtggga cccatctatt ttgttggtga atggagagga atgagagtg   61380
agactgaaag cataggatct tagtattagt tataatttga atagttattt tgaggttgca   61440
catgcagttt ttcatttgat ttgagcttct ttttgagat tgggttttat ttaggcagta   61500
gaaattataa tatacaggta gtaatacctc aggctctgtg ggccatatgt ctctgttgtt   61560
actactccaat tttgccgtgg tagcatgaga gcagccaaag aaaatatgtca catgaatgtt   61620
gctgtggttc aataaacttt attttatggg catgaaaatt tgaatttcat ataatttcta   61680
tatgtcatga aatattcttc ttcttttgat tttttttcaac cagttaaaaa ttgtaaaaaa   61740
tgttcttggt tcatgctggt catagttttgc tgaactctga tctgtaactg tgctctccag   61800
tagcggggcc acttgccatg tgtggctgtt gagcacttca aatgtggcta gtccagatgg   61860
agacagcaga tgtcaaagac ttagtacaag aaaaatgaaa gaaagaaaaa tagttcatta   61920
ataaccattt ttaattttt attatttgtt gaaaagatac tattttagat atataggggtt   61980
aagtaaaaata taaaaattaa tttcacctgc ttatttttac tttaaaaatt tgactactag   62040
aaatgaaaaa ttacacatat ggctcccatt ttatgtcttt tagacagccc tgatctagaa   62100
gaataagtca taggggacca acatttttat aggctatctt tatatcccat tgtgatggta   62160
tgctgggtgg ttgtatgttg ttgaatgagg tatagtggag gtgggaatt gattgcaaac   62220
ctatgatgtt tgaggaagag gcatttggat tttcttggtg gtgggggttg cggggcggg   62280
```

```
gtcatagttg actcacgtga cttttttggtc tccctgtcct agactgatct agagtctagg   62340
agtgtcttgg tacattcagg gccattagcc ttgattggag ctgaaggtct gccctatatt   62400
gttgactatt tggctttttt gatacttctc ttatgttaat tgaatggtga ggtgccttgt   62460
tatgagagtg gcctgtttct ttggtcagag aactatagaa aaaaagtttt atcgactgta   62520
aagaaacaca cattttttac tctggtggag tgctttatat caattatagt attagtactt   62580
ataaaatagt ttatacctta attattatta ttatttttcg agacggagtc tcactgtgtc   62640
actcaggctg gagtgcagtg gcatgatctc ggtcactgc aaccactgcc tcctgggttc    62700
aagcgattct cctgcctcag cctcctgagt agctgggatt acaggcatgc accaccatgc   62760
ccaacaattt ttgtattttt agtagagata ggattcacca tgctggccag gctggtcttg   62820
aactcctgac ctcaggtgat ccacctgcct ctgcctcccg agttctagaa ttacaggcgt   62880
gagccactac tcccagcctc ataccttaat tatataaagc tgaccaaatt agggatttct   62940
agtttttgggt gaaacaaagg gcttttcatc tgtcttaata tgtatttgga ttctaataaa   63000
tttaagttca aatagtacaa atttattaact ccttcacaac aattttattt ttcattttat   63060
tcagtggaag atgatagtga agtagattct ttaaaagatt tacccttgct tcttcgtctc   63120
aaaaagaaaa aaagatttac ccttgctttt cttttccagt attaccaaaa tttgaagtga   63180
ctttgcagac accattatat tgttctatga attctaagca tttaaatggt accatcacgg   63240
caaagtaagt gtcatttttc ttttgatatg actcaaaacc attataaaac tgtgtgacca   63300
aaagctgatt gtatacttca gaatattagg gcaattttg cttattaaaa taccttagtg     63360
gacagtaaat gactatttat aataaataat taagcatggg acagagctcc acatttcact   63420
gcatctatca ctctgcttgc aagccgaccc agtcttaaaa tatttcccat atttcttaga   63480
cttattaagg gatttatatt atagatagca ctgtttttt ttcagatgac atggacttga    63540
agccaccacg cctggctaat tttttttcct ttatagagat ggggtcttgc cattttctcc   63600
aggctggtct tgaactcctg gcctcacatg atactcctgc cttggtctcc taaagtgctg   63660
agactacagg catgttccac cactcctggg ctgatttgct ttttaaaaat tagtcaagct   63720
tttattttct gagtgattaa cttatcccaa atgcttcccg gttctatttg ggacaataat   63780
tgtatctttg tttcacaatt attataacca gcttggtgtt tggaaaacta aatctgcttc   63840
acattaaagt caaaattaaa aatttttatg tctgagagta cttttaaatta tattttggatt 63900
ttaaagatcc ttttactacc atgtgatata actctgttaa aatacaatat cctggcattc   63960
tagttttgct tttatttaat ctttagcacg atacaagtag agtcaggttt cgaagactct   64020
tgaatgagtg aatttgatgc tcaggttgct aaccagggtt tccactgact ttactgtttt   64080
tgtttggaag tgtggtgcat ttgaacttgg attttttttt ttttcttctt agtttggaat   64140
atgctatatt ttaagatttg ctttttgagtt gagttgatcc agatgagggg ctgtttctgt   64200
gttcagttaa tggattcagg aagccgccgt ttactgctgt gatttataga ctgcaaagca   64260
aaattgactt ccatgtctgg ctcagcattt cacaatagag atagaagcaa cccaggaaat   64320
gtacttaaaa aaggcttct gggccgggcg cagtggctca cgcctgtaat cccagcactt    64380
tgggaggccg aggcgggcgg gtcacaaggt caggagatcg agaccatctt ggctaacacg   64440
gtgaaacccc gtctctactg aaaatacaaa aaattagccg ggcgcggtgg cgggcgcctg   64500
tagtcccagc tactcgggag gctgaggcag gagaatggcc tgaacctggg aggcggagct   64560
tgcagtgagc cgagattgtg ccactgcagt ccggcctggg ctaaagagcg ggacccccgtc 64620
tcaaaaaaaa aaaaaaaaaa aaaaaaaaaa aagcctttct ggcagtaaaa tgtattgcct   64680
cttcttcaca tgaagagact ttcctataat gagagaggat aaaattaata catagaaaga   64740
aaagtagcag agaatatttg acttacgaag ctaagtttgg gccaggtgag gtggctcgtg   64800
cctataatcc cagcactttg gggggccaaa ctgggtggat cacttgaggt caggagttg    64860
agaccagcct ggccaatatg gtgaaactcc atttctactg aaaatacaaa aattagctgg   64920
gtgtagtggc agacgcctat aatcccagct attcgggagg ctgaagcaga gaattgattg   64980
aacctgggag gcagaggttg cagtgaccct agatcgcacc actgcactcc agcctgggtg   65040
acagacgaga actctgtctc aaaaaataaa ataaaataaa attcgctgga cgtggtggtg   65100
tgcgcttgtc atcccagcta ctcaggaggc tgaggcagga gaatctcttg aacccctgag   65160
gtggaggttg cagtgagccg agatcatgcc actgcatcca gcctgggtga cagagtgaga   65220
ctgtgtctaa acacacacac acacacacac acacacacac acacacacac acacacacac   65280
acacacaaac ccagaaacta agtttggtac tacagatttt aaaaattatt cttattttaa   65340
attttttggc aaaaaatcaa ttttttgacag ccatgagcac atttggtgct tcagaatcta  65400
tggtgtaata aaccttcctc gctaatattg aacatgtag caatagacca tggtgattgc    65460
actatcagct gacatttaaa aatcttctaa agctgcgaag tttcgtgggc attcagttaa   65520
tgggccagtc cagatttcta ggagtgaaag atttatgtaa tcttttaaaaa atcttttggac 65580
aggaaactgt cacttccaat tatgatcagg tattttctgg agtctttcag atggtcagag   65640
gttgggcaga gtgtgtgtta agaactgttt taagctacta tagttaaaag tcttcccatt   65700
ttggaaactt aatttcaagg atcaccattt attttttatt tatttattta ttttttgagt   65760
tggagtctca ctctgttgcc caggctggag tgcagtggca cgatcttggc tcactgcagc   65820
ctccacctcc tgggttcaaa cagttctctg cctcagcctc caagtagctg ggattacagg   65880
cacccaccac cacgcctggc taattttttt gcattttag tagagatggg gtttcaccat    65940
cttgccaggc tggtcttga actcctgacc tcgtgatcca ccagcctcgg cctcccaaag   66000
tgctgggatt acaggcatga gccaccgtgc ccatccagga tcaccgttta ttaaagacat   66060
ttttgttgtg tttagtttaa aaaattatag taggagtatg tttttaatgt aactttttcc   66120
tttttaaaat tttctcttttt tagtgttttg ccatcccata atgtattttt ttttaattta  66180
tttattttga cacagagtct tgctgtcttg ctgtgttgtc caggctggag tgcagtgatg   66240
cgatctcggc tcactgcaac ctccacttcc tgggttcaag cagttctcct gcctcagcct   66300
ccaaagtagc tgggagtaca ggtgcctgcc accatgccca gctgattttt gtatttttag   66360
tagagacagg gtttcactat gttggccagg ctggtcttgc actcctgacc tcgtgatcca   66420
cccgcctcgg cctcccaaag tgctgggatt acaggcgtga gccaccgctc cagcccaat    66480
gtaatttttt aaaatgttag attgctaatt gctaatgtat gctattgaaa gtagtatttt   66540
tattgtgttc tgacaatatc aagttgatac ataaaaagac tatgtttata attattcagg   66600
tatacatatg ggaagccagt gaaggagac gtaacgctta catttttacc tttatccttt     66660
tgggaaaga agaaaaatat tacaaaaaca tttaaggtaa cttttgcaga cactttataa    66720
cttgtgatgg gtaaaatatg tgtatttttc tagaaataag atttagtact gaattaacaa   66780
aaagttaagt gtaagaaaat caagagcttt ccagcattga acaaatgaga atttatgcaa   66840
ttatagcgat taaaatggta ccagagctat catattgttg tgcttagtt tgagttttat     66900
ttctaaaatt tgaattgcta aaatggtaaa taatactgaa cttttaaaca aaacagataa   66960
atggatctgc aaacttctct tttaatgatg aagagatgaa aaatgtaatg gattcttcaa   67020
```

```
atggactttc tgaatacctg gatctatctt ccctggacc agtagaaatt ttaaccacag    67080
tgacagaatc agttacaggt ttgtagactt taaagtggag gtaaaactat tcatgtgaca    67140
ctgctttatc atctttctta ttataactgg cactttcatt tgggagcatc attgactttc    67200
taaagatgct atttaatgtt gaaattgtta tgactgttag tctaagttgc aggatgattt    67260
tataagggggg accttatttt ctatgaaagt cactacttca accacatgtg atagctcttc    67320
ttaattttttt tttccatttc tactcttcc cctgaaaac tacatggaaa ggcttacatt    67380
ttcagctggt aaccttcttc tttttaaaat cactgaaatc tcagctgttc ctagacagtt    67440
ttcactttta ataagaaaat aaagttgagt ttccttggacc tttctgttac tatttcaaca    67500
actttagcca atccctgaaa gagcaaaaga ctattctttc attggcctta atttgctgct    67560
gttgtacatg tcactgcggt agaatggcag caatggtgct tagaggggat ccatagagaa    67620
cataatagaa ctgtgtggtg cttgtagtgt caaagtcaat atgggaatga ggcttatgtg    67680
ccctgatatt tttaaccctt tttgcaatag gttagatgga gagatttggt ggatagaagc    67740
tttgggtgaa acattacttt tgctttctaa attgtgcaat ttccaaaaaa ggtatttcaa    67800
gaaatgtaag cactaatgtg ttcttcaagc aacatgatta catcattgag tttttttgatt    67860
atactactgt cttgaagcca tctctcaact tcacagccac tgtaagttgg tatatttatt    67920
tccagtccat agcagtaagt tcagcttaat gaaatagaat gggaaataat attttcaatg    67980
cttttctaaa aatttaagcc aaaaagtata taactttgtc tctttagaca tgtgggggcat    68040
gtagattttgt ttccaaatga cctttgtcta tttttttctaa aaaagtagtt ttcaacaaca    68100
gtaaaaatat ttttttgaaaa tgtattttttt tttacaagca atttaagtta gatgtggatt    68160
gctacactga agcttttatt aattaattga aataattaca tggtagtcaa aaatttcaat    68220
ttcaatttgg ttttttataat gattaattgt agttctaaca aagatgttac attaaaaaat    68280
tatcaacaaa tctcattttt tggagataat gttgaattaa cacattaatt gtgtgaatgt    68340
tgacaatgag caaggcatgg tgttgggcag ggctatagaa ccaagaaggg ctcagtccct    68400
acctcaggt tcagttttt tgtgatggt acaggaaaat atatactaa ctataactca    68460
tggcagatta agattagtgt tacaaattaa tttctgtagg gatttaaagc agggggttgcc    68520
aaacttttc tgcaaaggggc tagagagtaa atatttttcag cttgtgaag atgtggtctt    68580
tgtcacagct actcagccct gccattgtag tgtgaaagca gccatagcca atttataaat    68640
aagtgagagt ggaatgtgtt ccagtaaaac tttgtttaca aacatactgg attggcctat    68700
cagcttgcag tagttggctg atctctgatt taaagaaagg aggagtcagg cctggcgtgg    68760
tggctcatgc ctgtaatccc agcactttgg gaggccgagg caggcggatc acctgaggtt    68820
aggagttcga gaccagcctg accaacatgg agaaacccca tctccactaa aaacacaaaa    68880
aattaggcgg gcgtggtggc acatgcctgt aattccaact actcgggagg ctgaggcaga    68940
agaatcgctt gaacccggga ggcggaggtt gtggtgagtg gagattgcgc cattgcactc    69000
cagcctgggc aacaaaagtg gaactccatt tcaaaaaaaa aaaaaaaaac aactaaaacg    69060
acaaagaaag aatggagggg tcacttgttg aatgggtcgg tagacgtttc aggtagtttc    69120
tgatttcaat gatcttaatt taggcagttt gaaaaggtca gtttaaaaaa ttgaggctgc    69180
aaatggtaat ttctgaatga gtagagtgaa accatgggcg ttcagagggg gagagttggc    69240
tgtgggatag gcatgggggt tactatggga tgctttatgg aagaggatgg tctaaactgt    69300
tttttaaaag attagttgtg ttttaaatgc ttgggcatgg gagtgggagg tgggggagcaa    69360
gataagaagt gagacaagaa ggagaggtct ggctggcaat ttcggggtgc actcaggtag    69420
tgtttgaggg agactgctca ggctgtgtgc aggaggatgg ctgtagccca ggagtggaggg    69480
gatgggcagc cttgtggtgg tagctgtggg agtggagagg atggaagaga gaagcatagg    69540
actttggtgt tcattggatt tgggggggggg ggagagggag ggaaaattca gaaatgtaaa    69600
gtcttgcaaa atcctgatgt tagcgaaaat aggaaaatga catggttgct catttttagat    69660
atgtgaattc aaggtgtcca ggatatccaa gtagaaattt cctgcaggta actggaggtg    69720
ttgggcatga actccagaga agggcaagga tgggaatttt ggctttaggg tacaatcaca    69780
gagatgacaa gctaagcaat aggattgctg agaccttgga ggaagggaga agaacagatg    69840
tccaaaattc ccacatttag ggagaggaaa gaggaactga aaaggacact gagaggatgc    69900
agaaagagag gtaggaagtg aagggggtta ttttggagcc gcggaagtta agggaatcca    69960
taatattaac aaggagtaa tcagtgatgt tggatgcctc ctagagagag gccactgaat    70020
ctgatatta tagtgctacc aataattttt gagagttcaa tttcatgaga atactacaga    70080
cggaaactgt atttaatcgt acttaaatcc tttgtgtttt taagatgttt tgttttgacc    70140
attaggtgaa ggtaactcgt gctgatggca accaactgac tcttgaagaa agaagaaata    70200
atgtagtcat aacagtgaca cagagaaact atactgagta ctggagcgga tctaacagtg    70260
gaaatcagaa aatggaagct gttcagaaaa taaattatac tgtcccccaa agtggaactt    70320
ttaagattga attcccaatc ctggaggatt ccagtgagct acagttgaag gtgccgtctg    70380
tttcccatca ttgtgtcact gcaacaacac cattacagtt gtaatcttgt ggtaggcact    70440
caacctgtca gaactgaaag tacataggaa gtggacacat gttctgtttt cacaaaatgg    70500
aggagagtgg taaaagtaat ttaatgacag tggctgaagg ttagactaaa tttttccttg    70560
taagttcatt ttgaagagca cagtaaaata tagcaatgtg aagatatgat ggagaatttc    70620
ctcaaatccc cagtctagtg tttgaggtca gtcatttgaa attttatttt ggcaggaatt    70680
gaaatgaaag ataaatatat atacatatat atatatacac acatatatat gtatatgtat    70740
atgtgtgtgt gtatatatat atatatatat tcctttcctg tgttttaaag ctatcagttt    70800
ctttacagta taagctataa aatgatgaaa atccaatgtc tggtgaatgt attttttcttg    70860
cattaaaaaa aagtgaagat gaatttggtc tttaataatt gttcagcagg taacatcttt    70920
tctcaaggtg ttactaaaga tgaacattta cagctccttt ttcttttatt ataggcctat    70980
ttccttggta gtaaaagtag catggcagtt catagtctgt ttaagtctcc tagtaagaca    71040
tacatccaac taaaaacaag agatgaaaat ataaggtaa tgcttacaat tcacttgaga    71100
attacaatat aattggacta tcttgctttt gatatgtaca tattaattaa ggttttttttc    71160
taggtgggat cgccttttga gttggtggtt agtggcaaca aacgattgaa ggagttaagc    71220
tatatggtaa tctcttatag aatctaaatt tatgatctat tatagaatca tcttttttatt    71280
cactttttaag ttctgggta catgtgcagg tttgttatat agctaaactc atgtcatggg    71340
ggtttgttgt acagattatt tcatcaccca ggtattaatc ctagtaccca ttagttatttt    71400
ttcctgatcc tctccctcct cctacctccc acccccccat aggacccagt gtcggttttt    71460
ccctctatg tgtccatgtg ttctcatcat ttagtgtgca cttataagtg agaatatgtg    71520
gtatttggtt ttctgttcct gcattagttt gctaaggata gtggcctcca gctccatcca    71580
tcttcctgca aaggacatga ttttattctt tttatagct gcatagtatt ccgtagtata    71640
tgtgcaccac gttttctttt tccagtccac ctttgatggg catttaggtt gagaatcatc    71700
ttaaatggtg tctaccttat atctcacacta aacttattaa tttttataac tcagcctcat    71760
```

```
accttttag    cctgtcgttt    taacattgca    atcaaataaa    aaacctttt    tatttcttca    71820
cctatgtttg    catttccaat    ttaaaataga    taactaaacc    ttgttttatg    tttaaaattt    71880
aaatttctat    ttgataagca    atatatattc    attatagaaa    attatacaat    gtaagaaaaa    71940
tgaaaaagaa    aataaaaagt    gctatccatg    accatgtaat    tttgctaatt    cagctttccc    72000
aatggtgccc    tgtattcctt    gcaatcaaaa    atagattctt    gactatgaag    ctactgttgc    72060
tccaatcagt    attactttaa    tcttaccatt    ttctttttct    cagtgtatgc    tctctgtgtt    72120
tgtcagagag    gttttcctgc    attccaaaag    actttgaagc    tggtttaatt    caagaatttg    72180
tgtgtatgca    tacaattatg    attaatgtag    cttcagatga    gatcctacta    ggtttggcaa    72240
taaattaaac    ccatctactg    ttcttttcag    gtagtatcca    ggggacagtt    ggtggctgta    72300
ggaaaacaaa    attcaacaat    gttctcttta    acaccagaaa    attcttggac    tccaaaagcc    72360
tgtgtaattg    tgtattatat    tgaagatgat    ggggaaatta    taagtgatgt    tctaaaaatt    72420
cctgttcagc    ttgtttttaa    aaataaggta    agatttaagg    taatgatgtt    taaaagaaaa    72480
ctttatatta    gtgaagtctg    agaaatgtaa    tatttcttta    gaaaagtatc    attaagccaa    72540
actggttaga    aatttatatt    attctatttc    tagaactagt    gttaaacttt    tcaatattta    72600
gcattacata    tatatttca    cttgtggagt    tattggggat    tgatagtcta    tttgtaaact    72660
atggttctgg    tctttaagac    tttaactcag    atcatgaagc    tgtttcagaa    ttttttcaaat    72720
ggttgaatta    atattgctca    ggagtgaaat    tccagtggta    acatagaatt    cgtgtggtgt    72780
tgatattgca    gtgatataaa    gggtgtggga    aggagtgagg    ccatctagga    taatacgtag    72840
aagcagagct    gggctttcat    taatctattt    aattagctgg    aaactagccc    agggcaactt    72900
ttcaatgagc    ttgattaccc    tgcatgtgag    gatctgtgtg    gagtctggtc    tccaagtgca    72960
ccagtgcctt    ttatagccta    atgtgaccag    cttgagtagg    aaatcccttt    ggaccccagc    73020
tctgaaaaga    aacctgattg    catcatctca    tgtatataag    aatgagccat    tgctgtcact    73080
aacaactgct    gccctctcca    tcctcttatg    taaaaaatta    ttcctttaaa    tagtgatttg    73140
cagagtatgg    ttcttctatt    tctttttcct    ttatttgtta    aaatatttga    gaagtaacag    73200
tagtgatctg    tactttcttt    tttaaaattt    gtatttattt    attttttgag    actaggttat    73260
aagactggct    aattttttgta    ttttcggtag    agagagggtt    ttgccatgtt    gctcaggttg    73320
gtctctaact    cctgggctca    ggagatccac    ctgcctcagc    ctctcaaggt    gccgggatta    73380
cagacatgag    ccactgcgcc    aggcctgtac    tttagttttg    ttgagaatta    ttactctcac    73440
tttgattgtt    aaaatataat    acaaacttct    atttttttag    cttatgaaaa    gagttcttaa    73500
aaagataaca    ctgtgttttg    ttagtggtag    agcacagttt    ttgacttcta    gtgatcctag    73560
taattgcctg    acaaaggtga    atttttaaagt    agaagttatg    gaggcttaaa    catctcagaa    73620
agcaagacca    ggttctaaag    ctggttacag    tgtaaaagat    cacggactt    gaggaagcag    73680
agtatatgaa    tagcatactt    tcaagtaatt    tcttagctat    aagagaaagg    aattagttc    73740
agttccattt    gcaactatat    atcttctct    tattttatg    tgataatcat    cacatttata    73800
aagaaacaac    ataattagaa    atggaatatg    tctaagcaag    agaaagttag    tgaatgttta    73860
ttaatgttca    gtaatgacta    tggaataaat    aaatgagctg    taggagcggc    aagagattta    73920
ggtttagaaa    tcatccacac    agaagtgcaa    gttgaagcca    tggggctctg    aggtacagag    73980
tatagagtga    gaagtacaag    gtctaagact    gagtcttgaa    catgctgctc    cctctccccc    74040
atgctttagt    gtgtaggtgg    agaaagtaac    ctacatacag    tggttttgaga    ggcatgtcag    74100
aaaaaaattg    cactggacaa    gttaaacagg    taaggaaggc    tttattcaag    actattgcaa    74160
tggaagagag    agatgataaa    ctcaactctg    ctgaaacaaa    aggcagaaga    gtttttaagc    74220
actgggtga    actcatatga    aagtgctgga    ggacattgtt    gggaggttgg    tcaatgtgat    74280
taggtagtct    gtgttttgcta    attagtactt    actgaagtta    ggtttccacc    ctcccacaga    74340
gaatgagatc    aattgggact    ctgtctttct    tgatgattat    acttcaaagg    gatggctctg    74400
aggaccttga    gaaagacatg    cctggggttgt    aaaactggcc    agaggctggg    aaaagattta    74460
catctcagag    agttggagaa    agaatttata    attgcatgtt    ttctaaaata    aatgctctaa    74520
gaaaagggag    ctcagggct    tatagttagg    aagaagccta    tctttgtaaa    gtcgagtcaa    74580
cttgagggga    atgttaaggc    cctctttgtc    aggcattata    atcattggca    cagcagaatg    74640
ttgagataga    gctagatgaa    atgaaaattc    ccagcagggg    ccaggcactg    tggctcacgc    74700
ctgtaatccc    agcactttgg    gaggccgagg    caggcggatc    acctgtggtc    aggagttgga    74760
gaccagcctg    gccaacatgg    tgaaaccctg    tctctactaa    aaaagttaca    aaaattagcc    74820
gggcatggtg    gtgggcgcct    gtaatcccag    ctacttggga    ggctgaggca    ggagaatcac    74880
ttgaacccag    gaggcaaagg    ttgcagtgag    ccgagattgt    gccattgtac    tctagcctgg    74940
gcaacaagag    ggaaactcca    tctcaaaac    aaaaaaagaa    aatgcccagt    aggcagggc    75000
ctcatgacaa    ggccatttgg    ttcagcggt    atgcgatgac    tgatgctctt    tataaagtat    75060
tagtaggtcc    aggaccatgc    tttcctgagg    gtaatggtga    ggaagtttag    aaggccatgg    75120
agacagagca    tgagggcctg    gactagtgtt    tgctctaacc    acccactccc    ttggaaaggc    75180
caccccctcac    cctcagtcca    ggtggttcta    tgagtccccg    aggagctctc    cttgccttca    75240
cttctgagct    cacgtcacca    acatgtaggc    atctgcagtt    tctttcctct    ttcgtgtttc    75300
tcctttgtat    actggccttc    cccaggtatg    ctagacactg    ctgtcttcta    ctcagcactg    75360
gctgggatct    gaggggtggg    agatggagaa    agggaagaaa    aaagatacag    aattaaagaa    75420
taattcagat    ttataccact    gtgagaagtt    ctatgacttg    caaacactct    gggcgtagtt    75480
tttttattcc    tttccctaga    gaagggttat    gcatggtttg    agaattatcc    ctgagccaag    75540
gcaaatgtag    aatctttgct    atattttggg    ccagtggtct    gctattggca    agaatatgct    75600
ttaaaaaagt    gaaataagtt    aatcctcctt    tctctctttt    ttagataaag    ctatattgga    75660
gtaaagtgaa    agctgaacca    tctgagaaag    tctccttag    gatctctgtg    acacagcctg    75720
actccatagt    tgggattgta    gctgttgaca    aaagtgaa    tctgatgaat    gcctctaatg    75780
atattacaat    ggaaaatgtg    agtttagcta    tttttttcatt    atgaaaatat    gtattacaag    75840
agaaagagga    aactttattg    tactacttta    aatattaaaa    gaaaattca    ttagttcctt    75900
tgcatgtgta    agtcaataat    tagtaaagct    tccaaataaa    aagtaatctg    tatcgtaatg    75960
gttatgttgg    aaagaagctt    atgtggttaa    gtgtccttgc    tctctttcat    cagaattatc    76020
acctaaagtt    agatgggagg    aataaaattct    ggaggtctgt    ggtacaacat    ggtgactgta    76080
gttaatgata    atgtaccata    tacttgaaaa    ttgctaaaag    agtagatttg    aaatgttctc    76140
accacaaaaa    atgatcagta    tgtagtatgc    aaggtgatag    atatgttaat    tagcttaatc    76200
attccacagt    atatacaaat    atcaatatat    cacattgtac    tccataaaata    tatacaataa    76260
aaaatgccac    ctatagtttt    ccttcatttt    catactacat    tttaagacac    tcaagaaagt    76320
actaggaaat    tgacttgcat    tattctgggt    tacgttggat    aagagagctt    tagataattt    76380
ttgaagtgtg    ttctattttg    gttatacgta    atggttataa    ataattacag    cacccattgt    76440
gccgggcatg    gtggctcatg    cctgtaatct    cagcactttg    ggaggccgag    gtgggtggat    76500
```

```
cacgaggtca ggagatcgag accatcttgg ctaacatggt gaaacccat  ctctactaaa   76560
aatacaaaaa attagccggg cgcggtggcg ggcgcctgta gtcccagcta ctcgggaggc   76620
tgaggcagga gaatggcatg aatcccagga ggcggagctt gcagcgagca gaaatcgtgc   76680
cactgcactc cagcctgggt gacagagcaa gactctgtct caaaaaaaaa aaaaaaaaaa   76740
aaaaaaatta cagttcccat tgaatcagga atttgcagta tattgagggg gtgaaatcat   76800
gttactctgc agaaaactta caaaccaaga agtatatgaa catctagcat tgcataaatg   76860
aatcccatat tcattagtca tttgattttt atttatatgt ccttgatata ttcttgtgta   76920
ccattgtcag ttgtaaacta gattgtataa ttttttgtcta ttaatggatt cagtagagtg   76980
attaacaata catcagaaag aaaactatat atagttgggt tgatttggtc attatattgt   77040
aaaatttagt ttacttcaga aaaattgtac attttcttca gtctacacaa ctatttttt    77100
caatctttc tttttttga aaactttttt ttttttaca accagttggt cattttctc       77160
tctttgactt ttcctgagtt cacattagtt ttatgtctgt agatcttgca tttgatttaa   77220
ctgaatataa tagtatctgt tattttatag cttttctaaat atcttggtaa atatattatt   77280
tcatttttc ttccctacat atgtgtatgt ttgtgtgtgt gtacgtgtgt gtatacatac     77340
acatacacac acaccccatc tgatgtgctg cgcactctgt ctctatttac atttatatat   77400
gtgtgttata tatatattta caagtatatt tatatataca tataatatat gcatatttac   77460
attaaatttt ttcagatatt aagattgctt tctcagcttt cttttggttc atattttcct   77520
ggtgtatttt tacatttctt attttcaacc ttttgtaaat tttaagtgt atctttttaaa   77580
tagcatatta ttatatttg cttttgtttt tcaatctaat ctaatagtca acatctttta    77640
ataagctttt atttaatcca cttataagta tggtaattct ttttctaatg gggactttt    77700
ctgcttttct atatttaaa attttagattc ttttctgtg ggctagatta aatttgtttt    77760
ggtgatttag aagttatgcg ttctattttt gttactctgt tagttacaaa ctgtacccat   77820
attaattat ccttgttggt ttctaaaggt tatcagtatt tgaatcttct agtatgctcc    77880
tattccttt ggtctctacc tctgtctcct ccttctcctc ctaccctggc cagatcattt    77940
tgctcgtgta cagattttag ttccatgtta ccatagattg cctttcaatc tatgctgttc   78000
tttcatttt taattgtgga aatctgtgtt gattatttct tcctccccat tttatttttt   78060
ctctccttct gggactttg ttttcagaa attggcactt ttacttcctc cttcacatct    78120
cttagttttt tgtttatgt tttctatctc tttgtcttt ctgtgttct ctgggagagt     78180
tcttcagtca actcagctta gtgatcattc attagctgta ttttaatcta ctttaatctc   78240
tcatattgtg tctttttaata cagctattat gtttttaata tctattattt ttcctttgtt 78300
tcttgttttt gttttatatt ctgatatttc ccattatctc cttgtgtata tttgctatgc   78360
gtatttaaa ttattgaatt gaactttca gtaattttgt gtcacatgct atatgttgtt    78420
tagttggatg tcttacttct acagtattta tactcttgg aagtctagct gatttggcag    78480
attctctgat aatatctatt ggtgaaggct gagcataagg ttccaatctg tgtaagtcct   78540
atgacccctt cctgagggga gaggactagc ctcatggact agagaattac tcttgatcct   78600
ttctgctgct tgcctctatt cagtgtttca ctcttaaacc cttggggaaa agagcaccag   78660
taagagaagg tctcctgagg ttatgattca ccagccctga gggtttggag gaggaggaga   78720
ggaagagtga atgcttgagg gacatgggtc tgtctgcatg ttttcttcac tttcccacac   78780
tagaaaggca gaggtgctga cctggtatta tcttttgata acttgcacag gccgtctgag   78840
ctgctactgc tgttgatttt ggcagtgaag ttgccaggac tgtgtgtcct gaggctaccc   78900
cctgagggga aataagagca aagtttaaaa acctctcctc cagcctgttt tctgactatg   78960
tctgctgctg tgtctagctg ccttctgcct tagactgaag cgatgcactt tctcccaaga   79020
ccaattcaag atgtccacca ctcttcctgg ggttttctca ctgtgcacgt taaagttttc   79080
tgcttgcttt tattgtttct ccagttggtt ctggaggagg gagtgaggat cctgtcatag   79140
tagactgttt tggcttcttt ttttttttg ttaaatttat atgtgttgtc aatagcctct   79200
tgaatgcctt ggaataattt cagtatgtgg atcttccagg aataattttt agacattagc   79260
cttctttcg ttagcctatg ctgcagcttt gacagtgctt tgtttattga gccagtgaga   79320
acaggaagat ttcttatga gatagatgct gcttttgctt tttttaaaat aaattttatt   79380
gtgtatattt gaggttatgt gtatatatat atatgtatat atgtatatat gaggtttattg 79440
tgtatacatg aggttatgga atacatatag gcagtatagt ggttactgta gtgaagcaaa   79500
tttacatatt tatcattttg catagctaca tttttgtgac aaaagcagtt aaaatcgatt   79560
taatgaaaac tccaaatatc atacaattct attaactata tctctcatgt tgtagattat   79620
ataactgcat ttttttcatcc cacatatctg ctattttgta tccccttgacc tctatattcc   79680
catttttcttc ttcctttccc cctcgcccct gtaaccatca tttgtttatc tatttattta   79740
tttaaacttt taagttcagg gatacatgtg caggtttgtt acataggcaa ccttgtgtca   79800
tagggggtttg ttgtacagat tatttcatta ctcaggtatg aagtccagta cccattagtt   79860
attttcatg atcctctccc tgctcccacc ctccaccctc tgacaatctc tactgtgtgt    79920
tgttcctctc tatgtgtcca tgtgttctca tcatttaact cccacttata agtgagaaca   79980
tgtgtatttt ggttttctgt tcctgagtta gtttgctaag gataatgacc tccagctcca   80040
tccatgtacc tgcaaaggag atgatcttgt tctttatggc tgcctagtat tccatggtgt   80100
acatgtacca cattttcttt atccagtcta tcattgacgg acatttagtt tgattccatg   80160
tctttgcttt tgtgaatagt gctgcaatga acatatgcat gcatacatct ttataatgaa   80220
attatttata ttccctttgga tatataccca ataatgggat tgctagtatt gaaatggtgt   80280
ttctgtctta agtctttgag gaattgtcac attgtcttat acaatggctg aattaattaa   80340
cactcctacc gacagtgtat aagtgttcct tttctctaca acctctccag catctgttat   80400
tttttgact tttaaatgat agctatccat tctgactggt gtgagatggt atctcattgt    80460
gtgtttttat tttatttttat tttttgaga caaagtctca ctctgttgct caggctggag   80520
tgcggtggtg tgatctcggc tcactgcaac ctctgcctcc caggttcaag taattctcct   80580
gcctcagcct cccgagtagc tgggactaca ggtgtcgcct ccacgcctgg ctaatttta   80640
aacttttttta gtagagaagg ggtttcacca tattggcctg gctggtctca aactcctgac   80700
cttgtgatcc atctcccttg gcctcctaaa gtgctgggat tgcaggcgtg agccaccacg   80760
caagtggcct ttttttttt tttttttt tttgacagag ccttgatctg tcacccaggc   80820
tggagtgcag tgatgtgatc ttggctcact gcaaccttca ccttctgggt tcaagcgatt   80880
ctcctgcctc agcctcccaa gtagctggga ttacaggcgt gagccaccat acccagctga   80940
tttttgtatt ttaatagaga cagggtttca ccatgttgga caggctggtt tcaaactcct   81000
gatctcaagt gatcctcctg ctttggcctc ccaaagtgct ggggttacag atgtgagcac   81060
tgtgcctggt ggcctcctta tggttctgat ttgcatttct ctaatgatca gtgatgttga   81120
gcttttctc atatgattgt aggcctcatg tatgcatgta tgcttctttt tgaaaagtgt   81180
ctgttcatat ccttttgccca tttttttttt tttttttt gagatggagt ttcccccttg    81240
```

```
ttgcccacgc tgcaacctcc acctcccggg ttcaagtgat tctcctgcct cagcctccca   81300
agtagctgga attacaggca tgtgccacca tgcttgctaa ttttgtattt tttagtagag   81360
atggggtttc ttcatgttgg tcagcctggt cttgaaaact cttgatctca ggtgatctgc   81420
ctaccttggc ctcccaaagt gctgggatta gaggcatgag ccactgtgcc tggccccttt   81480
gctgcttaa  aggaaatttt tttttcttgt aaatttgttt aagttcctta tagatgctgg   81540
atattagatc tttgtcagat gcacagtttg caaaaatttt ctcccatttt gtaggttgtt   81600
tactgtgttg atagtttctt tcactgtgca gatctctttc atttaatttg atcccatttg   81660
tcaattttg cttttgttgc aattgctttt gaaatctttg gctgttccta tgtcctgaat   81720
ggtattgcct aggttgtctt ccaggggttt tatagttttg ggttttacat ttaagttttt   81780
aatccatctt gcgttaattt ttgtatatga tgtaaggaag gggtccagtt tcagtcttct   81840
gcatatggct agccagctct cccagcacca tttattgaat aggaaatcct ttccccattg   81900
cttgttttg tcagatttgt tgaagatcag atagttgtag atgtgcagtc ttatttctgg    81960
gttctctatt ctgttccatt ggtctatgtg tctgtttttg tgtgagtacc atgctgtttt   82020
ggttactata gccttgtagt acagtttgaa ctctggtagc atgatgcctc cagcttttgt   82080
cttttgctt aggattgtct tggctatacg agctcttttt tggttccata tgaattttaa    82140
aatagttttc tctcgttctg tgaagaatgt agtagtttaa taggaatagc attgaataca   82200
taaattgctt tgggcagtat ggccatttta acaaattgat ttcttcctat ccatgagcat   82260
gggatgtttt cccattggtt tgttcatcta tgatttcctt gagcagtggt ttgtagttct   82320
ccttgtagag atcttttacc tccctagtta gctgtgttct taagtatttt atcttttctgt  82380
ggcagttgtg aatgggagtt tatttctgat ttggctctct gctgtgtgtt gttggtgtat   82440
aggaatgcta gtgattttca cacatcgagg cttttcctgaa gttgtttatc ggtttaagaa   82500
actttttggc tgagactata gggttttcta gatataggat tatgtcatct gcaaacaggg   82560
atagtttgac ttcctctctt cctatttgga tgcccttttgt ttcatttttt ctttcttttct  82620
tttgcctgat tgccctggcc agaacttcta gtactatgtt gaataggagc ggtgagagag   82680
ggcattcttg tcttgtgctg ataaccactg tttagatgct gcttcttgaa ttggtgtctg   82740
agcaagacg gaagcaaatc ttcatgtatt tgtattttgt gacagagttg gagtcatgga    82800
actctagcct tttctctcca atatgcctgg ctctggctcc cttgtctact gccagcttct   82860
ttgacacatt atgaattttt ttcttattt tattggtttc ttattggtgc ctgttctagt    82920
tgcttactgt ggatgcagcc atggttgttg ttagcattgc agaaatagtg gttgcaggtg   82980
tttaattta tgctggaatg tgtttttttc aacttagttt ttttttgtgat ttttaattct   83040
gactttgtct taatttgtct ggttaatgta aattttagg gagaagtatc aaaattatta   83100
cctaaaaagg tataatactt gattttatt gaagttaaat atatataaaa taaaatttgc   83160
tatttttacc attttaagtg tttaattcag tgacattaat tacttcacaa tgttatatga   83220
ccatcaccaa tatttccaaa acatttccat ggctccagac agagactctg taatcattaa   83280
gcaataaacta ctcatttccc cttccccaca gcccttggga acctctagtc tacttctgtc  83340
tttatgaatt tacctattct agatatttca catttatata atatttgccc ttttgtgtct   83400
ggcttatttc acttagcaca gtgttttcaa gattattcca tgttgtagca tgtatcagag   83460
cttcatttct tttttttttt ttgagacgga gtcttgctct gttacccagg ctggagtgca   83520
atagcgcgat cttggctcac tgcaacctcc gcctcccggg ttcaaaccat tctccttcct   83580
cagcctcccg agtagttggg actacaggcg cccaccacta cgcccagcta atttttttgta  83640
ttttttagtag agacggggtt tcactatgtt ggccaggctg gtctcaaact cctgacctca   83700
tgatccgccc gcctcggcct cccaaagtgc tgggattaca ggtgtgagcc accgcaccta   83760
gcctcagagc ttcatttctt tttacggctg aataatatgt tgttgtgat atataccaca    83820
ttttgtttat ccatttttct gctgatggac acaggttgtt tccacctttt tggctactgt   83880
aactattgct gcaatgaacg gtggcataca agtatctctt ggagttactg ttttcagtcc   83940
ttttgtgtat ataccagga gtggaattac tgggtcatat tctaattcta tgttaatttt    84000
ttgaggatct gacagtttta ctcttttagc ctgttttacc cactcttgct agcaatgagt   84060
actattctta aaaaaaaaag cattgctaat ggggtacatg caaatatctc attttttgaaa   84120
aaaccgtatc tcatgatgtt tgtcattgc attgctttga ttatcagtga ggctgaaatat   84180
ttttctgctt attaataact tatatttcta ctttttgtaaa ttgcctcttc agttttttttt  84240
ttttttttgta aatttaggtc actgacattt tgcagagttt atattaatct ccaacaaagt   84300
taacctgttt atctctgcca aaagtgtggg tcatttttaa tgctgacctc tgcctgttgg    84360
tcttgtcaaa cagtaacatc taagttctcc ctggcagaac tcaagtccag acttcttagg   84420
aactctggat tgctgaacag agtaaaagta agtataagta agaaatgtaa ttttggctga   84480
ctgactgata aacaaagcaa ttacatattc attactcctc aatttgtgtc attttcaaag   84540
ttgataaaca tgaaggctaa gtcttatcta agttacttgg aagaagtgtg gaaagttgtt   84600
atgaatccat tcattccgta tattttatct tctccttagg tggtccatga gttggaactt   84660
tataacacag gatattattt aggcatgttc atgaattctt ttgcagtctt tcaggtatgt   84720
tttgcttgct atattgaaaa gatattaata ttttttacta ttgcaaaccc tttcagaatt   84780
agtgatcatt ttgagatgtt aacctttttat taaatgtgtc actgaagcgc agtcttatgt   84840
aagtataatt tgaaatgaaa agataatcat ctttccagtt ttaaaagcaa atggaacaat   84900
tcaccattgg aaaagttaat ggaattgaca ttaaacaaat aattttttcct ttatgtatat   84960
gtatttccat ataaatatat tttatgtata tatataatat ataatatat tttatgtata    85020
tataatat atataatat tttatgtata tatataatat tatatatata tttatgtata    85080
tttccttgac tttgaaatgg ctcttatgca tgagtgtgtg tgtgtatgtg tgtgtgtgta   85140
agactgatgt gtgtatgtgt gtttgagaaa gatcaatgtg tatgtgcgtg tgtgtgttgg   85200
agagagatcg atatgtgtat gcgtgtgtgt gtgtgtttga gtgagaaaga tcgatgggca   85260
tgtgcgtgtg tgtgtttgag tgagaaaggt tgatgtgtgt gtgcgtgtgt gtgtgttt    85320
gagtgagaga cagaaaggtt gaatgtatgt gcatgtgtat acctaagctc tcaaaaatga   85380
gcacaagtga gtcaggagtt tgggagactg ccttgataat ttagtgagca tttaaacttg    85440
tgttttaaaa gaaaataaaa attattcttt ttaggaatgt ggactctggg tattgacaga   85500
tgcaaacctc acgaaggatt atattgatgg tgtttgtaag taatacatgg cgacatgctt   85560
gtatttgtct ttcacatgat attcaacatt acttatatag gtatggatat ttttagatg   85620
aacatagaga ttgtgatttt cattttttctc ttctcttctc ccaaaatgtt tggagtttaa   85680
tgtacttaga agtacatctg ggccatgaca tggaacgttc atctgagctc ctgtctagat   85740
atttgaagtg aatgctttcc ttttttctcta ggtaattctt tgaggtagtt atattttgg    85800
acatactgga agctgctttt cttctgattt gtatcacaaa ctgtcctatt cttttggaat   85860
tatttaaaag gagcaacata ttttttgaaat attttttgtac tccagctttt tgatgttcac   85920
ctagaaaata gcccagatgc catcatgcca taaagtattc tggtacacac acacacacac   85980
```

```
acacacagac acagacacac acacacacac agagacatag acacacacgc agacacacac   86040
acacacacac acccctcatc aatctgagtt cttcctgggc aggattatat ctgtacatcc   86100
tagtttcttg aattgccaaa tagagttggc tgccaagtaa taataagtgt gcttttagaa   86160
agacgtcata aaatgttttg actgaaggaa atgtataaat gtataaatta gaatggttaa   86220
cctagaagg gattctcttt tctttcaggt taagttatac taacatcatc ttgaaaggct    86280
tctagaactc tcacagtttc tatccctgaa ttccctgttt ctgtcaggta ttctgttatt   86340
ccatgctaag cccccgggtc tctttgggct ggttcttgcc ccaacaggac acctgatcct   86400
ctgtcctgaa acttaaaaga taattttata gtcttgaaga tgttatgaag tcattatgat   86460
ctctctacat taaagacatg tggtacattt agctttcctc atataaccct ctatcctaga   86520
caatcttcca agcatgtttt tccattttc agtctcagtt tttacccatc tttgttcttt    86580
tttacatatt gaatccttct tgatgccac tgtaataccc attctattgc cagtaatact    86640
tactgtatcc tttacctttt ctgaaaacct tcttctacct tttcactgta acagaaggaa   86700
cctgatactc tcactggcac attatgtctc tggacacctc aagtgattga cattcatttt   86760
gtatgtggag tttacaattc attctctcca gtgactgttt ttctaactac tgtcaatgtt   86820
tatttataga tgacaatgca gaatatgctg agaggtttat ggaggaaaat gaaggacata   86880
ttgtagatat tcatgacttt tctttgggta gcagtccaca tgtccgaaag cattttccag   86940
agacttggat ttggctagac accaacatgg ggtaaaaatt tataaagttc tttgcccata   87000
catattttgt ttagtgtttg ttttaaataa gctttgcccg cttttctaatg tttaagtaca   87060
aacatagtgt aactaagaac taagtagacc aaaaggattt tttaggaaat gatatttatt   87120
gaatctaaat acagttttg ataaagccac acataaatta tggcaggaag gtctcatcaa    87180
tgagaagata ggccttttt tttttttta actgaagggt gattttgact tccttgaagt    87240
ctcatgattc ttgttgaaga aaaattgctg ggagtacatt tgttgtcaca ggatgggaag   87300
cactcatgat tacctcctgt gacccctggc agtgctgcta actgaaccct gctcctcaca   87360
aagcattccc aggagtcaca gggagaaggg gcatgggtgg tggaaagaat tcagcttggc   87420
tgataaaccc cgtaccacct ggcctgataa ttgagcaggt aaatcatgaa atccacatag   87480
tattttatag tcagctgttt aaagatactt gagttaacac aggaaatctc aaggaa       87540
acaaataaca gcattgacag ggatacagag aaaaacttct gcaaatttag agaaaaaatt   87600
ggagttaagt ttgaaaatgt gtatttatta tctataaaaa atttgtgaaa aataataatt   87660
tattctgaag atgtaaattt tgcaggaaga ttttattaga atatggatca atatgcagta   87720
ttatgacctt atgatgacct attctttgaa aagttggagt ttactgtttt atacttaaac   87780
cttttaaatg gttttaaatt cagatatgta aacaataga aaaattgaaa ttcttccaaa    87840
aatagtttag attatttgg cttatttcaa aatgtatcag ttcttggttt tgtgatgttt     87900
atatttatta tcttgacttc agttacagga tttaccaaga atttgaagta actgtacctg   87960
attctatcac ttcttgggtg gctactggtt ttgtgatctc tgaggacctg ggtcttggac   88020
taacaactac tccagtggag gtattgtatt aaagagctgc ttatcagtat tacggtgaca   88080
ttaagctaat acagcgtcag ctcctcaatt tttttttaa atgactgctt ataatgttta    88140
tcacagttta gagattcctt ggctttgtct tttggttttt atctgtttta tatttaagaa   88200
tgtgagctat atatagctat ataaactgct aaatgtgcaa agtccgtatt aagatttggg   88260
tagaaaagtt tattattgac ctgaactaac catctccaaa ggccagaaga gagagaaaga   88320
aaaagagaga gagagaaaga ggagaggaga gagagagtga gtctttctat ttgtcctctt   88380
caagaatgaa cagaacttct caagatgttc cctagccaat attccatcat gtcttttggt   88440
caaattgcat catatattgt ttcctaagcc agtcactggc aggaggaata taatgaccat   88500
gagtggcctg aattttctca tttgaaattg aaatgtaatt ttgatttaca aaataatcgt   88560
attcatgaaa aatacagtgt agattgaaaa atgctttggg tttatataga aattggaatt   88620
agattgtaag ctcaggccac tataaacaga caattcagca acatgaatgt ctgaagggac   88680
attcaagaat cattaggaac atgggcaat ttttcattgt ctggggctgt cctgagtatt    88740
gcagactgtc acccactaac tacctatagc accttcgact catggtgaca atctaagaca   88800
ccttcacaaa tgtgcagata aactctagag ggagttactg ctgccagcaa aaccactggc   88860
ctaaactaac ccaggtttag ctttagatgc aggtgtgggg cttggccttt tctgtaggac   88920
ttggccaaca atatcagaat tgggtcactg aggaggaagc acatgtattc agatgtccca   88980
cacatttttct catctgtatg taaaaataaa tcatatatat gttttagaaa taattccaa    89040
tttcctcttt aaatttagtc aggaagcaca tgtattcaga tgtcccacac tagaacaggg   89100
gctgttggat ttggcagggc ttttaaagca gattggtgga gtcaatacag catgaaagaa   89160
gagcaaattg cttcgggatt agacaggctg ggttctagtt ctggctcctc tacttgccag   89220
caatatgaat ttgtactagt tacaaaaatc tcaaaaattt aattttcttt tctataaact   89280
aggagactaa cagtaaccttt atggggttgt aataaccaaa caaaataatt tatgtgaagt   89340
gtttggttgc tataaggcac ttaataaagt atagcaatta ttatgttaag taacataaat   89400
caagtcaatt tgccgtcatt catttgtgat aagttgctgt ttgctttctg ttgatagcaa   89460
gttgacattt ctagctgaag ttaaaagctt cacaggtttt ataaagattg catttaattg   89520
cataaaatgt gaagaatttt gacctgaata aaaaatatgta ctcgttgtgt tctttccagc   89580
tccaagcctt ccaaccattt ttcatttttt tgaatcttcc ctactctgtt atcagaggtg   89640
aagaatttgc tttggaaata actatattca attatttgaa agatgccact gaggtaatgt   89700
attcaagctt ttgttgatca tttacactac aggagaaaat cgaggtagca tgaagggatt   89760
gggttgtgta gtatctggc atttgggatt ctaagcactt tatacatttc tgggagcgtg    89820
aaaatagaca tgtcttgtca gtgatttctt ctgctaatta atgtctaagg atatcattag   89880
catgtctaca cattacctcc ttgaattttc agcataggtt ttcctctttt gccatgtaag   89940
ttccttattg tctctgaagc atgcctttct cttttcctgcc tccctgcatt ttcccctggt   90000
tttccccaca tctagaatgt gtggccactt ctcactgcca ctctgtgccc actgcagttt   90060
tgttttttt ttttttttga gacatgtgct tgctctgtgg cccaggctgg agtgcagtgg    90120
cgtgatctcg gctcactgca acttccacct cacaggttca agtgattctc ctgcctcagc   90180
ctccgagtag ctgggattac aagggtgcac caccacgccc agctaatttt tgtgtttttc   90240
atagagacag agtgttgcca tgttggccag gcgggtcttg atcaagtgat ctgcctgcct   90300
tggcctccca aagtactggc attacaggca tgagccactg cacccgactg ccattctgtt   90360
gttttag ccccccatgtt tatattttca aggattcact attggattca cgtaccttgt    90420
atctccttag ctagtcattt ccctggggag caggaattag gttcactgtt tgtgttgtgc   90480
ccacagtatg ttaaccaagt gactgatttt tcttcccca gaataagtag agatacgtaa    90540
ttaacttttat tacatggatg aaaatgacat gatatctttta ggcactttat atataatttt   90600
ttttaattta aattttaatt ttttaagctt tttattggca tatttggctg acaaagtggg   90660
aagtaaattt ttttaatttt ttaattttac ttttttaaccc agttatcatg gtaccatgta   90720
```

```
acaagcaaaa gatctagagt ctaaaggcct ggattcaatg tttaatctac cacttaccag   90780
caaatgactt aattgtagtt tcctcatctg taaaatggaa atgataatta ttacacccac   90840
aaaagatacc ttgagaagca gatgaaaaca tcaatgggaa aataaattcgt aaaatttaag   90900
gcctagataa atgctattat tgatgagact tgcaactttg ggataattta caaaagttta   90960
caaccaagat atgcttcagg actaatatct gagttgtact ttccttggaa taattttta    91020
cagagacttc aataaaattca ataacatttc atgctgtttt cttcaaattt ttctaatgag   91080
accagtatgt tccaggatga catagttaaa tcaagctagt agtaatatca atatatgaaa   91140
tagcctttct gtgcacatcc ttaccatcta atggcttcag atagtgagag aatttaaagt   91200
tagtgggagg actagaaatg gggctgaaga tcgcccttc cccatgtatc ttgaggttga    91260
ggggaaagca tagaaaagaa atgaagtttt tcctgatact ctttgatact ctccttggtc   91320
gaatctttgt ctcatctttt cgctagtctt gagcctcaca gatttgacag tacttaaact   91380
ggtgataaaa gagcactta ctgaaagca tctattatac aaaagctttg atttattttt     91440
ttctttcagg ttaaggtaat cattgagaaa agtgacaaat ttgatattct aatgacttca   91500
aatgaaataa atgccacagg ccaccagcag acccttctgg ttcccagtga ggatggggca   91560
actgttcttt ttcccatcag gccaacacat ctgggagaaa ttcctatcac agtcacagct   91620
cttttcaccca ctgcttctga tgctgtcacc cagatgattt tagtaaaggt aaatatttga   91680
tgtctgaaag aagtgaaatg gaaatacgta attaaaaagg aagcagaagg ttttttctct   91740
tggttaaatt tgttggcata tctagtaggt catcttcttt accctctgg taatgcctaa    91800
tcactttcta atctgtatgt aaaaatataa catttagaaa taattgccaa tttcctcttt   91860
aaatttagtc aggaatgtga ctataaagac taacgtctct tttgcagtca tttacatcta   91920
cagactgtgt tacgttggga tcctattaaa acacggccaa gtcgatttgt agatttgaaa   91980
ttttggaatt tttcagtgaa ggtaaaagag attttgtaga ttttcag agaagacatt      92040
ctagacagaa agataatgag catagtggat aaacacttgt attctgggt gaggcaaccc    92100
tgtgtttgaa tctcagctct gccaagtgtg attttgaaca aggcatttaa tctcccctc    92160
tttggataat aataggaact acctcaaagg gttttttcc ttacatttc atcttcttct     92220
ttgtcatttt caaggccagt ccatgagatg ccttatctaa tttaactaga acttactaac   92280
agatttgaag taagaataac aaaatggtac gcgctgtgtc atcagattta attcatttcc   92340
atggaaatgg tgcctattaa gtgtaaatcc tgtgaaaaac acgtttcagt taatgaaggg   92400
tactgtactt agtgagaaaa tctaaaagga aaaattaatc aaagttatgg taatttttg    92460
taatacagac taacaagaaa aactcattct gtgaaataa tgtattactt gtttaaataa    92520
aatatctaat ttaaagaaaa caaaataaga aatgataggg gcctatttag ccacacacaa   92580
acctcagaca caacaggtca gatgtttgtg ctcatatctg cgtatagttc tctgtaaaca   92640
tgtgagtaga gaccatgtta attgtgttca tttttttcaa caggctgaag aatagaaaa    92700
atcatattca caatccatct tattagactt gactgacaat aggctacaga gtaccctga    92760
aactttgagt ttctcatttc ctcctaaatac agtgactggc agtgaaagag ttcagatcac  92820
tgcaattggt aagaatagag tatatcacca tctattggtt taattgtata tgatcatata   92880
tgttgttctt gtaattatag atgtattttc ttattgagtc ctaataagaa gagatggcaa   92940
aagttttta ttgggcccaa caactcatta taatatgaag gctagcaaat tatgtatcct    93000
aaaactgttc tcaatcttca atgtgcataa gaatcacctg ggagtcttgt ttaaaagcaa   93060
attctggttt agtaggtctg gagtgggcc tgggaatctg cttttctaac aagctcctag    93120
gtgttggtga tactctggct tgtagaccac actttgagta gcaaggcctc actatactgt   93180
ggctggaggg aggtttcatt cctaagagca gagcttctgg cttctgtggc tctccaccac   93240
tggtgaatat cagaatcttc taaggagctc tgtaaataca gaaacatctg gtttctactc   93300
taaacctact aagtcagaat cacttgggct atggcttggt catgtatatc ttaaaaaact   93360
ttcacaagtg attctgataa ccaaaggttg agtactcctc cctagggcag ttctctgtgc   93420
aggatatgag taacctttac agtaggaagt tactcactga cttcggtcgc ctctcctagt   93480
tactttccat aacataatag tacttttcaa aaattggcaa tttataattg tataaattta   93540
tgggatacaa agtgatatta tggcttatga atgcaatgtg gaataactaa atcaagctgu   93600
ttgacgtagt catcacctca aatacttaac tgttttttt tgtgggaaga acatttgaaa    93660
tttgctgtct gagcattttt ttttttgag gcggagtctc gctctgtcgc ccaggctgga    93720
gtgcagtggc gcgaacttgg ctcactgcaa gctctgcttc ccaggttcac gccattctcc   93780
tgccacagcc tcccgagtag ttgggactac aggcacccgc caccatgcct ggctaatttt   93840
tttttttttgt atttttagt agagatgggg ttttcaccatg ttagccagga tggtctccat   93900
ctcctgactt catgatccac ccgcctcggc ctcccaaagt gctgggatta caggcgtgag   93960
ccaccgcgcc cggcctttt tttttttttt tcctttgatg gagtcttgct ctgtctccca    94020
ggctagagtg cagtggcagg atcttggctc actgcaacct ctgcctcttg gggttcaagc   94080
gagtctcctg cctcagcctc ctgagtagct ggaattacag gcacgtgcca ccacacccag   94140
ctagtttttg tagtttagt agagatgggc ttttgcagtg ttggcaggc tggtctcgaa      94200
cccctgaccc aaagtgctgg gattacaggt gtgagccatg gcactcagcc tttcttagca   94260
atttggaaat ttacaatact cttgttatta actatattta ccatgctaaa agtccttttt   94320
tttttttga gatggagtct ttctctgtag cccaggctgg agtgcagtgg tgtgatctcg    94380
gtttactgca accaccgcct actgggttta agcagttctt ataccttggc ctcctatgaa   94440
gatgggacta caggtgtgtg ccaccatgcc cggctaattt tttatatttt cattagagac   94500
gggattttcac catgttggcc aggctggtct caaaccctcc acctcaggtg atccacccac   94560
ctcagcctcc caaagtgcca ggattacagg catgagccat tgcgcccagc ctaaaagtac   94620
tttttaatta gacatagtgt ctacacaaat ggtgttatta atcagggttc tccagagaaa   94680
cagaaccaat aggagatact tacatataaa aggaggttta ttatgaggaa ttggctcatg   94740
caattatgga ggctgagaag tccccatgatc tgcttttcga agctggagac ccaggaaggc   94800
tggtagtact cactctgagt ccaaaggcct gtgaagcaga ggagctgatg atgtaaatcc   94860
cagtcctagg agaagatgag atgagatgtc tgagctcaag tagtgaggca ggaaaaaaag   94920
ggtgaattcc tccttcctca agcttttgtc tattcaggct gtcagtggat tggatggtgc    94980
ccacacacac tggggaggac aatctgctgg acccagtcca ccaattcaaa tgctaatgtc   95040
atctagaaac accctcacag acactcagaa gcaatgctta atctaggcac cccttggctc   95100
acttaagttg acacacaaaa ttaaccctca caaatgtttt gtttatatag ttgtgcttta   95160
caaataactg aagaaaacat tttaattaat gacgtctaat agtttgttag gtctttaagg   95220
tgttaggacc taaaacactt tttttacagtt cttttatatt tcactggcag atgtaatgct   95280
tttttattat aacccaaaca accaatccat aggcagagga cttatttgg aggcatatat    95340
atacatacat acatatatat atatatatat atatatatat atatatatat atacacacac   95400
acacatacat atatatatat atatatatat atatataatt tttttttgga agaggcaggg   95460
```

```
tttagctatg tttgccccag gctggacttg aacttcttga acttctgagc tcatgtagtc   95520
ctcctgcatc agccccttgc ataactggga ctacaggcat gcaccactgt gcctggccaa   95580
ttcttaaaag gaattaaata agctctctat ttagggaaat aaattctgct taagcatctc   95640
ccacagtgtt gggatgctgg gacatgcact acacatacat acacacacac acacgcacac   95700
atatacacag agggaaggag cctggctttt taaatatgta ccatcactcc ttacacagga   95760
acgattctgt ctgtcgtcat ggaaatacccc cgaggcttaa ttttttatgct tgatgtaaag   95820
aacggatttt caagttttat ttttacatgt tgtttttaaag acctattttg tatcccagaa   95880
tgtacgaatt ttagcttgct tctttgaact ttgatagtct atgttcactt tgaatattaa   95940
acacatagcc tgcagtggta ataaatataaac ctctattttt ttcttttgtat tcacatctaa   96000
aatttaagct atactggcac agcttcagtc tattcatatg aaacaggttc ttttcccttt   96060
tttttcatat tcattttta ggatcacatt ttcactaggt atttggactt ggcttggtat   96120
aagtttttcaa aataaactac atagaaagat actcttatct atacagctta acaatggcag   96180
ggccaaaatt agaactcagc cttcatattt ctgaattttt gctactttcc ctgagttgtg   96240
gtgttaggat gtgggtagag ggttttttaaa gcatgtgttt tgtttaattt tagattacta   96300
actttgaatc cttttccgaa tccttttgat cctgagatta attgaaatac ttatatttgt   96360
tgttactaaa cagaacacat tggaaaacac tacaatcctc attgttttt taaaaaatta   96420
tttctcaagt tcttgtggtg tattagtaag aaataagaat aaaattttgt ttgcgtgaag   96480
aatactacta ataaaatgtt tcttttcctgt atgagtgatg gtgtcttact gatcaattct   96540
gtacattttt ttaaagattt ttaaaaaaat tattttttgc ctaatttatg ccacatgctt   96600
aactgagcta aaaatgtcct cttttcatcac atgacctaca agttcagtac cagagcattg   96660
ttattttttt gaccagtctt cctaaaagct tggtgtaaag ttccaactct gttccaagca   96720
gtggaataat gatattgctt caatgacaga ggtcttctgt actcagtgga agtctctttg   96780
ccaccagcag gtcgttgtta ctgagtattt actgaatgaa ctgcatgtct tgtgcttcca   96840
ggagatgttc ttggtccttc catcaatggc ttagcctcat tgattcggat gccttatggc   96900
tgtggtgaac agaacatgat aaattttgct ccaaatattt acattttgga ttatctgact   96960
aaaaagaaac aactgacaga taatttgaaa gaaaaagctc tttcatttat gaggcaaggt   97020
aagcatttta gagacctaca tttgttcgta gaaaaaaatt tgttttttc aggtagggtt   97080
cattctagac catatttcaa aatagatgga ttttgtctta ggtaagtgat gggctacacg   97140
gtgttgacat gtgcaggaag tgcaaacaat ggaaagctgt tacaattctt cctttagcta   97200
actattcact cactgctgct aagatgtttg ttagtaatgg cttaagagtt agtttctggt   97260
gggagggctt gtattatact aagggatctg aaatttaaaa ctctttaaaa atctagaaga   97320
atactcattc atttattac acatttgtgg agtgttcctt agtgccagga tcagttttcg   97380
tgccaagaaa acagagggag ccagggcctc tcttcttaaa gaattcgctg ctcaatggag   97440
aagtggtttt gtatgtaaac agacgcagtg ccgtgtggtg gggaccttct cagtgcattt   97500
aaaatgatga ggaggacctg ctggaccctg aggaaatgtc atgctagtga agactgtatc   97560
ttgcacccttt gaaaggtgga aactgttcac aggcaccaga tcctttgttt tggcaacttg   97620
ttaataacag cagctaacat gagttgagtg tgcactgtgt ggcaggcagt gttctaaaca   97680
ctttacatct catacctcat tggaggctca ccattagtat tagcatgatc ctgtttttttt   97740
gcagatgagg aagctgaggt gcagaaaagt tagctaactt gcccagggtc atatagtcat   97800
acagagcttg gatttggact ctgagcctat gctcttgaca tccataccta ggaggaaaca   97860
aagagatgtg agacacgttt gatgttaata gtaaagtaaa tttgattttc tgaaatactc   97920
caaaagctta ccaaagttac agtctcagtt ttgtatttcc ttattagtgg acctctagca   97980
tcctctctct gtggctgagt tttttctctc gcacaatttg tatgatatat cccgtccatc   98040
aaattcatga ggattagaag ggttcacaca aactgattaa aaatgaggat tcactataat   98100
ctaagagaaa tatagttcaa cgcttttccaa ctcctaattt ttttagtttt tgttttttta   98160
taacaaatgg attaaatgaa aagtaggggc aagctattaa ttgattgcta attttctccat   98220
aggagaatta gaaaactcag taaagacgcc atttgtaatgt gagcttttct tccaggttcc   98280
attattgtgt agagaccttt ttattctaaa ataattctat gtaatgacag taataacaac   98340
taaatctgtt taaatgtttt atgcatgttt cattaattc tcacaaaaac tctaggagca   98400
ggtgtcctat tattattttcc attttataga tgaggaaatt gaggcacaga gaggttaaag   98460
aatttaccca tggtggtctg gttccaccgt ccaccttgt cctcagaaca ctatgggaa   98520
attctgattt gcagtgttct ctggtttta gaagcaatgg gatatgatgg aaaggaccag   98580
gaatcgggac gggatgcttg agtatcacca ccgtgtaaga agtctcactg gaggttttga   98640
taaaatatta agggaggaac atgggtcct gtagagaagg aggcaccaaa ggttagaata   98700
tgggggtgtca gattagactg aagtaagctg taaggtgttg gtttaagta gatgagctgg   98760
agtcagtgtc tgaagatctc cctgggatag gatggcacag acaaaggctg aatgggagtc   98820
aagggggttgc gggtcaggaa caatgcagtg tatgagatca caaaccaagg gagaccagcg   98880
tttagaatca gggctgagtg tggcctgagt tctgatgtgg ggaaggacat agtggtatat   98940
tttcccttag attagggcca gaccatgcag acactatgac cggccctgaa atgcaccagg   99000
tggttaggtc ctctgggata tttgtagaga tccagcagtt ggaatttcct gtatagagtt   99060
gcccatgtaa aattatccct gtttatacac atttgtggat tggtcgtgtt ttaaatatat   99120
acgtacaaga ataacctttg tcaaatttta ttataattaa atttaagtgg taccaagtgg   99180
tctctgtggt atattgtgtg ccatgctaaa cacaaatgag atctttacac attggcataa   99240
tggctgtaat taaggagata agtaaaaatt atttgggat gtcatgaatg aacgttgtac   99300
cttttgaaaa caagattcca atttgtattc aagatttagt ttttctggtt tgaagtagaa   99360
actacatagg aattagactg gtgctttata atttggcata cattctttgg gatagtttaa   99420
tacaataagg taaaatattt cagaaaatgc cacatataac tccatattta catatgcttt   99480
atgaactgta actctggcta atcaaatatt aatgctttaa acagaaagca taaattttac   99540
atagcttgaa acatggaagc agtgaaaact cattccttaa aaataatttc agtgtgtgtc   99600
ctagatactt ttgctgtgga tcagcagcca tcctacaaaa tgaatggtcc aaatcctcag   99660
tatctgttgt tttcccaaag cagtgctagt ccctcaggtc agtcctggcc aggtaggtgg   99720
ccaaactgta gttttttcaaa gtaacccaga aagggtctct actgattgcc tgagatccct   99780
cctcacatct gttggttgtt agaaggtaca gtggccagag tgcaaaaaaa gcatcgttct   99840
ctaaatgcca agcagtcctc ccaagtgtta agaatgccga gcgctacagc tgtaagtagg   99900
cgagtttccc cttgggagga agtagatcag gggcatagca ctggctgtgg aggcagtcac   99960
acctgggctt gagtcctggc tcccaccttg aacaggttc ttagtgtctc caaggcttgg   100020
tttttttacc tggaagacag ggataataaa agaaccccact tagtagggtt gttttttagga   100080
gtcagtgaga ataaaagaac ccacgtggta gggttgtttt gaggagtcag tgagatatgt   100140
cagcatttta ttcaacacgt agtaagtgca caacaaatat cagctatagt agaattagtt   100200
```

```
gcctctaact agggagttag aggttaatgt cagtgaataa atcctgtcca ttctccctct 100260
aaaaacctgt atgaaattct tctatttctc tccatcccac tgctaattgt tccattcaag 100320
catgattgct cactggacta ctccaatggc ttcctgacta gtcttttct gtgttccctc 100380
cccttcagta cattctccat ataatgtaaa agggatctta gaaaatgtca agatcctgtc 100440
acttgcttgc ttatgatcct gcagtgggct cccggcttca gcctacaggg tcctgggtga 100500
tctggcttgg cctccctcct tagcctcatc tggagctggc tgtatctgga acactctgag 100560
ctccatgctg cttcagggac atgatgcttt cccttccttc tcctggcatg cttttctccct 100620
aggtcttcc atggctgctc cttttcatca ttcagttgat gtttgcctca gagtggcctt 100680
ccctgaccac ttagtaactc caatttgtac tactccattt tatttcttca cttaacatta 100740
tttaaaatta tcctgtccat catctgtcct ggcatttaga gggggagctc tgtgacagtg 100800
gggaccatgt ttgaccttca ttgtatagct atgtgggcat ctcaataaat ccagaatggg 100860
cgaataactt attaccaata ttaacttttt tggactttag gtccatcatc ctaatgtgga 100920
tattgggtcc agaagatctc tgaagcgccc ccacagtgta gcatgatgat ctctgggcac 100980
taatggctcg acctggcctt ggcattctct tagcagctaa gaaatgtgac cagtgatttc 101040
catgtgctac tcttttgct ggtgaagtgg ctggtgaaag tcagcacagt ggagctcccc 101100
aaaaatacat catctcacat gctgaactaa attatatttc aaagtagtgg acgaaagctt 101160
cttggtataa tgcttttcat tatgaaatca gtgtctcatt tcagagactc tcttttttct 101220
tttgccatca catttgccaa agtccttta atatactgta gttgtttta ttttttaaga 101280
aattaaagtg gcttcagcgt gagtcatgat tatattttt aaatgtcatt tatgaacagc 101340
gcattgtttt acttaaatca tgcttggccc aggagttctg taacctaacc cattattttg 101400
ttggtcgaaa caacagctac atcattgaat gaagtgtctt tgctgtcaaa aaggaaaatg 101460
gaaccataac atgaaaactg ttttttgataa ggactggaaa tccagaacct gttaattgaa 101520
gatttaaacc atttgttttc ctcagatatt taaatcacag tgcctgcagt tcaactttttt 101580
aaagtgagac tcaaaccaag tctaattgaa aacactatat ttcctccatt gaaataaaaa 101640
taagagaaag aaagcttcag aattcggatg ttgccattgg tcacaagtat ggctagtggc 101700
catagcttaa aaaactgtga tgttctcact tccattca tgtcatagaa agtaaacaaa 101760
ttcataatga tttctttttaa tacagagaat tttttttatc agcttattac cagagaaaat 101820
tcttgaaata gtcacaaata gccgacttta cttcctttat ttacatgtaa ttttgacacg 101880
aggtaaatca agtcaaacta tgtttagaat gttactttt cattgtttgt gagcagtatt 101940
tttatcttta ttataataaa ttttgaaatt ttacattcat ggttatccca aagaaaattc 102000
ataacccaga acaggatgtg tcttatctgg cccctttatga agggctcatg ggtttttatc 102060
ttaagagcct ctggacttct tctgcatttc aatttcaga agtctatgaa agttctgagc 102120
atatgattac tttcaaact caagagccat tcctaaaatg attaacttaa aggtgatact 102180
cttatttctt cataactttt tggagagagc tatgtttttc ctttctcgt ctgttgtgat 102240
gcagagtctc caacttagat gactgcactg gaaggctgag ttgttgtatt aacaacaaac 102300
attatagacg agtcatcagt gtcctgtttt tttttttttc tttttttgt gatggagtct 102360
tgctctgtca tccagtctgg agtacagtgg tacgatcttg gctcactgca acctccgcct 102420
cccaggttca agcgattctc ctgcttcagc ctcccgagta gctgggacta caggtgtgtg 102480
ccaccacacc tggctaattt ttgtatttt agtagagacg ggactttgcc gtattagcca 102540
ggctggtttc aaactcctgt cctcaggtaa tccacccgcc ttggcctccc aaagtgctgg 102600
gattataggc atgagccact gtgcctggac ctgtttttgtt tatgggatgg aaattaggcc 102660
tgatacactg ggacgatttg gaggacagtc gagggatcca caatgatgca tgctggttta 102720
agatgaggaa ggaaacctca caggacactc ccacaaggga acataccaagt tctctccagg 102780
ttgtgaattt ctcccttact tttccatggg agcagagctg gtggttttgga ttctcggtgt 102840
tatctaagcc tgctcaagaa attcactgca aaactggtga ttgtctgtgg cctcttctct 102900
gggctggctg cctctagtgg aagaatggtg ctagttgttg atattaatgg ggaatgttgg 102960
aggtcagcca cctgaggggt aatttccata agcactgatc tcatctccat gatctcatct 103020
ctgaccagtt tcacaatatc tcatacttgg aactgccgtt gttgatgtga tctggggtg 103080
tggaggcaca tggtcctctc cttgaggttg gtctttctgt cacaaaagta cctcaaactt 103140
ttgtgtaggg attgagggcc tcaaacctat tttcttttt cttcttccct ctcctctcct 103200
tctcctctct tctttccttt tcctcttttt tcttaggttg aattcatagt taaactctgg 103260
ctatctggag aatttagtcc ttaattaaaa attgaggggag aatgtcctgg actctcttgc 103320
tgatttcttt tgtgaacatt aattattttg cttctctgtg atcctgget gcctctgaaa 103380
aatgagataa tatactgcat ttttaaaggt tatgtgaaaa ctaaacatg ataaaatgaa 103440
ctagagtagt gataatgcct atcatttaat tttttccact tttgtttatg ttttgaacat 103500
gtagaacatt aacatgcttc caaaagacaa acttatttg agacatatat tcaaagagt 103560
gtctcttctt cccctttct ttctccctac ctctccattgg taactatatc aggcggttct 103620
tgcattacta taaagaaata cccgagtctg ggtaattta aaggaaagag gtttaattgg 103680
ctcatgattc tgcaggctgt gcaggaagca tagcgccggc atttcccct aggaaggtct 103740
caggaagctt acagttgtgg cagaaggtga actgggaaca ggcacatcac atggtgaaaa 103800
caaggacaag agacagtg ttgtggggag gtgccacaca cttttaaatg accagatctt 103860
acagtaactc actcactatc tcaaggacag caccaagatc cagtcacctc ccactgggcc 103920
ttacctccaa cattgaggat tataattgaa catgagattt gtgtgggac aaatatacca 103980
gtaacctact tcattagttt ctagacctatc ttttctctct ctccttttgc gaaaataaat 104040
gtatacatat atgttttctc atttccccc gcaattttt ttttttttt aaagacaggg 104100
tgtctcccttt tgcccaggct gaagtgcagt ggcacaatca tggttcactg cagccttgac 104160
ttactgggct caggtgattc tcccacttca gccttctgaa caggtgggac tacaggcaca 104220
tgccaccatg ctaattttt ttttgtattt ttgtagagac aggcttttgt catattgcc 104280
aggctggtct caaactccta ggctcaagtg atccactcgc cttggcctcc caaagtgctg 104340
aaccttggca ataggtgaac cttggcgcct cgcctcattt cccctttta ttacacagaa 104400
gatagtatat ctatatgtac tattttacac tttgccttt tcacttaaca gtgtatccag 104460
gaaattactc tgcatcagtt gaccgagata ttcctcattc ttttttttac agctgcatag 104520
tactctgtca tgtgtgtgta ccatagttta tcaatcagt ctccagtttt ggggcactaa 104580
gattgttcc attatgttac aattacagat tgctgtgtaa tgaataatct tctgcgtata 104640
tatttttgta ttgttggagg tgtgtcttca gggtagattc ctagaactgg gattactggg 104700
tcagagggta aagacattcc cctacatggt agttgtaacc ttctgaattc cctctagcag 104760
tggatcagtg ctggtttcca tacagctcac ccaacagaag gagtggtcag acttttgaat 104820
cttaatgcta atctgatggg agagaaatgg tatctcagtg taggtttaat ttgagtttct 104880
cctgttatga agttgaatgt gttttctata ttaagatttg ttttatatt tttgtctttt 104940
```

```
gtgacttatc tgttttgcct tttattcact tattttata gggcttttta tcctttaccc     105000
taattttaa  aaagttcttt atatatgtat atacatgtaa gtaataacat ataaacatac     105060
ataaaaatta cataatattg atattagcta tttatccatc ttatatgttg caaatatggt     105120
cttaatttat ttgttaagcc ttgcttatag tgtgttttgc cttggaatag tttaaaaact     105180
ttaaaaaaat agtcaaatgc atcaattttt ttattttatt gcatctggtg cttagagagc     105240
cttcctctac acctatatta gagagtaatg cctattgttt gttgagagct ttccatgtaa     105300
aaggtactta ctgaagtctt ttcttctttt atcatgttta ataattggaa gagctctgtg     105360
atttactagg agacagtggc cttggagcca gtgagaagtt ggctaatgcc caacttcact     105420
ccctgttagc tgtgtgacca tgcacatggt atctgtatcc gctgagtttc agtctcatta     105480
tctgtgaaaa agggaataat aatagcatct atgtcagagg gtccttgtga gaattacctg     105540
agttaatcct gcaaaggact ttgaacagtt cctgacatct aatgagtgct gaatgaaagt     105600
tggctaatta ctgcaccgta ataattcaat tagaaacata aaggtataat ctaatgttcc     105660
cttcttcaaa ttaagcaaag ttttgtcatc actttaaatg tttatattc ttttaccata     105720
agtcttaaat atcaccatga aacagatgat cttgtttttct ttttttcttt atgcattttg     105780
ttttattgta acttaaatca gatacttaaa tctagggttt cttttggaaa gactcaggga     105840
gaagtttggg acttgaaggt gagaaacat taactgtaat ttcaaaccat taatgcttat     105900
gtttagttag tcaaatatga attttactta tagttctgga tgcttctaaa atatggtatt     105960
tataaagtca aatttgttta ttactgcagt ttactgggga aggatttcaa cattcacaa      106020
atgagtatgg ttgccaagct ttgccatgtc tgtgctgcaa agctcaggct gtgtgccctt     106080
acctgctaat agtggaattg tgtaatttt  agaaggattt ttggctatca gagagtcatt      106140
gataatgcct tgagctggaa atgttcctgc taatggttgc ttttttagtg ataagttatt     106200
gctatcttaa ctttattttt agcaagttag tttattgttg gttgtttggt gaatccttta     106260
gagtttggcc tatgttttct cacactggac tttgagatct gtatgcattg ctttgcaaat     106320
atgaaacatc tgctttttat ttgcaatcat ttatttgtaa ctatttgcaa atatgacaca     106380
tttgctttta ttaatgcaga tacgtgagcc ttaacccct  acctaattta cttctgtaat      106440
gatacttcat tgccaccact gagcatgtgt atatgtgtgt gtgtgtgtgt gtgtgtgtgt     106500
gtgtgtatat atatatatat attttttttt ttttttttt  tttagtgga  aacatggaat       106560
tggtgggtag gcaggcaagt tggtttttg  gtttacctca gttggccatg gccccaaaat      106620
ttaagagcca ccgttttaga ttattttgca tttcctcctc tgtattgctg gtctaagaat     106680
agaaaatact tttattttct acttttggcct taaacttaaa ttaatgatac cctacatagt     106740
atttttcttc tgtagcaaac agtgctagat gactaagcat tgaaacaatt ttgatgaaca     106800
ctagacagtt aaataaaagt ctgccttttaa tttgcttgct tttgaatggc tagaagcatc     106860
atctatgcca tagtgatctt ttaatttact ttaatttggg atatcacagg ctttttttt      106920
tttttttgag atggaatttt attttgctctt gttgctagg ctggagtgca atgacgcaaa      106980
tctcggctca ctgcaaccctc tgcttcctgg gttcaagcga ttctcctgcc tcagcctccc     107040
gagtagctgg gattacaggc atgtgccacc atgcccggct acttttttgta tttttaatag     107100
agatgggggtt tcaccatgtt ggtcaagctg gtctcgaagt cctgacttca ggcaatccac     107160
ctgcttcggc ctcccaaagc gctgggatta taggtgtgag ccactgcacc cggctgggat     107220
atcacagttt ttattttatg cattctgctt gaaaagtcct gcattttaa atttccaaca      107280
gcacttaaaa tagaaagtac tcaattattag ctcttggttt gatttcttct ttccccctct     107340
ctgcccatat ttcctcaata tgaagtcata attagaaact ttcatccatt gcaagttaat     107400
gattactttg actatctgtc tattttgtg  tctaggttac cagagagaac ttctctatca      107460
gagggaagat ggctcttca  gtgcttttgg gaattatgac ccttctggga gcacttggta      107520
agtgtttttg ccaactgaac aaatccgtgt catggaatgg gctttcacta ggtcacaata     107580
gccacgaaat tgacagatat atctctatat attatagact gggaggttgc ttttccttta     107640
gtctggcttt aaaagagat  tttctttta  aagtattatt tcaaacatt  aacaaatcaa       107700
atgttttat  ttagaaaaga taagttataa atcctctttt ttgtgttgt  gtgtgtgtgg       107760
aagaaacaga aataaaaata ctttatgatg atggtgcagc tgataaaatc agttagaaat     107820
gccgggtgat tgtgacacag cttttttctt aatcttccat gactaataca agtgttgtgt     107880
tactgcggtc aatgtagttt aagtttgtgt gtgtgtgtgt gtgtgtgtaa aaaacaaaca     107940
ctgatggaat taagtatgaa cagccagttt cctccagact ggaatctcta tgtggctagt     108000
tttggatgat taatctctct tcttgtactt atcttcaatt tcctatttta ctcagaaaaa     108060
gattgactca ctgtatcaat caggatagac taggagtgct gtggtaacaa ccaacctact     108120
caatctaagc aattaacaat gaagggattt cttgttcatg ctgcctttcc attgtggtca     108180
gcagggggct ctgcagctgc caacgtgtcc acgtctccaa aaggaggctc caggtttgcc     108240
acagcccgga aagaggaggc tggagtctat agcactggca attagagact tcatcctgag     108300
tgtatcattt ctactcattt tatccttctc agagctggtc acatggctat gcctaacctc     108360
actggggcag gaaagtgaat tcctctgtgt aaccaaagta aaagagaact gtatattatt     108420
gaatatcagt aatgtttacc acatgaaact ttatataaca tgaaacagat ctgcttcaaa     108480
ttttctcttg gccttggcct gactcaggat atagaaccat aaatagaaag ctttcagtgt     108540
tgtattgctt gatgttcttt ttacctcagt atagtgtttt gtagcaggga ctggcaaact     108600
tttctgtaaa gggtcagatt gtaagtattt caggcatttt gggccacgta gagtctccgt     108660
tgcatgctct tccctcttcc tccctctcct ccctctttct ttcctgtctt tgtctttttc     108720
ttttccttct tttaaaaccc gtcttaggt  ggtggtgttg gcaggtgggg gctgggttgg       108780
tgcacacata aacaggccct gggctgtatt tggcttgagg gccagattgg gccaggcag      108840
atttggccca caggctgcag ttggctaact cccattctat aggagagaaa atatcattt      108900
tccccacctg aagtactaca gtttgcttgt gaactatgta tgcattcttc acccacagct     108960
ttggggctga ctgaagcgtg ttggagctct tctttggtaa atatctagaa cagtccaaag     109020
atgaataacc ttggacaatt tatttaactc tcttggactg tcagattctc agtctacaaa     109080
ataatggagc tggattcaac agacacatta aaaaatgctc atcatcactg gccatcagag     109140
aaatgtaaat caaaaccaca atgagatacc atctcacacc agttagaatg gcgatcatta     109200
taaaggcagg aaacaacagg tgctggagaa gttgtggaga gataggaata cttttacact     109260
gttggtggga ccataaacta gttcaaccat tgtggagagc agtgtggtga ttcctcaagg     109320
atctagaaca agaaaatacca tttgacccag ctgtggggaa aagaaagaga gatcagattg     109380
ttaccgtgtc tgtgtagaaa gaagtagaca taggagactc cattttgttc tgtactaaga     109440
aaaattcttc tgccttgaga tgctgttaat ctgtaacctt accccaacc  ctgagctctc      109500
tgaaacatgt gctgtgtcaa ctcagggtta aagaattaag tgctgtgctt tagatatgca     109560
tacacataaa catctcaatg ccttaaagag cagtattgct gcccgcatgt cccacctcca     109620
gccctaaggc aggtttcccc tatctcagta gatggaacat acaatcggat tttataccga     109680
```

-continued

```
gacattccat tgcccaggga cgggcaggag acagatgcct tcctcttatc tcaactgcaa   109740
agaggtgttc cttctgctta tactaatcct cctcagcaca gacccttac gggtgttggg    109800
ctggggacg gtcaggtctt tcccttccca cgaggccaca tttcagacta tcacatgggg    109860
agaaccttg gacaatacct ggcttt cc ta ggcagaggtc cctgcagcct tccgcagtgt   109920
ttgtgtccct gggtacttga gattagggag tggtgatgac tcttaacgag catgctgcct   109980
tcaagcatct gtttaacaag gcacatctta cacagccctt aatccattta accctgagtt   110040
gacacagcac atgtttcaga gggcacgggg ttggggg taa ggttacagat taacagcatc   110100
tcaaggcaga agaattttc ttagtacaga acaaaatgga gtctcctatg tctacttctt    110160
tctacacaga cacagcaaca atctgatctc tctttctttt ccccacaccc agccatccca   110220
ttactgggta tatcccaaa ggattataaa tcatgctgct ataaagacac atgcacacgt    110280
atgtttattg cggcactatt cacaatagca aagacttgga accagcccaa atgtccatca   110340
atgatagact ggattaagaa aatgtggcac atatacacca tggaatacta tgcagccata   110400
aaaaaggatg agttcatgtc ctttgtaggg acatggatga agctggaaac catcattctc   110460
agcaaactat cgcaaggaca aaaaaccaaa caccacatgt tctcactcat aggtggaaat   110520
tgaacaatga gaacacttgg acacaggaag gggaacatta cacaccggga cctgttgtgg   110580
ggtggggga tgggggaggg atagcattag gagacatacc taatgtaaat gacgcgttaa   110640
tgggtgcagc acaccaacat ggcacatgta cacatatgta acaaacctgc acgttgtgca   110700
catgtacccct agaacttaaa tgtaataaaa taaaaataaa ataaaaattaa attaaattaa   110760
aaaatggagc tggattagat catttctaaa ttcctttca aatctgagat ttttgagtca    110820
acatggaatt tcttggccaa gcccaagtgg aaaccagttc tgcctgctag agagagttgc   110880
ttaccttgtc cctttgctct ttcttttttg attttttct ttccttgttc catcttcagt    110940
gattccccct ttgatgaatc ttctgatggg ggaaaaagtg ttgttgtttt gcttgctcgg   111000
tgttatttgg tggaccttat aaagtgtatt ttatgtaatt tttttctctt ttcataaagg    111060
ttgtcagctt ttgttttaag atgtttcctt gaagccgatc cttacataga tattgatcag   111120
aatgtgttac acagaacata cacttggctt aaaggacatc agaaatccaa cggtgaattt   111180
tgggatccag gaaagtgat tcatagtgag cttcaaggtg caataaaaag tccagtaaca    111240
cttacagcct atattgtaac ttctctcctg ggatatagaa agtatcaggt atttcgtatt    111300
taattaaata aatgatagat gggaaattca aggaaggtag gtcttaatgg gtcaaatatg   111360
tgtgtggaaa cttaacaagt tgcagcttta caacacatgt gaaatctgaa tttgagtact   111420
cttttgcttt gcatttgtgg ccatgttcca aaatctgaga ataaaacatt aacccactct   111480
ttcagaataa ctaagagaat tctaaaaatg cttttttaatg tatgtattgt acttgctatt    111540
ggtaagataa gtcaatacat gttttatcat tgaaaaagtt aatttctgag gggaagaaa    111600
attatttaaa atttgacaat gtgttctagc aagtttagat tgcaaaggat tttttactta   111660
taaaacatca tggaacagtt acaatatctg ttaatttagt gctgagaaca cccatacccct    111720
gaaaagtgtg ttgaatgggc atggatgct ggatgagaat gagtatgcgt ggaaaggtat    111780
gctgacgagc ttaagtttgc tccagagctg tcctggtgat tgatgccttt actgcttact   111840
gcctgctgca ttttatgaga tcaccaaagt cattctcttt attaggaccc ccactatttt   111900
cctattctac tagtaggcat gtagaagcta aacttttcct gaacttaggg ccgcactacc    111960
agagatcaaa tataagaaat atatttctca agcagtttgc tgttcttatc tgagtctgtg    112020
atactgagtg ggagaaacac tggcaaaagc tctactttt tcttctaggg aatgacacct    112080
gtttacttat aaaaactgaa aaacagtatt attttcaaaa tgcatggcaa atctttaaat    112140
gtcaatgatc atggttgatt ttcattgcct agtacaaggt caggtacttc atagacactg   112200
aacttatttt ttaaatgcat gttt caaagt actttttgt tcagtatgtg gtaatggttt   112260
actctgaata gtaaaaaca tacttttttt cttccaagcc taacattgat gtgcaagagt   112320
ctatccattt tttggagtct gaattcagta gaggaatttc agacaattat actctagccc   112380
ttataactta tgcattgtca tcagtgggga gtcctaaagc gaaggaagct ttgaatatgc   112440
tgacttggag agcagaacaa gaaggtaatg tgctgggcc acttgaggtt gttatgcttt    112500
atgaaatata taacttacat gagaaaaatt tttagccagg tttgaaattg attacatctg    112560
catcttttgg tgaaaagtaa aacacataat gagatcagga tgggcctgac atggccacaa    112620
tgcttctggt ctccccaggg tttttttaac agaatttcag ggctcagatg tctctttatt   112680
ttagatatgt gatgccctat gtcagttacc ctttgagtgt ctgataccat ttctggtttg   112740
gcagccttgt agtttgctaa gaccttgggt tctggagaga caggttaaat cctggttctg    112800
caacttacct ttatgaggtt cagttttccc aactgtaaag tggaaatggc acctatttta    112860
gagtggctgt gaggattaaa tgagataatg tgcaatgctg ctgcatagca aatgctcaaa    112920
aataggaact aaaatgctaa ttaaaagaaa tgtgaataac aaaaaatgct gctagtaagt    112980
ggattatgtg tatttatat acaaagtgga cagggatcca ggtgtgtgtg tgtgtgtgtg    113040
tgtgtgtgtg tgtgtgtgtg taagaaagag agagatggaa gtgggtgggc agaaataaga   113100
taatgtccag tgattcaaat ttctgttaat tcaagaaggg ataattgtag aaagtgttta   113160
gaggcttctg agactgtaaa aaatattgta ttaacagtaa cttagattga atccttgtta   113220
cctattccaa agctggggac tagaagatta ttgcttagag gctgaagcag tctttgacat   113280
tttttcttct tgtctgcttg gctaagtggt agttatttaa tattccacct aagtgtagtc    113340
atcatctaaa tagtaatatt tgagagaggg caccaagtag gatggtcctc tggggactag   113400
agcagaatta tctctaggaa ggttgttgag ttagctgggg atcctaattt ttttttcctgg    113460
gggcttgaac ctcaaactgt taacaccaac cttcagataa ttgaaatggg agagtccaga    113520
atattagagc tagttaatgg cagattccca gaataggatt cttttcaatg tgtcttaaaa    113580
tatttggg atggctggt cagataagta acgtgcatta tcttctgaaa tatattattt       113640
tttccttta tttatagcta tttagtcttg agccaaatat agggaatttc tcataggaaa    113700
actattttca tcaaaacatc ctcaaatgta ggcaatggga aaaggatgaa aatttacaag   113760
tatataggtt gagcatccct aatccaaaaa tctgaaatcc aaaatgctcc aatgagcatt   113820
tcctttgagt atcatgtcag tgctcaaaaa gtttcagatt tttgagcatt tcagattttg   113880
gaatgtatgt atgctgtaaa tattccaaaa attcaaacaa aacagaaatt ggacacactt    113940
ctggccccaa gcttttggaa taagatatac ttaacttgta atagtttaaa aaagcaacat   114000
ataggcacat gtatacatat gtatgtgtgt gtgtgtttgt gataaataaa tacatgtctg    114060
gcataaatat ataagtatat attttttatg ctagttaagt acaacttgga                114120
ccagagtagg aatatttaat ggtataaaat gtaattttc tggataattg atcagaatgt    114180
tattacttttt ctcttgcagg tggcatgcaa ttctgggtgt catcgagtc caaacttct     114240
gactcctggc agccacgctc cctggatatt gaagttgcag cctatgcact gctctcacac   114300
ttcttacaat ttcagacttc tgagggaatc ccaattatga ggtggctaag caggcaaaga   114360
aatagcttgg gtggttttgc atctactcag gtgagagatg atagttttt cccttttaaac   114420
```

```
tataatatat aatatagatt tatttattat atatatttta tatataatat atagtatata   114480
ttatataaat catatgttat atataaaaaa tattttttaaa agtatgtggt tgcattttt    114540
ccttgatttc ataaaattac ttggcagttt caaagtttag taacttaagc aaaaggctaa   114600
attgattaat tttaatttt ttctcctcat tactatgaat ttcatgtctg atatttatat    114660
ggaataaatc agttcccat ctgccacttt tcatctgtga taactgatat aagagtagat    114720
gttcagttcc atatagcaaa tattttctat tttcttttct tcttttttgga aaggaaaaac  114780
tgaaactttt aatttactga taatatgatc atttatgagc aaaattcagt gggatctaca   114840
gaaatgctac taggattaac aagtgaattt agtaacattg tggtataaaa aaatcattgt   114900
acagaaatcc attgtatcta tatataagca atggaaatgc aaatcaaaat agcataacat   114960
gtgaactgtt tagggattaa tctgacaaaa atcaataaga tctatacact aaaaactata   115020
aaacatttca gcaaacattt tctgagcctc tcctgtactc taggccaagg acattcaaat   115080
atgaatcagg gagcattcca ctctgaagga aggtgtgatga atatccagca acaaaatact  115140
actaaattta ctctttgaag accttgatat atacttatat gtacaaatgt ttttcttccc   115200
tcaacaggat accactgtgg ctttaaaggc tctgtctgaa tttgcagccc taatgaatac   115260
agaaaggaca aatatccaag tgaccgtgac ggggcctagc tcaccaagtc ctgtaaagtt   115320
tctgattgac acacacaacc gcttactcct tcagacagca gaggtgtggg caaggggcag   115380
ttatttaaaa atcagtgtag acaattcttt atgctgaaat actgctttat ttgtaatctg   115440
ttgatttcaa caaagacttg tttccagagc tctgtagagt aatagggaga agtggtgccc   115500
ttctttggct gaatttgctg agctctggaa gggtgggaa cttttggaaag attggtggaa   115560
caggagaaaa cacgggcact gtaacattgg gaaaggaatg aacatagaaa cctgttgagt   115620
ttctattctt cataggcact gtgctagatt actttacgta tgctattgca tttacttctc   115680
aaagtaactc taagaagtaa gtacatctat ccccatcata catatgataa aactgaggct   115740
gagagaggtt aagtgacttg ctcaagatca tgttactagt aacagtagag ctaggatttg   115800
aactcatcat tccaaagacc atgttctttt cagctgctcc acatgtcttc ttaggagaat   115860
tgatagaacc ggtagtagaa ttcttacttt aactggaata aagaatatg ctagttctta    115920
actttattcc cttgatcagt tttgtgggag gttaagtaca atggatgagg gtgataactt   115980
caattctgga aagtgatgaa gagtggtgat gataaaggaa aagaaagaat aaagttaggc   116040
acagtcatag acaatgtgtt attgtgttcc tgggagagcc aggggattag gccctgatta   116100
agggaggtca ggggagggag atgactttag tttcttgtct tttatgcttc agccccaaca   116160
ggaggacaga cttgtcagta gcactaatgt gccctcccat gggcagaggt gagggagctt   116220
ggggagtgtg cacttttcct ttcatcacct tgcttaccta tttgacccat agcttttgat   116280
atgtgagaca gtgcaaagct cttagtgctg tcagtgattg cttcttttcc taatgaggaa   116340
taggactgat ctgttttgct acttggaagg atctagatat ggaaaattag cctcattcac   116400
tttttttcac cttgattcag cttgctgtgg tacagccaac ggcagttaat atttccgcaa   116460
atggttttgg atttgctatt tgtcaggtat gtaacgatgc ttattttttt aagttaaata   116520
tgactttta taaattat ttggtttggg gctttattaa atcttagata acttgaatat      116580
aattcctaat gatttacatc tgtgacttaa gcaagatata tcactgtctt taataaaag    116640
tattagagat gttgccagcc aatgagtaga gagcaattat atagattgat tttctgtttg   116700
aaaagtattt cttggagatt attttgcttt tgaagtgagg gttaatgtcc tccaatatga   116760
ttcctgataa caaatacatg ttttacttat aatttcttaa tattcatctg agaatataga   116820
agtcaacatg gtagaattat tgacttgagg ggaggaattg tgtccctta atgtaaaatc    116880
ttatataata gtaaatataa caattaaagc ataattatgc tcaatcctct ggtacagaaa   116940
gaaaatataa agaaatctac attttttatag tgcagcagga gctacaataa aatggaagta   117000
gtatgaaaaa tactgaataa gataatcatc acactaaata gcacataaaa atattgagga   117060
ctttaagatc atctccattag aacccaaaga taatttgtga taggaccaaa aatgttgtg   117120
tgcttgggta gaaacaaacg accaaacaaa aacactgaaa cacttactga gaaagtaaaa   117180
aaatggctat tatggagaaa aagtacttttt ttcaaaaacc agaacaacca ttctagtaga  117240
gagaacaggt atacttgctg agtagggcgg gtataccttg ctaagcaggt ataattaga    117300
aacttccaaa taattctaag attattttgc attattctca gaatacagta aacattttt    117360
aaaactaaag gaaaaatgat cacaatgaaa aggaatggta ttcagtgaaa aggtcagaaa   117420
gagaaagtaa acaatttatt tcgatctta ctaacaaaga ccatgggaaa attctcattc    117480
tcaagctgtc ttgcaatcca agagtaaatc cagaagtaaa tatgctgtgt attctagata   117540
aaattgaaaa attatatgta cttaaatcac caagttggtt ggaattcatt tttgataaac   117600
caaatgtaga gaaattagtg aaaccaagtg atttttttact tgaggcttga agcacacagg   117660
ggtaaatgtg gtacctgttg gtcagaatgt tcatcaatcc catgttggtc tcaaaatgca   117720
gaaaacaaaa ggaagggact agtaggcacc tctcatgagg gaggaaaaaa attacaaaga   117780
agttggtcac tcagaaatgg gtattgagat ttcttacagt tgatatttt ataagtgctc    117840
tggaacaagg aaggcaaaga aaactcatga gtttgcagta aatattaccc tcttttgggt   117900
aataaaatac taaactgttg gaaataaact gcaagatctt ttgaagttcc ctgagtgagc   117960
agttgagctt tattgccaaa tgtaaaccct aatacttagt tatgatgggg cattaattat   118020
gacccaagag acagagtagt ccttgttgt ttcctgatag cattggtctc taaagggaca    118080
attgcatgcc accgaaaggg gaatgatgga aataatagaa agcatttctc caattttatg   118140
ggactgttct tcagctgctt caggaatact ctataattta atcattatac tttaagaaag   118200
agttgacaaa tgtccaaagt aagataacca gaaggatcga gtggatgaag gattatatca   118260
gtttggattg tggcagaata agaagattgc aactttttaga tttgaaaaat gaaggcttag   118320
aggattttt taagtatgca aatccatgag gggtattaga tgttagttct gaggggtgtg    118380
tgtgtatgtg tgtgcacgtg tgcatatgtg tatgtgtttt aggtataagt taaagaaaa    118440
cacaacctta caaagcaaca gtaagctta tgaaccttgt tataaaaaag gggatgaggt    118500
aaaacattta aatagattcc agtccatctg gagatgagat tggactagga agttttgagt   118560
acattcctaa gcttctgatt taggatccct ttgagaaaga cacgggtcct caggctctcc   118620
cagtgtgtct acggcacctt taacatcagt ggtgggtaca gagtagatgc tgagaaagac   118680
ccagttgact tgaaagctat catttatttt atcatctttg acaacattg tatgaacaaa    118740
aataatcctc agcaatgttc aactaaggct cttcaatgtt ttagttttga tttatcctac   118800
tgagagtttt gtaagttcta gttagagaaa aatgactcca tttgggcaac aggccttaga   118860
aattagtgaa tgctgtcaag aaagtttttt cctcaaggga atgtttgccc tctttggcaa   118920
accagtatcc ccaaatatca cccatagtgt tttattgtac ttgtttttgga atattactta   118980
acagttttct ccatttaaac ataatttat aaattttaat actatttgtt aatagtgata    119040
ctttgtgagc aagttaaatt aatttttttc tagtttgaag attaaaaatc ttactgggtc   119100
catccaaaga gaatcattac ctaatacagt atttagaagg caaaatgatg gaatttatg    119160
```

```
tccaacttgt tatttatgct agtttatttt ttacagctca atgttgtata taatgtgaag   119220
gcttctgggt cttctagaag acgaagatct atccaaaatc aagaagcctt tgatttagat   119280
gttgctgtaa aagaaaataa agatgatctc aatcatgtgg atttgaatgt gtgtacaagg   119340
taagtgtctg cttaggtctc tcttcttttt ttcctttaaa aaatagactt gaaggtttaa   119400
ttatgtatag ttgtctatat caatctaaga gttatattga acaaagaatt cagttatgca   119460
ctacacttca gattacaaac tagaaatact actaattata ttcaagcatt tattagatgc   119520
atacaaaaat tatttacaag ttttccctgg acgtataaca catttgaata gaacagtgta   119580
tatataaatt aataaaactc aggtctaatt taggaaaact ttaaattaag tcaatcatat   119640
ttaatacttc aaaaatggtt attttcttgtt atgagttatt tttctgtaga aataattatt   119700
tcgggttcat attgaaccttt aactgttagg cattttaaccc aaaacttttat gataacatgc   119760
aaattcaatc aagaggatag tttttttttta ggtacattga aaatattcca gtttaggagt   119820
ttctcatctt ggataattag acacttaaca gctgaagctt ctgggagtac tttttaagtt   119880
gactcttaaa ttgttctata tccaaagcat ctgagaatct tgttaataag gaaaaagggt   119940
tctacctcaa ccctaccgac ttcacagtaa gactgggaag ctgcagattt ttggtcattc   120000
cactgcacac aggagtttga gcacactcct tgtgaaagtt cttgaataga ggcttcactt   120060
tttttttcttt catgaatcta ttctcttaca tctgcattat ttggtattga gctgggactt   120120
aaagatgcac tggcattgag gagctgctgt ttgctcttct aaaatatccc atagtgtcct   120180
ggtttaactt agcttattgt tgggctagaa gtccctgatg tggtcctgag ctggcagatg   120240
ttcttcaagg tcatctctgg gtgttcatcc aggtggccag ccttcacagc tattgcctgg   120300
acccagtctc cgccattact gctactgtct gtctttatct ttggaccttc ttgttcatga   120360
ttttggggta aaatgtccca catttgtccc attcttcacc ttcttgggca ttttgggcca   120420
gcagcaaggg gatatcagaa tctctgtgtt ggcatccttt ccagctgaga aaaaagtagg   120480
actccaatta tttttttacga atcttccaat tggtctctgt tatagaataa caacttcaag   120540
ttattactat tattataaac aataacaacc tacagtaatt acaaacttat atgccaggca   120600
cggcaccaaa cactttttaca tgcatatcat ttaattctta caggaactct gtaaagtatg   120660
tgttattatt atccctgctt ttctcaaatt cctggcctca agtgatcctc ctgcgttggc   120720
ctcccaaagt gctgggctta caggcatgag ccactgtgcc ccacctattc ttgcttttct   120780
cattcattta tttattacct cagcaagtat tgcttgagtc tctactatgt gccaggcatg   120840
gtgtctgtgt gtcaggcgtg ggaatataat tgtaagccaa aaaagatgca agctctgcct   120900
tgtggaactt gctgtttgag ggggatacag aaattaatgg aaacaatccc ctaagcaagc   120960
ctaaaattct aattttgaaa agggcaaaga agaagaccct catggagtta agagagggag   121020
attttttacct cttaagagac atcaagtgaa gaaacatgag aaaaatgagg tggggaacca   121080
gaattcagac tgtgaagagg cctcagcatt tataggggtt catgtaagga tgcaggattt   121140
ccagttttaa gcatcaggaa tcaggtggac aacagagttt gggtggtagg tagagcctga   121200
agaagggaaa tgttttcatg tgaggggtagg ggttttataa aaaggattta aatgctgcta   121260
ctagttttct gagaaaaatc tggtatgaag gacaaataac atttaggtgt atttttttcag   121320
cagcacatta taaaaagatt acttgatatt tcagacactt tattcctatc aacagggtcc   121380
aagaccttac ctcataccag gctttctgtg tggcatgata gtttaacaaa ttctgcccca   121440
ggcttggtag agagatcaga tcaaccaagg tacttttaat atgtactgaa agtataatct   121500
gcattgtgct tttaaatgtt taagcatatt gactgttttt ttctcatcta tattttttttc   121560
tcatatgcaa acacctccag tttcaatcca tttattagtt ctcaataaca tctattttgg   121620
ctcagtgcat tgccagcaga tggtttcagt tgcttcggat tgcagagcca gctgaagtca   121680
gcagttgtac tgtatggctt ttcaatcagt catgtttggc aggcatgggt tttctgctct   121740
aaaaagcaag attttttctaa cagcccttttc ttcttttgcc atttaaaagg acaacaggta   121800
ctaacttaat gctatgattc ttttaaattg gaggcaaaca tcttttccata atcacttagc   121860
tgggctcctt ctgctctaaa tgaaaagctc ttgccatcaa ttcattttat aaaaatattt   121920
atttccaagc agacaaaatg ttgttggtgc ccagatcctt tgatgctcac atcacgtaca   121980
acagggcgag agaaggatgc agtgtaataa aactttccaa ggcttgtaat tccctcacgg   122040
tggccaaaga aaacagaaaa tgttcttcaa gtatatggga gaacaaaggg atggcttctc   122100
cctactggtc tgatgtttct aaaatcagac gaataaaagg ttgctaagac cttggatggg   122160
acctatcact aagtggtcaa gtgatgcctc ctttctcaggg cctggctttc agcttgcaag   122220
tttggtgctg tcaactttttg agaaaaggaa aagtgcaatt ctgtttggaa tcaccactag   122280
aaaatagagt tgtctgttga aaggatgtat attgtactgt cacagtttat aagcacaagc   122340
ctcttacatt gcaggcattg catactatct gtcagatgaa cacattgttg tatcattatt   122400
ccttatatgg ttaaaagttt caagattacc acacatgtaa gaaaatgata acctgttttta   122460
aaattctcta tagggaattt tatttgaact caaacagtgt ttggaataac atttggtggg   122520
tttgatttt gtatgaagat aatttgataa cagctatggg ttttttcctga ggagttttca   122580
ttcatcctcc ctctttgatt tagcttttcg ggcccgggta ggagtggcat ggctcttatg   122640
gaagttaacc tattaagtgg ctttatggtg ccttcagaag caatttctct gagcgagaca   122700
gtgaagaaag tggaatatga tcatgaaaca ctcaacctct atttagattc tgtaagtagt   122760
aaaacataag gtaactgttg acaaagccac tgtgttttgt attcaggtgt ctaccttact   122820
ttaagtatgt tttctttaat tcattgttat ttcaacttttt tgtgtccctg aatgagttta   122880
acatggcaac catatatttta tctccattag aaagacataa gtataaaatc agtttagaga   122940
gttgctatta atgacgagcc tgatgaaggc cttcataact aaatcttttat gtcatgccag   123000
atgtgaaata catagaaatt tccatagtat aattaaaaaa attcaaccca gatctgaatt   123060
tgagagcctg tctgcctcag ggagttgcct aggctggagt gcagtggtgc aatcgtagct   123120
cactgcaacc tccaactcct gggctcaagt gatcctccca ctgcaggctc ctgagtagct   123180
gggaccacag gtgcatgcca ccatgcctag ataatttcat gagaatttttt tgtggagata   123240
gggtctcatt ttgttgccca ggctggtttt gaactcctga cttcaagtga tcttctggtc   123300
ttggcttctc aaagtgttgg gattacaggt gtgagccgcc atgcctggct ggaagacgaa   123360
agtcttaatt acacattttta aaattcttcc atgaagcttt taacaaacct taagggggtt   123420
catattctta ccttgaaaaa ttaggtgcta aatcatggaa gactattctc agagatttga   123480
tcttgacata gaattgttac ataaccttcg tgtactcttt ccatgctgaa atgagtacta   123540
aagaataaag aataaaagtgc acacagtgtg tagggaaagg taagtgaaga attccagact   123600
ctacttggta tgtctcaaaa ctggtggtat gtaagtttat tcttttctta tagcatctat   123660
atgagcttca taggttgaac tgatattgag ttcatagtat tctaaggatt tcatattaca   123720
tgggtgggtt tgtatgtttc ttatttcagt tttgctaagt atgaatcaga aatatattgc   123780
tgaatatatg cttttaaaaa gatagttctt gaatggctctc atttgttttta gcacttcaaa   123840
accactttgg ttaaagccct gttaaaacta attcagtctc aatataatgt taaataacag   123900
```

```
tctctagatt cttttgctgt ttaggaatta tcttacatta agcactgctc aaaagccatt   123960
ggcctgattt ggaacttgaa aaacaaattt aaggttttag tttagttgtg taattggttt   124020
tggagtttgt cttctatctt tgatgctctt gttaatggtt attttaattt gagtgtccag   124080
tactctttga gtggtcagtt tgactttca tttactacta ttggcaaata agggaatgtt   124140
tgaaggaatt tactaatttc tgattcttta atgagtgttg ttgccaaatt ggccaaatct   124200
gtctctcttg gagacagata ggctggcttt gtgtacccca tctcagtcat tggctgtgga   124260
gtacagcccc atcttagtta cctcacctac tgggtgacat ggcttgcatg agctgagggt   124320
gattcccagg agaaggaggc tgctgtgagc cattagtagt aactgggggt ggggtgcacc   124380
atctgagaca ggagatctag gtgcatgcac cctaaggctt gctgcttact taaccactct   124440
aattctcagt atcccattca gcaaaatgga actaagaaca ataccttttt gtaagcattg   124500
ttttacaagt taaataagat agttcatagg aagtacttac tgcagtatct gacatgtaga   124560
aatcctccct aagtgttagt ctctgtttcc taaaatgatg agaaaaaaga aatgtcttta   124620
cttaatcatg aacacacagt gtgccaaccc cttaagactc ttttgtattt ctcaaggtaa   124680
atgaaaccca gttttgtgtt aatattcctg ctgtgagaaa ctttaaagtt tcaaataccc   124740
aagatgcttc agtgtccata gtggattact atgagccaag taagtatgct ctggagttct   124800
taatacttta gaaattaagc caggcattca ttcatttatt ggaagtgacc acacattgga   124860
ttggttctgt ggcgagggca ggatttggta ggagaaagta caggaggcgg ggggcagga   124920
agtgagcatt ccatttcagt gaagactatt gataatttac aagggtcaca tgataggttt   124980
tagcatatga aatttaaaaa tgatatattt tttcataatg ttttagattt ttaactcaca   125040
attataaact ttacaaagaa aaattggcat atagagtcca gttatgtctc atttgcaagg   125100
tattgcttct attccaagca cccattccat ctgtttccag ctttaaaatg ggagttctta   125160
atgtggcaca tatacaccat ggaatactat gcagctataa aaaaggatga gttcatgtcc   125220
tttgtaggga catggatgaa gctggaaacc attctcagca aactatcgca aggacaaaaa   125280
accaaatgct gcatgttcgc actcataggg gggaattgac caatgagaac acttggacac   125340
agagagggga tcatcacata ccagggcctg tcatggggtt ggggggaggag ggagggatag   125400
cattaggagt tatacctaat gtaaatgacg agttaacggg tgcagcacac caacatggca   125460
catgtataca tatgtaacaa acctgcacgt tgtgcacatg taccctagca cttaaagtat   125520
aataaaaaaa atgggagttc ttctaaaagt agagctacca tttgaccccca caatcccgtt   125580
actggatata tacccaaagg acaataaatt gttctaccaa aaagccacct gcactcatat   125640
gtttatcaca gcactaattc acaatagcaa agacaggtca tcgacctagg tgcccatcaa   125700
ctgtgaattg gataaataaa atgtggtaga tgtacatcat ggaatactat acagccataa   125760
aaaagaacta aattatgtct tttgcagcaa catggatgca gctgaaggtc attattctaa   125820
gtgaattaat gaagaaacag aaaaccaaat atcacatgtt ctcacttata gtgggagct   125880
gaacattggg tacacatgga cataaaaatg ggaacagtga acactgggga cttcaaaagt   125940
ggggagggag aggggaata agggctgaaa cactctctat tgggtacaat gttcattatt   126000
tgggtgacag gatcaataga agcccaaacc tcagcatcac ataatatacc cttgtaacaa   126060
acttgtacat gtaccctgaa acagtaaata aataagtaac aaataataaa taaaatggga   126120
cttcttcagg agagaacatg aacagcatct gcaatgcagt agcatcggct ggagttagct   126180
gtttcttttat tgagggagtc tggtgttttg ccgaaactta cacttgataa cagatttta   126240
aaagtgtgtc aagaaaaata tagcctgttt ggaaaataac ttgagcttct ttgatttac   126300
tggtaacttc ttatttgtat aaaatgatgg aaatttagga cgtaaaaata gagagctggt   126360
ctggagatgg cccaagttta ataggatgaa tccatgttca gtcagaggga ctttttgtat   126420
gtgatcctcg gcctaatgtt tctaattgta atatgtctta ttttgaataa gcgcttgtgg   126480
tggctcagaa tcatcacaat gcatgagaag catgaacatt tttgtgtgtt aggtagttgt   126540
agataattac actttaaatg agtgaacttt gttcccattg ttgttagtgt ttcatagagt   126600
attcaagact aaggtgtagc accagttctc tcctcatagt caacaagcca gttcctcttg   126660
tcttttgcct cctgttggca ctgaggaaga gggttcaccc aggttcttgt gggacatttg   126720
ggaaacactg gtgtggcact ttttttctag tggagggatg gaatacactg tggagaccca   126780
atgacagtaa ctagttgtcc aactttatta ctttacttag ttgcaaaatt ccccaattta   126840
tatttcttgg gtgcatgggg aacatttaa acatttaaga aacaaaaata attcagtcta   126900
tgcaaatttt tatggaaaac aacttactta tgaggaggcc attttaaaat gaaaatatgg   126960
gaaagatcag aataagctaa accttccaac ccatttaaa aaatctcaaa acacatttac   127020
gatatggaaa acagtctctg aaaaatcatg aataaatttg aaaatagaat atgttttta   127080
aaaattataa aactcattta tgttttacag tgagttcact gtggtgttat aggtacttta   127140
agtagttttt gtcatgttcg cttttagata ctatatgcg agtgttttaa aacaaggtat   127200
tgcataggca gtcttccctt catattatg tatttttta ctagagccca gggtaaatgc   127260
cccttttcag tagttctaat gattagaatt tgatttgagt gcatagagaa tgtcatccta   127320
aaaataaactc ttgaggaggt taaacagtcc ttaactgaaa attctccctg atgcagtaag   127380
agattaaagt ggtgcttgtg attgcagtgt gcagctgcag tctatttgct ctcttttaat   127440
gctggccaac tgctggtggt agacagattg gactgagcgc attgtttctc tcttggattt   127500
ggttagtact ttggaccact cttggacatt tcagttgttt cttgtaaaga aaataaaat   127560
taggttaaga atgaaaact cagaaaagtg tatcgaaatg ctcttatatt ttggcaaagt   127620
caatgttct aaacaaggga gccgtgtgaa ctgatgtctg cttctttgaa cagggagaca   127680
ggcggtgaca agttacaact ctgaagtgaa gctgtcctcc tgtgacctt gcagtgatgt   127740
ccagggctgc cgtccttgtg aggatgagc ttcaggctcc catcatcact cttcagtcat   127800
ttttattttc tgtttcaagc ttctgtactt tatggaactt tggctgtgat ttatttttaa   127860
aggactctgt gtaacactaa catttccagt agtcacatgt gattgttttg ttttcgtaga   127920
agaatactgc ttctattttg aaaaaagagt tttttttctt tctatggggt tgcagggatg   127980
gtgtacaaca ggtcctagca tgtatagctg catagatttc ttcacctgat ctttgtgttg   128040
aagatcagaa tgaatgcagt tgtgtgtcta tatttcccc tctcaaaatc ttttagaatt   128100
tttttggagg tgttttgtttt ctccagaata aaggtattac tttagaatag gtattctcct   128160
cattttgtga aagaaatgaa cctagattct taagcattat tacacatcca tgtttgctta   128220
aagatggatt tccctgggaa tgggagaaaa cagccagcag gaggagcttc atctgttccc   128280
tccccacctc caacctagcc ctactgccca cccacccca tgcccagtgg   128340
tctcagtaga tacttcttaa ctggaaattc tttcttttca gaatctaggt ggtgaatttt   128400
ttttaagtgg cacggtcttt ttctgcttga aatctgatca caccccccag ccattgccct   128460
ccctctcttt ttcctctgta gagaaatgtg aggggcagta catttactgt gcttttcaca   128520
ccatctcaga ggttgaggag catactgaaa attgccctgg ggggtgctgg gtgtgctgtc   128580
tccttccacc atcctcagcc ccacaccagc tctatttcag gggtgagagt cagagagcac   128640
```

```
tgcaatatgt gcttcatggg atttcgattc gaagatccta gaccaggag acactgtgag      128700
ccagggatac aacaaaatac taggtaagtc actgcagacc gacctccctg cagtttggga      128760
aagaagctgg gtttgtggag aatcagagca tcttgacatg actgctgacc taaagatccc      128820
tggcattggc cagggatcct gtggaacctc ttctagttca ggggtgtgag cattagactg      128880
ccagttgtct agtgacatct gatgcttgct gtgaacttt aagatccccg aatcctgagc       128940
acctcaatct ttaattgccc tgtattccga agggtaatat aatttatctg gatgaaatt      129000
ttaaagatga atcccccttt tttctttct tctctcttt ctttccttct cccttcttc       129060
tttgccttct aaatatactg aaatgattta gatatgtgtc aacaattaat gatcttttat      129120
tcaatctaag aaatggttta gttttttctct ttagctctat ggcatttcac tcaagtggac      129180
aggggaaaaa gtaattgcca tgggctccaa agaatttgct ttatgttttt agctatttaa      129240
aaataaatcc atcaaaaata aagtatgcaa atgtatcttt taaagttaat ttttaaaaat      129300
gctcttattt tagtgaattt tcagaaatta tagtggaatg gatgctcata tattgcttat      129360
ggatattttg gataccaaag taggaataac tgacattcag tattttaaag ctggcaaacc      129420
tgtacataga aaatagatcc ccagacagtg gtctatgaag agggcagtta agtatcaaat      129480
acttaatttt cttgccttt tttcttaagt ggggaaaagt ttctagatct cttacacctc      129540
tgacacaatc tgttctaaaa caggcacttg taatgttggg gcctccttgt aaacgtgttt      129600
ttgcccttta ctctctggga gttctttaaa ggtgaaatca tcttacaaag aaattggggg      129660
agggtcttgg caaaggactt tccccctcctc tttcctggcc tgggaacctt atactgacaa      129720
tcaatacttt atattttaaa gtatataatt tatagttaac ttctagtgta atatattagg      129780
aaacactaga atggaaaggc cattggaaga caggttgtat cttttttaga ccatatttcc      129840
ttgttttaaaa actatcattt gaatacttt ttggtgaaga actccatgtt ttcaagttaa      129900
aggtcaccct gtaggccagg cgcagtggct catgcctgta atcccagcac tctgggaggc      129960
tgaggcgggt gaatcacaag gttaggagtt tgaccagcc ctggccaata tggtgaaacc      130020
ccgtccctac taaaaataca aaatttagcc aggcgtggtg gcatgcacct gtagtcccac      130080
ctactcggga ggctgaggca ggagaatcac ttgaacctga gagacagagg ttgcagtgag      130140
ccgagatcac gccactgcac tccagcctgg gggacagagt gagattctgt ctcaaaaaac      130200
aaaaaaacaaa aaagtcacct tgtaactcat ctctttttat tgtaagttta ttaaaaaatga      130260
agaggacaac aatgagaagg aacataaagg gttagctagc actgtctcct ggtgcatggg      130320
gctgtgcaga tgtcccggcc acttcttcct tcatacttcc cttagagaac ttgctctgct      130380
acaagcagtg ggcttggact aaaagtgatt aaaataccac aggcataagg agaaaaggag      130440
tatatgtagt agtaataatt actagtataa attattttct tcacatgcta tgagtaataa      130500
tattaaaaaa ctcatttac cattaagatt cctatgctg aagctcttcc atttagaata       130560
ctgtcaatgt catttactgg tatgaactaa agtccccctt cttttccact cactgggaac      130620
cttagtaaaa caccagcata tcttacctct cttctgact ggccgatgct tccagagact       130680
gaatgttggg aaaacctagt agccaaacaa ttctaggaca gaataacatt tttatatttg      130740
gttccaccat cttattacat ttagttatag ttttaaaaaa gaaattcaag cccattaaaa      130800
tatgtctggt caatgaaatg cttccttta ttgtgttgtg ctattgtact ttgttttca        130860
aaacattgta aaaatagtat ctttggttta gtattttgga ttatatatta taatctgagg      130920
agtgttttgc ttatgtagaa tccagatata tttctgttac ctaggagatg ttacttacat      130980
atgtaatact gtatcctgca cgtggaaata ttcagaattg tagatagcat aactctccct      131040
gctcctattc ttttgagcct aggtataatt tttttttttt tttagaaaa agacatattt       131100
agctttaatt tctatttatg ctaaacatat ttataagtag tctgtcaata taataccaac      131160
tattttatt tttacataat tcaatttttt catttgacat gtctggcaga ctcaagacat      131220
taagtaaaaa attggaacta tgattttct ttgtcatttt ttaaaaaaga attatttat        131280
taacctgctg gcatataatc tggagttctt ttcacaacct tactttttct gatttgcttt      131340
attgaatgat tgaatactca tttctttcta aaaatatgtt gtaaattctc ccttggcaag      131400
atttctccct atgagggtag ttattatttg agtctgccaa gtggttacca tggggcaagg      131460
tgccatgatg tattcttggg tgcattggtt ttttgcgcat tgtaaattta agacacttat      131520
agtaagtgga ctcattcata gatgagtttc agaaaccttt t acgttctcgg tagaggcttc      131580
tgtcggacag gcagaagagt gtattcctca cttttttt tgtcttcaaa ttccagtaag        131640
gcatagcact tttaagaaat tagaatttt ctatcatcta tgcaaatgat attatgtta        131700
atattaaata tcttatgtta cactgggagt aatttgaggt gcaattatt ttattactac       131760
tttgaataga ggaccattat ccttctttct tcagaaact aagaagtaag tgtaactttt       131820
aaagtaagta tatatcagtg agagtaggct tgttttacaa ctatttctag ccagtgagtt      131880
gtgttttcat gtctcatcaa aagacaatac cacattgcat cattttacaa aatatgttgt      131940
cattttcatt tcagtttgtaa cataggaaaa tagatatttc ctagatgatt tctgagtttc      132000
ttactgcaaa aacagttat aaattggtat acatgtgtct ctgtaatagg gataatattg       132060
atatatctgt tgctacatat ttaagaatca ttctatctta tgttgtcttg aggccaagat      132120
ttaccacgtt tgcccagtgt attgaattgg tggtagaagg tagttccatg ttccatttgt      132180
agatctttaa gatttttatct ttgataactt taatagaatg tggctcagtt ctggtccttc      132240
aagcctgtat ggtttggatt ttcagtaggg gacagttgat gtggagtcaa tctctttggt      132300
acacaggaag ctttataaaa tttcattcac gaatctctta ttttgggaag ctgttttgca      132360
tatgagaaga acactgttga aataaggaac taaagcttta tatattgatc aaggtgattc      132420
tgaaagttt aatttttaat gttgtaatgt tatgttattg ttaattgtac tttatttgt       132480
attcaataga aaatcatgat ttattaataa aagcttaaat tctcatctat tt              132532

SEQ ID NO: 2          moltype = RNA   length = 9401
FEATURE               Location/Qualifiers
source                1..9401
                      mol_type = mRNA
                      organism = Homo sapiens
SEQUENCE: 2
atagttgcta tgaatttctc ctcacaagga tgggcctgtt tactcaccct gggcatcgtt        60
ggtagagcgc tagtgtaaac agcctgagga acccggtggg ccggggaagt gggcgcgctc       120
tgttctccgc ggccagctgg gacgccgggc caggtggggc cgcctgcgtt tagcaactgc       180
tttctcaccc cctggatttg cgatgtttgc cacagcagcg agaagcgcca ttgtaatggg       240
gatgggaggg gtggagcctc caagtcctgt ctcaatttag atctctcact ctgctgttag       300
gcgcgcccat ttcagattac taaactcgaa ttaagaggga aaaaaaatca gggaggaggt       360
ggcaagccac accccacggt gcccgcgaac ttccccggca gcggactgta gcccaggcag       420
```

-continued

```
acgccgtcga gatgcagggc ccaccgctcc tgaccgccgc ccacctcctc tgcgtgtgca    480
ccgccgcgct ggccgtggct cccgggcctc ggtttctggt gacagcccca gggatcatca    540
ggcccggagg aaatgtgact attggggtgg agcttctgga acactgccct tcacaggtga    600
ctgtgaaggc ggagctgctc aagacagcat caaacctcac tgtctctgtc ctggaagcag    660
aaggagtctt tgaaaaaggc tcttttaaga cacttactct tccatcacta cctctgaaca    720
gtgcagatga gatttatgag ctacgtgtaa ccggacgtac ccaggatgag attttattct    780
ctaatagtac ccgcttatca tttgagacca agagaatatc tgtcttcatt caaacagaca    840
aggccttata caagccaaag caagaagtga agtttcgcat tgttacactc ttctcagatt    900
ttaagcctta caaaacctct ttaaacattc tcattaagga ccccaaatca aatttgatcc    960
aacagtggtt gtcacaacaa agtgatcttg gagtcatttc caaaactttt cagctatctt   1020
cccatccaat acttggtgac tggtctattc aagttcaagt gaatgaccag acatactatc   1080
aatcatttca ggtttcagaa tatgtattac caaaatttga agtgactttg cagacaccat   1140
tatattgttc tatgaattct aagcatttaa atggtaccat cacggcaaag tatacatatg   1200
ggaagccagt gaaaggagac gtaacgctta cattttacc tttatccttt tggggaaaga   1260
agaaaaatat tacaaaaaca tttaagataa atggatctgc aaacttctct tttaatgatg   1320
aagagatgaa aaatgtaatg gattcttcaa atggactttc tgaatacctg gatctatctt   1380
cccctggacc agtagaaatt ttaaccacag tgacagaatc agttacaggt atttcaagaa   1440
atgtaagcac taatgtgttc ttcaagcaac atgattacat cattgagttt tttgattata   1500
ctactgtctt gaagccatct ctcaacttca cagccactgt gaaggtaact cgtgctgatg   1560
gcaaccaact gactcttgaa gaagaagaa ataatgtagt cataacagtg acacagagaa   1620
actatactga gtactggagc ggatctaaca gtggaaatca gaaatggaa gctgttcaga   1680
aaataaatta tactgtcccc caaagtggaa cttttaagat taattccca atcctggagg   1740
attccagtga gctacagttg aaggcctatt tccttggtag taaaagtagc atggcagttc   1800
atagtctgtt taagtctcct agtaagacat acatccaact aaaaacaaga gatgaaaata   1860
taaaggtggg atcgccttt gagttggtgg ttagtggcaa caaacgattg aaggagttaa   1920
gctatatggt agtatccagg ggacagttgg tggctgtagg aaaacaaaat tcaacaatgt   1980
tctctttaac accagaaaat tcttggactc caaaagcctg tgtaattgtg tattatattg   2040
aagatgatgg ggaaattata agtgatgttc taaaaattcc tgttcagctt gttttttaaaa   2100
ataagataaa gctatattgg agtaaagtga agctgaacc atctgagaaa gtctctctta   2160
ggatctctgt gacacagcct gactccatag ttgggattgt agctgttgac aaaagtgtga   2220
atctgatgaa tgcctctaat gatattacaa tggaaaatgt ggtccatgag ttggaacttt   2280
ataacacagg atattattta ggcatgttca tgaattcttt tgcagtcttt caggaatgtg   2340
gactctgggg attgacagat gcaaacctca cgaaggatta tattgatggt gtttatgaca   2400
atgcagaata tgctgagagg tttatggagg aaaatgaaga acatattgta gatattcatg   2460
actttctttt gggtagcagt ccacatgtcc gaaagcattt tccagagact tggatttggc   2520
tagacaccaa catgggttac aggatttacc aagaatttga agtaactgta cctgattcta   2580
tcacttcttg ggtggctact ggttttgtga tctctgagga cctgggtctt ggactaacaa   2640
ctactccagt ggagctccaa gccttccaac catttttcat tttttttgaat cttccctact   2700
ctgttatcga aggtgaagaa tttgctttgg aaataactat attcaattat ttgaaagatg   2760
ccactgaggt taaggtaatc attgagaaaa gtgacaaatt tgatattcta atgacttcaa   2820
atgaaataaa tgccacaggc caccagcaga cccttctggt tcccagtgag gatggggcaa   2880
ctgttctttt tcccatcagg ccaacacatc tgggagaaat tcctatcaca gtcacagctc   2940
ttcacccac tgcttctgat gctgtcaccc agatgatttt agtaaaggct gaaggaatag   3000
aaaaaatcata ttcacaatcc atcttattag acttgactga caataggcta cagagtaccc   3060
tgaaaacttt gagtttctca tttcctccta atacagtgac tggcagtgaa agagttcaga   3120
tcactgcaat tggagatgtt cttggtcctt ccatcaatgg cttagcctca ttgattcgga   3180
tgcctatgg ctgtggtgaa cagaacatga taaattttgc tccaaatatt tacatttgg   3240
attatctgac taaaaagaaa caactgacag ataatttgaa agaaaaagct cttttcattta   3300
tgaggcaagg ttaccagaga gaacttctct atcagaggga agatggctct ttcagtgctt   3360
ttgggaatta tgaccttct gggagcactt ggttgtcagc ttttgttta agatgtttcc   3420
ttgaagccga tccttacata gatattgatc agaatgtgtt acacagaaca tacacttggta   3480
ttaaaggaca tcagaaatcc aacggtgaat tttgggatcc aggaagagtg attcatagtg   3540
agcttcaagg tggcaataaa agtccagtaa cacttacagc ctatattgta acttctctcc   3600
tgggatatag aaagtatcag cctaacattg atgtgcaaga gtctatccat tttttggagt   3660
ctgaattcag tagaggaatt tcagacaatt atactctgac cctataact tatgcattgt   3720
catcagtggg gagtcctaaa gcgaaggaag ctttgaatat gctgacttgg agagcagaac   3780
aagaaggtgg catgcaattc tgggtgtcat cagagtccaa actttctgac tcctggcagc   3840
cacgctccct ggatattgaa gttgcagcct atgcactgct ctcacacttc ttacaatttc   3900
agacttctga gggaatccca attatgaggt ggctaagcag gcaaagaaat agcttgggtg   3960
gttttgcatc tactcaggat accactgtgg ctttaaaggc tctgtctgaa tttgcagccc   4020
taatgaatac agaaaggaca aatatccaag tgaccgtgac ggggcctagc tcaccaagtc   4080
ctcttgctgt ggtacagcca acggcagtta atatttccgc aaatggtttt ggatttgcta   4140
tttgtcagct caatgttgta tataatgtga aggcttctgg gtcttctaga agacgaagat   4200
ctatccaaaa tcaagaagcc tttgatttag atgttgctgt aaaagaaaat aaagatgatc   4260
tcaatcatgt ggatttgaat gtgtgtacaa gcttttcggg cccgggtagg agtggcatgg   4320
ctcttatgga agttaaccta ttaagtggct ttatggtgcc ttcagaagca atttctctga   4380
gcgagacagt gaagaaagtg gaatatgatc atggaaaact caacctctat ttagattctg   4440
taaatgaaac ccagttttgt gttaatattc ctgctgtgag aaacttttaaa gttcaaata   4500
cccaagatgc ttcagtgtcc atagtggatt actatgacct aaggagacag gcggtgagaa   4560
gttacaactc tgaagtgaag ctgtcctcct gtgacctttg cagtgatgtc cagggctgcc   4620
gtccttgtga ggatggagct tcaggctccc atcatcactc ttcagtcatt tttatttcct   4680
gtttcaagct tctgtacttt atggaacttt ggctgtgatt tattttttaaa ggactctgtg   4740
taacactaac atttccagta gtcacatgtg attgttttgt tttcgtagaa gaatactgct   4800
tctattttga aaaaagagtt tttttctttt ctatgggtgt gcagggatgg tgtacaacag   4860
gtcctagcat gtatagctgc atagatttct tcacctgatc tttgtgtgga agatcagaat   4920
gaatgcagtt gtgtgtctat attttccct ctcaaaatct tttagaattt ttttggaggt   4980
gtttgtttc tccagaataa aggtattact ttagaatagg tattctcctc attttgtgaa   5040
agaaatgaac ctagattctt aagcattatt acacatccat gtttgcttaa agatggattt   5100
ccctgggaat gggagaaaac agccagcagg aggagcttca tctgttccct tcccacctcc   5160
```

```
aacctagccc tactgcccac cccaccccaa cccaccccat gcccagtggt ctcagtagat    5220
acttcttaac tggaaattct ttcttttcag aatctaggtg gtgaattttt tttaagtggc    5280
acggtctttt tctgcttgaa atctgatcac acccccagc cattgccctc cctctctttt     5340
tcctctgtag agaaatgtga ggggcagtac atttactgtg cttttcacac catctcagag    5400
gttgaggagc atactgaaaa ttgccctggg gggtgctggg tgtgctgtct ccttcccaca    5460
tcctcagccc cacaccagct ctatttcagg ggtgagagtc agagagcact gcaatatgtg    5520
cttcatggga tttcgattcg aagatcctag accaggagag cactgtgagc cagggataca    5580
acaaatact aggtaagtca ctgcagaccg acctccctgc agtttgggaa agaagctggg     5640
tttgtgggaga atcagagcat cttgacatga ctgctgacct aaagatccct ggcattggcc    5700
agggatcctg tggaacctct tctagttcag gggtgtgagc attagactgc cagttgtcta    5760
gtgacatctg atgcttgctg tgaacttta agatccccga atcctgagca cctcaatctt    5820
taattgccct gtattccgaa gggtaatata atttatctgg atggaaattt taaagatgaa   5880
tccccctttt ttcttttctt ctctctttc tttccttctc ccttctttct ttgccttcta   5940
aatatactga aatgatttag atatgtgtca acaattaatg atcttttatt caatctaaga   6000
aatggtttag tttttctctt tagctctatg gcatttcact caagtggaca ggggaaaaag   6060
taattgccat gggctccaaa gaatttgctt tatgttttta gctatttaaa aataaatcca   6120
tcaaaataa agtatgcaaa tgtatctttt aaagttaatt tttaaaaatg ctcttattt     6180
agtgaatttt cagaaattat agtggaatgg atgctcatat attgcttatg gatattttgg   6240
ataccaaagt aggaataact gacattcagt attttaaagc tggcaaacct gtacatagaa   6300
aatagatccc cagacagtgg tctatgaaga gggcagttaa gtatcaaata cttaattttc   6360
ttgccttttt ttcttaagtg gggaaaagtt tctagatctc ttacacctct gacacaatct   6420
gttctaaaac aggcacttgt aatgttgggg cctccttgta aacgtgtttt tgcccttttac  6480
tctctgggag ttctttaaag gtgaaatcat cttacaaaga aattggggga gggtcttggc   6540
aaaggactt ccctcctct ttcctggcct gggaacctta tactgacaat caatacttta   6600
tattttaaag tatataattt atagttaact tctagtgtaa tatattagga aacactagaa    6660
tggaaaggcc attggaagac aggttgtatc ttttttagac catatttcct tgtttaaaaa    6720
ctatcatttg aatactttt tggtgaagaa ctccatgttt tcaagttaaa ggtcacctcg    6780
taggccaggc gcagtggctc atgcctgtaa tcccagcact ctgggaggct gaggcgggtg   6840
aatcacaagg ttaggagttt gagaccagcc tggccaatat ggtgaaaccc cgtccctact   6900
aaaaatacaa aatttagcca ggcgtggtgg catgcacctg tagtcccacc tactcgggag   6960
gctgaggcag gagaatcact tgaacctgag agacagaggt tgcagtgagc cgagatcacg   7020
ccactgcact ccagcctggg ggacagagtg agattctgtc tcaaaaaaca aaaaacaaaa   7080
aagtcacctt gtaactcatc tctttttatt gtaagtttat taaaaatgaa gaggacaaca    7140
atgagaagga acataaaggg ttagctagca ctgtctcctg gtgcatgggg ctgtgcagat   7200
gtcccggcca cttcttcctt catacttccc ttagagaact tgctctgcta caagcagtgg   7260
gcttggacta aaagtgatta aaataccaca ggcataagga gaaaaggagt atatgtagta   7320
gtaataatta ctagtataaa ttattttctt cacatgctat gagtaataat attaaaaaac   7380
tcattttacc attaagattc cttatgctga agctcttcca tttagaatac tgtcaatgtc   7440
atttactggt atgaactaaa gtccccctc ttttccactc actgggaacc ttagtaaaac   7500
accagcatat cttacctctc tttctgactg gccgatgctt ccagagactg aatgttggga   7560
aaacctagta gccaaacaat tctaggacag aataacatt ttatatttgg ttccaccatc    7620
ttattacatt tagttatagt tttaaaaag aaattcaagc ccattaaaat atgtctggtc    7680
aatgaaatgc ttccttttat tgtgttgtgc tattgtactt tgtttttcaa aacattgtaa   7740
aaatagtatc tttggtttag tattttggat tatatattat aatctgagga gtgttttgct   7800
tatgtagaat ccagatatat ttctgttacc taggagatgt tacttacata tgtaatactg   7860
tatcctgcac gtggaaatat tcagaattgt agatagcata actctccctg ctcctattct   7920
tttgagccta ggtataattt ttttttttt tttagaaaaa gacatattta gctttaatt    7980
ctatttatgc taaacatatt tataagtagt ctgtcaatat aataccaact attttttattt   8040
ttacataatt caattattc atttgacatg tctggcagac tcaagacatt aagtaaaaaa    8100
ttggaactat gattttctt tgtcattttt taaaaaagaa ttattttatt aacctgctgg     8160
catataatct ggagttcttt tcacaacctt acttttctg atttgcttta ttgaatgatt    8220
gaatactcat ttctttctaa aaatatgttg taaattctcc cttggcaaga tttctccta    8280
tgagggtagt tattatttga gtctgccaag tggttaccat ggggcaaggt gccatgatgt   8340
attcttgggt gcattggttt tttgcgcatt gtaaatttaa gacacttata gtaagtggac   8400
tcattcatag atgagtttca gaacctttta cgttctcggt agaggcttct gtcggacagg   8460
cagaagagtg tattcctcac tttttttttt gtcttcaaat tccagtaagg catagcactt    8520
ttaagaaatt agaattttc tatcatctat gcaaatgata tttatgttaa tattaaatat    8580
cttatgttac actgggagta atttgaggtg caattatttt tattactact ttgaatagag   8640
gaccattatc cttctttctt cagaaaacta agaagtaagt gtaacttta aagtaagtat    8700
atatcagtga gagtaggctt gttttacaac tatttctagc cagtgagttg tgtttttcatg  8760
tctcatcaaa agacaatacc acattgcatc attttacaaa atatgttgtc attttcattt   8820
cagttgtaac ataggaaaat agatatttcc tagatgattt ctgagtttct tactgcaaag   8880
aacagttata aattggtata catgtgtctc tgtaataggg ataattattga tatatctgtt  8940
gctacatatt taagaatcat tctatcttat gttgtcttga ggccaagatt taccacgttt    9000
gcccagtgta ttgaattggt ggtagaaggt agttccatgt tccatttgta gatctttaag    9060
attttatctt tgataacttt aatagaatgt ggctcagttc tggtccttca agcctgtatg    9120
gtttggattt tcagtagggg acagttgatg tggagtcaat ctcttggta cacaggaagc     9180
tttataaaat ttcattcacg aatctcttat tttgggaagc tgtttttgcat atgagaagaa    9240
cactgttgaa ataaggaact aaagcttat atattgatca aggtggattct gaaagtttta   9300
attttttaatg ttgtaatgtt atgttattgt taattgtact ttattatgta ttcaatagaa   9360
aatcatgatt tattaataaa agcttaaatt ctccatctatt t                        9401

SEQ ID NO: 3            moltype = RNA   length = 9221
FEATURE                 Location/Qualifiers
source                  1..9221
                        mol_type = mRNA
                        organism = Homo sapiens
SEQUENCE: 3
atagttgcta tgaatttctc ctcacaagga tgggcctgtt tactcaccct gggcatcgtt    60
```

-continued

```
ggtagagcgc tagtgtaaac agcctgagga acccggtggg ccggggaagt gggcgcgctc   120
tgttctccgc ggccagctgg gacgccgggc caggtggggc cgcctgcgtt tagcaactgc   180
tttctcaccc cctggatttg cgatgtttgc cacagcagcg agaagcgcca ttgtaatggg   240
gatgggaggg gtggagcctc caagtcctgt ctcaatttag atctctcact ctgctgttag   300
gcgcgcccat ttcagattac taaactcgaa ttaagaggaa aaaaaaatca gggaggaggt   360
ggcaagccac accccacggt gcccgcgaac ttccccggca gcggactgta gcccaggcag   420
acgccgtcga gatgcagggc ccaccgctcc tgaccgccgc ccacctcctc tgcgtgtgca   480
ccgccgcgct ggccgtggct cccgggcctc ggtttctggt gacagcccca gggatcatca   540
ggcccggagg aaatgtgact attggggtgg agcttctgga acactgccct tcacaggtga   600
ctgtgaaggc ggagctgctc aagacagcat caaacctcac tgtctctgtc ctggaagcag   660
aaggagtctt tgaaaaaggc tcttttaaga cacttactct tccatcagac cccaaatcaa   720
atttgatcca acagtggttg tcaacaacaa gtgatcttgg agtcatttcc aaaacttttc   780
agctatcttc ccatccaata cttggtgact ggtctattca agttcaagtg aatgaccaga   840
catactatca atcatttcag gtttcagaat atgtattacc aaaatttgaa gtgactttgc   900
agacaccatt atattgttct atgaattcta agcatttaaa tggtaccatc acggcaaagt   960
atacatatgg gaagccagtg aaaggagacg taacgcttac atttttacct ttatcctttt  1020
ggggaaagaa gaaaaatatt acaaaaacat ttaagataaa tggatctgca aacttctctt  1080
ttaatgatga agagatgaaa aatgtaatgg atttcttcaa tggactttct gaatacctgg  1140
atctatcttc ccctggacca gtagaaattt taaccacagt gacagaatca gttacaagta  1200
tttcaagaaa tgtaagcact aatgtgttct tcaagcaaca tgattacatc attgagtttt  1260
ttgattatac tactgtcttg aagccatctc tcaacttcac agccactgtg aaggtaactc  1320
gtgctgattac caaccaactg actcttgaag aagaagaaa taatgtagtc ataacagtga  1380
cacagagaaa ctatactgag tactggagcg gatctaacag tggaaatcag aaaatgaag  1440
ctgttcagaa aataaaattat actgtcccc aaagtggaac ttttaagatt gaattcccaa  1500
tcctggagga ttccagtgag ctacagttga aggcctattt ccttggtagt aaaagtagca  1560
tggcagttca tagtctgttt aagtctccta gtaagacata catccaacta aaaacaagag  1620
atgaaaatat aaaggtggga tcgcctttg agttggtggt tagtggcaac aaacgattga  1680
aggagttaag ctatatggta gtatccaggg gacagttggt ggctgtagga aaacaaaatt  1740
caacaatgtt ctctttaaca ccagaaaatt cttggactcc aaaagcctgt gtaattgtgt  1800
attatattga agatgatggg gaaattataa gtgatgttct aaaaattcct gttcagcttg  1860
ttttaaaaaa taagataaag ctatattgga gtaaagtgaa agctgaacca tctgagaaag  1920
tctctcttag gatctctgtg acacagcctg actccatagt tgggattgta gctgttgaca  1980
aaagtgtgaa tctgatgaat gcctctaatg atattacaat ggaaaatgtg gtccatgagt  2040
tggaacttta taacacagga tattatttag gcatgttcat gaattctttt gcagtctttc  2100
aggaatgtgg actctgggta ttgacagatg caaacctcac gaaggattat attgatggtg  2160
tttatgacaa tgcagaatat gctgagaggt ttatggagga aaatgaagga catattgtag  2220
atattcatga cttttctttg ggtagcagtc cacatgtccg aaagcatttt ccagagactt  2280
ggatttggct agacaccaac atgggttaca ggatttacca agaatttgaa gtaactgtac  2340
ctgattctat cacttcttgg gtggctactg gttttgtgat ctctgaggac ctgggtcttg  2400
gactaacaac tactccagtg gagctccaag ccttccaacc attttttcatt ttttttgaatc  2460
ttccctactc tgttatcaga ggtgaagaat ttgctttgga ataactata ttcaattatt  2520
tgaaagatgc cactgaggtt aaggtaatca ttgagaaag tgacaaattt gatattctaa  2580
tgacttcaaa tgaaataaat gccacaggcc accagcagcc cctctgctt cccagtgagg  2640
atggggcaac tgttctttttt cccatcaggc caacacatct gggagaaatt cctatcacag  2700
tcacagctct ttcacccact gcttctgatg ctgtcaccca gatgattta gtaaaggctg  2760
aaggaataga aaaatcatat tcacaatcca tcttattaga cttgactgac aataggctac  2820
agagtaccct gaaaactttg agtttctcat ttcctcctaa tacagtgact ggcagtgaaa  2880
gagttcagat cactgcaatt ggagatgttc ttggtccttc catcaatggc ttagcctcat  2940
tgattcggat gccttatggc tgtggtgaac agaacatgat aaatttttgct ccaaatattt  3000
acatttttgga ttatctgact aaaaagaaac aactgacaga taatttgaaa gaaaagctc  3060
tttcatttat gaggcaaggt taccagagag aacttctcta tcagagggaa ggggctcttt  3120
tcagtgcttt tgggaattat gacccttctg ggagcacttg gttgtcagct tttgttttaa  3180
gatgtttcct tgaagccgat ccttacatag atattgatca gaatgtgtta cacagaaacat  3240
acacttggct taaaggacat cagaaatcca acggtgaatt tgggatcca ggaagagtga  3300
ttcatagtga gcttcaaggt ggcaataaaa gtccagtaac acttacagcc tatattgtaa  3360
cttctctcct gggatataga aagtatcagc ctaacattga tgtgcaagag tctatccatt  3420
ttttggagtc tgaattcagt agaggaattt cagacaatta tactcagcc cttataactt  3480
atgcattgtc atcagtgggg agtcctaaag cgaaggaagc tttgaatatg ctgacttgga  3540
gagcagaaca agaaggtggc atgcaattct gggtgtcatc agagtccaaa ctttctgact  3600
cctggcagcc acgctccctg gatattgaag ttgcagccta tgcactgctc tcacacttct  3660
tacaatttca gacttctgag ggaatcccaa ttatgaggtg gctaagcagg caaagaaata  3720
gcttgggtgg ttttgcatct actcaggata ccactgtggc tttaaaggct ctgtctgaat  3780
ttgcagccct aatgaataca gaaaggacaa atatccaagt gaccgtgacg gggcctagct  3840
caccaagtcc tgtaaagttt ctgattgaca cacacaaccg cttactcctt cagacagtgg  3900
agcttgctgt ggtacagcca acggcagtta atatttccgc aaatggtttt ggatttgcta  3960
tttgtcagct caatgttgta tataatgtga aggcttctgg gtcttctaga agacgaagat  4020
ctatccaaaa tcaagaagcc tttgatttag atgttgctgt aaaagaaaat aaagatgatc  4080
tcaatcatgt ggatttgaat gtgtgtacaa gcttttcggg cccgggtagg agtggcatgg  4140
ctcttatgga agttaaccta ttaagtggct ttatggtgcc ttcagaagca atttctctga  4200
gcgagacagt gaagaaagtg gaatatgatc atggaaaact caacctctat ttagattctg  4260
taaatgaaac ccagttttgt gttaatattc ctgctgtgag aaactttaaa gtttcaaata  4320
cccaagatgc ttcagtgtcc atagtggatt actatgagcc aaggagacag gcggtgagaa  4380
gttacaactc tgaagtgaag ctgtcctcct gtgacctttg cagtgatgtc cagggctgcc  4440
gtccttgtga ggatggatct tcaggctccc atcatcactc ttcagtcatt tttattttct  4500
gtttcaagct tctgtacttt atggaacttt ggctgtgatt tattttttaaa ggactctgtg  4560
taacactaac atttccagta gtcacatgtg attgttttgt tttcgtagaa gaatactgct  4620
tctatttttga aaaagagtt tttttctttt ctatggggtt gcagggatgg tgtacaacag  4680
gtcctagcat gtatagctgc atagatttct tcacctgatc tttgtgtgga agatcagaat  4740
gaatgcagtt gtgtgtctat atttttcccct ctcaaaatct tttagaattt ttttggaggt  4800
```

```
gtttgttttc tccagaataa aggtattact ttagaatagg tattctcctc attttgtgaa  4860
agaaatgaac ctagattctt aagcattatt acacatccat gtttgcttaa agatggattt  4920
ccctgggaat gggagaaaac agccagcagg aggagcttca tctgttccct tcccacctcc  4980
aacctagccc tactgcccac cccaccccaa cccaccccat gcccagtggt ctcagtagat  5040
acttcttaac tggaaattct ttcttttcag aatctaggtg gtgaatttt tttaagtggc   5100
acggtctttt tctgcttgaa atctgatcac acccccagc cattgccctc cctctctttt   5160
tcctctgtag agaaatgtga ggggcagtac atttactgtg cttttcacac catctcagag  5220
gttgaggagc atactgaaaa ttgccctggg gggtgctggg tgtgctgtct ccttcccaca  5280
tcctcagccc cacaccagct ctatttcagg ggtgagagtc agagagcact gcaatatgtg  5340
cttcatggga tttcgattcg aagatcctag accagggaga cactgtgagc cagggataca  5400
acaaaatact aggtaagtca ctgcagaccg acctccctgc agtttgggaa agaagctggg  5460
tttgtgagaa atcagagcat cttgacatga ctgctgacct aaagatccct ggcattggcc  5520
agggatcctg tggaacctct tctagttcag gggtgtgagc attagactgc cagttgtcta  5580
gtgacatctg atgcttgctg tgaacttta agatcccga atctgagca cctcaatctt   5640
taattgccct gtattccgaa gggtaatata atttatctgg atggaaattt taaagatgaa  5700
tccccctttt ttcttttctt ctctcttttc tttccttctc cctttcttct ttgccttcta  5760
aatatactga aatgatttag atatgtgtca acaattaatg atcttttatt caatctaaga  5820
aatggtttag ttttctctt tagctctatg gcatttcact caagtggaca ggggaaaaag   5880
taattgccat gggctccaaa gaatttgctt tatgttttta gctatttaaa aataaatcca  5940
tcaaaaataa agtatgcaaa tgtatctttt aaagttaatt tttaaaaatg ctcttatttt  6000
agtgaatttt cagaaattat agtggaatgg atgctcatat attgcttatg gatattttgg  6060
ataccaaagt aggaataact gacattcagt attttaaagc tggcaaacct gtacatagaa   6120
aatagatccc cagacagtgg tctatgaaga gggcagttaa gtatcaaata cttaattttc   6180
ttgcctttt ttcttaagtg gggaaaagtt tctagatctc ttacacctct gacacaatct   6240
gttctaaaac aggcacttgt aatgttgggg cctccttgta aacgtgtttt tgccctttac   6300
tctctgggag ttcttttaaag gtgaaatcat cttacaaaga aattgggga gggtcttggc   6360
aaaggacttt cccctcctct ttcctggcct gggaaccttaa tactgacaat caatacttta   6420
tatttaaag tatataattt atagttaact tctagtgtaa tatattagga aacactagaa   6480
tggaaaggcc attggaagac aggttgtatc tttttttagac catatttcct tgtttaaaaa   6540
ctatcatttg aatactttt tggtgaagaa ctccatgttt tcaagttaaa ggtcacctcg   6600
taggccaggc gcagtggctc atgcctgtaa tcccagcact ctgggaggct gaggcgggtg   6660
aatcacaagg ttaggagttt gagaccagcc tggccaatat ggtgaaaccc cgtccctact   6720
aaaaatacaa aattttagcca ggcgtggtgg catgcacctg tagtcccacc tactcggagg   6780
gctgaggcag gagaatcact tgaacctgag agacagaggt tgcagtgagc cgagatcacg   6840
ccactgcact ccagcctggg ggacagagtg agattcgtc tcaaaaaca aaaaacaaaa   6900
aagtcacctt gtaactcatc tctttttatt gtaagtttat taaaaatgaa gaggacaaca   6960
atgagaagga acataaaggg ttagctagca ctgtctcctg gtgcatgggg ctgtgcagat   7020
gtcccggcca cttcttcctt catacttccc ttagagaact tgctctgcta caagcagtta   7080
gcttggacta aaagtgatta aaataccaca ggcataagga gaaaaggagt atatgtagta   7140
gtaataatta ctagtataaa ttatttttctt cacatgctat gagtaataat attaaaaaac   7200
tcattttacc attaagattc cttatgctga agctcttcca tttagaatac tgtcaatgtc   7260
atttactggt atgaactaaa gtcccccttc ttttccactc actgggaacc ttagtaaaac   7320
accagcatat cttacctctc tttctgactg gccgatgctt ccagagactg aatgttggga   7380
aaacctagta gccaaacaat tctaggacag aataacattt ttatatttgg ttccaccatc   7440
ttattacatt tagttatagt tttaaaaaag aaattcaagc ccattaaaat atgtctggtc   7500
aatgaaatgc ttccttttat tgtgttgtgc tattgtactt tgttttttcaa aacattgtaa   7560
aaatagtatc tttggtttag tattttggat tatatattat aatctgagga gtgttttgct   7620
tatgtagaat ccagatatat ttctgttacc taggagatgt tacttacata tgtaatactg   7680
tatcctgcac gtgaaatat tcagaattgt agatagcata actctccctg ctcctattct   7740
tttgagccta ggtataattt tttttttttt tttagaaaaa gacatattta gctttaattt   7800
ctatttatgc taaacatatt tataagtagt ctgtcaatat aataccaact attttatttt   7860
ttacataatt caattatttc atttgacatg tctggcagac tcaagacatt aagtaaaaaa   7920
ttggaactat gattttctt tgtcattttt taaaaagaa ttattttatt aacctgctgg   7980
catataatct ggagttctt tcacaacctt acttttctg atttgcttta ttgaatgatt   8040
gaatactcat ttcttttctaa aaatatgttg taaattctcc cttggcaaga tttctccta   8100
tgagggtagt tattatttga gtctgccaag tggttaccat ggggcaaggt gccatgatgt   8160
attcttgggt gcattggttt tttgcgcatt gtaaatttaa gacacttata gtaagtggac   8220
tcattcatag atgagtttca gaacctttta cgttctcggt agaggcttct gtcggacagg   8280
cagaagagtg tattcctcac ttttttttttt gtcttcaaat tccagtaagg catgccactt   8340
ttaagaaatt agaattttc tatcatctat gcaaatgata tttatgttaa tattaaatat   8400
cttatgttac actgggagta atttgaggtg caattatttt tattactact ttgaatagag   8460
gaccattatc cttcttttctt cagaaaacta agaagtaagt gtaactttta aagtaagtat   8520
atatcagtga gagtaggctt gttttacaac tatttctagc cagtgagttg tgttttcatg   8580
tctcatcaaa agacaatacc acattgcatc attttacaaa atatgttgtc atttttcattt   8640
cagttgtaac ataggaaaat agatatttcc tagatgattt ctgagtttct tactgcaaag   8700
aacagttata aattggtata catgtgtctc tgtaataggg ataatattga tatatctgtt   8760
gctacatatt taagaatcat tctatcttat gttgtcttga ggccaagatt taccacgttt   8820
gcccagtgta ttgaattggt ggtagaaggt agttccatgt tccattttgta gatcttttaag  8880
attttatctt tgataacttt aatagaatgt ggctcagttc tggtccttca agcctgtatg   8940
gtttggattt tcagtagggg acagttgatg tggagtcaat ctcttttggta cacaggaagc   9000
tttataaaat ttcattcacg aatctcttat tttgggaagc tgttttgcat atgagaagaa   9060
cactgttgaa ataaggaact aaagcttat atattgatca aggtgattct gaaagtttta   9120
atttttaatg ttgtaatgtt atgttattgt taattgtact ttattatgta ttcaatgaaa   9180
aatcatgatt tattaataaa agcttaaatt ctcatctatt t                       9221
```

SEQ ID NO: 4        moltype = RNA   length = 9031
FEATURE             Location/Qualifiers
source              1..9031
                    mol_type = mRNA organism = Homo sapiens
SEQUENCE: 4

```
agacgccgtc gagatgcagg gcccaccgct cctgaccgcc gcccacctcc tctgcgtgtg   60
caccgccgcg ctggccgtgg ctcccgggcc tcggtttctg gtgacagccc cagggatcat  120
caggcccgga ggaaatgtga ctattggggt ggagcttctg gaacactgcc cttcacaggt  180
gactgtgaag gcggagctgc tcaagacagc atcaaacctc actgtctctg tcctggaagc  240
agaaggagtc tttgaaaaag gctcttttaa gacacttact cttccatcac tacctctgaa  300
cagtgcagat gagatttatg agctacgtgt aaccggacgt acccaggatg agatttatt   360
ctctaatagt acccgcttat catttgagac caagagaata tctgtcttca ttcaaacaga  420
caaggcctta tacaagccaa agcaagaagt gaagtttcgc attgttacac tcttctcaga  480
ttttaagcct tacaaaacct cttttaaacat tctcattaag gaccccaaat caaatttgat  540
ccaacagtgg ttgtcacaac aaagtgatct tggagtcatt tccaaaactt ttcagctatc  600
ttcccatcca atacttggtg actggtctat tcaagttcaa gtgaatgacc agcatacta   660
tcaatcattt caggtttcag aatatgtatt accaaaattt gaagtgactt tgcagacacc  720
attatattgt tctatgaatt ctaagcattt aaatggtacc atcacggcaa agtatacata  780
tgggaagcca gtgaaaggag acgtaacgct tacattttta cctttatcct tttgggggaaa  840
gaagaaaaat attacaaaaa catttaagat aaatggatct gcaaacttct cttttaatga  900
tgaagagatg aaaaattgtaa tggattcttc aaatggactt tctgaataca ctggatctatc  960
ttcccctgga ccagtagaaa ttttaaccac agtgacagaa tcagttacag gtatttcaag 1020
aaatgtaagc actaatgtgt tcttcaagca acatgattac atcattgagt tttttgatta 1080
tactactgtc ttgaagccat ctctcaactt cacagccact gtgaaggtaa ctcgtgctga 1140
tggcaaccaa ctgactcttg aagaagaag aaataatgta gtcataacag tgacacagag 1200
aaactatact gagtactgga gcggatcaa cagtggaaat cagaaaatgg aagctgttca 1260
gaaaataaat tatactgtcc cccaaagtgg aactttaag attgaattcc caatcctgga 1320
ggattccagt gagctacagt tgaaggccta tttccttggt agtaaaagta gcatggcagt 1380
tcatagtctg tttaagtctc ctagtaagac atacatccaa ctaaaacaa gagatgaaaa 1440
tataaaggtg ggatcgcctt ttgagttggt ggttagtggc aacaaacgat tgaaggagtt 1500
aagctatatg gtagtatcca ggggacagtt ggtggctgta ggaaaacaaa attcaacaat 1560
gttctcttta acaccagaaa attcttggac tccaaaagcc tgtgtaattg tgtattatat 1620
tgaagatgat ggggaaatta taagtgatgt tctaaaaatt cctgttcagc ttgttttaa 1680
aaataagata aagctatatt ggagtaaagt gaaagctgaa ccatctgaga aagtctctct 1740
taggatctct gtgacacagc ctgactccaa agttgggatt gtagctgttg acaaaagtgt 1800
gaatctgatg aatgcctcta atgatattac aatggaaaat gtggtccatg agttggaact 1860
ttataacaca ggatattatt taggcatgtt catgaattcc tttgcagtct ttcaggaatg 1920
tggactctgg gtattgacag atgcaaacct cacgaaggat tatattgatg gtgtttatga 1980
caatgcagaa tatgctgaga ggtttatgga ggaaaatgaa ggacatattg tagatattca 2040
tgactttct ttgggtagca gtccacatgt ccgaaagcat tttccagaga cttggatttg 2100
gctagacacc aacatgggtt acaggattta ccaagaattt gaagtaactg tacctgattc 2160
tatccttct tgggtggcta ctggtttgt gatctctgag gacctgggtc ttggactaac 2220
aactactcca gtgagctcc aagccttcca accattttc attttttga atcttcccta 2280
ctctgttatc agaggtgaag aatttgcttt ggaaataact atattcaatt atttgaaaga 2340
tgccactgag gttaaggtaa tcattgagaa aagtgacaaa tttgatattc taatgacttc 2400
aaatgaaata aatgccacag gccaccagca gacccttctg gttcccagtg aggatgggc 2460
aactgttctt tttcccatca ggccaacaca tctgggagaa attcctatca cagtcacagc 2520
tctttcaccc actgcttctg atgctgtcac ccagatgatt ttagtaaagg ctgaaggaat 2580
agaaaaatca tattcacaat ccatcttatt agacttgact gacaataggc tacagagtac 2640
cctgaaaact ttgagtttct catttcctcc taatacagtg actggcagtg aaagagttca 2700
gatcactgca attggagatg ttcttggtcc ttccatcaat ggcttagcct cattgattcg 2760
gatgccttat ggctgtggtg aacagaacat gataaatttt gctccaaata tttacatttt 2820
ggattatctg actaaaaaga aacaactgac agataatttt aaagaaaaag ctctttcatt 2880
tatgaggcaa ggttaccaga gagaacttct ctatcagagg acagatggct cttcagtgc 2940
tttttgggaat tatgacccctt ctgggagcac ttggttgtca gcttttgttt taagatgttt 3000
ccttgaagcc gatccttaca tagatattga tcagaatgtg ttacacagaa catacacttg 3060
gcttaaagga catcagaaat ccaacggtga attttgggat ccaggaagag tgattcatag 3120
tgagcttcaa ggtggcaata aaagtccagt aacacttaca gcctatattg taacttctct 3180
cctgggatat agaaagtatc agcctaacat tgatgtgcaa gagtctatcc attttttgga 3240
gtctgaattc agtagaggaa tttcagacaa ttatactcta gcccttataa cttatgcatt 3300
gtcatcagtg gggagtccta aagcgaagga agctttgaat atgctgactt ggagagcaga 3360
acaagaaggt ggcatgcaat tctggtgtc atcagagtcc aaactttctg actcctggca 3420
gccacgctcc ctggatattg aagttgcagc ctatgcactg ctctcacact tcttacaatt 3480
tcagacttct gagggaatcc caattatgag gtggctaagc aggcaaagaa atagcttggg 3540
tggttttgca tctactcagg ataccactgt ggctttaaag gctctgtctg aatttgcagc 3600
cctaatgaat acagaaagga caaatatcca agtgaccgtg acggggccta gctcaccaag 3660
tcctgtaaag tttctgattg acacacacaa ccgcttactc cttcagacag cagagcttgc 3720
tgtggtacag ccaacggcag ttaatatttc cgcaaatgtt tttggatttg ctatttgtca 3780
gctcaatgtt gtatataatg tgaaggcttc tgggtcttct agaagacgaa gatctatcca 3840
aaatcaagaa gcctttgatt tagatgttgc tgtaaaagaa aataaagatg atctcaatca 3900
tgtggatttg aatgtgtgta caagcttttc gggcccgggt aggatggca tggctcttat 3960
ggaagttaac ctattaagtg gcttttatgg gccttcagaa gcaatttctc tgagcgagac 4020
agtgaagaaa gtggaatatg atcatgtgaaa actcaacctc tatttagatt ctgtaaatga 4080
aacccagttt tgtgttaata ttcctgctgt gagaaacttt aaagtttcaa atacccaaga 4140
tgcttcagtg tccatagtgg attactatga gccaaggaga caggcggtga gaagttacaa 4200
ctctgaagtg aagctgtcct cctgtgacct ttgcagtgat gtccagggct gccgtccttg 4260
tgaggatgga gcttcaggct cccatcatca cttttattt tctgtttcaa 4320
gcttctgtac tttatggaac tttgctgtg atttattttt aaaggactct gtgtaacact 4380
aacatttcca gtagtcacat gtgattgttt tgttttcgta aagaatact gcttctattt 4440
tgaaaaaga gttttttttc tttctatggg gttgcaggga tggtgtacaa caggtcctag 4500
catgtatagc tgcatagatt tcttcacctg atctttgtgt ggaagatcag aatgaatgca 4560
gttgtgtgtc tatattttcc cctctcaaaa tcttttagaa ttttttttgga ggtgtttgtt 4620
```

```
ttctccagaa taaaggtatt actttagaat aggtattctc ctcatttgt gaaagaaatg   4680
aacctagatt cttaagcatt attacacatc catgtttgct taaagatgga tttccctggg   4740
aatgggagaa aacagccagc aggaggagct tcatctgttc ccttcccacc tccaacctag   4800
ccctactgcc caccccaccc caacccaccc catgcccagt ggtctcagta gatacttctt   4860
aactggaaat tctttctttt cagaatctag gtggtgaatt tttttaagt ggcacggtct    4920
ttttctgctt gaaatctgat cacacccccc agccattgcc ctccctctct ttttcctctg   4980
tagagaaatg tgaggggcag tacatttact gtgcttttca caccatctca gaggttgagg   5040
agcatactga aaattgccct gggggtgct gggtgtgctg tctccttccc acatcctcag    5100
ccccacacca gctctatttc aggggtgaga gtcagagga actgcaatat gtgcttcatg    5160
ggatttcgat tcgaagatcc tagaccaggg agacactgtg agccagggat acaacaaaat   5220
actaggtaag tcactgcaga ccgacctccc tgcagtttgg gaaagaagct gggtttgtgg   5280
agaatcagag catcttgaca tgactgctga cctaaagatc cctggcattg gccagggatc   5340
ctgtggaacc tcttctagtt caggggtgtg agcattagac tgccagttgt ctagtgacat   5400
ctgatgcttg ctgtgaactt ttaagatccc cgaatcctga gcacctcaat cttttaattgc  5460
cctgtattcc gaagggtaat ataattttatc tggatggaaa ttttaaagat gaatcccct   5520
ttttctttt cttctctctt ttctttcctt ctcccttct tctttgcctt ctaaatatac    5580
tgaaatgatt tagatatgtg tcaacaatta atgatctttt attcaatcta agaaatggtt   5640
tagttttct ctttagctct atggcatttc actcaagtgg acaggggaaa aagtaattgc    5700
catgggctcc aaagaatttg ctttatgttt ttagctattt aaaaataaat ccatcaaaaa   5760
taaagtatgc aaatgtatct tttaaagtta attttaaaa atgctcttat tttagtgaat    5820
tttcagaaat tatagtggaa tggatgctca tatattgctt atggatattt tggataccaa   5880
agtaggaata actgacattc agtattttaa agctggcaaa cctgtacata gaaaatagat   5940
ccccagacag tggtctatga agagggcagt taagtatcaa atacttaatt ttcttgcctt   6000
ttttcttaa gtggggaaaa gtttctagat ctcttacacc tctgacacaa tctgttctaa    6060
aacaggcact tgtaatgttg gggcctcctt gtaaacgtgt ttttgccctt tactctctgg   6120
gagttcttta aaggtgaaat catcttacaa agaaattggg ggagggtctt ggcaaaggac   6180
tttcccctcc tctttcctgg cctgggaacc ttatactgac aatcaatact ttatatttta   6240
aagtatataa tttatagtta acttctagtg taatatatta ggaaacacta gaatggaaag   6300
gccattggaa gacaggttgt atctttttta gaccatattt ccttgtttaa aaactatcat   6360
ttgaatactt ttttggtgaa gaactccatg ttttcaagtt aaaggtcacc tcgtaggcca   6420
ggcgcagtgg ctcatgcctg taatcccagc actctgggag gctgaggcgg gtgaatcaca   6480
aggttaggag tttgagacca gcctggccaa tatggtgaaa cccgtccct actaaaaata    6540
caaaatttag ccaggcgtgg tggcatgcac ctgtagtccc acctactcgg gaggctgagg   6600
caggagaatc acttgaacct gagagacaga ggttgcagtg agccgagatc acgccactgc   6660
actccagcct gggggacaga gtgagattct gtctcaaaaa acaaaaaaca aaaaagtcac   6720
cttgtaactc atctcttttt attgtaagtt tattaaaaat gaagaggaca caatgagaa    6780
ggaacataaa gggttagcta gcactgtctc ctggtgcatg gggctgtgca gatgtcccgg   6840
ccacttcttc cttcatactt cccttagaga acttgctctg ctacaagcag tgggcttgga   6900
ctaaaagtga ttaaaaatacc acaggcataa ggagaaaagg agtatatgta gtagtaataa   6960
ttactagtat aaaattatttt cttcacatgc tatgagtaat aatattaaaa aactcatttt   7020
accattaaga ttccttatgc tgaagctctt ccatttagaa tactgtcaat gtcatttact    7080
ggtatgaact aaagtccccc ttcttttcca ctcactggga accttagtaa aacaccagca   7140
tatcttacct ctctttctga ctggccgatg cttccagaga ctgaatgttg ggaaaaccta   7200
gtagccaaac aattctagga cagaataaca ttttttatatt tggttccacc atcttattac   7260
atttagttat agttttaaaa aagaaattca agcccattaa aatatgtctg gtcaatgaaa   7320
tgcttccttt tattgtgttg tgctattgta ctttgttttt caaaacattg taaaaatagt    7380
atctttggtt tagtattttg gattatatat tataatctga ggtgttttt gcttatgtag    7440
aatccagata tatttctgtt acctaggaga tgttacttac atatgtaata ctgtatcctg   7500
cacgtggaaa tattcagaat tgtagatagc ataactctcc ctgctcctat tcttttgagc   7560
ctaggtataa tttttttttt tttttagaa aaagacatat ttagctttaa tttctatttta   7620
tgctaaacat atttataagt agtctgtcaa tataatacca actattttta ttttacata    7680
attcaattat ttcatttgac atgtctggca gactcaagag attaagtaaa aaattggaac   7740
tatgattttt ctttgtcatt tttaaaaaaa gaattatttt attaacctgc tggcatataa   7800
tctgagttc ttttcacaac cttactttt ctgatttgct ttattgaatg attgaatact    7860
catttctttc taaaaaatatg ttgtaaattc tcccttggca agatttctcc ctatgagggt   7920
agttattatt tgagtctgcc aagtggttac catgggggcaa ggtgccatga tgtattcttg   7980
ggtgcattgg ttttttgcgc attgtaaatt taagacactt atagtaagtg gactcattca   8040
tagatgagtt tcagaacctt ttacgttctc ggtagaggct tctgtcggac aggcagaaga   8100
gtgattcct cactttttt tttgtcttca aattccagta aggcatagca cttttaagaa     8160
attagaattt ttctatcatc tatgcaaatg atatttatgt taatattaaa tatcttatgt   8220
tacactggga gtaatttgag gtgcaattat ttttattact actttgaata gaggaccatt   8280
atccttcttt cttcagaaaa ctaagaagta agtgtaactt ttaaagtaag tatatatcag   8340
tgagagtagg cttgttttac aactatttct agccagtgag ttgtgttttc atgtctcatc   8400
aaaagacaat accacattgc atcattttac aaaatatgtt gtcattttca tttcagttgt   8460
aacataggaa aatagatatt tcctagatga tttctgagtt tcttactgca aagaacagtt   8520
ataaattggt atacatgtgt ctctgtaata gggataatat tgatatatct gttgctacat   8580
atttaagaat cattctatct tatgttgtct tgaggcaaag atttaccacg tttgcccagt   8640
gtattgaatt ggtggtagaa ggtagttcca tgttccattt gtagatcttt aagattttat   8700
ctttgataac tttaatagaa tgtggctcag ttctgtgtcct tcaagcctgt atggtttgga   8760
ttttcagtag gggacagttg atgtggagtc aatctctttg gtacacagga agctttataa    8820
aatttcattc acgaatctct tattttggga agctgttttg catatgagaa gaacactgtt   8880
gaaataagga actaaagctt tatatattga tcaaggtgat tctgaaagtt ttaattttta   8940
atgttgtaat gttatgttat tgttaattgt actttattat gtattcaata gaaaatcatg   9000
atttattaat aaaagcttaa attctcatct a                                 9031
SEQ ID NO: 5      moltype = RNA  length = 5883
FEATURE           Location/Qualifiers
source            1..5883
                  mol_type = mRNA
``` organism = Homo sapiens
SEQUENCE: 5

```
ctaaactcga attaagaggg aaaaaaaatc agggaggagg tggcaagcca caccccacgg   60
tgcccgcgaa cttccccggc agcggactgt agcccaggca gacgccgtcg agatgcaggg  120
cccaccgctc ctgaccgccg cccacctcct ctgcgtgtgc accgccgcgc tggccgtggc  180
tcccgggcct cggtttctgg tgacagcccc agggatcatc aggcccggag gaaatgtgac  240
tattggggtg gagcttctgg aacactgccc ttcacaggtg actgtgaagg cggagctgct  300
caagacagca tcaaacctca ctgtctctgt cctggaagca gaaggagtct ttgaaaaagg  360
ctcttttaag acacttactc ttccatcact acctctgaac agtgcagatg agatttatga  420
gctacgtgta accggacgta cccaggatga gattttattc tctaatagta cccgcttatc  480
atttgagacc aagagaatat ctgtcttcat tcaaacagac aaggcttat acaagccaaa  540
gcaagaagtg aagtttcgca ttgttacact cttctcagat tttaagcctt acaaaacctc  600
tttaaacatt ctcattaagg accccaaatc aaatttgatc caacagtggt tgtcacaaca  660
aagtgatctt ggagtcattt ccaaaacttt tcagctatct tcccatccaa tacttggtga  720
ctggtctatt caagttcaag tgaatgacca gacatattat caatcatttc aggtttcaga  780
atatgtatta ccaaaatttg aagtgacttt gcagacacca ttatattgtt ctatgaattc  840
taagcattta aatggtacca tcacggcaaa gtatacatat gggaagccag tgaaaggaga  900
cgtaacgctt acattttac ctttatcctt ttggggaaag aagaaaaata ttacaaaaac  960
atttaagata aatggatctg caaacttctc ttttaatgat gaagagatga aaatgtaat  1020
ggattcttca aatggacttt ctgaatacct ggatctatct tcccctggac cagtagaaat 1080
tttaaccaca gtgacagaat cagttacagg tatttcaaga aatgtaagca ctaatgtgtt 1140
cttcaagcaa catgattaca tcattgagtt ttttgattat actactgtct gtgaagccatc 1200
tctcaacttc acagccactg tgaaggtaac tcgtgctgat ggcaaccaac tgactcttga 1260
agaaagaaga aataatgtag tcataacagt gacacagaga aactatactg agtactggag 1320
cggatctaac agtggaaatc agaaaatgga agctgttcag aaaataaatt atactgtccc 1380
ccaaagtgga acttttaaga ttgaattccc aatcctggag gattccagtg agctacagtt 1440
gaaggcctat ttccttggta gtaaaagtag catggcagtt catagtctgt ttaagtctcc 1500
tagtaagaca tacatccaac taaaaacaag agatgaaaat ataaaggtgg gatcgccttt 1560
tgagttggtg gttagtggca acaaacgatt gaaggagtta agctatatgg tagtatccag 1620
gggacagttg gtggctgtag gaaaacaaaa ttcaacaatg ttctctttaa caccagaaaa 1680
ttcttggact ccaaaagcct gtgtaattgt gtattatatt gaagatgatg gggaaattat 1740
aagtgatgtt ctaaaaattc ctgttcagct tgttttttaaa aataagataa agctatattg 1800
gagtaaagtg aaagctgaac catctgagaa agtctctctt aggatctctg tgacacagcc 1860
tgactccata gttgggattg tagctgttga caaaagtgtg aatctgatga tgcctctaa  1920
tgatattaca atggaaaatg tggtccatga gttgaactt tataacacag gatattattt 1980
aggcatgttc atgaattctt ttgcagtctt tcaggaatgt ggactctggg tattgacaga 2040
tgcaaacctc acgaaggatt atattgatgg tgtttatgac aatgcagaat atgctgagag 2100
gtttatggag gaaaatgaag acatattgt agatattcat gacttttctt tgggtagcag 2160
tccacatgtc cgaaagcatt ttccagagac ttggatttgg ctagacacca acatgggtta 2220
caggatttac caagaatttg aagtaactgt acctgattct atcacttctt gggtggctac 2280
tggttttgtg atctctgagg acctgggtct tggactaaca actactccag tggagctcca 2340
agccttccaa ccattttttca ttttttttgaa tcttccctac tctgttatca gaggtgaaga 2400
atttgcttg gaaataacta tattcaatta tttgaaagat gccactgagg ttaaggtaat 2460
cattgagaaa agtgacaaat tgatattct aatgacttca aatgaaataa atgccacagg 2520
ccaccagcag ccccttctgg ttccagtga ggatggggca actgttcttt ttcccatcag 2580
gccaacacat ctgggagaaa ttcctatcac agtcacagct ctttcaccca ctgcttctga 2640
tgctgtcacc cagatgattt tagtaaaggc tgaaggaata gaaaaatcat attcacaatc 2700
catcttatta gacttgactg acaataggct acagagtacc ctgaaaactt tgagtttctc 2760
atttcctcct aatacagtga ctggcagtga aagagttcag atcactgcaa ttggagatgt 2820
tcttggtcct tccatcaatg gcttagcctc attgattcgg atgccttatg ctgtggtga  2880
acagaacatg ataaattttg ctccaaatat ttacattttg gattatctga ctaaaaagaa 2940
acaactgaca gataatttga agaaaaaagc tctttcattt atgaggcaag ttaccagag  3000
agaacttctc tatcagaggg aagatggctc tttcagtgct tttgggaatt atgcccttc  3060
tgggagcact tggttgtcag ctttttgttt aagatgtttc cttgaagccg atccttacat 3120
agatattgat cagaatgtgt tacacagaac atacacttgg ctttaaaggac atcagaaatc 3180
caacggtgaa ttttgggatc caggaagagt gattcatagt gagcttcaag gtggcaataa 3240
aagtccagta acacttacag cctatattgt aacttctctc ctgggatata gaaagtatca 3300
gcctaacatt gatgtgcaag agtctatcca tttttgggag tctgaattca gtagaggaat 3360
ttcagacaat tatactctag cccttataac ttatgcattg tcatcagtgg gggatcctaa 3420
agcgaaggaa gctttgaata tgctgacttg gagagcagaa caagaaggtg gcatgcaatt 3480
ctgggtgtca tcagagtcca aactttctga ctcctggcag ccacgctccc tggatattga 3540
agttgcagcc tatgcactgc tctcacactt cttacaattt cagacttctg agggaatccc 3600
aattatgagg tggctaagca ggcaaagaaa tagcttgggt ggtttgcat ctactcagga  3660
taccactgtg gcttttaagg ctctgtctga atttgcagcc ctaatgaata cagaaaggac 3720
aaatatccaa gtgaccgtga cggggcctag ctcaccaagt cctgtaaagt ttctgattga 3780
cacacacaac cgcttactcc ttcagacagc agagcttgct gtggtacagc aatggcagt  3840
taatatttcc gcaaatggtt ttggatttgc tatttgtcag ctcaatgttg tatataatgt 3900
gaaggcttct gggtcttcta gaagacgaag atctatccaa aatcaagaag cctttgattt 3960
agatgttgct gtaaaagaaa ataaagatga tctcaatcat gtggagttga atgtgtgtac 4020
aagcttttcg ggcccgggta ggagtggcat ggctcttatg gaagttaacc tattaagtgg 4080
ctttatggtg ccttcagaag caatttctct gagcgagaca gtgaagaaag tggaatatga 4140
tcatggaaaa ctcaacctct atttagattc tgtaaatgaa acccagtttt gtgttaatat 4200
tcctgctgtg agaaacttta aagttcaaa tacccaagat gcttcagtgt ccatagtgga 4260
ttactatgag ccaaggagac aggcggtgag aagttacaac tctgaagtga agctgtcctc 4320
ctgtgacctt tgcagtgatg tccagggctg ccgtccttgt gaggatgag cttcaggctc 4380
ccatcatcac tcttcagtca tttttatttt ctgtttcaag cttctgtact ttatggaact 4440
ttggctgtga tttattttta aaggactctg tgtaacacta cattccag tagtcacatg  4500
tgattgtttt gttttcgtag aagaatactg cttctatttt gaaaaagag tttttttttct 4560
ttctatgggg ttgcagggat ggtgtacaac aggtcctagc atgtatagct gcatagattt 4620
```

```
cttcacctga tctttgtgtg gaagatcaga atgaatgcag ttgtgtgtct atattttccc   4680
ctcacaaaat cttttagaat ttttttggag gtgtttgttt tctccagaat aaaggtatta   4740
ctttagaaat aggtattctc ctcattttgt gaaagaaatg aacctagatt cttaagcatt   4800
attacacatc catgtttgct taaagatgga tttccctggg aatgggagaa aacagccagc   4860
aggaggagct tcatctgttc ccttcccacc tccaacctag ccctactgcc cacccaccc   4920
caacccaccc catgcccagt ggtctcagta gatacttctt aactggaaat tctttctttt   4980
cagaatctag gtggtgaatt ttttttaagt ggcacggtct ttttctgctt gaaatctgat   5040
cacacccccc agccattgcc ctccctctct ttttcctctg tagagaaatg tgaggggcag   5100
tacattttact gtgcttttca caccatctca gaggttgagg agcatactga aaattgccct   5160
gggggggtgct gggtgtgctg tctccttccc acatcctcag ccccacacca gctctatttc   5220
agggggtgaga gtcagagagc actgcaatat gtgcttcatg ggatttcgat tcgaagatcc   5280
tagaccaggg agacactgtg agccaggat acaacaaaat actaggtaag tcactgcaga   5340
ccgacctccc tgcagtttgg gaaagaagct gggtttgtgg agaatcagag catcttgaca   5400
tgactgctga cctaaagatc cctggcattg gccaggatc ctgtggaacc tcttctagtt   5460
caggggtgtg agcattagac tgccagttgt ctagtgacat ctgatgcttg ctgtgaactt   5520
ttaagatccc cgaatcctga gcacctcaat ctttaattgc cctgtattcc gaagggtaat   5580
ataatttatc tggatggaaa ttttaaagat gaatcccct tttttctttt cttctctctt   5640
ttctttcctt ctcccttttct tctttgcctt ctaaatatac tgaaatgatt tagatatgtg   5700
tcaacaatta atgatctttt attcaatcta agaaatggtt tagtttttct ctttagctct   5760
atggcatttc actcaagtgg acaggggaaa aagtaattgc catgggctcc aaagaatttg   5820
ctttatgttt ttagctattt aaaaataaat ccatcaaaaa taaagtatgc aaatgtatct   5880
ttt                                                                5883

SEQ ID NO: 6             moltype = RNA   length = 4449
FEATURE                  Location/Qualifiers
source                   1..4449
                         mol_type = mRNA
                         organism = Homo sapiens
SEQUENCE: 6
aaaactcgaa ttaagaggga aagaaaatca gggaggaggt ggcaagccac accccacggt    60
gcccgcgaac ttccccggca gcggactgta gcccaggcag acgccgtcga gatgcagggc   120
ccaccgctcc tgaccgccgc ccacctcctc tgcgtgtgca ccgccgcgct ggccgtggct   180
cccgggcctc ggtttctggt gacagcccca gggatcatca ggcccggagg aaatgtgact   240
attggggtgg agcttctgga acactgccct tcacaggtga ctgtgaaggc ggagctgctc   300
aagacagcat caaacctcac tgtctctgtc ctggaagcag aaggagtctt tgaaaaaggc   360
tcttttaaga cacttactct tccatcacta cctctgaaca gtgcagatga gatttatgag   420
ctacgtgtaa ccggacgtac ccaggatgag atttttattct ctaatagtac ccgcttatca   480
tttgagacca agagaatatc tgtcttcatt caaacagaca aggccttata caagccaaag   540
caagaagtga agtttcgcat tgttacactc ttctcagatt ttaagcctta caaaacctct   600
ttaaacattc tcattaagga ccccaaatca aatttgatcc aacagtggtt gtcacaacaa   660
agtgatcttg gagtcatttc caaaactttt cagctatctt cccatccaat acttggtgac   720
tggtctattc aagttcaagt gaatgaccag acatatattc aatcatttca ggtttcagaa   780
tatgtattac caaaatttga agtgactttg cagacaccat tatattgttc tatgaattct   840
aagcatttaa atggtaccat cacggcaaag tatacatatg ggaagccagt gaaggagac   900
gtaacgctta cattttttacc tttatccttt tggggaaaga agaaaaatat tacaaaaaca   960
tttaagataa atggatctgc aaacttctct tttaatgatg aagagatgaa aaatgtaatg  1020
gattcttcaa atggacttc tgaatacctg gatctatctt ccctggacc agtagaaatt  1080
ttaaccacag tgacagaatc agttacaggt atttcaagaa atgtaagcac taatgtgttc  1140
ttcaagcaac atgattacat cattgagttt ttgattata ctactgtctt gaagccatct  1200
ctcaacttca cagccactgt gaaggtaact cgtgctgatg caaccaact gactcttgaa  1260
gaaagaagaa ataatgtagt cataacagtg acacagaaga actatactga gtactggaac  1320
ggatctaaca gtgaaaatca gaaaatggaa gctgttcaga aaataaatta tactgtcccc  1380
caaagtggaa cttttaagat tgaattccca atcctggagg attccagtga gctacagttg  1440
aaggcctatt tccttggtag taaaagtagc atggcagttc atagtctgtt taagtctcct  1500
agtaagacat acatccaact aaaaaacaaga gatgaaata taaaggtggg atcgcctttt  1560
gagttggtgg ttagtggcaa caacgattg aaggagttaa gctatatggt agtatccagg  1620
ggacagttgg tggctgtagg aaaacaaaat tcaacaatgt tctctcttaac accagaaaat  1680
tcttggactc caaaagcctg tgtaattgtg tattatattg aagatgatgg ggaaattata  1740
agtgatgttc taaaaattcc tgttcagctt ttttttaaaa ataagataaa gctatattgg  1800
agtaaagtga aagctgaacc atctgagaaa gtctctctta gatctctgt gacacagcct  1860
gactccatag ttgggattgt agctgttgac aaaagtgtga atctgatgaa tgcctctaat  1920
gatattacaa tggaaaatgt ggtccatgag ttggaacttt ataacacagg atattattta  1980
ggcatgttca tgaattcttt tgcagtcttt caggaatgtg gactctgggt attgacagat  2040
gcaaacctca cgaaggatta tattgatggt gtttatgaca atcagaata tgctgagagg  2100
tttatggagg aaaatgaagg acatattgta gatattcatg acttttcttt gggtagcagt  2160
ccacatgtcc gaaagcattt tccagagact tggattggc tagacaccaa catgggttcc  2220
aggatttacc aagaatttga agtaactgta cctgattcta tcacttcttg ggtggctact  2280
ggttttgtga tctctgagga cctgggtctt ggactaacaa ctactccagt ggagctccaa  2340
gccttccaac cattttttcat ttttttgaat cttccctact ctgttatcag aggtgaagaa  2400
tttgcttttgg aaataactat attcaattat ttgaaagatg ccactgaggt taaggtaatc  2460
attgagaaaa gtgacgaatt tgatattcta atgacttcaa atgaaataaa tgccacaggc  2520
caccagcaga cccttctggt tcccagtgag atggggcaa ctgttcttt tcccatcagg  2580
ccaacacatc tgggagaaat tcctatcaca gtcacagctc tttcacccac tgcttctgat  2640
gctgtcaccc agatgtttta gtaaaggct gaaggaatga aaaatcata ttcacaatcc  2700
atcttattag acttgactga caataggcta cagagtaccc tgaaaacttt gagtttctca  2760
tttcctcctta atacagtgac tggcagtgaa agagttcaga tcactgcaat tggagatgtt  2820
cttggtcctt ccatcaatgg cttagcctca ttgattcgga tgcttatgg ctgtggtgaa  2880
cagaacatga taaattttgc tccaaatatt tacatttgg attatctgac taaaagaaa  2940
caactgacag ataaatttgaa agaaaaagct ctttcattta tgaggcaagg ttaccagaga  3000
```

```
gaacttctct atcagaggga agatggctct ttcagtgctt ttgggaatta tgacccttct  3060
gggagcactt ggttgtcagc ttttgtttta agatgtttcc ttgaagccga tccttacata  3120
gatattgatc agaatgtgtt acacagaaca tacacttggc ttaaaggaca tcagaaatcc  3180
aacggtgaat tttgggatcc aggaagagtg attcatagtg agcttcaagg tggcaataaa  3240
agtccagtaa cacttacagc ctatattgta acttctctcc tgggatatag aaagtatcag  3300
cctaacattg atgtgcaaga gtctatccat tttttggagt ctgaattcag tagaggaatt  3360
tcagacaatt atactctagc ccttataact tatgcattgt catcagtggg gagtcctaaa  3420
gcgaaggaag ctttgaatat gctgacttgg agagcagaac aagaaggtgg catgcaattc  3480
tgggtgtcat cagagtccaa actttctgac tcctggcagc cacgctccct ggatattgaa  3540
gttgcagcct atgcactgct ctcacacttc ttacaatttc agacttctga gggaatccca  3600
attatgaggt ggctaagcag gcaaagaaat agcttgggtg gttttgcatc tactcaggat  3660
accactgtgg ctttaaaggc tctgtctgaa tttgcagccc taatgaatac agaaaggaca  3720
aatatccagg tgaccgtgac ggggcctagc tcaccaagtc ctgtaaagtt tctgattgac  3780
acacacaacc gcttactcct tcagacagca gagcttgctg tggtacagcc aacggcagtt  3840
aatatttccg caaatggttt tggatttgct atttgtcagc tcaatgttgt atataatgtg  3900
aaggcttctg ggtcttctag aagacgaaga tctatccaaa atcaagaagc ctttgattta  3960
gatgttgctg taaaagaaaa taaagatgat ctcaatcatg tggatttgaa tgtgtgtaca  4020
agcttttcgg gcccgggtag gagtggcatg gctcttatgg aagttaacct attaagtggc  4080
tttatggtgc cttcagaagc aatttctctg agcgagacag tgaagaaagt ggaatatgat  4140
catgaaaaac tcaacctcta tttagattct gtaaatgaaa cccagttttg tgttaatatt  4200
cctgctgtga gaaactttaa agtttcaaat acccaagatg cttcagtgtc catagtggat  4260
tactatgaac caaggagaca ggcggtgaga agttacaact gtcaagtgaa gctgtcctcc  4320
tgtgacccttt gcagtgatgt ccagggctgc cgtccttgtg aggatggagc ttcaggctcc  4380
catcatcact cttcagtcat ttttattttc tgtttcaagc ttctgtactt tatggaactt  4440
tggctgtga                                                          4449

SEQ ID NO: 7             moltype = RNA  length = 2273
FEATURE                  Location/Qualifiers
source                   1..2273
                         mol_type = mRNA
                         organism = Homo sapiens
SEQUENCE: 7
acacacccca cggtgcccgc gaacttcccc ggcagcggac tgtagcccag gcagacgccg   60
tcgagatgca gggcccaccg ctcctgaccg ccgcccacct cctctgcgtg tgcaccgccg  120
cgctggccgt ggctcccggg cctcggtttc tggtgacagc cccagggatc atcaggcccg  180
gaggaaatgt gactattggg gtggagcttc tggaacactg cccttcacag gtgactgtga  240
aggcggagct gctcaagaca gcatcaaacc tcactgtctc tgtcctggaa gcagaaggag  300
tctttgaaaa aggctctttt aagacactta ctcttccatc actacctctg aacagtgcag  360
atgagattta tgagctacgt gtaaccggac gtaccaggga tgagattta ttctctaata  420
gtacccgctt atcatttgag accaagagaa tatctgtctt cattcaaaca gacaaggcct  480
tatacaagcc aaagcaagaa gtgaagtttc gcattgttac actcttctca gattttaagc  540
cttacaaaac ctcttttaaac attctcatta aggaccccaa atcaaatttg atccaacagt  600
ggttgtcaca acaaagtgat cttggagtca tttccaaaac tttcagcta tcttccaatc  660
caatacttgg tgactggtct attcaagttc aagtgaatga ccagacatac tatcaatcat  720
ttcaggtttc agaatatgta ttaccaaaat ttgaagtgac tttgcagaca ccattatatt  780
gttctatgaa ttctaagcat ttaaatggta ccatcacggc aaagtataca tatgggaagc  840
cagtgaaagg agacgtaacg cttacatttt taccttatc cttttgggga aagaagaaaa  900
atattacaaa aacatttaag ataaatggat ctgcaaactt ctcttttaat gatgaagaga  960
tgaaaaatgt aatggattct tcaaatggac tttctgaata cctggatcta tcttcccctg 1020
gaccagtaga aattttaacc acagtgacag aatcagttac aggtatttca agaaatgtaa 1080
gcactaatgt gttcttcaag caacatgatt acatcattga gttttttgat tatactacta 1140
tcttgaagcc atctctcaac ttcacagcca ctgtgaaggt aactcgtgct gatggcaacc 1200
aactgactct tgaagaaaga agaaataatg tagtcataac agtgacacag agaaactata 1260
ctgagtactg gagcggatct aacagtgaaa tcagaaaat ggaagctgtt cagaaaataa 1320
attatactgt cccccaaagt ggaacttttta agattgaatt cccaatcctg gaggattcca 1380
gtgagctaca gttgaaggcc tatttccttg gtagtaaaag tagcatggca gttcatagtc 1440
tgtttaagtc tcctagtaag acatacatcc aactaaaaac aagagatgaa aatataaagg 1500
tgggatcgcc ttttgagttg gtggttagtg gcaacaaacg attgaaggag ttaagctata 1560
tggtagtatc caggggacag ttggtggctg taggaaaaca aaattcaaca atgttctctt 1620
taacaccaga aaattcttgg actccaaaag cctgtgtaat tgtgtattat attgaagatg 1680
atgggggaaat tataagtgat gttctaaaaa ttcctgttca gcttgttttt aaaaataaga 1740
taaagctata ttggagtaaa gtgaaagctg aaccatctga gaaagtctct cttaggatct 1800
ctgtgacaca gcctgactcc atagttggga ttgtagctgt tgacaaaagt gtgaatctga 1860
tgaatgcctc taatgatatt acaatggaaa atgtggtcca ttgtgaactt ataataca 1920
caggatatta tttaggcatg ttcatgaatt cttttgcagt ctttcaggaa tgtgggactct 1980
gggtattgac agatgcaaac ctcacgaagg attatattga tggtgtttat gacaatctct 2040
ttggtacaca ggaagcttta taaaatttca ttcacgaatc tcttatttt ggaagctgtt 2100
ttgcatatga gaagaacact gttgaaataa ggaactaaag ctttatatat tgatcaaggt 2160
gattctgaaa gttttaattt ttaatgttgt aatgtttatgt tattgttaat tgtactttat 2220
tatgtattca atagaaaatc atgatttatt aataaaagct taaattctca tct         2273

SEQ ID NO: 8             moltype = RNA  length = 4688
FEATURE                  Location/Qualifiers
source                   1..4688
                         mol_type = mRNA
                         organism = Homo sapiens
SEQUENCE: 8
gggactgtag cccaggcaga cgccgtcgag atgcagggcc caccgctcct gaccgccgcc   60
cacctcctct gcgtgtgcac cgccgcgctg gccgtggctc ccgggcctcg gtttctggtg  120
```

```
acagccccag ggatcatcag gcccggagga aatgtgacta ttggggtgga gcttctggaa    180
cactgccctt cacaggtgac tgtgaaggcg gagctgctca agacagcatc aaacctcact    240
gtctctgtcc tggaagcaga aggagtcttt gaaaaaggct cttttaagac acttactctt    300
ccatcactac ctctgaacag tgcagatgag atttatgagc tacgtgtaac cggacgtacc    360
caggatgaga tttttattctc taatagtacc cgcttatcat ttgagaccaa gagaatatct    420
gtcttcattc aaacagacaa ggccttatac aagccaaagc aagaagtgaa gtttcgcatt    480
gttacactct tctcagattt taagccttac aaaacctctt taaacattct cattaaggac    540
cccaaatcaa atttgatcca acagtggttg tcacaacaaa gtgatcttgg agtcatttcc    600
aaaactttc agctatcttc ccatccaata cttggtgact ggtctattca agttcaagtg    660
aatgaccaga catattatca atcatttcag gtttcagaat atgtattacc aaaatttgaa    720
gtgactttgc agacaccatt atattgttct atgaattcta agcatttaaa tggtaccatc    780
acggcaaagt atacatatgg gaagccagtg aaaggagacg taacgcttac attttttacct    840
ttatccttt ggggaaagaa gaaaaatatt acaaaaacat ttaagataaa tggatctgca    900
aacttctctt ttaatgatga agagatgaaa aatgtaatgg attcttcaaa tggactttct    960
gaatacctgg atctatcttc ccctggacca gtagaaattt taaccacagt gacagaatca   1020
gttacaggta tttcaagaaa tgtaagcact aatgtgttct tcaagcaaca tgattacatc   1080
attgagtttt ttgattatac cactgtcttg aagccatctc tcaacttcac agccactgtg   1140
aaggtaactc gtgctgatgg caaccaactg actcttgaga aagaagaaa taatgtagtc   1200
ataacagtga cacagagaaa ctatactgag tactggagcg atctaacag tggaaatcag   1260
aaaatggaag ctgttcagaa aataaattat actgtccccc aaagtggaac ttttaagatt   1320
gaattcccaa tcctggagga ttccagtgag ctacagttga aggcctattt ccttggtagt   1380
aaaagtagca tggcagttca tagtctgttt aagtctccta gtaagacata catccaacta   1440
aaacaagag atgaaaatat aaaggtggga tcgccttttg agttggtggt tagtggcaac   1500
aaacgattga aggagttaag ctatatggta gtatccaggg gacagttggt ggctgtagga   1560
aaacaaaatt caacaatgtt ctctttaaca ccagaaaatt cttggactcc aaaagcctgt   1620
gtaattgtgt attatattga agatgatggg gaaattataa gtgatgttct aaaaaattcct   1680
gttcagcttg tttttaaaaa taagataaag ctatattgga gtaaagtgaa agctgaacca   1740
tctgagaaag tctctcttag gatctctgtg acacagcctg actccatagt tgggattgta   1800
gctgttgaca aaagtgtgaa tctgatgaat gcctctaatg atattacaat ggaaaatgtg   1860
gtccatgagt tggaacttta taacacagga tattattttg acatgttcat gaattcttt   1920
gcagtctttc aggaatgtgg actctgggta ttgacagatg caaacctcac gaaggattat   1980
attgatggtg tttatgacaa tgcagaatat gctgagaggt ttatggagga aatgaagga    2040
catattgtag atattcatga cttttctttg ggtagcagtc cacatgtccg aaagcatttt   2100
ccagagactt ggatttggct agacaccaac atgggttaca ggattacca agaatttgaa   2160
gtaactgtac ctgattctat cacttcttgg gtggctactg gttttgtgat ctctgaggac   2220
ctgggtcttg gactaacaac tactccagtg gagctccaag ccttccaacc atttttcatt   2280
tttttgaatc ttccctactc tgttatcaga ggtgaagaat ttgctttgga ataactata    2340
ttcaattatt tgaaagatgc cactgaggtt aaggtaatca ttgagaaaag tgacaaattt   2400
gatattctaa tgacttcaag tgaaataaat gccacagcc accagcagac ccttctggtt   2460
cccagtgagg atgggcaac tgttctttt cccatcaggc caacacatct gggagaaatt   2520
cctatcacag tcacagctct ttcacccact gcttctgatg ctatcaccca gatgattta   2580
gtaaaggctg aaggaataga aaaatcatat tcacaatcca tcttattaga cttgactgac   2640
aatagctac agagtaccct gaaaagtttg agtttctcat ttcctcctaa tacagtgact   2700
ggcagtgaaa gagttcagat cactgcaatt ggagatgttc ttggtccttc catcaatggc   2760
ttagcctcat tgattcggat gccttatggc tgtggtgaac agaacatgat aaattttgct   2820
ccaaatattt acattttgga ttatctgact aaaaagaaac aactgacaga taatttgaaa   2880
gaaaaagctc tttcatttat gaggcaaggt taccagagga actttctcta tcagagggaa   2940
gatggctctt tcagtgcttt tgggaattat gaccctttctg ggagcacttg gttgtcagct   3000
tttgttttaa gatgtttcct tgaagccgat ccttacatag atattgatca gaatgtgtta   3060
cacagaacat acacttggct taaagacat cagaaatcca acggtgaatt tgggatcca    3120
ggaagagtga ttcatagtga gcttcaaggt ggcaataaaa gtccagcaac acttacgacg   3180
tatattgtaa cttctctcct gggatataga aagtatcagc ctaacattga tgtgcaagag   3240
tctatccatt ttttgagtc tgaattcagt agaggaattt cagacaatta tactctagcc   3300
cttataactt atgcattgtc atcagtgggg agtcctaaag cgaaggaagc tttgaatatg   3360
ctgacttgga gagcagaaca agaaggttgg ccatgcaattct gggtgtcatc agagtccaaa   3420
ctttctgact cctggcagcc acgctccctg gatattgaag ttgcagccta tgcactgctc   3480
tcacacttct tacaatttca gacttctgag ggaatcccaa ttatgaggtg gctaagcagg   3540
caaagaaata gcttgggtgg ttttgcatct actcaggata ccactgtggc tttaaaggct   3600
ctgtctgaat ttgcagccct aatgaataca gaaaggacaa atatccaagt gaccgtgacg   3660
gggcctagct caccaagtcc tgtaaagttt ctgattgaca cacacaaccg cttactcctt   3720
cagacagcag agcttgctgt ggtacagcca atggcagtta atattccgc aaatggtttt   3780
ggatttgcta tttgtcagct caatgttgta tataatgtga aggcttctgg gtcttctaga   3840
agacgaagat ctatccaaaa tcaagaagcc tttgatttag atgttgctgt aaaagaaaat   3900
aaagatgatc tcaatcatgt ggatttgaat gtgtgtacaa gctttttcgg cccgggtagg   3960
agtggcatgg ctcttatgga agttaaccta ttaagtggct ttatggtgcc ttcagaagca   4020
atttctctga gcgagacagt gaagaaagtg gaatatgatc atggaaaact caacctctat   4080
ttagattctg taaatgaaac ccagtttttgt gttaatattc ctgctgtgag aaactttaaa   4140
gtttcaaata cccaagtgca ttcagtgtcc atagtggatt actatgagcc aaggagacag   4200
gcggtgagaa gttcaaactc tgaagtgaag ctgtcctcct gtgacctttg cagtgatgtc   4260
cagggctgcc gtccttgtga ggatggagct tcaggctccc atcatcactc ttcagtcatt   4320
tttatttct gtttcaagct tctgtacttt atggaacttt ggctgtgatt tatttttaaa   4380
ggactctgtg taacactaac atttccagta gtcacatgtg attgttttgt tttcgtagaa   4440
gaatactgct tctattttga aaaagagtt tttttcttt ctatggggtt gcagggatgg   4500
tgtacaacag gtcctagcat gtatagctgc atagatttct tcacctgatc tttgtgttga   4560
agatcagaat gaatgcagtt gtgtgtctat attttcccct ctcaaaatct tttagaattt   4620
ttttggaggt gtttgtttc tccagaataa aggtattact ttagaaaaca aaaaaaaaa   4680
aaaaaaaa                                                            4688

SEQ ID NO: 9       moltype = RNA   length = 4369
```

```
FEATURE                 Location/Qualifiers
source                  1..4369
                        mol_type = mRNA
                        organism = Homo sapiens
SEQUENCE: 9
tgtagcccag gcagacgccg tcgagatgca gggcccaccg ctcctgaccg ccgcccacct   60
cctctgcgtg tgcaccgccg cgctggccgt ggctcccggg cctcggtttc tggtgacagc  120
cccagggatc atcaggcccg gaggaaatgt gactattggg gtggagcttc tggaacactg  180
cccttcacag gtgactgtga aggcggagct gctcaagaca gcatcaaacc tcactgtctc  240
tgtcctggaa gcagaaggag tctttgaaaa aggctctttt aagacactta ctcttccatc  300
actacctctg aacagtgcag atgagattta tgagctacgt gtaaccggac gtacccagga  360
tgagatttta ttctctaata gtacccgctt atcatttgag accaagagaa tatctgtctt  420
cattcaaaca gacaaggcct tatacaagcc aaagcaagaa gtgaagtttc gcattgttac  480
actcttctca gattttaagc cttacaaaac ctctttaaac attctcatta aggacccaa   540
atcaaatttg atccaacagt ggttgtcaca acaaagtgat cttggagtca tttccaaaac  600
ttttcagcta tcttcccatc caatacttgg tgactggtct attcaagttc aagtgaatga  660
ccagacatat tatcaatcat ttcaggtttc agaatatgta ttaccaaaat ttgaagtgac  720
tttgcagaca ccattatatt gttctatgaa ttctaagcat ttaaatggta ccatcacggc  780
aaagtataca tatgggaagc cagtgaaagg agacgtaacg cttacatttt tacctttatc  840
cttttgggga aagaagaaaa atattacaaa aacatttaag ataaatggat ctgcaaactt  900
ctcttttaat gatgaagaga tgaaaaatgt aatggattct tcaaatggac tttctgaata  960
cctggatcta tcttccccctg gaccagtaga aatttttaacc acagtgacag aatcagttac 1020
aggtatttca agaaatgtaa gcactaatgt gttcttcaag caacatgatt acatcattga 1080
gtttttgat tatactactg tcttgaagcc atctctcaac ttcacagcca ctgtgaaggt 1140
aactcgtgct gatggcaacc aactgactct tgaagaaaga agaataatg tagtcataac 1200
agtgacacag agaaactata ctgagtactg gagcggatcc aacagtgaaa atcagaaaat 1260
ggaagctgtt cagaaaataa attatactgt cccccaaagt ggaacttta agattgaatt 1320
cccaatcctg gaggattcca gtgagctaca gttgaaggcc tatttccttg gtagtaaaag 1380
tagcatggca gttcatagtc tgtttaagtc tcctagtaag acatacatcc aactaaaaac 1440
aagagatgaa aatataaagg tgggatcgcc ttttgagttg gtggttagtg gcaacaaacg 1500
attgaaggag ttaagctata tggtagtatc caggggacag ttggtggctg taggaaaaca 1560
aaattcaaca atgttctctt taacaccaga aaattcttgg actccaaaag cctgtgtaat 1620
tgtgtattat attgaagatg atggggaaat tataagtgat gttctaaaaa ttcctgttca 1680
gcttgttttt aaaaataaga taaagctata ttggagtaaa gtgaaagcta aaccatctga 1740
gaaagtctct cttaggatct ctgtgacaca gcctgactcc atagttggga ttgtagctga 1800
tgacaaaagt gtgaatctga tgaatgcctc taatgatatt acaatggaaa atgtggtcca 1860
tgagttggaa ctttataaca caggatatta tttaggcatg ttcatgaatt ctttttgcagt 1920
ctttcaggaa tgtggactct gggtattgac agatgcaaac ctcacgaagg attatattga 1980
tggtgtttat gacaatgcag aatatgctga gaggttttatg aggaaaaatg aaggacatat 2040
tgtagatatt catgactttt ctttgggtag cagtccacat gtccgaaagc attttccaga 2100
gacttggatt tggctagaca ccaacatggg ttccaggatt taccaagaat ttgaagtaac 2160
tgtacctgat tctatcactt cttgggtggc tactggtttt gtgatctctg aggacctggg 2220
tcttgactta acaactactc cagtggagct ccaagcctc caaccatttt tcattttttgt 2280
gaatcttccc tactctgtta tcagaggtga agaatttgct ttggaaataa ctatattcaa 2340
ttatttgaaa gatgccactg aggttaaggt aatcattgag aaaagtgaca aatttgatat 2400
tctaatgact tcaagtgaaa taaatgccac aggccaccag cagaccctc tggttcccag 2460
tgaggatggg gcaactgttc ttttttccat caggccacaa catctgggag aaattcctat 2520
cacagtcaca gctctctttcac ccactgcttc tgatgctatc acccagatga ttttagtaaa 2580
ggctgaagga atagaaaaat catattcaca atccatctta ttagacttga ctgacaaatag 2640
gctacagagt accctgaaaa ctttgagttt ctcatttcct cctaatacag tgactggcag 2700
tgaaagattt cagatcactg caattggaga tgttcttggt ccttccatca atggcttagc 2760
ctcattgatt cggatgcctt atggctgtgg tgaacagaac atgataaatt ttgctcccaa 2820
tatttacatt ttggattatc tgactaaaaa gaaacaactg acagataatt tgaaagaaaa 2880
agctctttca tttatgaggc aaggttacca gagagaactt ctctatcaga gggaagatgg 2940
ctctttcagt gcttttggga attatgaccc ttctgggagc acttggttgt cagctttttgt 3000
tttaagatgt ttccttgaag ccgatcctta catagatatt gatcagaatg tgttacacag 3060
aacatacact tggcttaaag gacatcagaa atccaacggt gaatttttggg atccaggaag 3120
agtgattcat agtgagcttc aaggtggcaa taaaagtcca gtaacactta cagcctatat 3180
tgtaacttct ctcctgggat atagaaagta tcagcctaac attgatgtgc aaagtctat  3240
ccatttttg gagtctgaat tcagtagagg aatttcagac aattatactc tagcccttat  3300
aacttatgca ttgtcatcag tggggagtcc taaagcgaag gaagctttga atatgctgac  3360
ttggagagca gaacaagaag gtggcatgca attctgggtg tcatcagagt ccaaactttc  3420
tgactcctgg cagccacgct ccctggatat tgaagttgca gcctatgcac tgctctcaca  3480
cttcttacaa tttcagactt ctgagggaat cccaattatg aggtgctaa gcaggcaaaa  3540
aatatgcttg ggtggttttg catctactca ggataccact gtggctttaa aggctctgtc  3600
tgaatttgca gccctaatga atacagaaag gacaaatatc caagtgaccg tgacggggcc  3660
tagctcacca agtcctcttg ctgtggtaca gccaacggca gttaatattt ccgcaaatgg  3720
ttttggattt gctatttgtc agctcaatgt tgtatataat gtgaaggctt ctgggtcttc  3780
tagaagacga agatctatcc aaaatcaaga agcctttgat ttagatgttg ctgtaaaaga  3840
aaataaagat gatctcaatc atgtggattt gaatgtgtgt acaagctttt cgggcccggg  3900
taggagtggc atggctctta tggaagttaa cctattaagt ggcttatgg tgccttcaga  3960
agcaatttct ctgagcgaga cagtgaagaa agtggaatat gatcatgaaa actcaacctc  4020
ctatttagat tctgtaaatg aaacccagtt ttgtgttaat attcctgctg tgagaaacttc  4080
taaaatttca aatacccaag atgcttcagt gtccatagtg gattactatg agccaaggag  4140
acaggcggtg agaagttaca actctgaagt gaagctgtcc tcctgtgacc tttgcagtga  4200
tgtccagggc tgccgtcctt gtgaggatgg agcttcaggc tcccatcatc actcttcagt  4260
catttttatt ttctgtttca agcttctgta ctttatggaa ctttggctgt gatttatttt  4320
taaaggactc tgtgtaacac taacattttcc agtagtcaca tgtgattgt              4369
```

| SEQ ID NO: 10 | moltype = RNA   length = 4237 |
|---|---|
| FEATURE | Location/Qualifiers |
| source | 1..4237 |
| | mol_type = mRNA |
| | organism = Homo sapiens |

SEQUENCE: 10

```
gaggcagacg ccgtcgagat gcagggccca ccgctcctga ccgccgccca cctcctctgc    60
gtgtgcaccg ccgcgctggc cgtggctccc gggcctcggt ttctggtgac agccccaggg   120
atcatcaggc ccggaggaaa tgtgactatt ggggtggagc ttctgaaca ctgccccttca   180
caggtgactg tgaaggcgga gctgctcaag acagcatcaa acctcactgt ctctgtcctg   240
gaagcagaag gagtctttga aaaaggctct tttaagacac ttactcttcc atcagacccc   300
aaatcaaatt tgatccaaca gtggttgtca caacaaagtg atcttggagt catttccaaa   360
acttttcagc tatcttccca tccaatactt ggtgactggt ctattcaagt tcaagtgaat   420
gaccagacat actatcaatc atttcaggtt tcagatatg tattaccaaa atttgaagtg   480
actttgcaga caccattata ttgttctatg aattctaagc atttaaatgg taccatcacg   540
gcaaagtata catatgggaa gccagtgaaa ggagacgtaa cgcttacatt tttaccttta   600
tccttttggg gaaagaagaa aaatattaca aaaacatttta agataaatgg atctgcaaac   660
ttctctcttta atgatgaaga gatgaaaaat gtaatggatt cttcaaatgg actttctgaa   720
tacctggatc tatcttcccc tggaccagta gaaattttaa ccacagtgac agaatcagtt   780
acaggtattt caagaaatgt aagcactaat gtgttcttca agcaacatga ttacatcatt   840
gagttttttg attatactac tgtcttgaag ccatctctca acttcacagc cactgtgaag   900
gtaactcgtg ctgatggcaa ccaactgact cttgaagaaa gaagaaataa tgtagtcata   960
acagtgacac agaaaacta tactgagtac tggagcggat ctaacagtgg aaatcagaaa  1020
atggaagctg ttcagaaaat aaattatact gtcccccaaa gtggaacttt taagattgaa  1080
ttcccaatcc tggaggattc cagtgagcta cagttgaagg cctattttcct tggtagtaaa  1140
agtagcatgg cagttcatag tctgtttaag tctcctagta agacatacat ccaactaaaa  1200
acaagagatg aaaatataaa ggtgggatcg cctttttgagt tggtggttag tgcaacaaa  1260
cgattgaagg agttaagcta tatggtagta tccaggggac agttgggtggc tgtaggaaaa  1320
caaaattcaa caatgttctc tttaacacca gaaaattctt ggactccaaa agcctgtgta  1380
attgtgtatt atattgaaga tgatgggaa attataagtg atgttctaaa aattcctgct  1440
cagcttgtttt ttaaaaataa gataaagcta tattggagta aagtgaaagc tgaaccatct  1500
gagaaagtct ctcttaggat ctctgtgaca cagcctgact ccatagttgg gattgtagct  1560
gttgacaaaa gtgtgaatct gatgaatgcc tctaatgata ttacaatgga aaatgtggtc  1620
catgagttgg aactttataa cacaggatat tattaaggca tgttcatgaa ttcttttgca  1680
gtctttcagg aatgtggact ctgggtattg acagatgtaa acctcacgga ggattatatt  1740
gatggtgttt atgacaatgc agaatatgct gagaggttta tggaggaaaa tgaaggacat  1800
attgtagata ttcatgactt ttctttgggt agcagtccac atgtccgaaa gcattttcca  1860
gagacttgga tttggctaga caccaacatg ggttacagga tttaccaaga atttgaagta  1920
actgtacctg attctatcac ttcttgggtg gctactggtt ttgtgatctc tgaggacctg  1980
ggtcttggac taacaactac tccagtggag ctccaagcct tccaaccatt tttcatttttt  2040
ttgaatcttc cctactctgt tatcagaggt gaagaatttg ctttggaaat aactatatttc  2100
aattatttga aagatgccac tgaggttaag gtaatcattg agaaaagtga caaatttgat  2160
attctaatga cttcaaatga aataaatgcc acaggccacc agcagaccct tctggttccc  2220
agtgaggatg gggcaactgt tctttttccc atcaggccaa cacatctggg agaaattcct  2280
atcacagtca cagctctttc acccactgct tctgatgctg tcacccagat gattttagta  2340
aaggctgaag gaatagaaaa atcatattca caatccatct tattagactt gactgacaat  2400
aggctacaga gtaccctgaa aactttgagt ttctcattttc ctcctaatac agtgactggc  2460
agtgaaagag ttcagatcac tgcaattgga gatgttcttg gtccttccat caatggctta  2520
gcctcattga ttcggatgcc ttatggctgt ggtgaacaga acatgataaa ttttgctcca  2580
aatatttaca ttttggatta tctgactaaa agaaacaac tgacagataa tttgaaagaa  2640
aaagctcttt catttatgag gcaaggttac cagagagaac ttctctatca gagggaagat  2700
ggctcttttca gtgcttttgg gaattatgac ccttctggga gcacttggtt gtcagccttt  2760
gttttaagat gttttcttga agccgatcct tacatagata ttgatcagaa tgtgttacac  2820
agaacataca cttggcttaa aggacatcag aaatccaacg tgaattttg ggatccagga  2880
agagtgattc atagtgagct tcaaggtggc aataaaagtc cagtaacact tacagcctat  2940
attgtaactt ctctcctggg atatagaaag tatcagccta acattgatgt gcaagagtct  3000
atccattttt tggagtctga attcagtaga ggaatttcag acaattatac tctagccctt  3060
ataacttatg cattgtcatc agtggggagt cctaaagcga aggaagcttt gaatatgctg  3120
acttggagag cagaacaaga aggtggcatg caattctggg tgtcatcaga gtccaaactt  3180
tctgactcct ggcagccacg ctccctggat attgaagttg cagcctatgc actgctctca  3240
cacttcttac aatttcagac ttctgaggga atcccaatta tgaggtggct aagcaggcaa  3300
agaaatagct tggggtggttt tgcatctact caggatacca ctgtggcttt aaaggctctg  3360
tctgaatttg cagccctaat gaatacgaaa aggacaaata tccaagtgac cgtgacgggg  3420
cctagctcac caagtcctgt aaagtttctg attgacacaa caaccgctt actccttcag  3480
acagcagagc ttgctgtggt acagccaatg gcagttaata tttccgcaaa tggttttga  3540
tttgctatttt gtcagctcaa tgttgtatat aatgtgaagg cttctgggtc ttctagaaga  3600
cgaagatcta tccaaaatca gaagcctttt gatttagat gttgctgtaa aagaaaataa  3660
agatgctctc aatcatgtgg atttgaatgt gtgtacaagc ttctcgggcc cgggtaggag  3720
tggcatggct cttatggaag ttaacctatt aagtggcttt atggtgcctt cagaagcaat  3780
ttctctgagc gagacagtga agaaagtgga atatgatcat ggaaaactca acctctatttt  3840
agattctgta aatgaaaccc agttttgtgt taatattcct gctgtgagaa actttaaagt  3900
tcaaatacc caagatgctt cagtgtccat agtggattac tatgagccaa ggagacaggc  3960
ggtgagaagt tacaactctg aagtgaagct gtcctcctgt gacctttgca gtgatgtcca  4020
gggctgccgt ccttgtgagg atggagcttc aggctccatt catccactct cagtcatttt  4080
tatttttctgt ttcaagcttc tgtacttttat ggaacttggg ctgtgattta ttttttaagg  4140
actctgtgta acactaacat ttccagtagt cacatgtgat tgttttgttt tcgtagaaga  4200
atactgcttc tattttgaaa aaaaaaaaaa aaaaaca                             4237
```

| SEQ ID NO: 11 | moltype = RNA   length = 4338 |
|---|---|

| FEATURE | Location/Qualifiers |
|---|---|
| source | 1..4338 |
| | mol_type = mRNA |
| | organism = Homo sapiens |

SEQUENCE: 11

```
atgcagggcc caccgctcct gaccgccgcc cacctcctct gcgtgtgcac cgccgcgctg   60
gccgtggctc ccgggcctcg gtttctggtg acagccccag ggatcatcag gcccggagga  120
aatgtgacta ttggggtgga gcttctggaa cactgcccct cacaggtgac tgtgaaggcg  180
gagctgctca agacagcatc aaacctcact gtctctgtcc tggaagcaga aggagtcttt  240
gaaaaaggct cttttaagac acttactctt ccatcactac ctctgaacag tgcagatgag  300
atttatgagc tacgtgtaac cggacgtacc caggatgaga ttttattctc taatagtacc  360
cgcttatcat ttgagaccaa gagaatatct gtcttcattc aaacagacaa ggccttatac  420
aagccaaagc aagaagtgaa gtttcgcatt gttcactact tctcagattt taagccttac  480
aaaacctctt taaacattct cattaaggac cccaaatcaa atttgatcca acagtggttg  540
tcacaacaaa gtgatcttgg agtcatttcc aaaacttttc agctatcttc ccatccaata  600
cttggtgact ggtctattca agttcaagtg aatgaccaga catattatca atcatttcag  660
gtttcagaat atgtattacc aaaatttgaa gtgactttgc agacaccatt atattgttct  720
atgaattcta agcatttaaa tggtaccatc acggcaaagt atacatatgg gaagccagtg  780
aaaggagacg taacgcttac atttttacct ttatcctttt ggggaaagaa gaaaaatatt  840
acaaaaacat ttaagataaa tggatctgca aacttctctt ttaatgatga agagatgaaa  900
aatgtaatgg attcttcaaa tggactttct gaatacctgg atctatcttc ccctggacca  960
gtagaaattt taaccacagt gacagaatca gttacaggta tttcaagaaa tgtaagcact 1020
aatgtgttct tcaagcaaca tgattacatc attgagtttt ttgattatac tactgtcttg 1080
aagccatctc tcaacttcac agccactgtg aaggtaactc gtgctgatgg caaccaactg 1140
actcttgaag aaagaagaaa taatgtagtc ataacagtga cacagagaaa ctatactgag 1200
tactggagcg gatctaacag tggaaatcag aaaatgcaag ctgttcagaa aataaattat 1260
actgtccccc aaagtggaac ttttaagatt gaattcccaa tcctggagga ttccagtgag 1320
ctacagttga aggcctattt ccttggtagt aaaagtagca tggcagttca tagtctgttt 1380
aagtctccta gtaagacata catccaacta aaaacaagag atgaaaatat aaaggtggga 1440
tcgcctttg agttggtggt tagtggcaac aaacgattga aggagttaag ctatatggta 1500
gtatccaggg gacagttggt ggctgtagga aaacaaaatt caacaatgtt ctctttaaca 1560
ccagaaaatt cttggactcc aaaagcctgt gtaattgtgt attatattga agatgatggg 1620
gaaattataa gtgatgttct aaaaattcct gttcagcttg ttttaaaaa taagataaag 1680
ctatattgga gtaaagtgaa agctgaacca tctgagaaag tctctcttag gatctctgtg 1740
acacagcctg actccatagt tgggattgta gctgttgaca aaagtgtgaa tctgatgaat 1800
gcctctaatg atattacaat ggaaatgtg tgccatgagt tggaacttta taacacagga 1860
tattatttag gcatgttcat aaattctttt gcagtctttc aggaatgtgg actctgggta 1920
ttgacagatg caaacctcac gaaggattat attgatggtg tttatgacaa tgcagaatat 1980
gctgagaggt ttattgagga aaatgaagga catattgtga atattcatga cttttctttg 2040
ggtagcagtc cacatgtccg aaagcatttt ccagagactt ggatttggct agacaccaac 2100
atgggttcca ggatttacca agaatttgaa gtaactgtac ctgattctat cacttcttgg 2160
gtggctactg gttttgtgat ctctgaggac ctgggtcttg gactaacaac tactccagtg 2220
gagctccaag ccttccaacc attttttcatt ttttgaatc ttccctactc tgttatcaga 2280
ggtgaagaat ttgctttgga ataactata ttcaattatt tgaaagatgc cactgaggtt 2340
aaggtaatca ttgagaaaag tgacaaattt gatattctaa tgacttcaag tgaaataaat 2400
gccacaagcc accagcagac ccttctggtt cccagtgagg atgggcaac tgttctttttt 2460
cccatcaggc caacacatct gggagaaatt cctatccaga tcacagctct ttcaccccact 2520
gcttctgatg ctatcacccca gatgatttta gtaaaggctg aaggaataga aaaatcatat 2580
tcacaatcca tcttattaga cttgactgac aataggctac agagtaccct gaaaactttg 2640
agtttctcat ttcctcctaa tacagtgact ggcagtgaaa gagttcagat cactgcaatt 2700
ggagatgttc ttggtccttc catcaatggc ttagcctcat tgattcggat gccttatgc 2760
tgtggtgaac agaacatgat aaattttgct ccaaatattt acattttgga ttatctgact 2820
aaaaagaaac aactgacaga taatttgaaa gaaaaagctc tttcatttat gaggcaaggt 2880
taccagagag aacttctcta tcagagggaa gatggctctt tcagtgcttt tgggaattat 2940
gaccccttctg ggagcacttg gttgtcagct tttgttttaa gatgtttcct tgaagccgat 3000
ccttacatag atattgatca gaatgtgtta cacagaacat acacttggct taaaggagat 3060
cagaaatcca acggtgaatt tgggatccca ggaagagtga ttcatagtga gcttcaaggt 3120
ggcaataaaa gtccagtaac acttacagcc tatattgtaa cttctctcct gggatataga 3180
aagtatcagc ctaacattga tgtgcaagag tctatccatt ttttggagtc tgaattcagt 3240
agaggaattt cagacaatta tactctagcc cttataactt atgcattgtc atcagtgggg 3300
agtcctaaag cgaaggaagc tttgaatatg ctgacttgga gagcagaaca agaaggtggc 3360
atgcaattct gggtgtcatc agagtccaaa ctttctgact cctggcagcc acgctccctg 3420
gatattgaag ttgcagccta tgcactgctc tcacacttct tacaatttca gacttctgag 3480
ggaatcccaa ttatgagtg gctaagcagg caaagaaata gcttgggtg tttttgcatct 3540
actcaggata ccactgtggc tttaaaggct ctgtctgaat ttgcagccct aatgaataca 3600
gaaaggacaa atatccaagt gaccgtgacg gggcctagct caccaagtcc tgtaaagttt 3660
ctgattgaca cacacaaccg cttactcctt cagacagcag agcttgctgt ggtacagcca 3720
acggcagtta atatttccgc aaatggtttt ggatttgcta tttgtcagct caatgttgta 3780
tataatgtga aggcttctgg gtcttctaga agacgaagta tatccaaaa tcaagaagcc 3840
tttgatttag atgttgctgt aaaagaaaat aaagatgatc tcaatcatgt ggatttgaat 3900
gtgtgtacaa gcttttcggg cccgggtagg agtggcatgg ctcttatgga agttaaccta 3960
ttaagtggcc ttatggtgcc ttcagaagca atttctctga gcgagacagt gaagaaagtg 4020
gaatatgatc atggaaaact caacctctat ttagattctg taaatgaaac ccagttttgt 4080
gttaatatc tgctgtgag aaactttaaa gttcaaata cccaagatgc ttcagtgtct 4140
atagtggatt actatgagcc aaggagacag gcggtgagaa gttacaactc tgaagtgaag 4200
ctgtcctcct gtgacctttg cagtgatgtc cagggctgcc gtccttgtga ggatggagct 4260
tcaggctccc atcatcactc ttcagtcatt tttatttcct gtttcaagct tctgtacttt 4320
atggaacttt ggctgtga                                                4338
```

```
SEQ ID NO: 12            moltype = RNA   length = 2938
FEATURE                  Location/Qualifiers
source                   1..2938
                         mol_type = mRNA
                         organism = Homo sapiens
SEQUENCE: 12
gttgacaaaa gtgtgaatct gatgaatgcc tctaatgata ttacaatgga aaatgtggtc   60
catgagttgg aactttataa cacaggatat tatttaggca tgttcatgaa ttcttttgca  120
gtcttttcagg aatgtggact ctgggtattg acagatgcaa acctcacgaa ggattatatt  180
gatggtgttt atgacaatgc agaatatgct gagaggttta tggaggaaaa tgaaggacat  240
attgtagata ttcatgactt ttctttgggt agcagtccac atgtccgaaa gcattttcca  300
gagacttgga tttggctaga caccaacatg ggttccagga tttaccaaga atttgaagta  360
actgtacctg attctatcac ttcttgggtg ctactggtt ttgtgatctc tgaggacctg  420
ggtcttggac taacaactac tccagtggag ctccaagcct tccaaccatt tttcattttt  480
ttgaatcttc cctactctgt tatcagaggt gaagaatttg ctttggaaat aactatattc  540
aattatttga aagatgccac tgaggttaag gtaatcattg agaaaagtga caaatttgat  600
attctaatga cttcaagtga aataaatgcc acaggccacc agcagaccct tctggttccc  660
agtgaggatg gggcaactgt tcttttttccc atcaggccaa cacatctggg agaaattcct  720
atcacagtca cagctctttc acccactgct tctgatgcta tcacccagat gatttttagta  780
aaggctgaag aatagaaaa atcatattca caatccatct tattagactt gactgacaat  840
aggctacaga gtaccctgaa aactttgagt ttctcatttc ctcctaatac agtgactggc  900
agtgaaagag ttcagatcac tgcaattgga gatgttcttg gtccttccat caatggctta  960
gcctcattga ttcggatgcc ttatggctgt ggtgaacaga acatgataaa ttttgctcca 1020
aatatttaca ttttggatta tctgactaaa aagaaacaac tgacagataa tttgaaagaa 1080
aaagctcttt catttatgag gcaaggttac cagagagaac ttctctatca gagggaagat 1140
ggctcttttca gtgcttttgg gaattatgac ccttctggga gcacttggtt gtcagctttt 1200
gttttaagat gtttccttga agccgatcct tacatagata ttgatcagaa tgtgttacac 1260
agaacataca cttggcttaa aggacatcag aaatccaacg gtgaattttg ggatccagga 1320
agagtgattc atagtgagct tcaaggtggc aataaaagtc cagtaacact tacagcctat 1380
attgtaactt ctctcctggg atatagaaag tatcagccta acttgatgt gcaagagtct 1440
atccattttt tggagtctga attcagtaga ggaatttcag acaattatac tctagcccctt 1500
ataacttatg cattgtcatc agtggggagt cctaaagcga aggaagcttt gaatatgctg 1560
acttggagag cagaacaaga aggtggcatg caattctggg tgtcatcaga gtccaaactt 1620
tctgactcct ggcagccacg ctccctggat attgaagttg cagcctatgc actgctctca 1680
cacttcttac aatttcagac ttctgaggga atcccaatta tgaggtggct aagcaggcaa 1740
agaaatagct tgggtggttt tgcatctact caggatacca ctgtggcttt aaaggctctg 1800
tctgaatttg cagccctaat gaatacgaaa aggacaaata tccaagtgac cgtgacgggg 1860
cctagctcac caagtcctgt aaagtttctg attgacacac acaaccgctt actccttcag 1920
acagcagagc ttgctgtggt acagccaacg gcagttaata tttccgcaaa tggttttgga 1980
tttgctattt gtcagctcaa tgttgtatat aatgtgaagg cttctgggtc ttctagaaga 2040
cgaagatcta tccaaaatca agaagccttt gatttagatt ttgctgtaaa agaaaataaa 2100
gatgatctca atcatgtgga tttgaatgtg tgtacaagct tttcgggccc gggtaggagt 2160
ggcatggctc ttatggaagt taaccatta agtggcttta tggtgcctca agaagcaatt 2220
tctctgagcg agacagtgaa gaaagtggaa tatgatcatg gaaaactcaa cctctattta 2280
gattctgtaa atgaaaccca gttttgtgtt aatattcctg ctgtgagaaa ctttaaagtt 2340
tcaaataccc aagatgcttc agtgtccata gtggattact atgagccaag gagacaggcg 2400
gtgagaagtt acaactctga agtgaagctg tcctcctgtg accttttgcag tgatgtccag 2460
ggctgccgtc cttgtgagga tggagcttca ggctcccatc atcactcttc agtcatttt 2520
attttctgtt tcaagcttct gtactttatg gaacttggc tgtgatttat ttttaaagga 2580
ctctgtgtaa cactaacatt tccagtagtc acatgtgatt gttttgtttt cgtagaagaa 2640
tactgcttct attttgaaaa aagagttttt tttcttcta tggggttgca gggatggtt 2700
acaacaggtc ctagcatgta tagctgcata gatttcttca cctgatcttt gtgtggaaga 2760
tcagaatgaa tgcagttgtg tgtctatatt ttcccctctc aaaatctttt agaattttt 2820
tggaggtgtt tgttttctcc agaataaagg tattacttta gaataaaaaa aaaaaaaaaa 2880
aaaaaaaaa aaaaaaaaa aaaaaaaaa aaaaaaaaa aaaaaaaaa aaaaaaa     2938

SEQ ID NO: 13            moltype = RNA   length = 2843
FEATURE                  Location/Qualifiers
source                   1..2843
                         mol_type = mRNA
                         organism = Homo sapiens
SEQUENCE: 13
ctgatgaatg cctctaatga tattacaatg gaaaatgtgg tccatgagtt ggaactttat   60
aacacaggat attatttagg catgttcatg aattcttttg cagtcttttca ggaatgtgga  120
ctctgggtat tgacagatgc aaacctcacg aaggattata ttgatggtgt ttatgacaat  180
gcagaatatg ctgagaggtt tatggaggaa aatgaaggac atattgtaga tattcatgac  240
ttttctttgg gtagcagtcc acatgtccga aagcattttc agagacttg atttggcta  300
gacaccaaca tgggttccag gatttaccaa gaatttgaag taactgtacc tgattctatc  360
acttcttggg tggctactgg ttttgtgatc tctgaggacc tgggtcttgg actaacaact  420
actccagtgg agctccaagc cttccaacca ttttttcattt ttttgaatct tccctactct  480
gttatcagag gtgaagaatt tgctttggaa ataactatat tcaattattt gaaagatgcc  540
actgaggtta aggtaatcat tgagaaaagt gacaaatttg atattctaat gacttcaagt  600
gaaataaatg ccacaggcca ccagcagacc cttctggttc ccagtgagga tggggcaact  660
gttctttttc ccatcaggcc aacacatctg ggagaaattc ctatcacagt cacagctctt  720
tcacccactg cttctgatgc tatcacccag atgattttag taaaggctga aggaatagaa  780
aaatcatatt cacaatccat cttattagac ttgactgaca ataggctaca gagtaccctg  840
aaaactttga gttctcatt tcctcctaat acagtgactg gcagtgaaag agttcagatc  900
actgcaattg gagatgttct tggtccttcc atcaatggct tagcctcatt gattcggatg  960
ccttatggct gtggtgaaca gaacatgata aattttgctc caaatattta cattttggat 1020
```

```
tatctgacta aaaagaaaca actgacagat aatttgaaag aaaaagctct ttcatttatg    1080
aggcaaggtt accagagaga acttctctat cagagggaag atggctcttt cagtgctttt    1140
gggaattatg acccttctgg gagcacttgg ttgtcagctt ttgttttaag atgtttcctt    1200
gaagccgatc cttacataga tattgatcag aatgtgttac acagaacata cacttggctt    1260
aaaggacatc agaaatccaa cggtgaattt tgggatccaa gaagagtgat tcatagtgag    1320
cttcaaggtg gcaataaaag tccagtaaca cttacagcct atattgtaac ttctctcctg    1380
ggatatagaa agtatcagcc taacattgat gtgcaagagt ctatccattt tttggagtct    1440
gaattcagta gaggaatttc agacaattat actctagccc ttataactta tgcattgtca    1500
tcagtgggga gtcctaaagc gaaggaagct ttgaatatgc tgacttggag agcagaacaa    1560
gaaggtggca tgcaattctg ggtgtcatca gagtccaaac tttctgactc ctggcagcca    1620
cgctccctgg atattgaagt tgcagcctat gcactgctct cacacttctt acaatttcag    1680
acttctgagg gaatcccaat tatgaggtgg ctaagcaggc aaagaaatag cttgggtggt    1740
tttgcatcta ctcaggatac cactgtggct ttaaaggctc tgtctgaatt tgcagcccta    1800
atgaatacag aaaggacaaa tatccaagtg accgtgacgg ggcctagctc accaagtcct    1860
gtaaagtttc tgattgacac acacaaccgc ttactccttc agacagcaga gcttgctgtg    1920
gtacagccaa cggcagttaa tatttccgca aatggttttg gatttgctat ttgtcagctc    1980
aatgttgtat ataatgtgaa ggcttctggg tcttctagaa gacgaagatc tatccaaaat    2040
caagaagcct ttgatttaga tgttgctgta aaagaaaata aagtgatct caatcatgtg    2100
gatttgaatg tgtgtacaag cttttcgggc ccgggtagga gtggcatggc tcttatggaa    2160
gttaacctat taagtggctt tatggtgcct tcagaagcaa tttctctgag cgagacagtg    2220
aagaaagtgg aatatgatca tggaaaactc aacctctatt tagattctgt aaatgaaacc    2280
cagttttgtg ttaatattcc tgctgtgaga aactttaaag tttcaaatac ccaagatgct    2340
tcagtgtcca tagtggatta ctatgagcca aggagacagg cggtgagaag ttacaactct    2400
gaagtgaagc tgtcctcctg tgacctttgc agtgatgtcc agggctgccg tccttgtgag    2460
aatggagctt caggctccca tcatcactct tcagtcattt ttattttctg tttcaagctt    2520
ctgtacttta tggaactttg gctgtgattt attttaaag gactctgtgt aacactaaca    2580
tttccagtag tcacatgtga ttgttttgtt ttcgtagaaa aatactgctt ctattttgaa    2640
aaaagagttt tttttctttc tatggggttg cagggatggt gtacaacagg tcctagcatg    2700
tatagctgca tagatttctt cacctgatct ttgtgtggaa gatcagaatg aatgcagttg    2760
tgtgtctata ttttcccctc tcaaaatctt ttagaatttt tttggaggtg tttgtttct    2820
ccagaataaa ggtattactt tag                                             2843
```

```
SEQ ID NO: 14           moltype = RNA   length = 8800
FEATURE                 Location/Qualifiers
source                  1..8800
                        mol_type = mRNA
                        organism = Homo sapiens
SEQUENCE: 14
agacgccgtc gagatgcagg gcccaccgct cctgaccgcc gcccacctcc tctgcgtgtg    60
caccgccgcg ctggccgtgg ctcccgggcc tcggtttctg gtgacagccc cagggatcat    120
caggcccgga ggaaatgtga ctattggggt ggagcttctg gaacactgcc cttcacaggt    180
gactgtgaag gcggagctgc tcaagacagc atcaaacctc actgtctctg tcctggaagc    240
agaaggagtc tttgaaaaag gctcttttaa gacacttact cttccatcag accccaaatc    300
aaatttgatc caacagtggt tgtcacaaca aagtgatcct ggagtcattt ccaaaacttt    360
tcagctatct tcccatccaa tacttggtga ctggtctatt caagttcaag tgaatgacca    420
gacatactat caatcatttc aggtttcaga atatgtatta ccaaaatttg aagtgacttt    480
gcagacaca ttatattgtt ctatgaattc taagcattta aatggtacca tcacggcaaa    540
gtatacatat gggaagccag tgaaggaga cgtaacgctt acattttac ctttatcctt    600
ttggggaaag aagaaaaata ttacaaaaac atttaagata aatggatctg caaacttctc    660
ttttaatgat gaagagatga aaatgtaat ggattcttca aatggacttt ctgaataacct    720
ggatctatct tcccctggac cagtagaaat tttaaccaca gtgacagaat cagttacagg    780
tatttcaaga aatgtaagca ctaatgtgtt cttcaagcaa catgattaca tcattgagtt    840
ttttgattat actactgtct tgaagccatc tctcaacttc acagccactg tgaaggtaac    900
tcgtgctgat ggcaaccaac tgactcttga agaaagaaga ataatgtag tcataacagt    960
gacacagaga aactatactg agtactggag cggatctaac agtggaaatc agaaaatgga    1020
agctgttcag aaaataaatt atactgtccc ccaaagtgga acttttaaga ttgaattccc    1080
aatcctggag gattccagtg agctacagtt gaaggcctat ttccttggta gtaaaagtag    1140
catggcagtt catagtctgt ttaagtctcc tagtaagaca tacatccaac taaaaacaag    1200
agatgaaaat ataaaggtgg gatcgccttt tgagttggtg gttagtgca acaaacgatt    1260
gaaggagtta agctatatgg tagtatccag gggacagttg gtggctgtag gaaaacaaaa    1320
ttcaacaatg ttctctcttaa caccagaaaa ttccttggact ccaaaagcct gtgtaattgt    1380
gtattatatt gaagatgatg gggaaattat aagtgatgtt ctaaaaattc ctgttcagct    1440
tgttttaaa aataagataa agctatattg gagtaaagtg aaagctgaac catctgagaa    1500
agtctctctt aggatctctg tgacacagcc tgactccata gttgggattg tagctgttga    1560
caaagtgtg aatctgatga atgcctctaa tgatattaca atggaaaatg tggtccatga    1620
gttgaacttt tataacacag gatattattt aggcatgttc atgaattctt ttgcagtctt    1680
tcaggaatgt ggactctggg tattgacaga tgcaaacctc acgaaggatt atattgatgg    1740
tgttttgac aatgcagaat atgctgagag gtttatggag gaaaatgaag gacatattgt    1800
agatattcat gacttttctt tgggtagcag tccacatgta gcgaaagcatt ttccagagac    1860
ttggatttgg ctagacacca acatgggtta caggatttac caagaatttg aagtaactgt    1920
acctgatct atcacttctt gggtggctac tggttttgtg atctctgagg acctgggtct    1980
tggactaaca actactccag tggagctcca agccttccaa ccattttca tttttttgaa    2040
tcttccctac tctgttatca gaggtgaaga atttgctttg gaataacta tattcaatta    2100
tttgaaagat gccactgagg ttaaggtaat cattgagaaa agtgacaaat ttgatattct    2160
aatgacttca aatgaaataa atgccacagg ccaccagcag accctctgg ttcccagtga    2220
ggatgggca actgttctt ttcccatcag gccaacacat ctgggagaaa ttcctatcac    2280
agtcacagct ctttcacccca ctgcttctga tgctgtcacc cagatgattt tagtaaaggc    2340
tgaaggaata gaaaaatcat attcacaatc catcttatta gacttgactg acaataggct    2400
acagagtacc ctgaaaactt tgagtttctc atttcctcct aatacagtga ctggcagtga    2460
```

```
aagagttcag atcactgcaa ttggagatgt tcttggtcct tccatcaatg gcttagcctc   2520
attgattcgg atgccttatg gctgtggtga acagaacatg ataaattttg ctccaaatat   2580
ttacattttg gattatctga ctaaaaagaa acaactgaca gataatttga aagaaaaagc   2640
tctttcattt atgaggcaag gttaccagag agaacttctc tatcagaggg aagatggctc   2700
tttcagtgct tttgggaatt atgacccttc tgggagcact tggttgtcag cttttgtttt   2760
aagatgtttc cttgaagccg atccttacat agatattgat cagaatgtgt tacacagaac   2820
atacacttgg cttaaaggac atcagaaatc aacggtgaa ttttgggatc caggaagagt    2880
gattcatagt gagcttcaag gtggcaataa aagtccagta acacttacag cctatattgt   2940
aacttctctc ctgggatata gaaagtatca gcctaacatt gatgtgcaag agtctatcca   3000
ttttttggag tctgaattca gtagaggaat ttcagacaat tatactctag ccctataac    3060
ttatgcattg tcatcagtgg ggagtcctaa agcgaaggaa gctttgaata tgctgacttg   3120
gagagcagaa caagaaggtg gcatgcaatt ctgggtgtca tcagagtcca aactttctga   3180
ctcctggcag ccacgctccc tggatattga agttgcagcc tatgcactgc tctcacactt   3240
cttacaattt cagacttctg agggaatccc aattatgagg tggctaagca ggcaaagaaa   3300
tagcttgggt ggttttgcat ctactcagga taccactgtg gctttaaagg ctctgtctga   3360
atttgcagcc ctaatgaata cagaaaggac aaatatccaa gtgaccgtga cggggcctag   3420
ctcaccaagt cctgtaaagt ttctgattga cacacacaac cgcttactcc ttcagacagc   3480
agagcttgct gtggtacagc caacggcagt taatatttcc gcaaatggtt ttggatttgc   3540
tatttgtcag ctcaatgttg tatataatgt gaaggcttct gggtcttcta gaagacgaag   3600
atctatccaa aatcaagaag cctttgattt agatgttgct gtaaaagaaa ataaagatga   3660
tctcaatcat gtggatttga atgtgtgtac aagcttttcg ggcccgggta ggagtggcat   3720
ggctcttatg gaagttaacc tattaagtgg cttttatgtg ccttcagaag caatttctct   3780
gagcgagaca gtgaagaaag tggaatatga tcatgaaaa ctcaacctct atttagattc     3840
tgtaaatgaa acccagtttt gtgttaatat tcctgctgtg agaaacttta aagtttcaaa   3900
tacccaagat gcttcagtgt ccatagtgga ttactatgag ccaaggagac aggcggtgag   3960
aagttacaac tctgaagtga agctgtcctc ctgtgacctt tgcagtgatg tccagggctg   4020
ccgtccttgt gaggatggag cttcaggctc ccatcatcac tcttcagtca tttttatttt   4080
ctgtttcaag cttctgtact ttatggaact ttggctgtga tttattttta aaggactctg   4140
tgtaacacta acatttccag tagtcacatg tgattgtttt gttttcgtag aagaatactg   4200
cttctatttt gaaaaagag ttttttttct ttctatgggt ttgcagggat ggtgtacaac     4260
aggtcctagc atgtatagct gcatagattt cttcacctga tctttgtgtg gaagatcaga   4320
atgaatgcag ttgtgtgtct atattttccc ctctcaaaat cttttagaat ttttttggag   4380
gtgtttgttt tctccagaat aaaggtatta ctttagaata ggtattctcc tcatttttgtg  4440
aaagaaatga acctagattc ttaagcatta ttacacatcc atgtttgctt aaagatggat   4500
ttccctggga atgggagaaa acagccagca ggaggagctt catctgttcc cttcccacct   4560
ccaacctagc cctactgccc accccacccc aacccacccc atgcccagtg gtctcagtag   4620
atacttctta actggaaatt cttctttttc agaatctagg tggtgaattt tttttaagtg   4680
gcacggtctt tttctgcttg aaatctgatc acacccccca gccattgccc tccctctctt   4740
tttcctctgt agagaaatgt gaggggcagt acatttactg tgcttttcac accatctcag   4800
aggttgagga gcatactgaa aattgccctg ggggtgctg ggtgtgctgt ctccttccca    4860
catcctcagc cccacaccag ctctatttca ggggtgagag tcagagagca ctgcaatatg   4920
tgcttcatgg gatttcgatt cgaagatcct agaccaggga gacactgtga gccagggata   4980
caacaaaata ctaggtaagt cactgcagac cgacctccct ggacttttggg aaagaagctg  5040
ggtttgtgga gaatcagagc atcttgacat gactgctgac ctaaagatcc ctggcattgg   5100
ccagggatcc tgtggaacct cttctagttc aggggtgtga gcattagact gccagttgtc   5160
tagtgacatc tgatgcttgc tgtgaacttt taagatcccc gaatcctgag cacctcaatc   5220
tttaattgcc ctgtattccg aagggtaata taatttatct ggatggaaat tttaaagatg   5280
aatccccctt ttttctttt ttctctcttt tctttccttc tccctttctt ctttgccttc    5340
taaatatact gaaatgattt agatatgtgt caacaattaa tgatctttta ttcaatctaa   5400
gaaatggttt agttttctc tttagctcta tggcatttca ctcaagtgga cagggggaaa    5460
agtaattgcc atgggctcca aagaatttgc tttatgtttt tagctattta aaaataaatc   5520
catcaaaaat aaagtatgca aatgtatctt ttaaagttaa tttttaaaaa tgctcttatt   5580
ttagtgaatt ttcagaaatt atagtggaat ggatgctcat atattgctta tggatatttt   5640
ggataccaaa gtaggaataa ctgacattca gtattttaaa gctggcaaac ctgtacatag   5700
aaaatagatc cccagacagt ggtctatgaa gagggcagtt aagtatcaaa tacttaatttt  5760
tcttgccttt ttttcttaag tggggaaaag tttctagatc tcttacacct ctgacacaat   5820
ctgttctaaa acaggcactt gtaatgttgg ggcctccttg taaacgtgtt tttgcccttt   5880
actctctggg agttctttaa aggtgaaatc atcttacaaa gaaattgggg gagggtcttg   5940
gcaaaggact ttcccctcct ctttcctggc ctgggaacct tatactgaca atcaatactt   6000
tatatttaa agtatataat ttatagttaa cttctagtgt aatatattag gaaacactag     6060
aatgaaagg ccattggaag acaggttgta tctttttag accatatttc cttgtttaaa      6120
aactatcatt tgaatacttt tttggtgaag aactccatgt tttcaagtta aagtcacct     6180
cgtaggccag gcgcagtggc tcatgcctgt aatcccagca ctctgggagg ctgaggcggg   6240
tgaatcacaa ggttaggagt ttgagaccag cctggccaat atggtgaaac cccgtcccta   6300
ctaaaaatac aaaatttagc caggcgtggt ggcatgcacc tgtagtccca cctactcgga   6360
aggctgaggc aggagaatca cttgaacctg agagacagag gttgcagtga gccgagatca   6420
cgccactgca ctccagcctg ggggacagag tgagattctg tctcaaaaaa caaaaaacaa   6480
aaaagtcacc ttgtaactca tctcttttta ttgtaagttt attaaaaatg aagaggacaa   6540
caatgagaag gaacataaag ggttagctag cactgtctcc tggtgcatgg ggctgtgcag   6600
atgtcccggc cacttcttcc ttcatacttc ccttagagaa cttgctctgc tacaagcagt   6660
gggcttggac taaaagtgat taaaatacca caggcataag gagaaaagga gtatatgtag   6720
tagtaataat tactagtata aattattttc ttcacatgct atgagtaata atattaaaaa   6780
actcattta ccattaagat tccttatgct gaagctcttc catttagaat actgtcaatg     6840
tcatttactg gtatgaacta aagtccccct tcttttccac tcactgggaa ccttagtaaa   6900
acaccagcat atcttacctc tctttctgac tggccgatga ttccagagac tgaatgttgg   6960
gaaaacctag tagccaaaca attctaggac agaataacat ttttatattt ggttccacca   7020
tcttattaca tttagttata gttttaaaaa agaaattcaa gcccattaaa atatgtctga   7080
tcaatgaaat gcttccttt attgtgttgt gctattgtac tttgtttttc aaaacattgt    7140
aaaaatagta tctttggttt agtattttgg attatatatt ataatctgag gagtgttttg   7200
```

```
cttatgtaga atccagatat atttctgtta cctaggagat gttacttaca tatgtaatac 7260
tgtatcctgc acgtggaaat attcagaatt gtagatagca taactctccc tgctcctatt 7320
cttttgagcc taggtataat tttttttttt tttttagaaa aagacatatt tagctttaat 7380
ttctatttat gctaaacata tttataagta gtctgtcaat ataataccaa ctattttat  7440
ttttacataa ttcaattatt tcatttgaca tgtctggcag actcaagaca ttaagtaaaa 7500
aattggaact atgattttc tttgtcattt tttaaaaaag aattatttta ttaacctgct  7560
ggcatataat ctgagttct tttcacaacc ttacttttc tgatttgctt tattgaatga   7620
ttgaatactc atttctttct aaaaatatgt tgtaaattct cccttggcaa gatttctccc 7680
tatgagggta gttattattt gagtctgcca agtggttacc atggggcaag gtgccatgat 7740
gtattcttgg gtgcattggt ttttgcgca ttgtaaattt aagacactta tagtaagtgg   7800
actcattcat agatgagttt cagaaccttt tacgttctcg gtagaggctt ctgtcggaca 7860
ggcagaagag tgtattcctc actttttttt ttgtcttcaa attccagtaa ggcatagcac 7920
tttaagaaa ttagaatttt tctatcatct atgcaaatga tatttatgtt aatattaaat   7980
atcttatgtt acactgggag taatttgagg tgcaattatt tttattacta ctttgaatag 8040
aggaccatta tccttcttc ttcagaaaac taagaagtaa gtgtaactt taaagtaagt    8100
atatatcagt gagagtaggc ttgtttaca actatttcta gccagtgagt tgtgttttca   8160
tgtctcatca aaagacaata ccacattgca tcattttaca aaatatgttg tcattttcat  8220
ttcagttgta acataggaaa atagatattt cctagatgat ttctgagttt cttactgcaa  8280
agaacagtta taaattggta tacatgtgtc tctgtaatag ggataatatt gatatatctg  8340
ttgctacata tttaagaatc attctatctt atgttgtctt gaggccaaga tttaccacgt  8400
ttgcccagtg tattgaattg gtggtagaag gtagttccat gttccatttg tagatcttta  8460
agattttatc tttgataact ttaatagaat gtggctcagt tctggtcctt caagcctgta  8520
tggtttggat tttcagtagg ggacagttga tgtggagtca atctctttgg tacacaggaa 8580
gctttataaa atttcattca cgaatctctt attttgggaa gctgttttgc atatgagaag  8640
aacactgttg aaataaggaa ctaaagcttt atatattgat caaggtgatt ctgaaagttt  8700
taatttttaa tgttgtaatg ttatgttatt gttaattgta ctttattatg tattcaatag  8760
aaaatcatga tttattaata aaagcttaaa ttctcatcta                        8800

SEQ ID NO: 15            moltype = RNA   length = 8980
FEATURE                  Location/Qualifiers
source                   1..8980
                         mol_type = mRNA
                         organism = Homo sapiens
SEQUENCE: 15
agacgccgtc gagatgcagg gcccaccgct cctgaccgcc gcccacctcc tctgcgtgtg   60
caccgccgcg ctggccgtgg ctcccggggcc tcggtttctg gtgacagccc cagggatcat 120
caggcccgga ggaaatgtga ctattggggt ggagcttctg gaacactgcc cttcacaggt  180
gactgtgaag gcggagctgc tcaagacagc atcaaacctc actgtctctg tcctggaagc  240
agaaggagtc tttgaaaaag gctctttaa gacacttact cttccatcac tacctcctga  300
cagtgcagat gagatttatg agctacgtgt aaccggacgt acccaggatg agattttatt  360
ctctaatagt acccgcttat catttgagac caagagaata tctgtcttca ttcaaacaga  420
caaggcctta tacaagccaa agcaagaagt gaagtttcgc attgttacac tcttctcaga  480
ttttaagcct tacaaaacct ctttaaacat tctcattaag gaccccaaat caaatttgat  540
ccaacagtgg ttgtcacaac aaagtgatct tggagtcatt tccaaaactt ttcagctatc  600
ttcccatcca atacttggtg actggtctat tcaagttcaa gtgaatgacc agacatacta  660
tcaatcatt caggttcag aatatgtatt accaaaattt gaagtgactt tgcagacacc   720
attatattgt tctatgaatt ctaagcattt aaatggtacc atcacggcaa agtatacata  780
tgggaagcca gtgaaaggag acgtaacgct tacatttta cctttatcct tttggggaaa   840
gaagaaaaat attacaaaaa catttaagat aaatggatct gcaaacttct cttttaatga  900
tgaagagatg aaaaatgtaa tggatcttc aaatggactt tctgaatacc tggatctatc  960
ttccctgga ccagtagaaa ttttaaccac agtgacagaa tcagttacag gtatttcaag 1020
aaatgtaagc actaatgtgt tcttcaagca acatgattac atcattgagt ttttgatta  1080
tactactgtc ttgaagccat ctctcaactt cacagccact gtgaaggtaa ctcgtgctga 1140
tggcaaccaa ctgactcttg aagaagaag aaataatgta gtcataacag tgacacagag 1200
aaactatact gagtactgga gcggatctaa cagtggaaat cagaaaatgg aagctgttca 1260
gaaaataaat tatactgtcc cccaaagtgg aacttttaag attgaattcc caatcctgga 1320
ggattccagt gagctacagt tgaaggccta tttccttggt agtaaagta gcatggcagt   1380
tcatagtctg tttaagtctc ctagtaagac atacatccaa ctaaaaacaa gagatgaaaa 1440
tataaaggtg ggatcgcctt ttgagttggt ggttagtggc aacaaacgat tgaaggagtt 1500
aagctatatg gtagtatcca ggggacagtt ggtggctgta ggaaaacaaa attcacaat  1560
gttctcttta acaccagaaa attcttggac tccaaaagcc tgtgtaattg tgtattatat 1620
tgaagatgat ggggaaatta taagtgatgt tctaaaaatt cctgttcagc ttgttttaa  1680
aaataagata aagctatatt ggagtaaagt gaaagctgaa ccatctgaga aagtctctct 1740
taggatctct gtgacacagc ctgactccat agttgggatt gtagctgttg acaaaagtgt 1800
gaatctgatg aatgcctcta atgatattac aatggaaaat gtggtccatg agttggaact 1860
ttataacaca ggatattatt taggcatgtt catgaattct tttgcagtct ttcaggaatg 1920
tggactctgg gtattgacag atgcaaacct cacgaaggat tatattgatg tgtttatga   1980
caatgcagaa tatgctgaga ggtttatgga ggaaatgaa ggacatattg tagatattca   2040
tgacttttct ttgggtagca gtcccacatgt ccgaaagcat tttccagaga cttggatttg  2100
gctagacacc aacatgggtt acaggatta ccaagaattt gaagtaactg tacctgattc   2160
tatcacttct tgggtggcta ctggttttgt gatctctgag gacctggtc ttggactaac   2220
aactactcca gtggagctcc aagccttcca accatttttc atttttttga atcttcccta  2280
ctctgttatc agaggtgaag aatttgcttt ggaaataact atatcaatt atttgaaaga   2340
tgccactgag gttaaggtaa tcattgagaa aagtgacaaa tttgattc taatgacttc   2400
aaatgaaata aatgccacag gccaccagca gaccctctg gttccagtg aggatgggc    2460
aactgttctt tttcccatca ggccaacaca tctgggagaa attcctatca cagtcacagc 2520
tctttcaccc actgcttctg atgctgtcac ccagatgatt ttagtaaagg ctgaaggaat 2580
agaaaaatca tattcacaat ccatcttatt agacttgact gacaataggc tacagagtac 2640
cctgaaaact ttgagtttct cattccttct taatacagtg actggcagtg aaagagttca 2700
```

```
gatcactgca attggagatg ttcttggtcc ttccatcaat ggcttagcct cattgattcg  2760
gatgccttat ggctgtggtg aacagaacat gataaatttt gctccaaata tttacatttt  2820
ggattatctg actaaaaaga aacaactgac agataaattg aaagaaaaag ctctttcatt  2880
tatgaggcaa ggttaccaga gagaacttct ctatcagagg gaagatggct cttttcagtgc  2940
ttttgggaat tatgacccctt ctgggagcac ttggttgtca gcttttgttt taagatgttt  3000
ccttgaagcc gatccttaca tagatattga tcagaatgtg ttacacagaa catacacttg  3060
gcttaaagga catcagaaat ccaacggtga attttgggat ccaggaagag tgattcatag  3120
tgagcttcaa ggtggcaata aaagtccagt aacacttaca gcctatattg taacttctct  3180
cctgggatat agaaagtatc agcctaacat tgatgtgcaa gagtctatcc attttttgga  3240
gtctgaattc agtagaggaa tttcagacaa ttatactcta gcccttataa cttatgcatt  3300
gtcatcagtg gggagtccta aagcgaagga agctttgaat atgctgactt ggagagcaga  3360
acaagaaggt ggcatgcaat tctgggtgtc atcagagtcc aaactttctg actcctggca  3420
gccacgctcc ctggatattg aagttgcagc ctatgcactg ctctcacact tcttacaatt  3480
tcagacttct gagggaatcc caattatgag gtggctaagc aggcaaagaa atagcttgag  3540
tggtttttgca tctactcagg ataccactgt ggctttaaag gctctgtctg aatttgcagc  3600
cctaatgaat acagaaagga caaatatcca agtgaccgtg acgggccta gctcaccaag  3660
tcctcttgct gtggtacagc caacggcagt taatatttcc gcaaatggtt ttggatttgc  3720
tatttgtcag ctcaatgttg tatataatgt gaaggcttct gggtcttcta gaagacgaag  3780
atctatccaa aatcaagaag cctttgattt agatgttgct gtaaaagaaa ataaagatga  3840
tctcaatcat gtggatttga atgtgtgtac aagcttttcg ggcccgggta ggagtggcat  3900
ggctcttatg gaagttaacc tattaagtgg ctttatggtg ccttcagaag caatttctct  3960
gagcagagaca gtgaagaaag tggaatatga tcatgaacaa ctcaacctct atttagattc  4020
tgtaaatgaa acccagtttt gtgttaatat tcctgctgtg agaaacttta aagtttcaaa  4080
tacccaagat gcttcagtgt ccatagtgga ttactatgag ccaaggagac aggcggtgag  4140
aagttacaac tctgaagtga agctgtcctc ctgtgacctt tgcagtgatg tccagggctg  4200
ccgtccttgt gaggatggag cttcaggctc ccatcatgca tcttcagtca tttttattt  4260
ctgtttcaag cttctgtact ttatggaact ttggctgtga tttatttta aaggactctg  4320
tgtaacacta acatttccag tagtcacatg tgattgtttt gttttcgtag aagaatactg  4380
cttctatttt gaaaaagag ttttttttct ttctatgggg ttgcagggat ggtgtacaac  4440
aggtcctagc atgtatagct gcatagattt cttcacctga tctttgtgtg gaagatcaga  4500
atgaatgcag ttgtgtgtct atatttttccc ctctcaaaat cttttagaat tttttttggag  4560
gtgtttgttt tctccagaat aaaggtatta ctttagaata ggtattctcc tcattttgtg  4620
aaagaaatga acctagattc ttaagcatta ttacacatcc atgtttgctt aaagatggat  4680
ttccctggga atgggagaaa acagccagca ggaggagctt catctgttcc cttcccacct  4740
ccaacctagc cctactgccc accccacccc aaccaccc atgcccagtg gtctcagtag  4800
atacttctta actggaaatt cttctttttc agaatctagg tggtgaattt tttttaagtg  4860
gcacggtctt tttctgcttg aaatctgatc acaccccca gccattgccc tcctctctt  4920
tttcctctgt agagaaatgt gaggggcagt acatttactg tgcttttcac accatctcag  4980
aggttgagga gcatactgaa aattgccctg gggggtgctg ggtgtgctgt ctccttccca  5040
catcctcagc cccacaccag ctctatttca ggggtgagag tcagagagca ctgcaatatg  5100
tgcttcatgg gatttcgatt cgaagatcct agaccaggga gacactgtga gccagggata  5160
caacaaaata ctaggtaagt cactgcagac cgacctccct gcagtttggg aaagaagctg  5220
ggtttgtgga gaatcagagc atcttgcat gactgctgac ctaaagatcc ctggcattgg  5280
ccagggatcc tgtggaacct cttcctagttc aggggtgtga gcattagact gccagttgtc  5340
tagtgacatc tgatgcttgc tgtgaacttt taagatcccc gaatcctgag cacctcaatc  5400
tttaattgcc ctgtattccg aagggtaata taatttatct ggatgaaat tttaaagatg  5460
aatcccccctt ttttcttttc ttctctcttt tcttttcttt ctttgccttc  5520
taaatatact gaaatgattt agatatgtgt caacaattaa tgatctttta ttcaatctaa  5580
gaaatggttt agtttttctc tttagctcta tggcatttca ctcaagtgga caggggaaaa  5640
agtaattgcc atgggctcca aagaatttgc tttatgtttt tagctattta aaaataaatc  5700
catcaaaaat aaagtatgca aatgtatctt ttaaagttaa tttttaaaaa tgctcttatt  5760
ttagtgaatt ttcagaaatt atagtggaat ggatgctcat atattgctta tggatatttt  5820
ggataccaaa gtaggaataa ctgacattca gtatttaaa gctggcaaac ctgtacatag  5880
aaaatagatc cccagacagt ggtctatgaa gagggcagtt aagtatcaaa acttaattt  5940
tcttgccttt ttttcttaag tggggaaaag tttctagatc ttctacacct ctgacacaat  6000
ctgttctaaa acaggcactt gtaatgttgg ggcctccttg taaacgtgtt tttgcccttt  6060
actctctggg agttctttaa aggtgaaatc atcttacaaa gaaattgggg gagggtcttg  6120
gcaaaggact ttcccctcct cttttcctggc ctgggaacct tatactgaca atcaatactt  6180
tatattttaa agtatataat ttatagttaa cttctagtgt aatatattag gaaacactag  6240
aatggaaagg ccattggaag acaggttgta tctttttttag accatatttc cttgtttaaa  6300
aactatcatt tgaatacttt tttggtgaag aactccatgt tttcaagtta aaggtcacct  6360
cgtaggccag cgcagtggc tcatgcctgt aatcccagca ctctgggagg ctgaggcggg  6420
tgaatcacaa ggttaggagt ttgagaccag cctggccaat atggtgaaac cccgtcccta  6480
ctaaaaatac aaaatttagc caggcgtggt ggcatgcacc tgtagtccca cctactcggg  6540
aggctgaggc aggagaatca cttgaacctg agagacagag gttgcagtga gccgagatca  6600
cgccactgca ctccagcctg gggacagag tgagattctg tctcaaaaaa caaaaaacaa  6660
aaaagtcacc ttgtaactca tctcttttta ttgtaagttt attaaaaatg aagaggacaa  6720
caatgagaag gaacataaag ggttagctag cactgtctcc tggtcatgg ggctgtgcag  6780
atgtcccgc cacttcttcc ttcatacttc cttagagaa cttgctctgc tacaagcagt  6840
gggcttggac taaaagtgat taaaataccaa caggcataag gagaaaagga gtatatgtag  6900
tagtaataat tactagtata aattattttc ttcacatgct atgagtaata atattaaaaa  6960
actcattta ccattaagat tccttatgct gaagctcttc catttagaat actgtcaatg  7020
tcatttactg gtatgaacta aagtccccct tcttttccac tcactgggaa ccttagtaaa  7080
acaccagcat atcttacctc tcttctgac tggccgatgc ttccagagac tgaatgttgg  7140
gaaacctag tagccaaaca attctaggac agaataacat ttttatattt ggttccacca  7200
tcttattaca tttagtttata gttttaaaaa agaaattcaa gcccattaaa atatgtctgg  7260
tcaatgaaat gcttcctttt attgtgttgt gctattgtac tttgtttttc aaaacattgt  7320
aaaaatagta tctttggttt agtattttgg attatatatt ataatctgag gagtgttttg  7380
cttatgtaga atccagatat atttctgtta cctaggagat gttacttaca tatgtaatac  7440
```

```
tgtatcctgc acgtggaaat attcagaatt gtagatagca taactctccc tgctcctatt   7500
cttttgagcc taggtataat tttttttttt ttttagaaa aagacatatt tagctttaat    7560
ttctatttat gctaaacata tttataagta gtctgtcaat ataataccaa ctattttat    7620
ttttacataa ttcaattatt tcatttgaca tgtctggcag actcaagaca ttaagtaaaa   7680
aattggaact atgattttc tttgtcattt tttaaaaaag aattatttta ttaacctgct    7740
ggcatataat ctggagttct tttcacaacc ttactttttc tgatttgctt tattgaatga   7800
ttgaatactc atttctttct aaaaatatgt tgtaaattct cccttggcaa gatttctccc   7860
tatgagggta gttattattt gagtctgcca agtggttacc atggggcaag gtgccatgat   7920
gtattcttgg gtgcattggt tttttgcgca ttgtaaattt aagacactta tagtaagtgg   7980
actcattcat agatgagttt cagaaccttt tacgttctcg gtagaggctt ctgtcggaca   8040
ggcagaagag tgtattcctc actttttttt ttgtcttcaa attccagtaa ggcatagcac   8100
ttttaagaaa ttagaatttt tctatcatct atgcaaatga tatttatgtt aatattaaat   8160
atcttatgtt acactgggag taatttgagg tgcaattatt tttattacta ctttgaatag  8220
aggaccatta tccttctttc ttcagaaaac taagaagtaa gtgtaacttt taaagtaagt   8280
atatatcagt gagagtaggc ttgttttaca actatttcta gccagtgagt tgtgtttca    8340
tgtctcatca aaagacaata ccacattgca tcattttaca aaatatgttg tcattttcat   8400
ttcagttgta acataggaaa atagatattt cctagatgat ttctgagttt cttactgcaa   8460
agaacagtta taaattggta tacatgtgtc tctgtaatag ggataatatt gatatatctg   8520
ttgctacata tttaagaatc attctatctt atgttgtctt gaggccaaga tttaccacgt   8580
ttgcccagtg tattgaattg gtggtagaag gtagttccat gttccatttg tagatcttta   8640
agattttatc tttgataact ttaatagaat gtggctcagt tctggtcctt caagcctgta   8700
tggtttggat tttcagtagg ggacagttga tgtggagtca atctcttttgg tacacaggaa   8760
gctttataaa atttcattca cgaatctctt attttgggaa gctgtttttgc atatgagaag   8820
aacactgttg aaataaggaa ctaaagcttt atatattgat caaggtgatt ctgaaagttt   8880
taatttttaa tgttgtaatg ttatgttatt gttaattgta ctttattatg tattcaatag   8940
aaaatcatga tttattaata aaagcttaaa ttctcatcta                         8980

SEQ ID NO: 16          moltype = DNA   length = 9401
FEATURE                Location/Qualifiers
source                 1..9401
                       mol_type = genomic DNA
                       organism = Homo sapiens
SEQUENCE: 16
atagttgcta tgaatttctc ctcacaagga tgggcctgtt tactcaccct gggcatcgtt    60
ggtagagcgc tagtgtaaac agcctgagga acccggtggg ccggggaagt gggcgcgctc   120
tgttctccgc ggccagctgg gacgccgggc caggtggggc cgcctgcgtt tagcaactgc   180
tttctcaccc cctggatttg cgatgtttgc cacagcagcg agaagcgcca ttgtaatggg   240
gatgggaggg gtggagcctc caagtcctgt ctcaatttag atctctcact ctgctgttag   300
gcgcgcccat ttcagattac taaactcgaa ttaagaggga aaaaaatca ggaggaggt    360
ggcaagccac accccacggt gcccgcgaac ttccccggca gcggactgta gcccaggcag   420
acgccgtcga gatgcagggc ccaccgctcc tgaccgccgc ccacctcctc tgcgtgtgca   480
ccgccgcgct ggccgtggct cccgggcctc ggttctggt gacagcccca gggatcatca    540
ggcccggagg aaatgtgact attgggtgg agcttctgga acactgccct tcacaggtga   600
ctgtgaaggc ggagctgctc aagacagcat caaacctcac tgtctctgtc ctggaagcag   660
aaggagtctt tgaaaaaggc tcttttaaga cacttactct tccatcacta cctctgaaca   720
gtgcagatga gatttatgag ctacgtgtaa ccggacgtac ccaggatgag attttattct   780
ctaatagtac ccgcttatca tttgagacca agagaatatc tgtcttcatt caaacagaca   840
aggcccttata caagcaaaag caagaagtga agtttcgcat tgttacactc ttctcagatt   900
ttaagcctta caaaaacctct ttaaacattc tcattaagga ccccaaatca aatttgatcc    960
aacagtggtt gtcacaacaa agtgatcttg gagtcatttc caaaactttt cagctatctt   1020
cccatccaat acttggtgac tggtctattc aagttcaagt gaatgaccag acatactatg   1080
aatcattttca ggtttcagaa tatgtattac caaaatttga agtgactttg cagacaccat   1140
tatattgttc tatgaattct aagcatttaa atggtaccat cacggcaaag tatacatatg   1200
ggaagccagt gaaaggagac gtaacgctta cattttttacc tttatccttt tggggaaaga   1260
agaaaatat tacaaaaaca tttaagataa atggatctgc aaacttctct tttaatgatg   1320
aagagatgaa aaatgtaatg gattcttcaa atggactttc tgaatacctg gatctatctt   1380
cccctggacc agtagaaatt ttaaccacag tgacagaatc agttacaggt atttcaagaa   1440
atgtaagcac taatgtgttc ttcaagcaac atgattacat cattgagttt ttttgattata   1500
ctactgtctt gaagccatct ctcaacttca gcccactgt gaaggtaact cgtgctgatg   1560
gcaaccaact gactcttgaa gaaagaagaa ataatgtagt cataacagtg acacagagaa   1620
actatactga gtactggagc ggatctaaca gtggaaatca gaaatggaa gctgttcaga   1680
aaataaatta tactgtcccc caagtgaaa cttttaagat tgaattccca atcctggagg   1740
attccagtga gctacagttg aaggcctatt tccttgtag taaaagtagc atggcagttc   1800
atagtctgtt taagtctcct agtaagacat acatccaact aaaaacaaga gatgaaaata   1860
taaaggtggg atcgccttttt gagttggtgg ttagtggcaa caaacgattg aaggagttaa   1920
gctatatggt agtatccagg ggacagttgg tggctgtagg aaaacaaaat tcaacaatgt   1980
tctctttaac accagaaaat tcttggactc caaaagcctg tgtaattgtg tattatattg   2040
aagatgatgg ggaaattata agtgatgttc taaaaattcc tgttcagctt gttttttaaaa   2100
ataagataaa gctatattgg atgaagtga aagctgaacc atctcgaaaa gtctctctta   2160
ggatctctgt gacacagcct gactccatag ttgggattgt agctgttgac aaaagtgtga   2220
atctgatgaa tgcctctaat gatattacaa tggaaaatgt ggtccatgag ttgaactttt   2280
ataacacagg atattattta ggcatgttca tgaattcttt tgcagtcttt caggaatgtg   2340
gactctgggt attgacagat gcaaacctca cgaaggatta tattgatggt gtttatgaca   2400
atgcagaata tgctgagagg tttatggagg aaaatgaagg acatattgta gatatcatg   2460
actttttctt gggtagcagt ccacatgtcc gaaagcattt tccagagact tggattgc    2520
tagacaccaa catgggttac aggatttacc aagaatttga agtaactgta cctgattcta   2580
tcacttcttg ggtggctact ggttttgtga tctctgagga cctgggtctt ggactaacaa   2640
ctactccagt ggagctccaa gccttccaac catttttcat ttttttgaat cttccctact   2700
ctgttatcag aggtgaagaa tttgctttgg aaataactat attcaattat ttgaaagatg   2760
```

```
ccactgaggt taaggtaatc attgagaaaa gtgacaaatt tgatattcta atgacttcaa   2820
atgaaataaa tgccacaggc caccagcaga cccttctggt tcccagtgag gatggggcaa   2880
ctgttctttt tcccatcagg ccaacacatc tgggagaaat tcctatcaca gtcacagctc   2940
tttcacccac tgcttctgat gctgtcaccc agatgatttt agtaaaggct gaaggaatag   3000
aaaaatcata ttcacaatcc atcttattag acttgactga caataggcta cagagtaccc   3060
tgaaaacttt gagtttctca tttcctccta atacagtgac tggcagtgaa agagttcaga   3120
tcactgcaat tggagatgtt cttggtcctt ccatcaatgg cttagcctca ttgattcgga   3180
tgccttatgg ctgtggtgaa cagaacatga taaattttgc tccaaatatt tacatttgg    3240
attatctgac taaaaagaaa caactgacag ataatttaga agaaaaagct ctttcattta   3300
tgaggcaagg ttaccagaga gaacttctct atcagaggga agatggctct ttcagtgctt   3360
ttgggaatta tgacccttct gggagcactt ggttgtcagc ttttgtttta agatgtttcc   3420
ttgaagccga tccttacata gatattgatc agaatgtgtt acacagaaca tacacttggc   3480
ttaaaggaca tcagaaatcc aacggtgaat tttgggatcc aggaagagtg attcatagtg   3540
agcttcaagg tggcaataaa agtccagtaa cacttacagc ctatattgta actctctct    3600
tgggatatag aaagtatcag cctaacattg atgtgcaaga gtctatccat tttttggagt   3660
ctgaattcag tagaggaatt tcagacaatt atactctagc cctataaact tatgcattgt   3720
catcagtggg gagtcctaaa gcgaaggaag ctttgaatat gctgacttgg agagcagaac   3780
aagaaggtgg catgcaattc tgggtgtcat cagagtccaa acttctgac tcctggcagc    3840
cacgctccct ggatattgaa gttgcagcct atgcactgct ctcacacttc ttacaatttc   3900
agacttctga gggaatccca attatgaggt ggctaagcag gcaaagaaat agcttgggtg   3960
gttttgcatc tactcaggat accactgtgg ctttaaaggc tctgtctgaa tttgcagccc   4020
taatgaatac agaaaggaca aatatccaag tgaccgtgac ggggcctagc tcaccaagtc   4080
ctcttgctgt ggtacagcca acggcagtta atatttccgc aaatggtttt ggatttgcta   4140
tttgtcagct caatgttgta tataatgtga aggcttctgg gtcttctaga agacgaagat   4200
ctatccaaaa tcaagaagcc tttgatttag atgttgctgt aaaagaaaat aaagatgatc   4260
tcaatcatgt ggatttgaat gtgtgtacaa gcttttcggg cccgggtagg agtggcatgg   4320
ctcttatgga agttaaccta ttaagtggct ttatggtgcc ttcagaagca atttctctga   4380
gcgagacagt gaagaaagtg gaatatgatc atggaaaact caacctctat ttagattctg   4440
taaatgaaac ccagttttgt gttaatattc ctgctgtgag aaactttaaa gtttcaaata   4500
cccaagatgc ttcagtgtcc atagtggatt actatgagcc aaggagacag gcggtgagaa   4560
gttacaactc tgaagtgaag ctgtcctcct gtgacctttg cagtgatgtc cagggctgcc   4620
gtccttgtga ggatgagct tcaggctccc atcatcactc ttcagtcatt tttattttct    4680
gtttcaagct tctgtacttt atggaacttt ggctgtgatt tattttaaa ggactctgtg    4740
taacactaac atttccagta gtcacatgtg attgttttgt tttcgtagaa gaatactgct   4800
tctattttga aaaagagttt tttttctttt ctatggggtt gcagggatgg tgtacaacag   4860
gtcctagcat gtatagctgc atagatttct tcacctgatc tttgtgtgga agatcagaat   4920
gaatgcagtt gtgtgtctat attttcccct ctcaaaatct tttagaattt tttggaggt    4980
gtttgttttc tccagaataa aggtattact ttagaatagg tattctcctc atttttgtgaa   5040
agaaatgaac ctagattctt aagcattatt acacatccat gtttgcttaa agatggattt   5100
ccctgggaat gggagaaaac agccagcagg aggagcttca tctgttccct tcccacctcc   5160
aacctagccc tactgcccac cccaccccaa cccacccccat gcccagtggt ctcagtagat   5220
acttcttaac tggaaattct ttcttttcag aatctaggtg gtgaatttt tttaagtggc    5280
acggtctttt tctgcttgaa atctgatcac accccccagc cattgccctc cctctcttt    5340
tcctctgtag agaaatgtga ggggcagtac atttactgtg cttttcacac catctccagg   5400
gttgaggagc atactgaaaa ttgccctggg gggtgctggg tgtgctgtct ccttcccaca   5460
tcctcagccc cacaccagct ctatttcagg ggtgagagtc agagagcact gcaatatgtg   5520
cttcatggga tttcgattcg aagatcctag accagggaga cactgtgagc cagggataca   5580
acaaaatact aggtaagtca ctgcagaccg acctccctgc agtttgggaa agaagctggg   5640
tttgtggaga atcagagcat cttgacatga ctgctgacct aaagatccct ggcattggcc   5700
agggatcctg tggaacctct tctagttcag gggtgtgagc attagactgc cagttgtcta   5760
gtgacatctg atgcttgctg tgaacttttta agatcccga atcctgagca cctcaatctt   5820
taattgccct gtattccgaa gggtaatata atttatctgg atggaaattt taaagatgaa   5880
tcccccttt ttcttttctt ctctcttttc tttcctttctc cctttcttct ttgccttcta    5940
aatatactga aatgatttag atatgtgtca acaattaatg atcttttatt caatctaaga   6000
aatggtttag ttttctctt tagctctatg gcatttcact caagtggaca ggggaaaaag    6060
taattgccat gggctccaaa gaatttgctt tatgtttta gctatttaaa aataaatcca    6120
tcaaaaataa agtatgcaaa tgtatctttt aaagttaatt tttaaaaatg ctcttatttt   6180
agtgaatttt cagaaattat agtggaatgg atgctcatat attgcttatg gatatttggg   6240
ataccaaagt aggaataact gacattcagt attttaaagc tggcaaacct gtacatgaaa   6300
aatagatccc cagacagtgg tctatgagga gggcagttaa gtatcaaata cttaattttc   6360
ttgccttttt ttcttaagtg gggaaagtt tctagatctc ttacacctct gacacaatct    6420
gttctaaaac aggcacttgt aatgttgggg cctccttgta aacgtgtttt tgcccttttac   6480
tctctgggag ttcttaaag gtgaaatcat cttacaaaga aattgggga gggtcttggc     6540
aaaggacttt cccctcctct ttcctgcct gggaaccttta tctgacaat caatacttta    6600
tattttaaag tatataattt atagttaact tctagtgtaa tatattagga aacactagaa   6660
tggaaaggcc attggaagac aggttgtatc ttttttagac catatttcct tgtttaaaaa   6720
ctatcatttg aatactttt tggtgaagaa ctccatgttt tcaagtttaaa ggtcacctcg    6780
taggccaggc gcagtggctc atgcctgtaa tcccagcact ctgggaggct gaggcggtg    6840
aatcacaagg ttaggagttt gagaccagcc tggccaatat ggtgaaaccc cgtccctact   6900
aaaaatacaa aatttagcca ggcgtggtgg catgcacctg tagtcccacc tactcggag    6960
gctgaggcag gagaatcact tgaacctgag agacagaggt tgcagtgagc cgagatcacg   7020
ccactgcact ccagcctggg ggacagagtg agattctgtc tcaaaaaaca aaaacaaaa    7080
aagtcacctt gtaactcatc tcttttttatt gtaagtttat taaaaatgaa gaggcacaaca  7140
atgagaagga acataaaggg ttagctagca ctgtctccgg tgcatgggg ctgtgcagat    7200
gtcccggcca cttcttcctt catacttccc ttagagaact tgctctgcta caagcagtgg   7260
gcttggacta aaagtgatta aaataccaca ggcataagga gaaaggagt atatgtagta    7320
gtaataatta ctagtataaa ttatttttctt cacatgctat gagtaataat attaaaaaac   7380
tcattttacc attaagattc cttatgctga agctcttcca tttagaatac tgtcaatgtc   7440
atttactggt atgaactaaa gtcccccttc ttttccactc actgggaacc ttagtaaaac   7500
```

```
accagcatat cttacctctc tttctgactg gccgatgctt ccagagactg aatgttggga   7560
aaacctagta gccaaacaat tctaggacag aataacattt ttatatttgg ttccaccatc   7620
ttattacatt tagttatagt tttaaaaaag aaattcaagc ccattaaaat atgtctggtc   7680
aatgaaatgc ttcctttat tgtgttgtgc tattgtactt tgttttcaa aacattgtaa    7740
aaatagtatc tttggtttag tattttggat tatatattat aatctgagga gtgttttgct  7800
tatgtagaat ccagatatat ttctgttacc taggagatgt tacttacata tgtaatactg  7860
tatcctgcac gtggaaatat tcagaattgt agatagcata actctccctg ctcctattct  7920
tttgagccta ggtataattt tttttttttt tttagaaaaa gacatattta gctttaattt  7980
ctatttatgc taaacatatt tataagtagt ctgtcaatat aataccaact attttattt   8040
ttacataatt caattatttc atttgacatg tctggcagac tcaagacatt aagtaaaaaa  8100
ttggaactat gattttcctt tgtcatttt taaaaaagaa ttatttatt aacctgctgg    8160
catataatct ggagttcttt tcacaacctt actttttctg atttgcttta ttgaatgatt  8220
gaatactcat ttctttctaa aaatatgttg taaattctcc cttggcaaga tttctcccta  8280
tgagggtagt tattatttga gtctgccaag tggttaccat ggggcaaggt gccatgatgt  8340
attcttgggt gcattggttt tttgcgcatt gtaaattaa gacacttata gtaagtggac   8400
tcattcatag atgagtttca gaacctttta cgttctcggt agaggcttct gtcggacagg  8460
cagaagagtg tattcctcac tttttttttt gtcttcaaat tccagtaagg catagcactt  8520
ttaagaaatt agaatttttc tatcatctat gcaaatgata tttatgttaa tattaaatat  8580
cttatgttac actgggagta atttgaggtg caattatttt tattactact ttgaatagag  8640
gaccattatc cttctttctt cagaaaacta agaagtaagt gtaactttta aagtaagtat  8700
atatcagtga gagtaggctt gttttacaac tatttctagc cagtgagttg tgttttcatg  8760
tctcatcaaa agacaatacc acattgcatc attttacaaa atatgttgtc atttttcattt 8820
cagttgtaac ataggaaaat agatatttcc tagatgattt ctgagtttct tactgcaaag  8880
aacagttata aattggtata catgtgtctc tgtaatagg ataatattga tatatctgtt   8940
gctacatatt taagaatcat tctatcttat gttgtcttga ggccaagatt taccacgttt  9000
gcccagtgta ttgaattggt ggtagaaggt agttccatgt tccatttgta gatctttaag  9060
attttatctt tgataacttt aatagaatgt ggctcagttc tggtccttca agcctgtatg  9120
gtttggattt tcagtagggg acagttgatg tggagtcaat ctctttggta cacaggaagc  9180
tttataaaat ttcattcacg aatctcttat tttgggaagc tgttttgcat atgagaagaa  9240
cactgttgaa ataaggaact aaagctttat atattgtaca aggtgattct gaaagtttta  9300
attttaatg ttgtaatgtt atgttattgt taattgtact ttattatgta ttcaatagaa   9360
aatcatgatt tattaataaa agcttaaatt ctccatctatt t                     9401

SEQ ID NO: 17           moltype = DNA   length = 9221
FEATURE                 Location/Qualifiers
source                  1..9221
                        mol_type = genomic DNA
                        organism = Homo sapiens
SEQUENCE: 17
atagttgcta tgaatttctc ctcacaagga tgggcctgtt tactcaccct gggcatcgtt    60
ggtagagcgc tagtgtaaac agcctgagga acccggtggg ccggggaagt gggcgcgctc   120
tgttctccgc ggccagctgg gacgccggc caggtgggc cgcctgcgtt tagcaactgc    180
tttctcaccc cctggatttg cgatgtttgc cacagcaggg agaagcgcca ttgtaatgcg  240
gatgggaggg gtggagcctc caagtcctgt ctcaatttag atctctcact ctgctgttaa  300
gcgcgcccat ttcagattac taaactcgaa ttaagaggga aaaaaaatca gggaggaggt   360
ggcaagccac accccacggt gcccgcgaac ttccccggca gcggactgta gcccaggcag   420
acgccgtcga gatgcagggc ccaccgctcc tgaccgcctc cacctcctc tgcgtgtgca    480
ccgccgcgct ggccgtggct cccgggcctc ggtttctggt gacagcccca gggatcatca   540
ggcccggagg aaatgtggact attggggtgg agcttctgga acactgccct tcacaggtga  600
ctgtgaaggc ggagctgctc aagacagcat caaacctcac tgtctctgtc ctggaagcag   660
aaggagtctt tgaaaaaggc tcttttaaga cacttactct tccatcagac cccaaatcaa   720
atttgatcca acagtggttg tcacaacaaa gtgatcttgg agtcatttcc aaaacttttc   780
agctatcttc ccatccaata cttggtgact ggtctattca agttcaagtg aatgaccaga   840
catactatca atcatttcag gtttcagaat atgtattacc aaaatttgaa gtgactttgc   900
agacaccatt atattgttct atgaattcta agcatttaaa tggtaccatc acggcaaagt   960
atacatatgg gaagccagtg aaaggagacg taacgcttac attttaacct ttatccttttt 1020
ggggaaagaa gaaaaatatt acaaaaacat ttaagataaa tggatctgca aacttctctt  1080
ttaatgatga agagatgaaa aatgtaatgg attcttcaaa tggactttct gaatacctgg  1140
atctatcttc ccctggacca gtagaaattt taaccacagt gacagaatca gttacaggta  1200
tttcaagaaa tgtaagcact aatgtgttct tcaagcaaca tgattacatc attgagtttt  1260
ttgattatac tactgtcttg aagccatctc tcaacttcac agccactgtg aaggtaactc  1320
gtgctgatgg caaccaactg actcttgaag aagaagaaa taatgtagtc ataacagtga   1380
cacagagaaa ctatactgag tactggagcg gatctaacag tggaaatcag aaaatggaag  1440
ctgttcagaa aataaattat actgtccccc aaagtgaact tttaagatt gaattcccaa   1500
tcctggagga ttccagtgag ctacagttga aggcctattt ccttggtagt aaaagtagca  1560
tggcagttca tagtctgttt aagtctccta gtaagacata catccaacta aaaacaagag  1620
atgaaaatat aaaggtggga tcgccttttg agttggtggt tagtggcaac aaacgattga   1680
aggagttaag ctatatggta gtatccaggg gacagttggt ggctgtagga aaacaaaatt   1740
caacaagtgt tctctttaaca ccagaaaatt cttggactac aaaagcctgt gtaattgtgt  1800
attatattga agatgatggg gaaattataa gtgatgttct aaaaaattcct gttcagcttg  1860
ttttaaaaa taagataaag ctatattgga gtaaagtgaa agctgaacca tctgagaaag   1920
tctctcttag gatctctgtg acacagcctg actccatagt tgggattgta gctgttgaca  1980
aaagtgtgaa tctgatgaat gcctctaatg atatttacaat ggaaaatgtg gtccatgagt  2040
tggaacttta taacacagga tattattttag gcatgttcat gaatttttcttg gcagtctitt 2100
aggaatgtgg actctgggta ttgacagatg caaacctcac gaaggattat attgatggta   2160
tttatgacaa tgcagaatat gctgagaggt ttatggagga aaatgaagga catattgtag   2220
atattcatga cttttctttg gtagcagtc cacatgtccg aaagcatttt ccagagactt    2280
ggatttggct agacaccaac atgggttaca ggatttacca agaatttgaa gtaactgtac   2340
ctgattctat cacttcttgg gtggctactg gttttgtgat ctctgaggac ctgggtcttg   2400
```

```
gactaacaac tactccagtg gagctccaag ccttccaacc attttttcatt tttttgaatc    2460
ttccctactc tgttatcaga ggtgaagaat ttgctttgga ataaactata ttcaattatt    2520
tgaaagatgc cactgaggtt aaggtaatca ttgagaaaag tgacaaattt gatattctaa    2580
tgacttcaaa tgaaataaat gccacaggcc accagcagac ccttctggtt cccagtgagg    2640
atggggaac tgttctttt cccatcaggc caacacatct gggagaaatt cctatccacag    2700
tcacagctct ttcacccact gcttctgatg ctgtcaccca gatgatttta gtaaaggctg    2760
aaggaataga aaaatcatat tcacaatcca tcttattaga cttgactgac aataggctac    2820
agagtaccct gaaaactttg agtttctcat ttcctcctaa tacagtgact ggcagtgaaa    2880
gagttcagat cactgcaatt ggagatgttc ttggtccttc catcaatggc ttagcctcat    2940
tgattcggat gccttatggc tgtggtgaac agaacatgat aaattttgct ccaaatattt    3000
acattttgga ttatctgact aaaaagaaac aactgacaga taatttgaaa gaaaaagctc    3060
tttcatttat gaggcaaggt taccagagag aacttctcta tcagagggaa gatggctctt    3120
tcagtgcttt tgggaattat gacccttctg ggagcacttg gttgtcagct tttgttttaa    3180
gatgtttcct tgaagccgat cctacatag atattgatca gaatgtgtca cacagaacat    3240
acacttggct taaaggacat cagaaatcca acggtgaatt ttgggatcca ggaagagtga    3300
ttcatagtga gcttcaaggt ggcaataaaa gtccagtaac acttacagcc tatattgtaa    3360
cttctctcct gggatataga aagtatcagc ctaacattga tgtgcaagag tctatccatt    3420
ttttggagtc tgaattcagt agaggaattt cagacaatta tactctagcc cttataactt    3480
atgcattgtc atcagtgggg agtcctaaag cgaaggaagc tttgaatatg ctgacttgga    3540
gagcagaaca agaaggtggc atgcaattct gggtgtcatc agagtccaaa ctttctgact    3600
cctggcagcc acgctccctg gatattgaag ttgcagccta tgcactgctc tcacacttct    3660
tacaatttca gacttctgag ggaatcccaa ttatgaggtg gctaagcagg caaagaaata    3720
gcttgggtgg ttttgcatct actcaggata ccactgttggc tttaaaggct ctgtctgaat    3780
ttgcagccct aatgaataca gaaaggacaa atatccaagt gaccgtgacg gggcctagct    3840
caccaagtcc tgtaaagttt ctgattgaca cacacaaccg cttactcctt cagacagcag    3900
agcttgctgt ggtacagcca acggcagtta atatttccgc aaatggtttt ggatttgcta    3960
tttgtcagct caatgttgta tataatgtga aggcttctgg gtcttctaga agacgaagat    4020
ctatccaaaa tcaagaagcc tttgatttag atgttgctgt aaaagaaaat aaagatgatc    4080
tcaatcatgt ggatttgaat gtgtgtacaa gcttttcggg cccgggtagg agtggcatgg    4140
ctcttatgga agttaaccta ttaagtggct ttatggtgac ttcagaagca atttctctga    4200
gcgagacagt gaagaaagtg aatatgatc atggaaaact caacctctat ttagattctg    4260
taaatgaaac ccagtttgt gttaatattc ctgctgtgag aaactttaaa gtttcaaata    4320
cccaagatgc ttcagtgtcc atagtggatt actatgagcc aaggagacag gcggtgagaa    4380
gttacaactc tgaagtgaag ctgcctcct gtgacctttg cagtgatgtc cagggctgcc    4440
gtccttgtga ggatggagct tcaggctccc atcatcactc ttcagtcatt tttatttct    4500
gtttcaagct tctgtacttt atggaacttt ggctgtgatt tatttttaaa ggactctgtg    4560
taacactaac atttccagta gtcacatgtg attgttttgt tttcgtagaa gaatactgct    4620
tctattttga aaaagagtt ttttttcttt ctatgggggt gcaggatgg tgtacaacag    4680
gtcctagcat gtatagctgc atagatttct tcacctgatc tttgtgtgga agatcagaat    4740
gaatgcagtt gtgtgtctat attttccct ctcaaaatct tttagaattt ttttggaggt    4800
gtttgttttc tccagaataa aggtattact ttagaatagg tattctcctc attttgtgaa    4860
agaaatgaac ctagattctt aagcattatt acacatccat gtttgcttaa agatggattt    4920
ccctgggaat gggagaaaac agccagcagg aggagcttca tctgttccct tcccacctcc    4980
aacctagccc tactgcccac cccacccaa cccaccccat gcccagtggt ctcagtagat    5040
acttcttaac tggaaattct ttctttcag aatctaggtg gtgaattttt tttaagtggc    5100
acggtctttt tctgcttgaa atctgatcac accccccagc cattgccctc cctctcttt    5160
tcctctgtag agaaatgtga ggggcagtac atttactgtg cttttcacac catctcagag    5220
gttgaggagc atactgaaaa ttgccctggg gggtgctggg tgtgctgtct ccttcccaca    5280
tcctcagccc cacaccagct ctatttcagg ggtgagagtc agagagcact gcaatatgtg    5340
cttcatggga tttcgattcg aagatcctag accaggagaa cactgtgagc cagggataca    5400
acaaaatact aggtaagtca ctgcagaccg acctccctgc agtttgggaa agaagctggg    5460
tttgtggaga atcagagcat cttgacatga ctgctgacct aaagatccct ggcattggcc    5520
agggatcctg tggaacctct tctagttcag gggtgtgagc attagactgc cagttgtcta    5580
gtgacatctg atgcttgctg tgaactttta agatccccga atcctgagca cctcaatctt    5640
taattgccct gtattccgaa gggtaatata atttatctgg atggaaattt taaagatgaa    5700
tcccccttt ttcttttctt ctctcttttc tttccttctc cctttcttct ttgccttcta    5760
aatatactga aatgatttag atatgtgtca acaattaatg atcttttatt caatctaaga    5820
aatggtttag ttttttctctt tagctctatg gcatttcact caagtggaca ggggaaaaag    5880
taattgccat gggctccaaa gaatttgctt tatgttttta gctatttaaa aataaatcca    5940
tcaaaaataa agtatgcaaa tgtatctttt aaagttaatt tttaaaaatg ctcttatttt    6000
agtgaatttt cagaaattat agtggaatgg atgctcatat attgcttatg gatattttgg    6060
ataccaaagt aggaataact gacattcagt attttaaagc tggcaaacct gtacatagaa    6120
aatagatccc cagacagtgg tctatgaaga gggcagttaa gtatcaaata cttaattttc    6180
ttgccttttt ttcttaagtg gggaaaagtt tctagatctc ttacacctct gacacaatct    6240
gttctaaaac aggcacttgt aatgttgggg cctccttgta aacgtgtttt tgccctttac    6300
tctctgggag ttcttaaag gtgaaatcat cttacaaaga aattgggga gggtcttggc    6360
aaaggactt cccctcctct ttcctggcct gggaaccta tactgacaat caatacttta    6420
tatttaaag tatataattt atagttaact ttagtgtaa tatattagga aacactagaa    6480
tggaaaggcc attggaagac aggttgtatc tttttttagac catatttcct tgtttaaaaa    6540
ctatcatttg aatactttt tggtgaagaa ctccatgttt tcaagttaaa ggtcacctcg    6600
taggccaggc gcagtggctc atgcctgtaa tcccagcact ctgggaggct gaggcgggtg    6660
aatcacaagg ttaggagttt gagaccagcc tggccaatat ggtgaaaccc cgtccctact    6720
aaaaatacaa aatttagcca ggcgtggtgg catgcacctg tagtcccacc tactcgggag    6780
gctgaggcag gagaatcact tgaacctgag agacaggagt tgcagatcacg    6840
ccactgcact ccagcctggg ggacagagtg agattctgtc tcaaaaaaca aaaaacaaaa    6900
aagtcaccctt gtaactcatc tctttttatt gtaagtttat taaaaatgaa gaggacaaca    6960
atgagaagga acataaaggg ttagctagca ctgtctcctg gtgcatgggg ctgtgcagat    7020
gtcccggcca cttcttcctt catacttccc ttagagaact tgctctgcta caagcagtgg    7080
gcttggacta aaagtgatta aaataccaca ggcataagga gaaaggagt atatgtagta    7140
```

```
gtaataatta ctagtataaa ttattttctt cacatgctat gagtaataat attaaaaaac  7200
tcattttacc attaagattc cttatgctga agctcttcca tttagaatac tgtcaatgtc  7260
atttactggt atgaactaaa gtcccccttc ttttccactc actgggaacc ttagtaaaac  7320
accagcatat cttacctctc tttctgactg gccgatgctt ccagagactg aatgttggga  7380
aaacctagta gccaaacaat tctaggacag aataacatt ttatatttgg ttccaccatc   7440
ttattacatt tagttatagt tttaaaaag aaattcaagc ccattaaaat atgtctggtc   7500
aatgaaatgc ttcctttat tgtgttgtgc tattgtactt tgttttcaa acattgtaa     7560
aaatagtatc tttggtttag tattttggat tatatattat aatctgagga gtgttttgct  7620
tatgtagaat ccagatatat ttctgttacc taggagatgt tacttacata tgtaatactg  7680
tatcctgcac gtggaaatat tcagaattgt agatagcata actctccctg ctcctattct  7740
tttgagccta ggtataattt ttttttttt tttagaaaaa gacatattta gctttaattt   7800
ctatttatgc taaacatatt tataagtagt ctgtcaatat aataccaact attttttattt 7860
ttacataatt caattatttc atttgacatg tctggcagca tcaagacatt aagtaaaaaa  7920
tggaactat gatttttctt tgtcatttt taaaaaagaa ttattttatt aacctgctgg    7980
catataatct ggagttcttt tcacaacctt acttttctg atttgcttta ttgaatgatt   8040
gaatactcat ttcttctaa aaatatgttg taaattctcc cttggcaaga tttctcccta   8100
tgagggtagt tattatttga gtctgccaag tggttaccat ggggcaaggt gccatgatgt  8160
attcttgggt gcattggttt tttgcgcatt gtaaatttaa gacacttata gtaagtggac  8220
tcattcatag atgagtttca gaacctttta cgttctcggt agaggcttct gtcggacagg  8280
cagaagagtg tattcctcac ttttttttt gtcttcaaat tccagtaagg catagcactt   8340
ttaagaaatt agaattttc tatcatctat gcaaatgata tttatgttaa tattaaatat   8400
cttatgttac actgggagta atttgaggtg caattatttt tattactact ttgaatagag  8460
gaccattatc cttctttctt cagaaaacta agaagtaagt gtaacttta aagtaagtat    8520
atatcagtga gagtaggctt gttttacaac tatttctagc cagtgagttg tgttttcatg  8580
tctcatcaaa agacaatacc acattgcatc attttacaaa atatgttgtc attttcattt  8640
cagttgtaac ataggaaaat agatatttcc tagatgattt ctgagtttct tactgcaaag  8700
aacagttata aattggtata catgtgtctc tgtaataggg ataatattga tatatctgtt  8760
gctacatatt taagaatcat tctatcttat gttgtcttga ggccaagatt taccacgttt  8820
gcccagtgta ttgaattggt ggtagaaggt agttccatgt tccatttgta gatctttaag  8880
attttatctt tgataacttt aatagaatgt ggctcagttc tggtccttca agcctgatg   8940
gtttggattt tcagtagggg acagttgatg tggagtcaat ctctttggta cacaggaagc  9000
tttataaaat ttcattcacg aatctcttat ttttgggaagc tgtttgcat atgagaagaa  9060
cactgttgaa ataaggaact aaagcttat atattgatca aggtgattct gaaagtttta   9120
atttttaatg ttgtaatgtt atgttattgt taattgtact ttattatgta ttcaatagaa  9180
aatcatgatt tattaataaa agcttaaatt ctcatctatt t                      9221
```

```
SEQ ID NO: 18           moltype = DNA   length = 9031
FEATURE                 Location/Qualifiers
source                  1..9031
                        mol_type = genomic DNA
                        organism = Homo sapiens
SEQUENCE: 18
agacgccgtc gagatgcagg gcccaccgct cctgaccgcc gcccacctcc tctgcgtgtg   60
caccgccgcg ctggccgtgg ctcccgggcc tcggtttctg gtgacagccc cagggatcat   120
caggcccgga ggaaatgtga ctattggggt ggagcttctg gaacactgcc ttcacaggt   180
gactgtgaag gcggagctgc tcaagacagc atcaaacctc actgtctctg tcctggaagc  240
agaaggagtc tttgaaaaag gctcttttaa gacacttact cttccatcac tacctctgaa  300
cagtgcagat gagatttatg agctacgtgt aaccggacgt acccaggatg agattttatt  360
ctctaatagt acccgcttat catttgagac caagagaata tctgtcttca ttcaaaacaga 420
caaggcctta tacaagccaa agcaagaagt gaagtttcgc attgttacac tcttctcaga  480
ttttaagcct tacaaaacct cttttaaacat tctcattaag gacccaaat caaatttgat   540
ccaacagtgg ttgtcacaac aaagtgatct tggagtcatt tccaaaactt ttcagctatc  600
ttcccatcca atacttggtg actggtctat tcaagttcaa gtgaatgacc agacatacta  660
tcaatcattt caggtttcag aatatgtatt accaaaattt gaagtgactt tgcagacacc  720
attatattgt tctatgaatt ctaagcattt aaatggtacc atcacggcaa agtatacata  780
tgggaagcca gtgaaaggag acgtaacgct tacatttta cctttatcct tttgggaaaa   840
gaagaaaaat attacaaaaa catttaagat aaatgatct gcaaactct cttttaatga    900
tgaagagatg aaaaatgtaa tggattcttc aaatggactt tctgaatacc tggatctatc   960
ttcccctgga ccagtagaaa tttttaaccac agtgacagaa tcagttacag gtatttcaag  1020
aaatgtaagc actaatgtgt tcttcaagca acatgattac atcattgagt ttttttgatta 1080
tactactgtc ttgaagccat ctctcaactt cacagccact gtgaaggtaa ctcgtgctga  1140
tggcaaccaa ctgactcttg aagaagaag aaataatgta gtcataacag tgacacagag   1200
aaactatact gagtactgga gcggatctaa cagtggaaat cagaaaatgg aagctgttca   1260
gaaaataaat tatactgtcc cccaaagtgg aacttttaag attgaattcc caatcctgga  1320
ggattccagt gagctacagt tgaaggccta tttccttggt agtaaaagta gcatggcagt   1380
tcatagtctg tttaagtctc ctagtaagac atacatccaa ctaaaaacaa gagatgaaaa   1440
tataaaggtg ggatcgcctt ttgagttggt ggttagtggc aacaaacgat tgaaggagtt   1500
aagctatatg gtagtatcca ggggacagtt ggtggctgta ggaaaacaaa attcaacaat   1560
gttctcttta acaccagaaa attcttggac tccaaaagcc tgtgtaattg tgtattataa   1620
tgaagatgat ggggaaatta taagtgatgt tctaaaaatt cctgttcagc ttgtttttaa  1680
aaataagata aagctatatt ggagtaaagt gaaagctgaa ccatctgaga aagtctctct   1740
taggatctct gtgacacagc ctgactccat agttgggatt gtagctgttg acaaaagtgt   1800
gaatctgatg aatgcctcta atgatattac aatggaaaat gtggtccatg agttggaact  1860
ttataacaca ggatattatt taggcatgtt catgaattct tttgcgaatg ttcaggaatg  1920
tggactctgg gtattgacag atgcaaacct cacgaaggat tatattgatg gtgtttatga  1980
caatgcagaa tatgctgaga ggtttatgga ggaaatgaa ggacatattg tagatattca   2040
tgactttcct ttgggtagca gtccacatgt ccgaaagcat tttccagaga cttggatttg  2100
gctagacacc aacatggggt acaggattta ccaagaattt gaagtaactg tacctgattc  2160
tatcacttct tgggtggcta ctggttttgt gatctctgag gacctgggtc ttggactaac  2220
```

```
aactactcca gtggagctcc aagccttcca accattttc attttttga atcttccta      2280
ctctgttatc agaggtgaag aatttgcttt ggaaataact atattcaatt atttgaaaga    2340
tgccactgag gttaaggtaa tcattgagaa aagtgacaaa tttgatattc taatgacttc    2400
aaatgaaata aatgccacag gccaccagca gacccttctg gttcccagtg aggatggggc    2460
aactgttctt tttcccatca ggccaacaca tctgggagaa attcctatca cagtcacagc    2520
tctttcaccc actgcttctg atgctgtcac ccagatgatt ttagtaaagg ctgaaggaat    2580
agaaaaatca tattcacaat ccatcttatt agacttgact gacaataggc tacagagtac    2640
cctgaaaact ttgagtttct catttcctcc taatacagtg actggcagtg aaagagttca    2700
gatcactgca attggagatg ttcttggtcc ttccatcaat ggcttagcct cattgattcg    2760
gatgccttat ggctgtggtg aacagaacat gataaatttt gctccaaata tttacatttt    2820
ggattatctg actaaaaaga aacaactgac agataatttg aaagaaaaag ctctttcatt    2880
tatgaggcaa ggttaccaga gagaacttct ctatcagagg gaagatggct ctttcagtgc    2940
ttttgggaat tatgacccttt ctgggagcac ttggttgtca gcttttgttt taagatgttt   3000
cctgaaagcc gatccttaca tagatattga tcagaatgtg ttacacagaa catacacttg    3060
gcttaaagga catcagaaat ccaacgtgta attttgggat ccaggaagag tgattcatag    3120
tgagcttcaa ggtggcaata aaagtccagt aacacttaca gcctatattg taacttctct    3180
cctgggatat agaaagtatc agcctaacat tgatgtgcaa gagtctatcc attttttgga    3240
gtctgaattc agtagaggaa tttatactcta gcccttataa cttatgcatt                3300
gtcatcagtg gggagtccta aagcgaagga agctttgaat atgctgactt ggagagcaga    3360
acaagaaggt ggcatgcaat tctgggtgtc atcagagtcc aaactttctg actcctggca    3420
gccacgctcc ctggatattg aagttgcagc ctatgcactg ctctcacact tcttacaatt    3480
tcagacttct gagggaatcc caattatgag gtggctaagc aggcaaagaa atagcttgag    3540
tggttttgca tctactcagg ataccactgt ggctttaaag gctctgtctg aatttgcagc    3600
cctaatgaat acagaaagga caaatatcca agtgaccgtg acggggccta gctcaccaag    3660
tcctgtaaag tttctgattg acacacacaa ccgcttactc cttcagacag cagagcttgc    3720
tgtggtacag ccaacggcag ttaatatttc cgcaaatgct tttggatttg ctatttgtca    3780
gctcaatgtt gtatataatg tgaaggcttc tgggtcttct agaagacgaa gatctatcca    3840
aaatcaagaa gcctttgatt tagatgttgc tgtaaaagaa aataaagatg atctcaatca    3900
tgtggatttg aatgtgtgta caagcttttc gggcccgggt aggagtggca tggctcttat    3960
ggaagttaac ctattaagtg gcttatggt gccttcagaa gcaatttctc tgagcgagac    4020
agtgaagaaa gtggaatatg atcatgaaa actcaacctc tatttagatt ctgtaaatga    4080
aacccagttt tgtgttaata ttcctgctgt gagaaacttt aaagtttcaa atacccaaga    4140
tgcttcagtg tccatagtgg attactatga gccaaggaga caggcggtga gaagttacaa    4200
ctctgaagtg aagctgtcct cctgtgacct ttgcagtgat gtccagggct gccgtccttg    4260
tgaggatgga gcttcaggct cccatcatca ctcttcagtc atttttattt tctgtttcaa    4320
gcttctgtac tttatggaac tttggctgtg atttatttttt aaaggactct gtgtaacact   4380
aacatttcca gtagtcacat gtgattgttt tgttttcgta gaagaatact gcttctattt    4440
tgaaaaaaga gttttttttc tttctatggg gttgcaggga tggtgtacaa caggtcctag    4500
catgtatagc tgcatagatt tcttcacctg atctttgtgt ggaagatcag aatgaatgca    4560
gttgtgtgtc tatattttcc cctctcaaaa tcttttagaa ttttttttgga ggtgtttgtt   4620
ttctccagaa taaaggtatt actttagaat aggtattctc ctcattttgt gaaagaaatg    4680
aacctagatt cttaagcatt attacacatc catgtttgct taaagatgga tttccctggg    4740
aatgggaaa aacagccagc aggaggagct tcatctgttc cctcccaac tccaacctag     4800
ccctactgcc caccccaccc caacccaccc catgcccagt ggtctcagta gatacttctt    4860
aactggaaat tctttcttttt cagaatctag gtggtgaatt tttttaagt ggcacggtct    4920
ttttctgctt gaaatctgat cacacccccc agccattgcc ctccctctct ttttcctctg    4980
tagagaaatg tgaggggcag tacatttact gtgcttttca caccatctca gaggttgagg    5040
agcatactga aaattgccct ggggggtgct gggtgtgctg tctccttccc acatcctcag    5100
ccccacacca gctctatttc aggggtgaga gtcagagagc actgcaatat gtgcttcatg    5160
ggatttcgat tcgaagatcc tagaccaggg agacactgtg agccagggat acaacaaaat    5220
actaggtaag tcactgcaga ccgacctccc tgcagtttgg gaaagaagct gggttttgtgg   5280
agaatcagag catcttgaca tgactgctga cctaaagatc cctggcattg gccaggatc    5340
ctgtggaacc tcttctagtt caggggtgtg agcattagac tgccagttgt ctagtgacat    5400
ctgatgcttc ctgtgaactt ttaagatccc cgaatcctga gcacctcaat ctttaattgc    5460
cctgtattcc gaagggtaat ataatttatc tggatgggaa ttttaaagat gaatccccct    5520
ttttctttt cttctctctt tcttttcctt ctccctttct tctttgcctt ctaaatatac    5580
tgaaatgatt tagatatgtg tcaacaatta atgatctttt attcaatcta agaaatggtt    5640
tagttttttct ctttagctct atggcatttc actcaagtgg acaggggaaa aagtaattgc   5700
catgggctcc aaaagatttg ctttatgttt ttagctattt aaaaataaat ccatcaaaaa    5760
taaagtatgc aaatgtatct ttttaagtta atttttaaaa atgctcttat tttagtgaat    5820
tttcagaaat tatagtggaa tggatgctca tatattgctt atggatattt tggataccaa    5880
agtaggaata actgacattc agtatttaa agctggcaaa cctgtacata gaaaatagat    5940
ccccagacag tggtctatga agagggcagt taagtatcaa atacttaatt ttcttgcctt    6000
tttttcttaa gtggggaaaa gttttctagat ctcttacacc tctgacacaa tctgttctaa   6060
aacaggcact tgtaatgttg gggcctcctt gtaaacgtgt ttttgccctt tactctctgg    6120
gagttcttta aaggtgaaat catcttacaa agaaattggg ggagggtctt ggcaaaggac    6180
tttcccctcc tctttcctgg cctgggaacc ttatactgac aatcaatact ttatatttta    6240
aagtatataa tttatagtta acttctagtg taatatatta ggaaacacta gaatgaaaag    6300
gccattggaa gacaggttgt atctttttta gaccatatttt ccttgtttaa aaactatcat   6360
ttgaatactt ttttggtgaa gaactccatg ttttcaagtt aaaggtcacc tcgtaggcca    6420
ggcgcagtgg ctcatgcctg taatcccagc actctgggag gctgaggcgg gtgaatcaca    6480
aggttaggag tttgagacca gcctggccaa tatggtgaaa ccccgtccct actaaaaata    6540
caaaatttag ccaggcgtgg tggcatgcac ctgtagtccc acctactcgg gaggctgagg    6600
caggagaatc acttgaacct gagacgagga ggttgcagtg agccgagatc acgccactgc    6660
actccagcct gggggacaga gtgagattct gtctcaaaaa acaaaaaaca aaaaagtcac    6720
cttgtaactc atctctttt attgtaagtt tattaaaaat gaagaggaca caatgagaa     6780
ggaacataaa gggttagcta gcactgtctc tggtgcatg ggctgtgca gatgtcccgg     6840
ccacttcttc cttcatactt cccttagaga acttgctctg ctacaagcag tgggcttgga    6900
ctaaaagtga ttaaaatacc acaggcataa ggagaaaagg agtatatgta gtagtaataa    6960
```

```
ttactagtat aaattatttt cttcacatgc tatgagtaat aatattaaaa aactcatttt    7020
accattaaga ttccttatgc tgaagctctt ccatttagaa tactgtcaat gtcatttact    7080
ggtatgaact aaagtccccc ttcttttcca ctcactggga accttagtaa aacaccagca    7140
tatcttacct ctctttctga ctggccgatg cttccagaga ctgaatgttg ggaaaaccta    7200
gtagccaaac aattctagga cagaataaca ttttatatt tggttccacc atcttattac     7260
atttagttat agttttaaaa aagaaattca agcccattaa aatatgtctg gtcaatgaaa    7320
tgcttccttt tattgtgttg tgctattgta ctttgttttt caaaacattg taaaaatagt    7380
atctttggtt tagtattttg gattatatat tataatctga ggagtgtttt gcttatgtag    7440
aatccagata tatttctgtt acctaggaga tgttacttac atatgtaata ctgtatcctg    7500
cacgtggaaa tattcagaat tgtagatagc ataactctcc ctgctcctat tcttttgagc    7560
ctaggtataa ttttttttttt tttttagaa aaagacatat ttagctttaa tttctattta    7620
tgctaaacat atttataagt agtctgtcaa tataatacca actatttta ttttacata     7680
attcaattat ttcatttgac atgtctggca gactcaagac attaagtaaa aaattggaac    7740
tatgattttt cttttgtcatt ttttaaaaaa gaattatttt attaacctgc tggcatataa   7800
tctggagttc ttttcacaac cttactttt ctgatttgct ttattgaatg attgaatact     7860
catttctttc taaaaaatatg ttgtaaattc tcccttggca agatttctcc ctatgagggt   7920
agttattatt tgagtctgcc aagtggttac catggggcaa ggtgccatga tgtattcttg    7980
ggtcattgg tttttgcgc attgtaaatt taagacactt atagtaagtg gactcattca      8040
tagatgagtt tcagaacctt ttacgttctc ggtagaggct tctgtcggac aggcagaaga    8100
gtgtattcct cacttttttt tttgtcttca aattccagta aggcatagca cttttaagaa    8160
attagaattt ttctatcatc tatgcaaatg atatttatgt taatattaaa tatcttatgt    8220
tacactggga gtaatttgag gtgcaattat ttttattact actttgaata gaggaccatt    8280
atccttcttt cttcagaaaa ctaagaagta agtgtaactt ttaaagtaag tatatatcag    8340
tgagagtagg cttgtttttac aactatttct agccagtgag ttgtgttttc atgtctcatc   8400
aaaagacaat accacattgc atcatttttac aaaatatgtt gtcattttca tttcagttgt   8460
aacataggaa aatagatatt tcctagatga tttctgagtt tcttactgca aagaacagtt    8520
ataaattggt atacatgtgt ctctgtaata gggataatat tgatatatct gttgctacat    8580
atttaagaat cattctatct tatgttgtct tgaggccaag atttaccacg tttgcccagt    8640
gtattgaatt ggtggtagaa ggtagttcca tgttccatt gtagatcttt aagatttat      8700
ctttgataac tttaatagaa tgtggctcag ttctggtcct tcaagcctgt atggtttgga    8760
ttttcagtag gggacagttg atgtggagtc aatctctttg gtacacagga agctttataa    8820
aatttcattc acgaatctct tattttggga agctgtttg catatgagaa gaacactgtt     8880
gaaataagga actaaagctt tatatattga tcaaggtgat tctgaaagtt ttaatttta     8940
atgttgtaat gttatgttat tgttaattgt actttattat gtattcaata gaaaatcatg    9000
atttattaat aaaagcttaa attctcatct a                                   9031

SEQ ID NO: 19         moltype = DNA   length = 5883
FEATURE               Location/Qualifiers
source                1..5883
                      mol_type = genomic DNA
                      organism = Homo sapiens
SEQUENCE: 19
ctaaactcga attaagaggg aaaaaaaatc agggaggagg tggcaagcca caccccacgg     60
tgcccgcgaa cttccccggc agcggactgt agcccaggca gacgccgtcg agatgcaggg    120
cccaccgctc ctgaccgccg cccacctcct ctgcgtgtgc accgccgcgc tggccgtggc    180
tcccgggcct cggtttctgg tgacagcccc agggatcatc aggcccggag gaaatgtgac    240
tattggggtg gagcttctgg aacactgccc ttcacaggtg actgtgaagg cggagctgct    300
caagacagca tcaaacctca ctgtctctgt cctggaagca gaaggagtct ttgaaaaagg    360
ctcttttaag acacttactc ttccatcact acctctgaac agtgcagatg agatttatga    420
gctacgtgta accggacgta cccaggatga gattttattc tctaatagta cccgcttatc    480
atttagacc aagagaatat ctgtcttcat tcaaacagac aaggcctttat acaagccaaa    540
gcaagaagtg aagtttcgca ttgttacact cttctcagat tttaagcctt acaaaaccct    600
tttaaacatt ctcattaagg accccaaatc aaatttgatc caacagtggt tgtcacaaca    660
aagtgatctt ggagtcattt ccaaaacttt tcagctatct tccatccaa tacttggtga     720
ctggtctatt caagttcaag tgaatgacca gacatattat caatcatttc aggttttcaga   780
atatgtatta ccaaaatttg aagtgacttt gcagacacca ttatattgtt ctatgaattc    840
taagcatttta aatggtacca tcacggcaaa gtatacatat gggaagccag tgaaaggaga   900
cgtaacgctt acatttttac cttatatcctt ttggggaaag aagaaaaata ttacaaaaac    960
atttagaata aatggatctg caaacttctc ttttaatgat gaagagatga aaaatgtaat   1020
ggattcttca aatggactttt ctgaataacct ggatctatct ccccctggac cagtagaaat   1080
tttaaccaca gtgacagaat cagttacagg tatttcaaga aatgtaagca ctaatgtgtt   1140
cttcaagcaa catgattaca tcattgagtt ttttgattat actactgtct gaagccatc    1200
tctcaacttc acagccactg tgaaggtaac tcgtgctgat ggcaaccaac tgactcttga   1260
agaaagaaga aataatgtag tcataacagt gacacagaaa aactatactg agtactggag  1320
cggatctaac agtggaaatc agaaaatgga agctgttcag aaaataaatt atactgtccc   1380
ccaaagtgga actttaagaa ttgaatttcc aatcctggag gattccagtg agctacagtt    1440
gaaggcctat ttccttggta gtaaaagtag catggcagtt catgtctgt ttaagtctcc    1500
tagtaagaca tacatccaac taaaaacaag agatgaaaat ataaaggtgg gatcgcctt     1560
tgagttggtg gttagtggca acaaacgatt gaaggagtta agctatatg tagtatccag    1620
gggacagttg gtggcgtag gaaaacaaaa ttcaacaatg ttctctttaa caccagaaaa    1680
ttcttggact ccaaaagcct gtgtaattgt gtattatt gaagatgatg gggaaattat      1740
aagtgatgtt ctaaaattc ctgttcagct tgttttaaaa ataagataa agctatattg      1800
gagtaaagtg aaagctgaac catctgagaa agtctctctt aggatctctg tgacacagcc    1860
tgactccata gttgggattg tagctgttga caaagtgtg aatctgatga tgcctctaa       1920
tgatattaca atggaaaatg tggtccatga gttggaactt tataacacag gatattttt     1980
aggcatgttc atgaattctt ttgcagtctt tcaggaatgt ggactctggg tattgacaga   2040
tgcaaacctc acgaaggatt atattgatgg tgtttatgac aatgcagaat atgctgagag    2100
gtttatggag gaaaatgaag gacatattgt agatattcat gacttttctt tgggtagcag    2160
tccacatgtc cgaaagcatt ttccagagac ttggattgg ctagacacca acatgggtta    2220
```

```
caggatttac caagaatttg aagtaactgt acctgattct atcacttctt gggtggctac  2280
tggttttgtg atctctgagg acctgggtct tggactaaca actactccag tggagctcca  2340
agccttccaa ccattttttca tttttttgaa tcttccctac tctgttatca gaggtgaaga  2400
atttgctttg gaaataacta tattcaatta tttgaaagat gccactgagg ttaaggtaat  2460
cattgagaaa agtgacaaat ttgatattct aatgacttca aatgaaataa atgccacagg  2520
ccaccagcag acccttctgg ttcccagtga ggatgtgggca actgttcttt ttcccatcag  2580
gccaacacat ctgggagaaa ttcctatcac agtcacagct ctttcaccca ctgcttctga  2640
tgctgtcacc cagatgattt tagtaaaggc tgaaggaata gaaaaatcat attcacaatc  2700
catcttatta gacttgactg acaataggct acagagtacc ctgaaaactt tgagtttctc  2760
atttcctcct aatacagtga ctggcagtga aagagttcag atcactgcaa ttggagatgt  2820
tcttggtcct tccatcaatg gcttagcctc attgattcgg atgccttatg ctgtggtga   2880
acagaacatg ataaattttg ctccaaatat ttacattttg gattatctga ctaaaaagaa  2940
acaactgaca gataatttga agaaaaaagc tctttcattt atgaggcaag gttaccagag  3000
agaacttctc tatcagaggg aagatggctc tttcagtgct tttgggaatt atgaccsttc  3060
tgggagcact tggttgtcag cttttgttt aagatgttc cttgaagccg atccttacat   3120
agatattgat cagaatgtgt tacacagaac atacactttgg cttaaaggac atcagaaatc  3180
caacggtgaa ttttgggatc caggaagagt gattcatagt gagcttcaag gtggcaataa  3240
aagtccagta acacttacag cctatattgt aacttctctc ctgggatata gaaagtatca  3300
gcctaacatt gatgtgcaag agtctatcca tttttttggag tctgaattca gtagaggaat  3360
ttcagacaat tatactctag cccttataac ttatgcattg tcatcagtgg ggagtcctaa  3420
agcgaaggaa gctttgaata tgctgacttg gagagcagaa caagaaggtg gcatgcaatt  3480
ctgggtgtca tcagagtcca aactttctga ctcctggcag ccacgctccc tggatattga  3540
agttgcagcc tatgcactgc tctcacactt cttacaattt cagacttctc agggaatccc  3600
aattatgagg tggctaagca ggcaaagaaa tagcttgggt ggtttttgcat ctactcagga  3660
taccactgtg gctttaaagg ctctgtctga atttgcagcc ctaatgaata cagaaaggac  3720
aaatatccaa gtgaccgtga cggggcctag ctcaccaagt cctgtaaagt ttctgattga  3780
cacacacaac cgcttactcc ttcagacagc agagcttgct gtggtacagc caatggcagt  3840
taatatttcc gcaaatggtt ttggattttgc tatttgtcag ctcaatgttg tatataatgt  3900
gaaggcttct gggtcttcta aagacgaag atctatccaa aatcaagaag cctttgattt  3960
agatgttgct gtaaaagaaa ataaagatga tctcaatcat gtggatttga atgtgtgtac  4020
aagcttttcg ggcccgggta ggagtggcat ggctcttatg gaagttaacc tattaagtgg  4080
ctttatggtg ccttcagaag caatttctct gagcgagaca gtgaagaaag tggaatgatga 4140
tcatggaaaa ctcaacctct atttagattc tgtaaatgaa acccagtttt gtgttaatat  4200
tcctgctgtg agaaacttta aagtttcaaa tacccaagat gcttcagtgt ccatagtgga  4260
ttactatgag ccaaggagac aggcggtgag aagttacaac tctgaagtga agctgtcctc  4320
ctgtgacctt tgcagtgatg tccagggctg ccgtccttgt gaggatggag cttcaggctc  4380
ccatcatcac tcttcagtca tttttattttt ctgtttcaag cttctgtact ttatggaact  4440
ttggctgtga tttattttta aaggactctg tgtaacacta acatttccag tagtcacatg  4500
tgattgtttt gttttcgtag aagaatactg cttctatttt gaaaaaagag ttttttttct  4560
ttctatgggg ttgcagggat ggtgtacaac aggtcctagc atgtatagct gcatagattt  4620
cttcacctga tctttgtgtg gaagatcaga atgaatgcag ttgtgtgtct atattttccc  4680
ctcacaaaat cttttagaat tttttttggag gtgtttgttt tctccagaat aaaggtatta  4740
ctttagaaat aggtattctc ctcatttttgt gaaagaaatg aacctagatt cttaagcatt  4800
attacacatc catgtttgct taaagatgga tttccctggg aatggagaaa aacagccagc  4860
aggaggagct tcatctgttc ccttcccacc tccaacctag ccctactgcc caccccaccc  4920
caacccaccc catgcccagt ggtctcagta gatacttctt aactggaaat tcttttcttttt 4980
cagaatctag gtggtgaatt ttttttaagt ggcacggtgat tttctgctt gaaatctgat  5040
cacaccccccc agccattgcc ctccctctct tttttcctctg tagagaaatg tgaggggcag  5100
tacattact gtgcttttca caccatctca gaggttgagg agcatactga aaattgccct  5160
gggggggtgct ggtgtgctg tctccttccc acatcctcag ccccacacca gctctatttc  5220
aggggtgaga gtcagagagc actgcaatat gtgcttcatg ggatttcgat tcgaagatcc  5280
tagaccaggg agacactgtg agccagggat acaacaaaat actaggtaag tcactgcaga  5340
ccgacctccc tgcagtttgg gaaagaagct gggtttgtgg agaatcagag catcttgaca  5400
tgactgctga cctaaagatc cctggcattg gccaggggatc ctgtgaaacc tcttctagtt  5460
caggggtgtg agcattagac tgccagttgt ctagtagacat ctgatgcttg ctgtgaactt  5520
ttaagatccc cgaatcctga gcacctcaat ctttaattgc cctgtattcc gaagggtaat  5580
ataatttatc tggatggaaa ttttaaagat gaatcccccct ttttttctttt cttctctctt  5640
ttcttttcctt ctccctttct tctttgcctt ctaaatatac tgaaatgatt tagatatgtg  5700
tcaacaatta atgatcttttt attcaatcta agaaatggtt tagttttttct ctttagctct  5760
atggcatttc actcaagtgg acagggggaaa aagtaattgc catgggctcc aaagaatttg  5820
ctttatgttt ttagctattt aaaaataaat ccatcaaaaa taaagtatgc aaatgtatct  5880
ttt                                                                5883

SEQ ID NO: 20         moltype = DNA    length = 4449
FEATURE               Location/Qualifiers
source                1..4449
                      mol_type = genomic DNA
                      organism = Homo sapiens
SEQUENCE: 20
aaaactcgaa ttaagaggga agaaaatca gggaggaggt ggcaagccac accccacggt    60
gcccgcgaac ttccccggca gcggactgta gcccaggcag acgccgtcga gatgcagggc   120
ccaccgctcc tgaccgccgc ccacctcctc tgcgtgtgca ccgccgcgct ggccgtggct   180
cccgggcctc ggtttctggt gacagcccca gggatcatca ggcccggagg aaatgtgact   240
attggggtgg agcttctgga acactgcccct tcacaggtgg gtgaaggcc ggagctgctc   300
aagacagcat caaacctcac tgtctctgtc ctggaagcag aaggagtctt tgaaaaaggc   360
tcttttaaga cacttactct tccatcacta cctctgaaca gtgcagatga gatttatgag   420
ctacgtgtaa ccgaacgtac ccaggatgag attttattct ctaatagtac ccgcttatca   480
tttgagacca agagaatatc tgtcttcatt caaacagaca aggccttata caagccaaag   540
caagaagtga agtttcgcat tgttacactc ttctcagatt ttaagcctta caaaaccctct  600
```

```
ttaaacattc tcattaagga ccccaaatca aatttgatcc aacagtggtt gtcacaacaa    660
agtgatcttg gagtcatttc caaaacttt cagctatctt cccatccaat acttggtgac    720
tggtctattc aagttcaagt gaatgaccag acatattatc aatcatttca ggtttcagaa    780
tatgtattac caaaatttga agtgactttg cagacaccat tatattgttc tatgaattct    840
aagcatttaa atggtaccat cacggcaaag tatacatatg ggaagccagt gaaaggagac    900
gtaacgctta cattttttacc tttatccttt tggggaaaga agaaaaatat tacaaaaaca    960
tttaagataa atggatctgc aaacttctct tttaatgatg aagagatgaa aaatgtaatg   1020
gattcttcaa atggactttc tgaatacctg gatctatctt cccctggacc agtagaaatt   1080
ttaaccacag tgacagaatc agttacaggt atttcaagaa atgtaagcac taatgtgttc   1140
ttcaagcaac atgattacat cattgagttt tttgattata ctactgtctt gaagccatct   1200
ctcaacttca cagccactgt gaaggtaact cgtgctgatg caaccaact gactcttgaa    1260
gaaagaagaa ataatgtagt cataacagtg acacagagaa actatactga gtactggagc   1320
ggatctaaca gtggaaatca gaaaatggaa gctgttcaga aaataaatta tactgtcccc   1380
caaagtggaa cttttaagat tgaattccca atcctggagt attccagtga gctacagttg   1440
aaggcctatt tccttggtag taaaagtagc atggcagttc atagtctgtt taagtctcct   1500
agtaagacat acatccaact aaaaacaaga gatgaaaata taaggtgggg atcgcctttt   1560
gagttggtgg ttagtggcaa caaacgattg aaggagttaa gctatatggt agtatccagg   1620
ggacagttgg tggctgtagg aaaacaaaat tcaacaatgt tctctttaac accagaaaat   1680
tcttggactc caaaagcctg tgtaattgtg tattatattg aagatgatgg ggaaattata   1740
agtgatgttc taaaaattcc tgttcagctt gttttaaaa ataagataaa gctatattgg   1800
agtaaagtga aagctgaacc atctgagaaa gtctctctta ggatctctgt gacacagcct   1860
gactccatag ttgggattgt agctgttgac aaaagtgtga atctgatgaa tgcctctaat   1920
gatattacaa tggaaaatgt ggtccatgag ttggaacttt ataacacagg atattatta    1980
ggcatgttca tgaattcttt tgcagtcttt caggaatgtg gactctgggt attgacagat   2040
gcaaacctca cgaaggatta tattgatggt gtttatgaca atgcagaata tgctgagagg   2100
tttatggagg aaaatgaagg acatattgta gatattcatg acttttcttt gggtagcagt   2160
ccacatgtcc gaaagcattt tccagagact tggatttggc tagacaccaa catgggttcc   2220
aggatttacc aagaatttga agtaactgta cctgattcta tcacttcttg ggtggctact   2280
ggttttgtga tctctgagga cctgggtctt ggactaacaa ctactccagt ggagctccaa   2340
gccttccaac cattttttcat ttttttgaat cttccctact ctgttatcag aggtgaagaa   2400
tttgctttgg aaataactat attcaattat ttgaaagatg ccactgaggt taaggtaatc   2460
attgagaaaa gtgacgaatt tgatattcta atgacttcaa atgaaataaa tgccacaggc   2520
caccagcaga cccttctggt tcccagtgag gatggggcaa ctgttctttt tcccatcagg   2580
ccaacacatc tgggagaaat tcctatcaca gtcacagctc tttcacccac tgcttctgat   2640
gctgtcaccc agatgatttt agtaaaggct gaaggaatag aaaaatcata ttcacaatcc   2700
atcttattag acttgactga caataggcta cagagtaccc tgaaaacttt gagtttctca   2760
tttcctccta atacagtgac tggcagtgaa agagttcaga tcactgcaat tggagatgtt   2820
cttggtcctt ccatcaatgg cttagcctca ttgattcgga tgccttatgg ctgtggtgaa   2880
cagaacatga taaatttttgc tccaaatatt tacatttttgg attatctgac taaaaagaaa   2940
caactgacag ataatttgaa agaaaaagct cttttcattta tgaggcaagg ttaccagaga   3000
gaacttctct atcagaggga agatggctct ttcagtgctt ttgggaatta tgacccttct   3060
gggagcactt ggttgtcagc ttttgtttta agatgtttcc ttgaagccga tccttacata   3120
gatattgatc agaatgtgtt acacagaaca tacacttggc ttaaaggaca tcagaaatcc   3180
aacggtgaat tttgggatcc aggaagagtg attcatagtg agcttcaagg tggcaataaa   3240
agtccagtaa cacttacagc ctatattgta acttctctcc tgggatatag aaagtatcag   3300
cctaacattg atgtgcaaga gtctatccat ttttttggagt ctgaattcag tagaggaatt   3360
tcagacaatt atactctagc ccttataact tatgcattgt catcagtgg gagtcctaaa   3420
gcgaaggaag ctttgaatat gctgacttgg agagcagaac aagaaggtgg catgcaattc   3480
tgggtgtcat cagagtccaa actttctgac tcctggcagc cacgctccct ggatattgaa   3540
gttgcagcct atgcactgct ctcacacttc ttacaatttc agacttctga gggaatccca   3600
attatgaggt ggctaagcag gcaaagaaat agcttgggtg gtttttgcatc tactcaggat   3660
accactgtgg ctttaaaggc tctgtctgaa tttgcagccc taatgaatac agaaaggaca   3720
aatatccagg tgaccgtgac ggggcctagc tcaccaagtc ctgtaaagtt tctgattgac   3780
acacacaacc gcttactcct tcagacagca gagcttgctg tggtacagcc aacggcagtt   3840
aatatttccg caaatggttt tggatttgct atttgtcagc tcaatgttgt atataatgtg   3900
aaggcttctg ggtcttctag aagacgaaga tctatccaaa atcaagaagc ctttgattta   3960
gatgttgctg taaaagaaaa taagatgat ctcaatcatg tggatttgaa tgtgtgtaca    4020
agcttttcgg gccgggtag gagtggcatg gctcttatgg aagttaacct attaagtggc   4080
tttatggtgc cttcagaagc aatttctctg agcgagacag tgaagaaagt ggaaatgat    4140
catggaaaac tcaacctcta tttagattct gtaaatgaaa cccagttttg tgttaatatt   4200
cctgctgtga gaaactttaa agtttcaaat acccaagatg cttcagtgtc catagtggat   4260
tactatgagc caaggagaca ggcggtgaga agttacaact ctgaagtgaa gctgtcctcc   4320
tgtgacctttt gcagtgatgt ccagggctgc cgtccttgtg aggatggagc ttcaggctcc   4380
catcatcact cttcagtcat ttttatttc tgtttcaagc ttctgtactt tatggaactt   4440
tggctgtga                                                           4449

SEQ ID NO: 21           moltype = DNA   length = 2273
FEATURE                 Location/Qualifiers
source                  1..2273
                        mol_type = genomic DNA
                        organism = Homo sapiens
SEQUENCE: 21
acacaccca cggtgcccgc gaacttcccc ggcagcggac tgtagcccag gcagacgccg     60
tcgagatgca gggcccaccg ctcctgaccg ccgcccacct cctctgcgtg tgcaccgccg    120
cgctggccgt ggctcccggg cctcggtttc tggtgacaga cccagggatc atcaggcccg    180
gaggaaatgt gactattggg gtggagcttc tggaacactg cccttcacag gtgactgtga    240
aggcggagct gctcaagaca gcatcaaacc tcactgtctc tgtcctggaa gcagaaggag    300
tctttgaaaa aggctctttt aagacactta ctcttccatc actacctctg aacagtcag    360
atgagattta tgagctacgt gtaaccggac gtaccccagga tgagatttta ttctctaata    420
```

```
gtacccgctt atcatttgag accaagagaa tatctgtctt cattcaaaca gacaaggcct    480
tatacaagcc aaagcaagaa gtgaagtttc gcattgttac actcttctca gattttaagc    540
cttacaaaac ctctttaaac attctcatta aggaccccaa atcaaatttg atccaacagt    600
ggttgtcaca acaaagtgat cttggagtca tttccaaaac ttttcagcta tcttcccatc    660
caatacttgg tgactggtct attcaagttc aagtgaatga ccagacatac tatcaatcat    720
ttcaggtttc agaatatgta ttaccaaaat ttgaagtgac tttgcagaca ccattatatt    780
gttctatgaa ttctaagcat ttaaatggta ccatcacggc aaagtataca tatgggaagc    840
cagtgaaagg agacgtaacg cttacatttt tacctttatc cttttgggga aagaagaaaa    900
atattacaaa aacatttaag ataaatggat ctgcaaactt ctcttttaat gatgaagaga    960
tgaaaaatgt aatggattct tcaaatggac tttctgaata cctgatctca tcttcccctg   1020
gaccagtaga aattttaacc acagtgacag aatcagttac aggtatttca agaaatgtaa   1080
gcactaatgt gttcttcaag caacatgatt acatcattga gttttttgat tatactactg   1140
tcttgaagcc atctctcaac ttcacagcca ctgtgaaggt aactcgtgct gatggcaacc   1200
aactgactct tgaagaaaga agaaataatg tagtcataac agtgacacag agaaactata   1260
ctgagtactg gagcggatct aacagtggaa atcagaaaat ggaagctgtt cagaaaataa   1320
attatactgt cccccaaagt ggaacttta agattgaatt cccaatcctg gaggattcca   1380
gtgagctaca gttgaaggcc tatttccttg gtagtaaaaa tagcatggca gttcatagtc   1440
tgtttaagtc tcctagtaag acatacatcc aactaaaaac aagagatgaa aatataaagg   1500
tgggatcgcc ttttgagttg gtggttagtg gcaacaaacg attgaaggag ttaagctata   1560
tggtagtatc caggggacag ttggtggctg taggaaaaca aaattcaaca atgttctctt   1620
taacaccaga aaattcttgg actccaaaag cctgtgtaat tgtgtattat attgaagatg   1680
atgggaaat tataagtgat gttctaaaaa ttcctgttca gcttgttttt aaaaataaga   1740
taaagctata ttggagtaaa gtgaaagctg aaccatctga gaaagtctct cttaggatct   1800
ctgtgacaca gcctgactcc atagttggga ttgtagctgt tgacaaaagt gtgaatctga   1860
tgaatgcctc taatgatatt acaatggaaa atgtggtcca tgagttggaa ctttataaca   1920
caggatatta tttaggcatg ttcatgaatt cttttgcagt cttcaggaa tgtggactct   1980
gggtattgac agatgcaaac ctcacgaagg attatattga tggtgtttat gacaatctct   2040
ttggtacaca ggaagcttta taaaattca ttcacgaatc tcttatttg ggaagctgtt   2100
ttgcatatga gaagaacact gttgaaataa ggaactaaag ctttatatat tgatcaaggt   2160
gattctgaaa gttttaattt taatgttgt aatgtattat tattgttat tgtacttat   2220
tatgtattca atagaaaatc atgattatt aataaaagct taaattctca tct         2273
```

SEQ ID NO: 22          moltype = DNA   length = 4688
FEATURE              Location/Qualifiers
source               1..4688
                      mol_type = genomic DNA
                      organism = Homo sapiens
SEQUENCE: 22

```
gggactgtag cccaggcaga cgccgtcgag atgcagggcc caccgctcct gaccgccgcc     60
cacctcctct gcgtgtgcac cgccgcgctg gccgtggctc ccgggcctcg gtttctggtg    120
acagccccag ggatcatcag gcccggagga aatgtgacta ttggggtgga gcttctggaa    180
cactgcccctt cacaggtgac tgtgaaggcg agctgctcca agacagcatc aaacctcact    240
gtctctgtcc tggaagcaga aggagtcttt gaaaaaggct cttttaagac acttactctt    300
ccatcactac ctctgaacag tgcagatgag atttatgagc tacgtgtaac cggacgtacc    360
caggatgaga ttttattctc taatagtacc cgcttatcat ttgagaccaa gagaatatct    420
gtcttcattc aaacagacaa ggcctttatac aagccaaagc aagaagtgaa gtttcgcatt    480
gttacactct tctcagattt taagccttac aaaacctctt taaacattct cattaaggac    540
cccaaatcaa atttgatcca acagtggttg tcaacaaaa gtgatcttgg agtcattcc    600
aaaactttc agctatcttc catccaata cttggtgact ggtctattca agttcaagtg    660
aatgaccaga catattatca atcatttcag gtttcagaat atgtattacc aaaatttgaa    720
gtgactttgc agacaccatt atattgttct atgaattcta agcatttaaa tggtaccatc    780
acggcaaagt atacatatgg gaagccagtg aaaggagacg taacgcttac attttttacc    840
ttatcctttt ggggaaagaa gaaaatatt acaaaaacat ttaagataaa tggatctgca    900
aacttctctt ttaatgatga gagatgaaa atgtaatgg attcttcaaa tggactttct    960
gaatacctgg atctcatctt cccctggacc agtagaaatt taaccacagt gacagaatca   1020
gttacaggta tttcaagaaa tgtaagcact aatgtgttct tcaagcaaca tgattacatc   1080
attgagtttt tgattatac cactgtcttg aagccatctc tcaacttcac agccactgtg   1140
aaggtaactc gtgctgatgg caaccaactg actcttgaag aaagaagaaa taatgtagtc   1200
ataacagtga cacagagaaa ctatactgag tactggagcg gatctaacag tggaaatcag   1260
aaaatggaag ctgttcagaa aataaattat actgtccccc aaagtggaac ttttaagatt   1320
gaattcccaa tcctggagga ttccagtgag ctacagttga aggcctattt ccttggtagt   1380
aaaagtagca tggcagttca tagtctgttt aagtctccta gtaagacata tccaacta   1440
aaaacaagag atgaaaatat aaaggtggga tcgccttttg agttggtggt tagtggcaac   1500
aaacgattga aggagttaag ctatatggta gtatccaggg gacagttggt ggctgtagga   1560
aaacaaaatt caacaatgtt ctctttaaca ccagaaaatt cttggactcc aaaagcctgt   1620
gtaattgtgt attatattga agatgatggg aaattataa gtgatgttct aaaaattcct   1680
gttcagcttg tttttaaaaa taagataag ctatattgga gtaaagtgaa agctgaacca   1740
tctgagaaag tctctcttag gatctctgtg acacagcctg actccatagt tgggattgta   1800
gctgttgaca aaagtgtgaa tctgatgaat gcctctaatg atattacaat ggaaaatgta   1860
gtccatgagt tggaacttta taacacagga tattatttag gcatgttcat gaattctttt   1920
gcagtctttc aggaatgtgg actctgggta ttgacagatg caaacctcac gaaggattat   1980
attgatggtg tttatgacaa tgcagaatat gctgagaggt ttatggagga aaatgaagga   2040
catattgtag atattcatga cttttctttg ggtagcagtc cacatgtccg aaagcatttt   2100
ccagagactt ggatttggct agacaccaac atgggttcca tgatttacca agaatttgaa   2160
gtaactgtac ctgattctat cacttcttgg gtggctactg gttttgtgat ctctgaggac   2220
ctgggtcttg gactaacaac tactccagtg gagctccaag cctccaacc attttttcatt   2280
tttttgaatc ttccctactc tgttatcaga ggtgaagaat ttgctttgga aataactata   2340
ttcaattatt tgaagatgc cactgaggtt aaggtaatca ttgagaaaag tgacaaattt   2400
gatattctaa tgacttcaag tgaaataaat gccacaggcc accagcagac ccttctggtt   2460
```

-continued

```
cccagtgagg atgggcaac tgttcttttt cccatcaggc caacacatct gggagaaatt   2520
cctatcacag tcacagctct ttcacccact gcttctgatg ctatcaccca gatgatttta   2580
gtaaaggctg aaggaataga aaaatcatat tcacaatcca tcttattaga cttgactgac   2640
aataggctac agagtaccct gaaaactttg agtttctcat ttcctcctaa tacagtgact   2700
ggcagtgaaa gagttcagat cactgcaatt ggagatgttc ttggtccttc catcaatggc   2760
ttagcctcat tgattcggat gccttatggc tgtggtgaac agaacatgat aaattttgct   2820
ccaaatattt acattttgga ttatctgact aaaaagaaac aactgacaga taatttgaaa   2880
gaaaaagctc tttcatttat gaggcaaggt taccagagag aacttctcta tcagagggaa   2940
gatggctctt tcagtgcttt tgggaattat gacccttctg ggagcacttg gttgtcagct   3000
tttgttttaa gatgtttcct tgaagccgat ccttacatag atattgatca gaatgtgtta   3060
cacagaacat acacttggct taaaggacat cagaaatcca acggtgaatt ttgggatcca   3120
ggaagagtga ttcatagtga gcttcaaggt ggcaataaaa gtccagcaac acttacagcc   3180
tatattgtaa cttctctcct gggatataga aagtatcagc ctaacattga tgtgcaagag   3240
tctatccatt ttttggagtc tgaattcagt agaggaattt cagacaatta tactctagcc   3300
cttataactt atgcattgtc atcagtgggg agtcctaaag cgaaggaagc tttgaatatg   3360
ctgacttgga gagcagaaca agaaggtggc atgcaattct gggtgtcatc agagtccaaa   3420
cttttctgact cctggcagcc acgctccctg gatattgaag ttgcagccta tgcactgctc   3480
tcacacttct tacaatttca gacttctgag ggaatcccaa ttatgaggtg gctaagcagg   3540
caaagaaata gcttgggtgg ttttgcatct actcaggata ccactgtggc tttaaaggct   3600
ctgtctgaat ttgcagccct aatgaataca gaaaggacaa atatccaagt gaccgtgacg   3660
gggcctagct caccaagtcc tgtaaagttt ctgattgaca cacacaaccg cttactcctt   3720
cagacagcag agcttgctgt ggtacagcca atggcagtta atatttccgc aaatggtttt   3780
ggatttgcta tttgtcagct caatgttgta tataatgtga aggcttctgg gtcttctaga   3840
agacgaagat ctatccaaaa tcaagaagcc tttgatttag atgttgctgt aaaagaaaat   3900
aaagatgatc tcaatcatgt ggatttgaat gtgtgtacaa gcttttcggg cccgggtagg   3960
agtggcatgg ctcttatgga agttaaccta ttaagtgct ttcagaaagca cagtgatgtc   4020
atttctctga gcgagacagt gaagaaagtg gaatatgatc atggaaaact caacctctat   4080
ttagattctg taaatgaaac ccagttttgt gttaatattc ctgctgtgag aaactttaaa   4140
gtttcaaata cccaagatgc ttcagtgtcc atagtggatt actatgagcc aaggagacag   4200
gcggtgagaa gttacaactc tgaagtgaag ctgtcctcct gtgaccttg cagtgatgtc   4260
cagggctgcc gtccttgtga ggatggagct tcaggctccc atcatcactc ttcagtcatt   4320
tttattttct gtttcaagct tctgtacttt atggaacttt ggctgtgatt tatttttaaa   4380
ggactctgtg taacactaac atttccagta gtcacatgtg attgttttgt tttcgtagaa   4440
gaatactgct tctattttga aaaaagagtt ttttttcttt ctatggggtt gcagggatgg   4500
tgtacaacag gtcctagcat gtatagctgc atagatttct tcacctgatc tttgtgtgaa   4560
agatcagaat gaatgcagtt gtgtgtctat attttcccct ctcaaaatct tttagaattt   4620
ttttggaggt gtttgtttc tccagaataa aggtattact ttagaaaaca aaaaaaaaaa   4680
aaaaaaaa                                                          4688

SEQ ID NO: 23           moltype = DNA  length = 4369
FEATURE                 Location/Qualifiers
source                  1..4369
                        mol_type = genomic DNA
                        organism = Homo sapiens
SEQUENCE: 23
tgtagcccag gcagacgccg tcgagatgca gggcccaccg ctcctgaccg ccgcccacct    60
cctctgcgtg tgcaccgccg cgctggccgt ggctcccgtg cctggtttc tggtgacagc   120
cccagggatc atcaggcccg gaggaaatgt gactattggg gtggagcttc tggaacactg   180
cccttcacag gtgactgtga aggcggagct gctcaagaca gcatcaaacc tcactgtctc   240
tgtcctggaa gcagaaggag tctttgaaaa aggctctttt aagacactta ctcttccatc   300
actacctgtc aacagtgcag atgagattta tgagctacgt gtaaccggac gtacccagga   360
tgagattttt ttctctaata gtacccgctt atcatttgag accaagagaa tatctgtctt   420
cattcaaaca gacaaggcct tatacaagcc aaagcaagaa gtgaagtttc gcattgttac   480
actcttctca gattttaagc cttacaaaac ctctttaaac attctcatta aggaccccaa   540
atcaaatttg atccaacagt ggttgtcaca acaaagtgat cttggagtca tttccaaaac   600
ttttcagcta tcttcccatc caatacttgg tgactggtct attcaagttc aagtgaatga   660
ccagacatat tatcaatcat tcagttttc agaatatgta ttaccaaaat ttgaagtgac   720
tttgcagaca ccattatatt gttctatgaa ttctaagcat ttaaatggta ccatcacggc   780
aaagtataca tatgggaagc cagtgaaagg agacgtaacg cttacatttt taccttatc   840
cttttgggga aagaagaaaa atattacaaa aacatttaag ataaatggat ctgcaaactt   900
ctctttttaat gatgaagaga tgaaaaatgt aatggattct tcaaatggac tttctgaata   960
cctggatcta tcttccctg gaccagtaga aattttaacc acagtgacag aatcagttac  1020
aggtatttca agaaatgtaa gcactaatgt gttcttcaag caacatgatt acatcattga  1080
gtttttttgat tatactactg tcttgaagcc atctctcaac ttcacagcca ctgtgaaggt  1140
aactcgtgct gatggcaacc aactgactct tgaagaaaga gaaaatgta tagtcataac  1200
agtgacacag agaaactata ctgagtactg gagcggatct aacagtggaa atcagaaaat  1260
ggaagctgtt cagaaaataa attatactgt cccccaaagt ggaacttta agattgaatt  1320
cccaatcctg gaggattcca gtgagctaca gttgaaggcc tatttccttg gtagtaaaag  1380
tagcatggca gttcatagtc tgtttaagtc tcctagtaag acatacatcc aactaaaaac  1440
aagagatgaa aatataaagg tgggatcgcc ttttgagttg gtggttagtg caacaaacg  1500
attgaaggag ttaagctata tggtagtatc caggggacag ttggtggctg tagaaaaca  1560
aaattcaaca atgttctctt taacaccaga aaattcttgg actccaaaag cctgtgtaat  1620
tgtgtattat attgaagatg atggggaaat ataagtgat gttctaaaaa ttcctgttca  1680
gcttgttttt aaaaataaga taagctataa ttggagtaag tgaaagctga aaccatctga  1740
gaaagtctct cttaggatct ctgtgacaca gcctgactcc atagttggga ttgtagctgt  1800
tgacaaaagt gtgaatctga tgaatgcctc taatgatatt acaatggaaa atggtggtcca  1860
tgagttggaa ctttataaca caggatatta tttaggcatg ttcatgaatt cttttgcagt  1920
cttttcaggaa tgtggactct gggtattgac agatgcaaac ctcacgaagg attatattga  1980
tggtgtttat gacaatgcag aatatgctga gaggtttatg gaggaaaatg aaggacatat  2040
```

```
tgtagatatt catgactttt ctttgggtag cagtccacat gtccgaaagc attttccaga  2100
gacttggatt tggctagaca ccaacatggg ttccaggatt taccaagaat ttgaagtaac  2160
tgtacctgat tctatcactt cttgggtggc tactggtttt gtgatctctg aggacctggg  2220
tcttggacta caactactc cagtggagct ccaagcctt caaccatttt tcattttttt  2280
gaatcttccc tactctgtta tcagaggtga agaatttgct ttggaaataa ctatattcaa  2340
ttatttgaaa gatgccactg aggttaaggt aatcattgag aaaagtgaca aatttgatat  2400
tctaatgact tcaagtgaaa taaatgccac aggccaccag cagacccttc tggttcccag  2460
tgaggatggg gcaactgttc tttttcccat caggccaaca catctgggag aaattcctat  2520
cacagtcaca gctcttcac ccactgcttc tgatgctatc acccagatga ttttagtaaa  2580
ggctgaagga atagaaaaat catattcaca atccatctta ttagacttga ctgacaatag  2640
gctacagagt accctgaaaa ctttgagttt ctcatttcct cctaatacag tgactggcag  2700
tgaaagagtt cagatcactg caattggaga tgttcttggt ccttccatca atggcttagc  2760
ctcattgatt cggatgcctt atggctgtgg tgaacagaac atgataaatt ttgctccaaa  2820
tatttacatt ttggattatc tgactaaaaa gaaacaactg acagataatt tgaaagaaaa  2880
agctctttca tttatgaggc aaggttacca gagagaactt ctctatcaga gggaagatgg  2940
ctctttcagt gcttttggga attatgaccc ttctgggagc acttggttgt cagcttttgt  3000
tttaagatgt ttccttgaag ccgatcctta catagatatt gatcagaatg tgttacacag  3060
aacatacact tggcttaaag gacatcagaa atccaacggt gaattttggg atccaggaag  3120
agtgattcat agtgagcttc aaggtggcaa taaaagtcca gtaacactta cagcctatat  3180
tgtaacttct ctcctgggat atagaaagta tcagcctaac attgatgtgc aagagtctat  3240
ccatttttg gagtctgaat tcagtagagg aatttcagac aattatactc tagccctat  3300
aacttatgca ttgtcatcag tggggagtcc taaagcgaag gaagcttga atatgctgac  3360
ttggagagca gaacaagaag gtggcatgca attctgggtg tcatcagagt ccaaactttc  3420
tgactcctgg cagccacgct ccctggatat tgaagttgca gcctatgcac tgctctcaca  3480
cttcttacaa tttcagactt ctgagggaat cccaattatg aggtggctaa gcaggcaaag  3540
aaatagccttg ggtggttttg catctactca ggataccact gtggctttaa aggctctgtc  3600
tgaatttgca gccctaatga atacagaaag gacaaatatc caagtgaccg tgacggggcc  3660
tagctcacca agtcctcttg ctgtggtaca gccaacggca gttaatattt ccgcaaatgg  3720
ttttggattt gctatttgtc agctcaatgt tgtatataat gtgaaggctt ctgggtcttc  3780
tagaagacga agatctatcc aaaatcaaga agcctttgat ttagatgttg ctgtaaaaga  3840
aaataaagat gatctcaatc atgtggattt gaatgtgtgt acaagctttt cgggcccggg  3900
taggagtggc atggctctta tggaagttaa cctattaagt ggcttatgg tgccttcaga  3960
agcaatttct ctgagcgaga cagtgaagaa agtggaatat gatcatgaa aactcaacct  4020
ctatttagat tctgtaaatg aaacccagtt ttgtgttaat attcctgctg tgagaaactt  4080
taaagtttca aatacccaag atgcttcagt gtccatagtg gattactatg agccaaggag  4140
acaggcggtg agaagttaca actctgaagt gaagctgtcc tcctgtgacc tttgcagtga  4200
tgtccagggc tgccgtcctt gtgaggatgg agcttcaggc tcccatcatc actcttcagt  4260
catttttatt ttctgtttca agcttctgta ctttatggaa ctttggctgt gatttatttt  4320
taaaggactc tgtgtaacac taacatttcc agtagtcaca tgtgattgt          4369
```

```
SEQ ID NO: 24          moltype = DNA   length = 4237
FEATURE                Location/Qualifiers
source                 1..4237
                       mol_type = genomic DNA
                       organism = Homo sapiens
SEQUENCE: 24
gaggcagacg ccgtcgagat gcagggccca ccgctcctga ccgccgccca cctcctctgc  60
gtgtgcaccg ccgcgctggc cgtggctccc gggcctcggt ttctggtgac agccccaggg  120
atcatcaggc ccggaggaaa tgtgactatt ggggtggagc ttctggaaca ctgcccttca  180
caggtgactg tgaaggcgga gctgctcaag acagcatcaa acctcactgt ctctgtcctg  240
gaagcagaag gagtctttga aaaaggctct tttaagcact tactcttcc atcagaccgc  300
aaatcaaatt tgatccaaca gtggttgtca caacaaagtg atcttggagt catttccaaa  360
acttttcagc tatcttccca tccaatactt ggtgactggt ctattcaagt tcaagtgaat  420
gaccagacat actatcaatc atttcaggtt tcagaatatg tattaccaaa atttgaagtg  480
actttgcaga caccattata ttgttctatg aattctaagc atttaaatg taccatcacg  540
gcaaagtata catatgggaa gccagtgaaa ggagacgtaa cgcttacatt ttacctttta  600
tcctttggg gaaagaagaa aaatattaca aaaacattta agataaatgg atctgcaaac  660
ttctctcttt a atgatgaaga gatgaaaaat gtaatggatt cttcaaatgg actttctgaa  720
tacctggatc tatcttcccc tggaccagta gaaatttaa ccacagtgac agaatcagtt  780
acaggtattt caagaaatgt aagcactaat gtgttcttca agcaacatga ttacatcatt  840
gagtttttg attatactac tgtcttgaag ccatctctca acttcacagc cactgtgaag  900
gtaactcgtg ctgatggcaa ccaactgact cttgaagaaa gaagaataa tgtagtcata  960
acagtgacac agagaaacta tactgagtac tggagcggat ctaacagtgg aaatcagaaa  1020
atggaagctg ttcagaaaat aaattatact gtccccacaa gtggaactt taagattgaa  1080
ttcccaatcc tggaggattc cagtgagcta cagttgaagg cctatttcct tggtagtaaa  1140
agtagcatgg cagttcatag tctgttaag tctcctagta agacatacat ccaactaaaa  1200
acaagagatg aaaatataaa ggtgggatcg cctttgagt tggtgttag tggcaacaaa  1260
cgattgaagg agttaagcta tatggtagta tccaggggac agttggtggc tgtaggaaaa  1320
caaaattcaa caatgttctc tttaacacca gaaaattctt ggactccaaa agcctgtgta  1380
attgtgtatt atattgaaga tgatgggaa attataagtg atgttctaaa aattcctgtt  1440
cagcttgttt ttaaaaataa gataaagcta tattggagta aagtgaaagc tgaaccatct  1500
gagaaagtct ctcttaggat ctctgtgaca cagcctgact ccatagtgg gattgtagct  1560
gttgacaaaa gtgtgaatct gatgaatgcc tctaatgata ttacaatgga aaatgtggtc  1620
catgagttga aactttataa cacaggatat tatttaggca tgttcatgaa ttcttttgca  1680
gtctttcagg aatgtggact ctgggtattg acagatgcaa acctcacgaa ggattatatt  1740
gatggtgttt atgacaatgc agaatatgct gagaggttta tggaggaaaa tgaaggacat  1800
attgtagata ttcatgactt tctttgggt agcagtccac atgtccgaaa gcattttcca  1860
gagacttgga tttggctaga caccaacatg ggttacagga tttaccaaga atttgaagta  1920
actgtacctg attctatcac ttcttgggtg gctactggtt ttgtgatctc tgaggacctg  1980
```

-continued

```
ggtcttggac taacaactac tccagtggag ctccaagcct tccaaccatt tttcattttt  2040
ttgaatcttc cctactctgt tatcagaggt gaagaatttg ctttggaaat aactatattc  2100
aattatttga aagatgccac tgaggttaag gtaatcattg agaaaagtga caaatttgat  2160
attctaatga cttcaaatga aataaatgcc acaggccacc agcagaccct tctggttccc  2220
agtgaggatg gggcaactgt tcttttttccc atcaggccaa cacatctggg agaaattcct  2280
atcacagtca cagctctttc acccactgct tctgatgctg tcacccagat gattttagta  2340
aaggctgaag gaatagaaaa atcatattca caatccatct tattagactt gactgacaat  2400
aggctacaga gtaccctgaa aactttgagt ttctcatttc ctcctaatac agtgactggc  2460
agtgaaagag ttcagatcac tgcaattgga gatgttcttg gtccttccat caatggctta  2520
gcctcattga ttcggatgcc ttatggctgt ggtgaacaga acatgataaa ttttgctcca  2580
aatatttaca ttttggatta tctgactaaa aagaaacaac tgacagataa tttgaaagaa  2640
aaagctcttt catttatgag gcaaggttac cagagagaac ttctctatca gagggaagat  2700
ggctcttttca gtgcttttgg gaattatgac ccttctggga gcacttggtt gtcagccttt  2760
gttttaagat gtttccttga agccgatcct tacatagata ttgatcagaa tgtgttacac  2820
agaacataca cttggcttaa aggacatcag aaatccaacg gtgaattttg ggatccagga  2880
agagtgattc atagtgagct tcaaggtggc aataaaagtc cagtaacact tacagcctat  2940
attgtaactt ctctcctggg atatagaaag tatcagccta acattgatgt gcaagagtct  3000
atccattttt tggagtctga attcagtaga ggaatttcaa ccaattatac tctagcccttt  3060
ataacttatg cattgtcatc agtggggagt cctaaagcga aggaagcttt gaatatgctg  3120
acttggagag cagaacaaga aggtggcatg caattctggg tgtcatcaga gtccaaactt  3180
tctgactcct ggcagccacg ctccctggat attgaagttg cagcctatgc actgctctca  3240
cacttcttac aatttcagac ttctgaggga atcccaatta tgaggtggct aagcaggcaa  3300
agaaatagct tgggtggttt tgcatctact caggatacca ctgtggcttt aaaggctctg  3360
tctgaatttg cagccctaat gaatacgaaa aggacaaata tccaagtgac cgtgacgggg  3420
cctagctcac caagtcctgt aaagtttctg attgacacac acaaccgctt actccttcag  3480
acagcagagc ttgctgtggt acagccaatg gcagttacta tttccgcaaa tggttttgga  3540
tttgctattt gtcagctcaa tgttgtatat aatgtgaagg cttctgggtc ttctagaaga  3600
cgaagatcta tccaaaatca agaagccttt tgatttagat gttgctgtaa aagaaaataa  3660
agatgatctc aatcatgtgg atttgaatgt gtgtacaagc ttttcgggcc cgggtaggag  3720
tggcatggct cttatggaag ttaacctatt aagtggcttt atggtgcctt cagaagcaat  3780
ttctctgagc gagacagtga agaaagtgga atatgatcat ggaaaactca acctctatt   3840
agattctgta aatgaaaccc agttttgtgt taatattcct gctgtgagaa actttaaagt  3900
ttcaaatacc caagatgctt cagtgtccat agtggattac tatgagccaa ggagacaggc  3960
ggtgagaagt tacaactctg aagtgaagct gtcctcctgt gaccttttgca gtgatgtcca  4020
gggctgccgt ccttgtgagg atgggagcttc aggctcccat catcactctt cagtcatttt  4080
tatttttctgt ttcaagcttc tgtacttat ggaactttgg ctgtgattta tttttaaagg  4140
actctgtgta acactaacat ttccagtagt cacatgtgat tgttttgttt tcgtagaaga  4200
atactgcttc tattttgaaa aaaaaaaaaa aaaaaca                            4237
```

```
SEQ ID NO: 25          moltype = DNA   length = 4338
FEATURE                Location/Qualifiers
source                 1..4338
                       mol_type = genomic DNA
                       organism = Homo sapiens
SEQUENCE: 25
atgcagggcc caccgctcct gaccgccgcc cacctcctct gcgtgtgcac cgccgcgctg    60
gccgtgggct c ccgggcctcg gtttctggtg acagcccag ggatcatcag gcccggagga   120
aatgtgacta ttggggtgga gcttctggaa cactgcccctt cacaggtgac tgtgaaggcg   180
gagctgctca agacagcatc aaacctcact gtctctgtcc tggaagcaga aggagtctttt  240
gaaaaaggct cttttaagac acttactctt ccatcactac ctctgaacag tgcagatgag   300
atttatgagc tacgtgtaac cggacgtacc caggatgaga ttttattctc taatagtacc   360
cgcttatcat ttgagaccaa gagaatatct gtcttcattc aaacagacaa ggccttatac   420
aagccaaagc aagaagtgaa gtttcgcatt gttacactct tctcagattt taagccttac   480
aaaacctctt taaacattct cattaaggac cccaaatcaa atttgatcca acagtggttg   540
tcacaacaaa gtgatcttgg agtcatttcc aaaacttttc agctatcttc ccatccaata   600
cttggtgact ggtctattca agttcaagtg aatgaccaga catattatca atcatttcag   660
gtttcagaat atgtattacc aaaatttgaa gtgactttgc agacaccatt atattgttct   720
atgaattcta agcatttaaa tggtaccatc acggcaaagt atacatatgg gaagccagtg   780
aaaggagacg taacgcttac atttttaacct ttatccttt gggaaagaa gaaaaatatt    840
acaaaaacat ttaagataaa tggatctgca aacttctctt ttaatgatga agagatgaaa   900
aatgtaatgg attcttcaaa tggactttct gaatacctgg atctatcttc ccctggacca   960
gtagaaattt taaccacagt gacagaatca gttacaggta tttcaagaaa tgtaagcact  1020
aatgtgttct tcaagcaaca tgattacatc attgagtttt ttgattatac tactgtcttg  1080
aagccatctc tcaacttcac agccactgtg aaggtactgc gtgctggtca caccaactg   1140
actcttgaag aaagaagaa taatgtagtc ataacagtga cacagagaaa ctatactgag  1200
tactggagcg atctaacag tggaaatcag aaaatggaag ctgttcagaa aataaattat  1260
actgtccccc aaagtggaac ttttaagatt gaattcccaa tcctggagga ttccagtgag  1320
ctacagttga aggcctattt ccttggtagt aaaagtagca tggcagttca tagtctgttt  1380
aagtctccta gtaagacata catccaacta aaacaggag atgaaaatat aaaggtggta  1440
tcgccttttg agtggtggt tagtggcaac aaacgattga aggagttaag ctatatggta  1500
gtatccaggg gacagttggt ggctgtagga aaacaaaatt caacaatgtt ctctttaaca  1560
ccagaaaatt cttggactcc aaaagcctgt gtaattgtgt attatattga agatgatggg  1620
gaaattaaa gtgatgttct aaaaattcct gttcagcttg ttttaaaaa taagataaag  1680
ctatattgga gtaaagtgaa agctgaacca tctgagaaag tctctcttag gatcctgttg  1740
acacagcctg actccatagt tgggattgta gctgttgaca aaagtgtgaa tctgatgaat  1800
gcctctaatg atattacaat ggaaaatgtg tccatgagt tggaacttta taacacagga  1860
tattatttag gcatgttcat aaattctttt gcagtctttc aggaatgtgg actctgggta  1920
ttgacagatg caaacctcac gaaggattat attgatggtg tttatgacaa tgcagaatat  1980
gctgagaggt ttatggagga aaatgaagga catattgtag atattcatga cttttctttg  2040
```

```
ggtagcagtc cacatgtccg aaagcatttt ccagagactt ggatttggct agacaccaac  2100
atgggttcca ggatttacca agaatttgaa gtaactgtac ctgattctat cacttcttgg  2160
gtggctactg gttttgtgat ctctgaggac ctgggtcttg gactaacaac tactccagtg  2220
gagctccaag ccttccaacc attttcatt ttttgaatc ttccctactc tgttatcaga  2280
ggtgaagaat ttgctttgga aataactata ttcaattatt tgaaagatgc cactgaggtt  2340
aaggtaatca ttgagaaaag tgacaaattt gatattctaa tgacttcaag tgaaataaat  2400
gccacaagcc accagcagac ccttctggtt cccagtgagg atgggcaac tgttctttt  2460
cccatcaggc caacacatct gggagaaatt cctatcacag tcacagctct ttcacccact  2520
gcttctgatg ctatcaccca gatgattta gtaaaggctg aaggaataga aaaatcatat  2580
tcacaatcca tcttattaga cttgactgac aataggctac agagtaccct gaaaactttg  2640
agtttctcat ttcctcctaa tacagtgact ggcagtgaaa gagttcagat cactgcaatt  2700
ggagatgttc ttggtccttc catcaatggc ttagcctcat tgattcggat gccttatggc  2760
tgtggtgaac agaacatgat aaattttgct ccaaatattt acattttgga ttatctgact  2820
aaaaagaaac aactgacaga taatttgaaa gaaaagctc tttcatttat gaggcaaggt  2880
taccagagag aacttctcta tcagagggaa gatggctctt tcagtgcttt tgggaattat  2940
gacccttctg ggagcacttg gttgtcagct tttgttttaa gatgtttcct tgaagccgat  3000
ccttacatag atattgatca gaatgtgtta cacagaacac acacttggct taaaggacat  3060
cagaaatcca acggtgaatt tgggatcca ggaaagtga ttcatagtga gcttcaaggt  3120
ggcaataaaa gtccagtaac acttacagcc tatattgtaa cttctctcct gggatataga  3180
aagtatcagc ctaacattga tgtgcaagag tctatccatt ttttggagtc tgaattcagt  3240
agaggaattt cagacaatta tactctagcc cttataactt atgcattgtc atcagtgggg  3300
agtcctaaag cgaaggaagc tttgaatatg ctgacttgga gagcagaaca ggaaggtggc  3360
atgcaattct gggtgtcatc agagtccaaa ctttctgact cctggcagcc acgctccctg  3420
gatattgaag ttgcagccta tgcactgctc tcacacttct tacaatttca gacttctgag  3480
ggaatcccaa ttatgaggtg gctaagcagg caaagaaata gcttgggtgg ttttgcatct  3540
actcaggata ccactgtggc tttaaaggct ctgtctgaat ttgcagccct aatgaataca  3600
gaaaggacaa atatccaagt gaccgtgacg gggcctagct caccaagtcc tgtaaagttt  3660
ctgattgaca cacacaaccg cttactcctt cagacagcag agcttgctgt ggtacagcca  3720
acggcagtta atatttccgc aaatggtttt ggatttgcta tttgtcagct caatgttgta  3780
tataatgtga aggcttctgg gtcttctaga agacaagat ctatccaaaa tcaagaagcc  3840
tttgatttag atgttgctgt aaaagaaaat aaagatgatc tcaatcatgt ggatttgaat  3900
gtgtgtacaa gcttttcggg cccgggtagg agtggcatgg ctcttatgga agttaaccta  3960
ttaagtggct ttatggtgcc ttcagaagca atttctctga cgagacagt gaagaaagtg  4020
gaatatgatc atggaaaact caacctctat ttagattctg taaatgaaac ccagttttgt  4080
gttaatattc ctgctgtgag aaactttaaa gtttcaaata cccaagatgc ttcagtgtct  4140
atagtggatt actatgagcc aaggagacag gcggtgagaa gttacaactc tgaagtgaag  4200
ctgtcctcct gtgacctttg cagtgatgtc cagggctgcc gtccttgtga ggatggagct  4260
tcaggctccc atcatcactc ttcagtcatt tttattttct gtttcaagct tctgtacttt  4320
atggaacttt ggctgtga                                                4338

SEQ ID NO: 26        moltype = DNA    length = 2938
FEATURE              Location/Qualifiers
source               1..2938
                     mol_type = genomic DNA
                     organism = Homo sapiens
SEQUENCE: 26
gttgacaaaa gtgtgaatct gatgaatgcc tctaatgata ttacaatgga aaatgtggtc  60
catgagttgg aactttataa cacaggatat tatttaggca tgttcatgaa ttcttttgca  120
gtctttcagg aatgtggact ctgggtattg acagatgcaa acctcacgaa ggattatatt  180
gatggtgttt atgacaatgc agaatatgct gagaggttta tggaggaaaa tgaaggacat  240
attgtagata ttcatgactt ttctttgggt agcagtccac atgtccgaaa gcattttcca  300
gagacttgga tttggctaga caccaacatg ggttccagga tttaccaaga atttgaagta  360
actgtacctg attctatcac ttcttgggtg ctactggttt tgtgatctc tgaggacctg  420
ggtcttggac taacaactac tccagtggag ctccaagcct ccaaccatt tttcattttt  480
ttgaatcttc cctactctgt tatcagaggt gaagaatttg cttggaaat aactatattc  540
aattatttga aagatgccac tgaggttaag gtaatcattg agaaaagtga caaatttgat  600
attctaatga cttcaagtga aataaatgcc acaggccacc agcagaccct tctggttccc  660
agtgaggatg ggcaactgt tcttttccc atcaggccaa cacatctggg agaaattcct  720
atcacagtca gctctttc acccactgct tctgatgcta tcacccagat gattttagta  780
aaggctgaag gaatagaaaa atcatattca atccatct tattagactt gactgacaat  840
aggctacaga gtaccctgaa aactttgagt ttctcatttc ctcctaatac agtgactggc  900
agtgaaagag ttcagatcac tgcaattgga gatgttcttg gtccttccat caatggctta  960
gcctcattga ttcggatgcc ttatggctgt ggtgaacaga acatgataaa ttttgctcca  1020
aatatttaca ttttggatta tctgactaaa aagaaacagt tgacagataa tttgaaagaa  1080
aaagctcttt catttatgag gcaaggttac cagagagaac ttctctatca gagggaagat  1140
ggctctttca gtgcttttgg aattatgac ccttctggga cttggtt gtcagctttt  1200
gttttaagat gtttccttga agccgatcct tacatagata ttgatcagaa tgtgttacac  1260
agaacacact tggcttaa aggacatcag aaatccaacg gtgaatttgg ggatccagga  1320
agagtgatc atagtgagct tcaaggtggc aataaaagtc cagtaacact tacagcctat  1380
attgtaactt ctctcctggg atatagaaag tatcagccta acattgatgt gcaagagtct  1440
atccattttt tggagtctga attcagtaga ggaatttcag acaattatac tctagccctt  1500
ataacttatg cattgtcatc agtggggagt cctaaagcga aggaagcttt gaatatgctg  1560
acttggagag cagaacaaga aggtggcatg caattctggg tgtcatcaga gtccaaactt  1620
tctgactcct ggcagccacg ctccctggat attgaagttg cagcctatgc actgctctca  1680
cacttcttac aatttcagac ttctgaggga atcccaatta tgaggtggct aagcaggcaa  1740
agaaatagct gggtggtttt gcatctact caggatacca ctgtggcttt aaaggctctg  1800
tctgaatttg cagccctaat gaatacagaa aggacaaata tccaagtgac cgtgacgggg  1860
cctagctcac caagtcctgt aaagtttctg attgacacac acaaccgctt actccttcag  1920
acagcagagc ttgctgtggt acagccaacg gcagttaata tttccgcaaa tggttttgga  1980
```

-continued

```
tttgctattt gtcagctcaa tgttgtatat aatgtgaagg cttctgggtc ttctagaaga    2040
cgaagatcta tccaaaatca agaagccttt gatttagatg ttgctgtaaa agaaaataaa    2100
gatgatctca atcatgtgga tttgaatgtg tgtacaagct tttcgggccc gggtaggagt    2160
ggcatggctc ttatggaagt taacctatta agtggcttta tggtgccttc agaagcaatt    2220
tctctgagcg agacagtgaa gaaagtggaa tatgatcatg gaaaactcaa cctctattta    2280
gattctgtaa atgaaaccca gttttgtgtt aatattcctg ctgtgagaaa ctttaaagtt    2340
tcaaataccc aagatgcttc agtgtccata gtggattact atgagccaag gagacaggcg    2400
gtgagaagtt acaactctga agtgaagctg tcctcctgtg acctttgcag tgatgtccag    2460
ggctgccgtc cttgtgagga tggagcttca ggctcccatc atcactcttc agtcatttt    2520
attttctgtt tcaagcttct gtactttatg gaactttggc tgtgatttat tttaaagga    2580
ctctgtgtaa cactaacatt tccagtagtc acatgtgatt gttttgtttt cgtagaagaa    2640
tactgcttct attttgaaaa aagagttttt tttctttcta tggggttgca gggatggtgt    2700
acaacaggtc ctagcatgta tagctgcata gatttcttca cctgatcttt gtgtggaaga    2760
tcagaatgaa tgcagttgtg tgtctatatt ttcccctctc aaaatctttt agaatttttt    2820
tggaggtgtt tgtttctcc agaataaagg tattacttta gaataaaaaa aaaaaaaaaa    2880
aaaaaaaaaa aaaaaaaaaa aaaaaaaaaa aaaaaaaaaa aaaaaaaaaa aaaaaaa      2938

SEQ ID NO: 27          moltype = DNA   length = 2843
FEATURE                Location/Qualifiers
source                 1..2843
                       mol_type = genomic DNA
                       organism = Homo sapiens
SEQUENCE: 27
ctgatgaatg cctctaatga tattacaatg gaaaatgtgg tccatgagtt ggaactttat      60
aacacaggat attatttagg catgttcatg aattcttttg cagtctttca ggaatgtgga     120
ctctgggtat tgacagatgc aaacctcacg aaggattata ttgatggtgt ttatgacaat     180
gcagaatatg ctgagaggtt tatggaggaa aatgaaggac atattgtaga tattcatgac     240
ttttctttgg gtagcagtcc acatgtccga aagcatttc cagagacttg gatttggcta     300
gacaccaaca tgggttccag gatttaccaa gaatttgaag taactgtacc tgattctatc     360
acttcttggg tggctactgg tttttgtgatc tctgaggacc ttgtgcttgg actaacaact     420
actccagtgg agctccaagc cttccaacca ttttcattt ttttgaatct tccctactct     480
gttatcagag gtgaagaatt tgctttggaa ataactatat tcaattattt gaaagatgcc     540
actgaggtta aggtaatcat tgagaaaagt gacaaatttg atattctaat gacttcaagt     600
gaaataaatg ccacaggcca ccagcagacc ccttcggttc ccagtgagga tggggcaaat     660
gttctttttc ccatcaggcc aacacatctg ggagaaattc ctatcacagt cacagctctt     720
tcacccactg cttctgatgc tatcacccag atgatttag taaaggctga aggaatagaa     780
aaatcatatt cacaatccat cttattagac ttgactgaca ataggctaca gagtaccctg     840
aaaactttga gttctctcatt tcctcctaat acagtgactg gcagtgaaag agttcagatc     900
actgcaattg gagatgttct tggtcttcc atcaatggct tagcctcatt gattcggatg     960
ccttatgget gtggtgaaca gaacatgata aatttttgctc caaatattta catttttggat    1020
tatctgacta aaaagaaaca actgacagat aatttgaaag aaaaagctct ttcatttatg    1080
aggcaaggtt accagagaga acttctctat cagagggaag atggctcttt cagtgctttt    1140
gggaattatg acccttctgg gagcacttgg ttgtcagctt ttgttttaag atgtttcctt    1200
gaagccgatc cttacataga tattgatcag aatgtgttac acagaacata cacttggctt    1260
aaaggacatc agaaatccaa cggtgaattt tgggatccag gaagagtgat tcatagtgag    1320
cttcaaggtg gcaataaaag tccagtaaca cttacagcct atattgtaac ttctctcctg    1380
ggatatagaa agtatcagcc taacattgat gtgcaagagt ctatccattt tttgagtct    1440
gaattcagta gaggaaattc agacaattat actctagccc ttataactta tgcattgtca    1500
tcagtgggga gtcctaaagc gaaggaagct ttgaatatgc tgacttggag agcagaacaa    1560
gaaggtggca tgcaattctg ggtgtcatca gagtccaaac tttctgactc ctggcagcca    1620
cgctccctgg atattgaagt tgcagcctat gcactgctct cacacttctt acaatttcag    1680
acttctgagg gaatcccaat tatgaggtgg ctaagcaggc aaagaaatag cttgggtggt    1740
tttgcatcta ctcaggatac cactgtggct ttaaaggctc tgtctgaatt tgcagccct    1800
atgaatacag aaaggacaaa tatccaagtg accgtgacgg ggcctagctc accaagtcct    1860
gtaaagtttc tgattgacac acacaaccgc ttactcctic agacagcaga gcttgctgtg    1920
gtacagccaa cggcagttaa tatttccgca aatggttttg gatttgctat ttgtcagctc    1980
aatgttgtat ataatgtgaa ggcttctggg tcttctagaa gacgaagatc tatccaaaat    2040
caagaagcct tgatttaga tgttgctgta aagaaaata aagatgatct caatcatgtg    2100
gatttgaatg tgtgtacaag cttttcgggc ccgggtagga gtggcatgg tcttatggaa    2160
gttaacctat taagtggctt tatggtgcct tcagaagcaa tttctctgag cgagacagtg    2220
aagtgaagc tgtcctcctg tgacctttgc agtgatgtcc tcctgtgag    2280
aatggagctt caggctccca tcatcactct tcagtcattt ttatttctg tttcaagctt    2520
ctgtacttta tggaactttg gctgtgattt atttttaaag gactctgtgt aacactaaca    2580
tttccagtag tcacatgtga ttgttttgtt tcgtagaag aatactgctt ctattttgaa    2640
aaagagtttt ttttctttc tatggggttg cagggatggt gtacaacagg tcctagcatg    2700
tatagctgca tagatttctt cacctgatct ttgtgtggaa gatcagaatg aatgcagttg    2760
tgtgtctata ttttcccctc tcaaaatctt ttagaatttt tttggaggtg tttgtttct    2820
ccagaataaa ggtattactt tag                                            2843

SEQ ID NO: 28          moltype = DNA   length = 8800
FEATURE                Location/Qualifiers
source                 1..8800
                       mol_type = genomic DNA
                       organism = Homo sapiens
SEQUENCE: 28
agacgccgtc gagatgcagg gcccaccgct cctgaccgcc gcccacctcc tctgcgtgtg       60
```

-continued

```
caccgccgcg ctggccgtgg ctcccgggcc tcggtttctg gtgacagccc cagggatcat    120
caggcccgga ggaaatgtga ctattggggt ggagcttctg gaacactgcc cttcacaggt    180
gactgtgaag gcggagctgc tcaagacagc atcaaacctc actgtctctg tcctggaagc    240
agaaggagtc tttgaaaaag gctcttttaa gacacttact cttccatcag accccaaatc    300
aaatttgatc caacagtggt tgtcacaaca aagtgatctt ggagtcattt ccaaaacttt    360
tcagctatct tcccatccaa tacttggtga ctggtctatt caagttcaag tgaatgacca    420
gacatactat caatcatttc aggtttcaga atatgtatta ccaaaatttg aagtgacttt    480
gcagacacca ttatattgtt ctatgaattc taagcatttg aatggtacca tcacggcaaa    540
gtatacatat gggaagccag tgaaaggaga cgtaacgctt acattttac ctttatcctt     600
ttggggaaag aagaaaaata ttacaaaaac atttaagata aatggatctg caaacttctc    660
ttttaatgat gaagagatga aaaatgtaat ggattcttca aatggacttt ctgaatacct    720
ggatctatct tcccctggac cagtagaaat tttaaccaca gtgacagaat cagttacagg    780
tatttcaaga aatgtaagca ctaatgtgtt cttcaagcaa catgattaca tcattgagtt    840
ttttgattat actactgtct tgaagccatc tctcaacttc acagccactg tgaaggtaac    900
tcgtgctgat ggcaaccaac tgactcttga agaagaagaa aataatgtag tcataacagt    960
gacacagaga aactatactg agtactggag cggatctaac agtggaaatc agaaaatgga   1020
agctgttcag aaaataaatt atactgtccc ccaaagtgga acttttaaga ttgaattccc   1080
aatcctggag gattccagtg agctacagtt gaaggcctat ttccttggta gtaaaagtag   1140
catggcagtt catagtctgt ttaagtctcc tagtaagaca tacatccaac taaaaacaag   1200
agatgaaaat ataaaggtgg gatcgccttt tgagttggtg gttagtggca caaacgatt    1260
gaaggagtta agctatatgg tagtatccag gggacagttg gtggctgtag gaaaacaaaa   1320
ttcaacaatg ttctctttaa caccagaaaa ttcttggact ccaaaagcct gtgtaattgt   1380
gtattatatt gaagatgatg gggaaattat aagtgatgtt ctaaaaattc ctgttcagct   1440
tgttttaaa aataagataa agctatattg gagtaaagtg aaagctgaac catctgagaa    1500
agtctctctt aggatctctg tgacacagcc tgactccata gttgggattg tagctgttga   1560
caaaagtgtg aatctgatga atgcctctaa tgatattaca atggaaaatg tggtccatga   1620
gttggaactt tataacacag atattattt aggcatgttc atgaattctt ttgcagtctt    1680
tcaggaatgt ggactctggg tattgacaga tgcaaacctc acgaaggatt atattgatgg   1740
tgtttatgac aatgcagaat atgctgagag gtttatggag gaaaatgaag gacatattgt   1800
agatattcat gactttctt tgggtagcag tccacatgct cgaaagcatt ttccagagac    1860
ttggatttgg ctagacacca acatgggtta caggatttac caagaatttg aagtaactga   1920
acctgattct atcacttctt gggtggctac tggttttgtg atctctgagg acctgggtct   1980
tggactaaca actactccag tggagctcca agccttccaa ccatttttca tttttttgaa   2040
tcttccctac tctgttatca gaggtgaaga atttgctttg gaaataacta tattcaatta   2100
tttgaaagat gccactgagg ttaaggtaat cattgagaaa agtgacaaat ttgatattct   2160
aatgacttca aatgaaataa atgccacagg ccaccagcag acccttctgg ttcccagtga   2220
ggatggggca actgttcttt ttcccatcag gccaacacat ctgggagaaa ttcctatcac   2280
agtcacagct ctttcaccca ctgcttctga tgctgtcacc cagatgattt tagtaaaggc   2340
tgaaggaata gaaaatcat attcacaatc catcttata gacttgactg acaataggct     2400
acagagtacc ctgaaaactt tgagtttctc atttcctcct aatacagtga ctggcagtga   2460
aagagttcag atcactgcaa ttggagatgt tcttggtcct tccatcaatg gcttagcctc   2520
attgattcgg atgccttatg gctgtggtga acagaacatg ataaatttg ctccaaatat    2580
ttacattttg gattatctga ctaaaaagaa acaactgaca gataatttga agaaaaagc    2640
tctttcattt atgaggcaag gttaccagag agaacttctc tatcagaggg aagatggctc   2700
tttcagtgct tttgggaatt atgacccttc tgggagcact tggttgtcag cttttgtttt   2760
aagatgtttc cttgaagccg atccttacat agatattgat cagaatgtgt tacacagaac   2820
atacactgg cttaaaggac atcagaaatc caacggtgaa ttttgggatc caggaagagt    2880
gattcatagt gagcttcaag gtggcaataa aagtccagta acacttacag cctatattgt   2940
aacttctctc ctgggatata gaaagtatca gcctaacatt gatgtgcaag agtctatcca   3000
ttttttggag tctgaattca gtagaggaat ttcagacaat tatactctag cccttataac   3060
ttatgcattg tcatcagtgg ggagtcctaa agcgaaggaa gctttaaagg ctctgtctga   3120
gagagcagaa caagaaggtg gcatgcaatt ctgggtgtca tcagagtcca aacttttctga  3180
ctcctggcag ccacgctccc tggatattga agttgcagcc tatgcactgc tctcacactt   3240
cttacaattt cagacttctg agggaatccc aattatgagg tggctaagca ggcaaagaaa   3300
tagcttgggt ggttttgcat ctactcagga taccactgtg gctttaaagg ctctgtctga   3360
atttgcagcc ctaatgaata cagaaaggac aaatatccaa gtgaccgtga cggggcctag   3420
ctcaccaagt cctgtaaagt ttctgattga cacacacaac cgcttactcc ttcagacagc   3480
agagcttgct gtggtacagc caacggcagt taatatttcc gcaaatggtt ttggatttgc   3540
tatttgtcag ctcaatgttg tatataatgt gaaggcttct gggtcttcta gaagacgaag   3600
atctatccaa aatcaagaag cctttgattt agatgttgct gtaaaagaaa ataaagatga   3660
tctcaatcat gtggatttga atgtgtgtac aagcttttcg ggcccgggta ggagtggcat   3720
ggctcttatg gaagttaacc tattaagtgg ctttatggtg ccttcagaag caatttctct   3780
gagcgagaca gtgaagaaag tggaaatatga tcatggaaaa ctcaacctct atttagattc   3840
tgtaaatgaa acccagtttt gtgttaatat tcctgctgtg agaaactta aagtttcaaa    3900
tacccaagat gcttcagtgt ccatagtgga ttactatgga ccaaggagac aggcggtgag   3960
aagttacaac tctgaagtga agctgtcctc ctgtgacctt tgcagtgatg tccaggctg    4020
ccgtccttgt gaggatggag cttcaggctc ccatcatcac tcttcagtca ttttattt     4080
ctgtttcaag cttctgtact ttatgaaact ttggctgtga tttttcgtag aaggactctg   4140
tgtaacacta acatttccag tagtcacatg tgattgtttt gttttcgtag aagaatactg   4200
cttctatttt gaaaaagag tttttttct ttctatgggg ttgcagggat ggtgtacaac     4260
aggtcctagc atgtatagct gcatagattt cttcacctga tctttgtgtg gaagatcaga   4320
atgaatgcag ttgtgtgtct atattttccc ctctcaaaat cttttagaat tttttggag    4380
gtgtttgttt tctccagaat aaaggtatta ctttagaata ggtattctcc tcattttgtg   4440
aaagaaatga acctagattc ttaagcatta ttaacacatc atgttttgctt aaagatggat   4500
ttccctggga atgggagaaa acagccagca ggaggagctt catctgttcc cttcccacct   4560
ccaacctagc cctactgccc accccacccc aacccacccc atgcccagtg gtctcagtag   4620
atacttcttca actggaaatt cttctttttc agaatctagg tggtgaattt tttttaagtg   4680
gcacggtctt tttctgcttg aaatctgatc acccccccca gccattgccc tccctctctt   4740
tttcctctgt agagaaatgt gaggggcagt acatttactg tgcttttcac accatctcag   4800
```

```
aggttgagga gcatactgaa aattgccctg gggggtgctg ggtgtgctgt ctccttccca   4860
catcctcagc cccacaccag ctctatttca ggggtgagag tcagagagca ctgcaatatg   4920
tgcttcatgg gatttcgatt cgaagatcct agaccaggga gacactgtga gccaggggata  4980
caacaaaata ctaggtaagt cactgcagac cgacctccct gcagtttggg aaagaagctg   5040
ggtttgtgga gaatcagagc atcttgacat gactgctgac ctaaagatcc ctggcattgg   5100
ccagggatcc tgtggaacct cttctagttc aggggtgtga gcattagact gccagttgtc   5160
tagtgacatc tgatgcttgc tgtgaacttt taagatcccc gaatcctgag cacctcaatc   5220
tttaattgcc ctgtattccg aagggtaata taatttatct ggatgaaat tttaaagatg    5280
aatcccccctt ttttcttttc ttctctcttt tctttccttc tcccttttctt ctttgccttc  5340
taaatatact gaaatgattt agatatgtgt caacaattaa tgatctttta ttcaatctaa   5400
gaaatggttt agttttttctc tttagctcta tggcatttca ctcaagtgga cagggggaaaa 5460
agtaattgcc atgggctcca aagaatttgc tttatgtttt tagctattta aaaataaatc   5520
catcaaaaat aaagtatgca aatgtatctt ttaaagttaa ttttttaaaaa tgctcttatt  5580
ttagtgaatt ttcagaaatt atagtggaat ggatgctcat atattgctta tggatatttt  5640
ggataccaaa gtaggaataa ctgacattca gtattttaaa gctggcaaac ctgtacatag   5700
aaaatagatc cccagacagt ggtctatgaa gagggcagtt aagtatcaaa tacttaattt   5760
tcttgccttt ttttcttaag tggggaaaag tttctagatc tcttacacct ctgacacaat   5820
ctgttctaaa acaggcactt gtaatgttgg ggcctccttg taaacgtgtt tttgcccttt   5880
actctctggg agttctttaa aggtgaaatc atcttacaaa gaaattgggg gagggtcttg   5940
gcaaaggact ttcccctcct ctttcctggc ctgggaacct tatactgaca atcaatactt   6000
tatattttaa agtatataat ttatagttaa cttctagtgt aatatattag gaaacactag   6060
aatggaaagg ccattggaag acaggttgta tcttttttag accatatttc cttgtttaaa   6120
aactatcatt tgaatacttt tttggtgaag aactccatgt tttcaagtta aaggtcacct   6180
cgtaggccag gcgcagtggc tcatgcctgt aatcccagca ctctggggagg ctgaggcggg  6240
tgaatcacaa ggttaggagt ttgagaccag cctggccaat atggtgaaac cccgtcccta   6300
ctaaaaatac aaaatttagc caggcgtggt ggcatgcacc tgtagtccca cctactcggga 6360
aggctgaggc aggagaatca cttgaacctg agagacagag gttgcagtga gccgagatca   6420
cgccactgca ctccagcctg ggggacagag tgagattctg tctcaaaaaa caaaaaacaa   6480
aaaagtcacc ttgtaactca tctcttttta ttgtaagttt attaaaaatg aagaggacaa   6540
caatgagaag gaacataaag ggttagctag cactgtctcc tggtgcatgg ggctgtgcag   6600
atgtcccggc cacttcttcc ttcatacttc cctttagagaa cttgctctgc tacaagcagt   6660
gggcttggac taaaagtgat taaaatacca caggcataag gagaaaagga gtatatgtag   6720
tagtaataat tactagtata aattattttc ttcacatgct atgagtaata atattaaaaa   6780
actcattta ccattaagat tccttatgct gaagctcttc cattagaat actgtcaatg    6840
tcatttactg gtatgaacta aagtcccct tcttttccac tcactgggaa ccttagtaaa   6900
acaccagcat atcttacctc tctttctgac tggccgatgc ttccagagac tgaatgttgg  6960
gaaaacctag tagccaaaca attctaggac agaataacat ttttatattt ggttccacca   7020
tcttattaca tttagttata gttttaaaaa agaaattcaa gcccattaaa atatgtctgg   7080
tcaatgaaat gcttcctttt attgtgttgt gctattgtac tttgtttttc aaaacattgt   7140
aaaaaatagta tctttggttt agtattttgg attatatatt ataatctgag gagtgtttttg 7200
cttatgtaga atccagatat atttctgtta cctaggagat gttacttaca tatgtaaatac  7260
tgtatcctgc acgtggaaat attcagaatt gtagatagca taactctccc tgctcctatt   7320
cttttgagcc taggtataat tttttttttt tttttagaaa aagacatatt tagcttttaaa  7380
ttctatttat gctaaacata tttataagta gtctgtcaat ataataccaa ctatttttat  7440
ttttacataa ttcaattatt tcatttgaca tgtctggcag actcaagaca ttaagtaaaa   7500
aattggaact atgattttc tttgtcattt tttaaaaaag aattatttta ttaacctgct   7560
ggcatataat ctggagttct tttcacaacc ttacttttttc tgatttgctt tattgaatga  7620
ttgaatactc atttctttct aaaaatatgt tgtaaattct cccttggcaa gatttctccc    7680
tatgagggta gttattattt gagtctgcca agtggttacc atggggcaag gtgccatgat   7740
gtattcttgg gtgcattggt ttttttgcgca ttgtaaattt aagacactta tagtaagtgg  7800
actcattcat agatgagttt cagaacctttt tacgttctcg gtagaggctt ctgtcggaca   7860
ggcagaagag tgtattcctc actttttttttt ttgtcttcaa attccagtaa ggcatagcac 7920
ttttaagaaa ttagaatttt tctatcatct atgcaaatga tatttatgtt aatattaaat   7980
atcttatgtt acactgggag taatttgagg tgcaattatt tttattacta ctttgaatag   8040
aggaccatta tccttctttc ttcagaaaac taagaagtaa gtgtaacttt taaagtaagt   8100
atatatcagt gagagtaggc ttgttttaca actatttcta gccagtgagt tgtgttttca   8160
tgtctcatca aaagacaata ccacattgca tcattttaca aaatatgttg tcattttcat   8220
ttcagttgta acataggaaa atagatattt cctagatgat ttctgagttt cttactgcaa   8280
agaacagtta taaattggta tacatgtgtc tctgtaatag ggataatatt gatatatctg   8340
ttgctacata tttaagaatc attctatctt atgttgtctt gaggccaaga tttaccacgt   8400
ttgcccagtg tattgaattg gtggtagaag gtagttccat gttccatttg tagatcttta   8460
agattttatc tttgataact ttaatagaat gtggctcagt tctggtcctt caagcctgta   8520
tggtttggat tttcagtagg ggacagttga tgtggagtca atctctttgg tacacaggaa   8580
gctttataaa atttcattca cgaatctctt attttgggaa gctgttttgc atatgaagaa   8640
aacactgttg aaataaggaa ctaaagcttt atatattgat caaggtgatt ctgaaagttt   8700
taattttttaa tgttgtaatg ttatgttatt gttaattgta ctttattatg tattcaatag   8760
aaaatcatga tttattaata aaagcttaaa ttctcatcta                          8800

SEQ ID NO: 29        moltype = DNA   length = 8980
FEATURE              Location/Qualifiers
source               1..8980
                     mol_type = genomic DNA
                     organism = Homo sapiens
SEQUENCE: 29
agacgccgtc gagatgcagg gcccaccgct cctgaccgcc gcccacctcc tctgcgtgtg    60
caccgccgcg ctgccgtgg ctcccgggcc tcggtttctg gtgacagccc cagggatcat   120
caggcccgga ggaaatgtga ctattggggt ggagcttctg gaacactgcc ttcacaggtt   180
gactgtgaag gcggagctgc tcaagacagc atcaaacctc actgtctctg tcctggaagc   240
agaaggagtc tttgaaaaag gctcttttaa gacacttact cttccatcac tacctctgaa   300
```

```
cagtgcagat gagatttatg agctacgtgt aaccggacgt acccaggatg agattttatt    360
ctctaatagt acccgcttat catttgagac caagagaata tctgtcttca ttcaaacaga    420
caaggcctta tacaagccaa agcaagaagt gaagtttcgc attgttacac tcttctcaga    480
ttttaagcct tacaaaacct ctttaaacat tctcattaag gaccccaaat caaatttgat    540
ccaacagtgg ttgtcacaac aaagtgatct tggagtcatt tccaaaactt ttcagctatc    600
ttcccatcca atacttggtg actggtctat tcaagttcaa gtgaatgacc agacatacta    660
tcaatcattt caggtttcag aatatgtatt accaaaattt gaagtgactt tgcagacacc    720
attatattgt tctatgaatt ctaagcattt aaatggtacc atcacggcaa agtatacata    780
tgggaagcca gtgaaaggag acgtaacgct tacattttta cctttatcct tttgggggaaa   840
gaagaaaaat attacaaaaa catttaagat aaatggatct gcaaacttct cttttaatga    900
tgaagagatg aaaaatgtaa tggattcttc aaatggactt tctgaatacc tggatctatc    960
ttcccctgga ccagtagaaa ttttaaccac agtgacagaa tcagttacag gtatttcaag   1020
aaatgtaagc actaatgtgt tcttcaagca acatgattac atcattgagt tttttgatta   1080
tactactgtc ttgaagccat ctctcaactt cacagccact gtgaaggtaa ctcgtgctga   1140
tggcaaccaa ctgactcttg aagaaagaag aaataatgta gtcataacag tgacacagag   1200
aaactatact gagtactgga gcggatctaa cagtggaaat cagaaaatgg aagctgttca   1260
gaaaataaat tatactgtcc cccaaagtgg aacttttaag attgaattcc caatcctgga   1320
ggattccagt gagctacagt tgaaggccta tttccttagt agtaaaagta gcatggcagt   1380
tcatagtctg tttaagtctc ctagtaagac atacatccaa ctaaaaacaa gagatgaaaa   1440
tataaaggtg ggatcgcctt ttgagttggt ggttagtggc aacaaacgat tgaaggagtt   1500
aagctatatg gtagtatcca ggggacagtt ggtggctgta ggaaaacaaa attcaacaat   1560
gttctctttta acaccagaaa attcttggac tccaaaagcc tgtgtaattg tgtattatat   1620
tgaagatgat ggggaaatta taagtgatgt tctaaaaatt cctgttcagc ttgttttttaa   1680
aaataagata aagctatatt ggagtaaagt gaaagctgaa ccatctgaga aagtctctct   1740
taggatctct gtgacacagc ctgactccat agttgggatt gtagctgttg acaaaagtgt   1800
gaatctgatg aatgcctcta atgatattac aatggaaaat gtggtccatg agttggaact   1860
ttataacaca ggatattatt taggcatgtt catgaattct tttgcagtct ttcaggaatg   1920
tggactctgg gtattgacag atgcaaacct cacgaaggat tatattgatg gtgtttatga   1980
caatgcagaa tatgctgaga ggtttatgga ggaaaatgaa ggacatattg tagatattca   2040
tgacttttct ttgggtagca gtcccacatgt ccgaaagcat tttccagaga cttggatttg   2100
gctagacacc aacatgggtt acaggattta ccaagaattt gaagtaactg tacctgattc   2160
tatcacttct tgggtggcta ctggttttgt gatctctgag gacctgggtc ttggactaac   2220
aactactcca gtggagctcc aagccttcca accatttttc attttttga atcttcccta   2280
ctctgttatc agaggtgaag aatttgcttt ggaaataact attcaatt atttgaaaga   2340
tgccactgag gttaaggtaa tcattgagaa aagtgacaaa tttgatattc taatgacttc   2400
aaatgaaata aatgccacag gccaccagca gaccccttctg gttcccagtg aggatggggc   2460
aactgttctt tttcccatca ggccaacaca tctgggagaa attcctatca cagtcacagc   2520
tcttctcaccc actgcttctg atgctgtcac ccagatgatt ttagtaaagg ctgaaggaat   2580
agaaaaatca tattcacaat ccatcttatt agacttgact gacaataggc tacagagtac   2640
cctgaaaact ttgagtttct catttcctcc taatacagtg actggcagtg aaagagttca   2700
gatcactgca attggagatg ttcttggtcc ttccatcaat ggcttagcct cattgattcg   2760
gatgcctttat ggctgtggtg aacagaacat gataaatttt gctccaaata tttacatttt   2820
ggattatctg actaaaaaga aacaactgac agataatttg aaagaaaaag ctctttcatt   2880
tatgaggcaa ggttaccaga gagaacttct ctatcagagg gaagatggct ctttcagtgc   2940
ttttgggaat tatgacccctt ctgggagcac ttggttgtca gcttttgttt taagatgttt   3000
ccttgaagcc gatccttaca tagatattga tcagaatgtg ttacacagaa catacacttg   3060
gcttaaagga catcagaaat ccaacggtga attttggagt ccaggaaagg tgattcatag   3120
tgagcttcaa ggtggcaata aaagtccagt aacacttaca gcctatattg taacttctct   3180
cctgggatat agaaagtatc agcctaacat tgatgtgcaa gagtctatcc attttttgga   3240
gtctgaattc agtagaggaa tttcagacaa ttatactcta gcccttataa cttatgcatt   3300
gtcatcagtg gggagtccta aagcgaagga agcttggaat atgctgactt ggagagcaga   3360
acaagaaggt ggcatgcaat tctgggtgtc atcagagtcc aaactttctg actcctggca   3420
gccacgctcc ctggatattg aagttgcagc ctatgcactg ctctcacact tcttacaatt   3480
tcagacttct gagggaatcc caattatgag gtggctaagc aggcaaagaa atagcttggg   3540
tggttttgca tctactcagg ataccactgt ggctttaaag gctctgtctg aatttgcagc   3600
cctaatgaat acagaaagga caaatatcca agtgaccgtg acggggccta gctcaccaag   3660
tcctcttgct gtggtacagc aacggcagt taatatttcc gcaaatggtt ttggatttgc   3720
tatttgtcag ctcaatgttg tatataatgt gaaggcttct gggtcttcta aagacgaag   3780
atctatccaa aatcaagaag cctttgattt agatgttgct gtaaaagaaa ataaagatga   3840
tctcaatcat gtgggatttga atgtgtgtac aagcttccg ggcccgggta ggagtggcat   3900
ggctcttatg gaagttaacc tattaagtgg ctttatggtg ccttcagaag caatttctct   3960
gagcgagaca gtgaagaaag tggaatatga tcatggaaaa ctcaacctct atttagattc   4020
tgtaaatgaa acccagtttt gtgttaatat tcctgctgtg agaaactta aagttttcaa   4080
tacccaagat gcttcagtgt ccatagtgga ttactatgga ccaaggagac aggcggttga   4140
aagttacaac tctgaagtga agctgtcctc ctgtgacctt tgcagtgatg tccagggctg   4200
ccgtcccttgt gaggatggag cttcaggctc ccatcatcac tcttcagtca tttttatttt   4260
ctgtttcaag cttctgtact ttatggaact ttggctgtga tttattttta aaggactctg   4320
tgtaacacta acatttccag tagtcacatg tgattgttt gttttcgtag aagaatactg   4380
cttctatttt gaaaaaagag ttttttttct ttctatgggg ttgcagggat gggtacacac   4440
aggtcctagc atgtatagct gcatagattt cttcacctga tctttgtgtg gaagatcaga   4500
atgaatgcag ttgtgtgtct atatttccc ctctcaaaat cttttagaat ttttttggag   4560
gtgtttgttt tctccagaat aaaggtatta ctttagaata ggtattctcc tcatttttgtg   4620
aaagaaatga acctagattc ttaagcatta ttacacatcc atgtttgctt aaagatggat   4680
ttccctggga atgggagaaa acagccagca ggaggagctt catctgttcc cttcccacct   4740
ccaacctagc cctactgccc accccacccc aacccacccc atgccagtg gtctcagtag   4800
atacttctta actggaaatt ctttcttttc agaatctagg tggtgaattt ttttaagtg   4860
gcacggtctt tttctgcttg aaatctgatc acacccccca gccattgccc tcctctcttt   4920
tttcctctgt agagaaatgt gaggggcagt acatttactg tgcttttcac accatctcag   4980
aggttgagga gcatactgaa aattgccctg gggggtgctg ggtgtgctgt ctccttccca   5040
```

-continued

```
catcctcagc cccacaccag ctctatttca ggggtgagag tcagagagca ctgcaatatg    5100
tgcttcatgg gatttcgatt cgaagatcct agaccaggga gacactgtga gccaggggata   5160
caacaaaata ctaggtaagt cactgcagac cgacctccct gcagtttggg aaagaagctg    5220
ggtttgtgga gaatcagagc atcttgacat gactgctgac ctaaagatcc ctggcattgg    5280
ccagggatcc tgtggaacct cttctagttc aggggtgtga gcattagact gccagtttgc    5340
tagtgacatc tgatgcttgc tgtgaacttt taagatcccc gaatcctgag cacctcaatc    5400
tttaattgcc ctgtattccg aagggtaata taatttatct ggatgaaaat tttaaagatg    5460
aatccccctt ttttctttc ttctctcttt tcttcctttc tccctttctt ctttgccttc     5520
taaatatact gaaatgattt agatatgtgt caacaattaa tgatcttta ttcaatctaa     5580
gaaatggttt agttttctc tttagctcta tggcatttca ctcaagtgga caggggaaaa     5640
agtaattgcc atgggctcca aagaaattgc tttatgtttt tagctattta aaaataaatc    5700
catcaaaaat aaagtatgca aatgtatctt ttaaagttaa tttttaaaaa tgctcttatt    5760
ttagtgaatt ttcagaaatt atagtggaat ggatgctcat atattgctta tggatatttt   5820
ggataccaaa gtaggaataa ctgacattca gtattttaaa gctggcaaac ctgtacatag    5880
aaaatagatc cccagacagt ggtctatgaa gagggcagtt aagtatcaaa tacttaattt    5940
tcttgccttt ttttcttaag tggggaaaag tttctagatc tcttacacct ctgacacaat    6000
ctgttctaaa acaggcactt gtaatgttgg ggcctccttg taaacgtgtt tttgcccttt    6060
actctctggg agttctttaa aggtgaaatc atcttacaaa gaaattgggg gagggtcttg    6120
gcaaaggact ttccctcct ctttcctggc ctgggaacct tatactgaca atcaatactt      6180
tatattttaa agtatataat ttatagttaa cttctagtgt aatatattag gaaacactag    6240
aatgaaaggg ccattggaag acaggttgta tcttttttag accatatttc cttgtttaaa    6300
aactatcatt tgaatacttt tttggtgaag aactccatgt ttcaagtta aaggtcacct     6360
cgtaggccag gcgcagtggc tcatgcctgt aatcccagca ctctgggagg ctgaggcggg    6420
tgaatcacaa ggtcaggagt ttgagaccag cctggccaat atggtgaaac cccgtcccta    6480
ctaaaaatac aaaatttagc caggcgtggt ggcatgcacc tgtagtccca cctactcggg    6540
aggctgaggc aggagaatca cttgaacctg agagacagga gttgcagtga gccgagatca    6600
cgccactgca ctccagcctg ggggacagag tgagattctg tctcaaaaaa caaaaaacaa    6660
aaaagtcacc ttgtaactca tctctttta ttgtaagttt attaaaaatg aagaggacaa      6720
caatgagaag gaacataaag ggttagctag cactgtctcc tggtgcatgg ggctgtgcag    6780
atgtcccggc cacttcttcc ttcatacttc ccttagagaa cttgctctgc tacaagcagt    6840
gggcttggac taaaagtgat taaaatacca caggcataag gagaaaagga gtatatgtag    6900
tagtaataat tactagtata aattattttc ttcacatgct atgagtaata atattaaaaa    6960
actcatttta ccattaagat tccttatgct gaagctcttc catttagaat actgtcaatg    7020
tcatttactg gtatgaacta aagtccccct tctttccca tcactgggaa ccttagtaaa     7080
acaccagcat atcttacctc tcttctgac tggccgatgc ttccagagac tgaatgttgc      7140
gaaaacctag tagccaaaca attctaggac agaataacat ttttatattt ggttccacca    7200
tcttattaca tttagttata gttttaaaaa agaaattcaa gcccattaaa atatgtctgg    7260
tcaatgaaat gcttcctttt attgtgttgt gctattgtac tttgttttc aaaacattgt      7320
aaaaatagta tctttggttt agtattttgg attatatatt ataatctgag gagtgttttg    7380
cttatgtaga atccagatat atttctgtta cctaggagat gttacttaca tatgtaaatac    7440
tgtatcctgc acgtggaaat attcagaatt gtagatagca taactctccc tgctcctatt    7500
cttttgagcc taggtataat tttttttttt ttttagaaa aagacatatt tagctttaat      7560
ttctatttat gctaaacata tttataagta gtctgtcaat ataataccaa ctattttat     7620
ttttacataa ttcaattatt tcatttgaca tgtctggcag actcaagaca ttaagtaaaa    7680
aattggaact atgattttc tttgtcattt tttaaaaaag aattatttta ttaacctgct     7740
ggcatataat ctggagttct tttcacaacc ttacttttc tgatttgctt tattgaatga     7800
ttgaatactc attcttct aaaaaatatgt tgtaaattct cccttggcaa gatttctccc     7860
tatgagggta gttattattt gagtctgcca agtggttacc atggggcaag gtgccatgat    7920
gtattcttgg gtgcattggt tttttgcgca ttgtaaattt aagacactta tagtaagtgg    7980
actcattcat agatgagttt cagaaccttt tacgttctcg gtagaggctt ctgtcggaca    8040
ggcagaagag tgtattcctc acttttttt ttgtcttcaa attccagtaa gcatagcac       8100
ttttaagaaa ttagaatttt tctatcatct atgcaaatga tatttatgtt aatattaaat    8160
atcttatgtt acactgggag taatttgagg tgcaattatt tttattacta ctttgaatag    8220
aggaccatta tccttcttc ttcagaaaac taagaagtaa gtgtaacttt taaagtaagt      8280
atatatcagt gagagtaggc ttgttttaca actatttcta gccagtgagt tgtgttttca    8340
tgtctcatca aaagacaata ccacattgca tcatttaca aaatatgttg tcattttcat     8400
ttcagttgta acataggaaa atagatattt cctagatgat ttctgagttt cttactgcaa    8460
agaacagtta taaattggta tacatgtgtc tctgtaatag gataatatt gatatatctg     8520
ttgctacata tttaaggaaa atttctatctt atgttgtcct gaggccaaga tttaccacgt    8580
ttgcccagtg tattgaattg gtggtagaag gtagttccat gttccatttg tagatcttta    8640
agattttatc tttgataact ttaatagaat gtggctcagt tctggtcctt caagcctgta    8700
tggtttggat tttcagtagg ggacagttga tgtggagtca atctctttgg tacacaggaa    8760
gctttataaa atttcattca cgaatctctt attttgggaa gctgttttgc atatgagaag    8820
aacactgttg aaatattgat ctaaagcttt atatattgat caaggtgatt ctgaaagttt    8880
taattttaa tgttgtaatg ttatgttatt gttaattgta ctttattatg tattcaatag     8940
aaaatcatga tttattaata aaagcttaaa ttctcatcta                          8980
```

SEQ ID NO: 30        moltype = AA length = 1428
FEATURE          Location/Qualifiers
source           1..1428
                mol_type = protein
                organism = Homo sapiens
SEQUENCE: 30

```
MQGPPLLTAA HLLCVCTAAL AVAPGPRFLV TAPGIIRPGG NVTIGVELLE HCPSQVTVKA     60
ELLKTASNLT VSVLEAEGVF EKGSFKTLTL PSLPLNSADE IYELRVTGRT QDEILFSNST   120
RLSFETKRIS VFIQTDKALY KPKQEVKFRI VTLFSDFKPY KTSLNILIKD PKSNLIQQWL   180
SQQSDLGVIS KTFQLSSHPI LGDWSIQVQV NDQTYYQSFQ VSEYVLPKFE VTLQTPLYCS   240
MNSKHLNGTI TAKYTYGKPV KGDVTLTFLP LSFWGKKKNI TKTFKINGSA NFSFNDEEMK   300
NVMDSSNGLS EYLDLSSPGP VEILTTVTES VTGISRNVST NVFFKQHDYI IEFFDYTTVL   360
```

```
KPSLNFTATV KVTRADGNQL TLEERRNNVV ITVTQRNYTE YWSGSNSGNQ KMEAVQKINY    420
TVPQSGTFKI EFPILEDSSE LQLKAYFLGS KSSMAVHSLF KSPSKTYIQL KTRDENIKVG    480
SPFELVVSGN KRLKELSYMV VSRGQLVAVG KQNSTMFSLT PENSWTPKAC VIVYYIEDDG    540
EIIISDVLKIP VQLVFKNKIK LYWSKVKAEP SEKVSLRISV TQPDSIVGIV AVDKSVNLMN   600
ASNDITMENV VHELELYNTG YYLGMFMNSF AVFQECGLWV LTDANLTKDY IDGVYDNAEY    660
AERFMEENEG HIVDIHDFSL GSSPHVRKHF PETWIWLDTN MGYRIYQEFE VTVPDSITSW    720
VATGFVISED LGLGLTTTPV ELQAFQPFFI FLNLPYSVIR GEEFALEITI FNYLKDATEV    780
KVIIEKSDKF DILMTSNEIN ATGHQQTLLV PSEDGATVLF PIRPTHLGEI PITVTALSPT    840
ASDAVTQMIL VKAEGIEKSY SQSILLDLTD NRLQSTLKTL SFSFPPNTVT GSERVQITAI    900
GDVLGPSING LASLIRMPYG CGEQNMINFA PNIYILDYLT KKKQLTDNLK EKALSFMRQG    960
YQRELLYQRE DGSFSAFGNY DPSGSTWLSA FVLRCFLEAD PYIDIDQNVL HRTYTWLKGH   1020
QKSNGEFWDP GRVIHSELQG GNKSPVTLTA YIVTSLLGYR KYQPNIDVQE SIHFLESEFS   1080
RGISDNYTLA LITYALSSVG SPKAKEALNM LTWRAEQEGG MQFWVSSESK LSDSWQPRSL   1140
DIEVAAYALL SHFLQFQTSE GIPIMRWLSR QRNSLGGFAS TQDTTVALKA LSEFAALMNT   1200
ERTNIQVTVT GPSSPSPLAV VQPTAVNISA NGFGFAICQL NVVYNVKASG SSRRRSIQN    1260
QEAFDLDVAV KENKDDLNHV DLNVCTSFSG PGRSGMALME VNLLSGFMVP SEAISLSETV   1320
KKVEYDHGKL NLYLDSVNET QFCVNIPAVR NFKVSNTQDA SVSIVDYYEP RRQAVRSYNS   1380
EVKLSSCDLC SDVQGCRPCE DGASGSHHHS SVIFIFCFKL LYFMELWL                1428

SEQ ID NO: 31          moltype = AA  length = 1368
FEATURE                Location/Qualifiers
source                 1..1368
                       mol_type = protein
                       organism = Homo sapiens
SEQUENCE: 31
MQGPPLLTAA HLLCVCTAAL AVAPGPRFLV TAPGIIRPGG NVTIGVELLE HCPSQVTVKA     60
ELLKTASNLT VSVLEAEGVF EKGSFKTLTL PSDPKSNLIQ QWLSQQSDLG VISKTFQLSS    120
HPILGDWSIQ VQVNDQTYYQ SFQVSEYVLP KFEVTLQTPL YCSMNSKHLN GTITAKYTYG    180
KPVKGDVTLT FLPLSFWGKK KNITKTFKIN GSANFSFNDE EMKNVMDSSN GLSEYLDLSS    240
PGPVEILTTV TESVTGISRN VSTNVFFKQH DYIIEFFDYT TVLKPSLNFT ATVKVTRADG    300
NQLTLEERRN NVVITVTQRN YTEYWSGSNS GNQKMEAVQK INYTVPQSGT FKIEFPILED    360
SSELQLKAYF LGSKSSMAVH SLFKSPSKTY IQLKTRDENI KVGSPFELVV SGNKRLKELS    420
YMVVSRGQLV AVGKQNSTMF SLTPENSWTP KACVIVYYIE DDGEIISDVL KIPVQLVFKN    480
KIKLYWSKVK AEPSEKVSLR ISVTQPDSIV GIVAVDKSVN LMNASNDITM ENVVHELELY    540
NTGYYLGMFM NSFAVFQECG LWVLTDANLT KDYIDGVYDN AEYAERFMEE NEGHIVDIHD    600
FSLGSSPHVR KHFPETWIWL DTNMGYRIYQ EFEVTVPDSI TSWVATGFVI SEDLGLGLTT    660
TPVELQAFQP FFIFLNLPYS VIRGEEFALE ITIFNYLKDA TEVKVIIEKS DKFDILMTSN    720
EINATGHQQT LLVPSEDGAT VLFPIRPTHL GEIPITVTAL SPTASDAVTQ MILVKAEGIE    780
KSYSQSILLD LTDNRLQSTL KTLSFSFPPN TVTGSERVQI TAIGDVLGPS INGLASLIRM    840
PYGCGEQNMI NFAPNIYILD YLTKKKQLTD NLKEKALSFM RQGYQRELLY QREDGSFSAF    900
GNYDPSGSTW LSAFVLRCFL EADPYIDIDQ NVLHRTYTWL KGHQKSNGEF WDPGRVIHSE    960
LQGGNKSPVT LTAYIVTSLL GYRKYQPNID VQESIHFLES EFSRGISDNY TLALITYALS   1020
SVGSPKAKEA LNMLTWRAEQ EGGMQFWVSS ESKLSDSWQP RSLDIEVAAY ALLSHFLQFQ   1080
TSEGIPIMRW LSRQRNSLGG FASTQDTTVA LKALSEFAAL MNTERTNIQV TVTGPSSPSP   1140
VKFLIDTHNR LLLLQTAELA VQPTAVNISA NGFGFAICQL NVVYNVKASG SSRRRSIQN    1200
QEAFDLDVAV KENKDDLNHV DLNVCTSFSG PGRSGMALME VNLLSGFMVP SEAISLSETV   1260
KKVEYDHGKL NLYLDSVNET QFCVNIPAVR NFKVSNTQDA SVSIVDYYEP RRQAVRSYNS   1320
EVKLSSCDLC SDVQGCRPCE DGASGSHHHS SVIFIFCFKL LYFMELWL                1368

SEQ ID NO: 32          moltype = AA  length = 1445
FEATURE                Location/Qualifiers
source                 1..1445
                       mol_type = protein
                       organism = Homo sapiens
SEQUENCE: 32
MQGPPLLTAA HLLCVCTAAL AVAPGPRFLV TAPGIIRPGG NVTIGVELLE HCPSQVTVKA     60
ELLKTASNLT VSVLEAEGVF EKGSFKTLTL PSLPLNSADE IYELRVTGRT QDEILFSNST    120
RLSFETKRIS VFIQTDKALY KPKQEVKFRI VTLFSDFKPY KTSLNILIKD PKSNLIQQWL    180
SQQSDLGVIS KTFQLSSHPI LGDWSIQVQV NDQTYYQSFQ VSEYVLPKFE VTLQTPLYCS    240
MNSKHLNGTI TAKYTYGKPV KGDVTLTFLP LSFWGKKKNI TKTFKINGSA NFSFNDEEMK    300
NVMDSSNGLS EYLDLSSPGP VEILTTVTES VTGISRNVST NVFFKQHDYI IEFFDYTTVL    360
KPSLNFTATV KVTRADGNQL TLEERRNNVV ITVTQRNYTE YWSGSNSGNQ KMEAVQKINY    420
TVPQSGTFKI EFPILEDSSE LQLKAYFLGS KSSMAVHSLF KSPSKTYIQL KTRDENIKVG    480
SPFELVVSGN KRLKELSYMV VSRGQLVAVG KQNSTMFSLT PENSWTPKAC VIVYYIEDDG    540
EIIISDVLKIP VQLVFKNKIK LYWSKVKAEP SEKVSLRISV TQPDSIVGIV AVDKSVNLMN   600
ASNDITMENV VHELELYNTG YYLGMFMNSF AVFQECGLWV LTDANLTKDY IDGVYDNAEY    660
AERFMEENEG HIVDIHDFSL GSSPHVRKHF PETWIWLDTN MGYRIYQEFE VTVPDSITSW    720
VATGFVISED LGLGLTTTPV ELQAFQPFFI FLNLPYSVIR GEEFALEITI FNYLKDATEV    780
KVIIEKSDKF DILMTSNEIN ATGHQQTLLV PSEDGATVLF PIRPTHLGEI PITVTALSPT    840
ASDAVTQMIL VKAEGIEKSY SQSILLDLTD NRLQSTLKTL SFSFPPNTVT GSERVQITAI    900
GDVLGPSING LASLIRMPYG CGEQNMINFA PNIYILDYLT KKKQLTDNLK EKALSFMRQG    960
YQRELLYQRE DGSFSAFGNY DPSGSTWLSA FVLRCFLEAD PYIDIDQNVL HRTYTWLKGH   1020
QKSNGEFWDP GRVIHSELQG GNKSPVTLTA YIVTSLLGYR KYQPNIDVQE SIHFLESEFS   1080
RGISDNYTLA LITYALSSVG SPKAKEALNM LTWRAEQEGG MQFWVSSESK LSDSWQPRSL   1140
DIEVAAYALL SHFLQFQTSE GIPIMRWLSR QRNSLGGFAS TQDTTVALKA LSEFAALMNT   1200
ERTNIQVTVT GPSSPSPVKF LIDTHNRLLL QTAELAVVQP TAVNISANGF GFAICQLNVV   1260
YNVKASGSSR RRSIQNQEA FDLDVAVKEN KDDLNHVDLN VCTSFSGPGR SGMALMEVNL   1320
LSGFMVPSEA ISLSETVKKV EYDHGKLNLY LDSVNETQFC VNIPAVRNFK VSNTQDASVS   1380
IVDYYEPRRQ AVRSYNSEVK LSSCDLCSDV QGCRPCEDGA SGSHHSSVI FIFCFKLLYF   1440
```

```
MELWL                                                                   1445

SEQ ID NO: 33            moltype = AA  length = 665
FEATURE                  Location/Qualifiers
source                   1..665
                         mol_type = protein
                         organism = Homo sapiens
SEQUENCE: 33
MQGPPLLTAA HLLCVCTAAL AVAPGPRFLV TAPGIIRPGG NVTIGVELLE HCPSQVTVKA    60
ELLKTASNLT VSVLEAEGVF EKGSFKTLTL PSLPLNSADE IYELRVTGRT QDEILFSNST   120
RLSFETKRIS VFIQTDKALY KPKQEVKFRI VTLFSDFKPY KTSLNILIKD PKSNLIQQWL   180
SQQSDLGVIS KTFQLSSHPI LGDWSIQVQV NDQTYYQSFQ VSEYVLPKFE VTLQTPLYCS   240
MNSKHLNGTI TAKYTYGKPV KGDVTLTFLP LSFWGKKKNI TKTFKINGSA NFSFNDEEMK   300
NVMDSSNGLS EYLDLSSPGP VEILTTVTES VTGISRNVST NVFFKQHDYI IEFFDYTTVL   360
KPSLNFTATV KVTRADGNQL TLEERRNNVV ITVTQRNYTE YWSGSNSGNQ KMEAVQKINY   420
TVPQSGTFKI EFPILEDSSE LQLKAYFLGS KSSMAVHSLF KSPSKTYIQL KTRDENIKVG   480
SPFELVVSGN KRLKELSYMV VSRGQLVAVG KQNSTMFSLT PENSWTPKAC VIVYYIEDDG   540
EIISDVLKIP VQLVFKNKIK LYWSKVKAEP SEKVSLRISV TQPDSIVGIV AVDKSVNLMN   600
ASNDITMENV VHELELYNTG YYLGMFMNSF AVFQECGLWV LTDANLTKDY IDGVYDNLFG   660
TQEAL                                                               665

SEQ ID NO: 34            moltype = AA  length = 1374
FEATURE                  Location/Qualifiers
source                   1..1374
                         mol_type = protein
                         organism = Homo sapiens
SEQUENCE: 34
EADAVEMQGP PLLTAAHLLC VCTAALAVAP GPRFLVTAPG IIRPGGNVTI GVELLEHCPS    60
QVTVKAELLK TASNLTVSVL EAEGVFEKGS FKTLTLPSDP KSNLIQQWLS QQSDLGVISK   120
TFQLSSHPIL GDWSIQVQVN DQTYYQSFQV SEYVLPKFEV TLQTPLYCSM NSKHLNGTIT   180
AKYTYGKPVK GDVTLTFLPL SFWGKKKNIT KTFKINGSAN FSFNDEEMKN VMDSSNGLSE   240
YLDLSSPGPV EILTTVTESV TGISRNVSTN VFFKQHDYII EFFDYTTVLK PSLNFTATVK   300
VTRADGNQLT LEERRNNVVI TVTQRNYTEY WSGSNSGNQK MEAVQKINYT VPQSGTFKIE   360
FPILEDSSEL QLKAYFLGSK SSMAVHSLFK SPSKTYIQLK TRDENIKVGS PFELVVSGNK   420
RLKELSYMVV SRGQLVAVGK QNSTMFSLTP ENSWTPKACV IVYYIEDDGE IISDVLKIPV   480
QLVFKNKIKL YWSKVKAEPS EKVSLRISVT QPDSIVGIVA VDKSVNLMNA SNDITMENVV   540
HELELYNTGY YLGMFMNSFA VFQECGLWVL TDANLTKDYI DGVYDNAEYA ERFMEENEGH   600
IVDIHDFSLG SSPHVRKHFP ETWIWLDTNM GYRIYQEFEV TVPDSITSWV ATGFVISEDL   660
GLGLTTTPVE LQAFQPPFIF LNLPYSVIRG EEFALEITIF NYLKDATEVK VIIEKSDKFD   720
ILMTSNEINA TGHQQTLLVP SEDGATVLFP IRPTHLGEIP ITVTALSPTA SDAVTQMILV   780
KAEGIEKSYS QSILLDLTDN RLQSTLKTLS FSFPPNTVTG SERVQITAIG DVLGPSINGL   840
ASLIRMPYGC GEQNMINFAP NIYILDYLTK KKQLTDNLKE KALSFMRQGY QRELLYQRED   900
GSFSAFGNYD PSGSTWLSAF VLRCFLEADP YIDIDQNVLH RTYTWLKGHQ KSNGEFWDPG   960
RVIHSELQGG NKSPVTLTAY IVTSLLGYRK YQPNIDVQES IHFLESEFSR GISDNYTLAL  1020
ITYALSSVGS PKAKEALNML TWRAEQEGGM QFWVSSESKL SDSWQPRSLD IEVAAYALLS  1080
HFLQFQTSEG IPIMRWLSRQ RNSLGGFAST QDTTVALKAL SEFAALMNTE RTNIQVTVTG  1140
PSSPSPVKFL IDTHNRLLLQ TAELAVVQPM AVNISANGFG FAICQLNVVY NVKASGSSRR  1200
RRSIQNQEAF DLDVAVKENK DDLNHVDLNV CTSFSGPGRS GMALMEVNLL SGFMVPSEAI  1260
SLSETVKKVE YDHGKLNLYL DSVNETQFCV NIPAVRNFKV SNTQDASVSI VDYYEPRRQA  1320
VRSYNSEVKL SSCDLCSDVQ GCRPCEDGAS GSHHHSSVIF IFCFKLLYFM ELWL        1374

SEQ ID NO: 35            moltype = AA  length = 854
FEATURE                  Location/Qualifiers
source                   1..854
                         mol_type = protein
                         organism = Homo sapiens
SEQUENCE: 35
VDKSVNLMNA SNDITMENVV HELELYNTGY YLGMFMNSFA VFQECGLWVL TDANLTKDYI    60
DGVYDNAEYA ERFMEENEGH IVDIHDFSLG SSPHVRKHFP ETWIWLDTNM GSRIYQEFEV   120
TVPDSITSWV ATGFVISEDL GLGLTTTPVE LQAFQPPFIF LNLPYSVIRG EEFALEITIF   180
NYLKDATEVK VIIEKSDKFD ILMTSNEINA TGHQQTLLVP SEDGATVLFP IRPTHLGEIP   240
ITVTALSPTA SDAITQMILV KAEGIEKSYS QSILLDLTDN RLQSTLKTLS FSFPPNTVTG   300
SERVQITAIG DVLGPSINGL ASLIRMPYGC GEQNMINFAP NIYILDYLTK KKQLTDNLKE   360
KALSFMRQGY QRELLYQRED GSFSAFGNYD PSGSTWLSAF VLRCFLEADP YIDIDQNVLH   420
RTYTWLKGHQ KSNGEFWDPG RVIHSELQGG NKSPVTLTAY IVTSLLGYRK YQPNIDVQES   480
IHFLESEFSR GISDNYTLAL ITYALSSVGS PKAKEALNML TWRAEQEGGM QFWVSSESKL   540
SDSWQPRSLD IEVAAYALLS HFLQFQTSEG IPIMRWLSRQ RNSLGGFAST QDTTVALKAL   600
SEFAALMNTE RTNIQVTVTG PSSPSPVKFL IDTHNRLLLQ TAELAVVQPT AVNISANGFG   660
FAICQLNVVY NVKASGSSRR RRSIQNQEAF DLDVAVKENK DDLNHVDLNV CTSFSGPGRS   720
GMALMEVNLL SGFMVPSEAI SLSETVKKVE YDHGKLNLYL DSVNETQFCV NIPAVRNFKV   780
SNTQDASVSI VDYYEPRRQA VRSYNSEVKL SSCDLCSDVQ GCRPCEDGAS GSHHHSSVIF   840
IFCFKLLYFM ELWL                                                     854

SEQ ID NO: 36            moltype = AA  length = 847
FEATURE                  Location/Qualifiers
source                   1..847
                         mol_type = protein
                         organism = Homo sapiens
SEQUENCE: 36
```

```
MNASNDITME NVVHELELYN TGYYLGMFMN SFAVFQECGL WVLTDANLTK DYIDGVYDNA    60
EYAERFMEEN EGHIVDIHDF SLGSSPHVRK HFPETWIWLD TNMGSRIYQE FEVTVPDSIT   120
SWVATGFVIS EDLGLGLTTT PVELQAFQPF FIFLNLPYSV IRGEEFALEI TIFNYLKDAT   180
EVKVIIEKSD KFDILMTSSE INATGHQQTL LVPSEDGATV LFPIRPTHLG EIPITVTALS   240
PTASDAITQM ILVKAEGIEK SYSQSILLDL TDNRLQSTLK TLSFSFPPNT VTGSERVQIT   300
AIGDVLGPSI NGLASLIRMP YGCGEQNMIN FAPNIYILDY LTKKKQLTDN LKEKALSFMR   360
QGYQRELLYQ REDGSFSAFG NYDPSGSTWL SAFVLRCFLE ADPYIDIDQN VLHRTYTWLK   420
GHQKSNGEFW DPGRVIHSEL QGGNKSPVTL TAYIVTSLLG YRKYQPNIDV QESIHFLESE   480
FSRGISDNYT LALITYALSS VGSPKAKEAL NMLTWRAEQE GGMQFWVSSE SKLSDSWQPR   540
SLDIEVAAYA LLSHFLQFQT SEGIPIMRWL SRQRNSLGGF ASTQDTTVAL KALSEFAALM   600
NTERTNIQVT VTGPSSPSPV KFLIDTHNRL LLQTAELAVV QPTAVNISAN GFGFAICQLN   660
VVYNVKASGS SRRRRSIQNQ EAFDLDVAVK ENKDDLNHVD LNVCTSFSGP GRSGMALMEV   720
NLLSGFMVPS EAISLSETVK KVEYDHGKLN LYLDSVNETQ FCVNIPAVRN FKVSNTQDAS   780
VSIVDYYEPR RQAVRSYNSE VKLSSCDLCS DVQGCRPCEN GASGSHHSS VIFIFCFKLL   840
YFMELWL                                                            847
```

SEQ ID NO: 37          moltype = DNA   length = 21
FEATURE                Location/Qualifiers
misc_feature           1..21
                       note = Synthetic sequence; gRNA Recognition Sequence
source                 1..21
                       mol_type = other DNA
                       organism = synthetic construct
SEQUENCE: 37
gcctccaagt cctgtctcaa t                                            21

SEQ ID NO: 38          moltype = DNA   length = 21
FEATURE                Location/Qualifiers
misc_feature           1..21
                       note = Synthetic sequence; gRNA Recognition Sequence
source                 1..21
                       mol_type = other DNA
                       organism = synthetic construct
SEQUENCE: 38
ggtaccatca cggcaaagta t                                            21

SEQ ID NO: 39          moltype = DNA   length = 21
FEATURE                Location/Qualifiers
misc_feature           1..21
                       note = Synthetic sequence; gRNA Recognition Sequence
source                 1..21
                       mol_type = other DNA
                       organism = synthetic construct
SEQUENCE: 39
gtaccatcac ggcaaagtat a                                            21

SEQ ID NO: 40          moltype = DNA   length = 21
FEATURE                Location/Qualifiers
misc_feature           1..21
                       note = Synthetic sequence; gRNA Recognition Sequence
source                 1..21
                       mol_type = other DNA
                       organism = synthetic construct
SEQUENCE: 40
gctacagttg aaggcctatt t                                            21

SEQ ID NO: 41          moltype = DNA   length = 21
FEATURE                Location/Qualifiers
misc_feature           1..21
                       note = Synthetic sequence; gRNA Recognition Sequence
source                 1..21
                       mol_type = other DNA
                       organism = synthetic construct
SEQUENCE: 41
gattgaagga gttaagctat a                                            21

SEQ ID NO: 42          moltype = DNA   length = 21
FEATURE                Location/Qualifiers
misc_feature           1..21
                       note = Synthetic sequence; gRNA Recognition Sequence
source                 1..21
                       mol_type = other DNA
                       organism = synthetic construct
SEQUENCE: 42
ggtcttggac taacaactac t                                            21

SEQ ID NO: 43          moltype = DNA   length = 21
FEATURE                Location/Qualifiers
misc_feature           1..21

```
                        note = Synthetic sequence; gRNA Recognition Sequence
source                  1..21
                        mol_type = other DNA
                        organism = synthetic construct
SEQUENCE: 43
gaaagatgcc actgaggtta a                                              21

SEQ ID NO: 44           moltype = DNA  length = 21
FEATURE                 Location/Qualifiers
misc_feature            1..21
                        note = Synthetic sequence; gRNA Recognition Sequence
source                  1..21
                        mol_type = other DNA
                        organism = synthetic construct
SEQUENCE: 44
gcatctactc aggataccac t                                              21

SEQ ID NO: 45           moltype = DNA  length = 21
FEATURE                 Location/Qualifiers
misc_feature            1..21
                        note = Synthetic sequence; gRNA Recognition Sequence
source                  1..21
                        mol_type = other DNA
                        organism = synthetic construct
SEQUENCE: 45
ggtacagcca acggcagtta a                                              21

SEQ ID NO: 46           moltype = DNA  length = 21
FEATURE                 Location/Qualifiers
misc_feature            1..21
                        note = Synthetic sequence; gRNA Recognition Sequence
source                  1..21
                        mol_type = other DNA
                        organism = synthetic construct
SEQUENCE: 46
ggctcttatg gaagttaacc t                                              21

SEQ ID NO: 47           moltype = DNA  length = 21
FEATURE                 Location/Qualifiers
misc_feature            1..21
                        note = Synthetic sequence; gRNA Recognition Sequence
source                  1..21
                        mol_type = other DNA
                        organism = synthetic construct
SEQUENCE: 47
gacaggcggt gagaagttac a                                              21

SEQ ID NO: 48           moltype = DNA  length = 21
FEATURE                 Location/Qualifiers
misc_feature            1..21
                        note = Synthetic sequence; gRNA Recognition Sequence
source                  1..21
                        mol_type = other DNA
                        organism = synthetic construct
SEQUENCE: 48
gcccagtggt ctcagtagat a                                              21

SEQ ID NO: 49           moltype = DNA  length = 19
FEATURE                 Location/Qualifiers
misc_feature            1..19
                        note = Synthetic sequence; gRNA Recognition Sequence
source                  1..19
                        mol_type = other DNA
                        organism = synthetic construct
SEQUENCE: 49
gccgatcctt acatagata                                                 19

SEQ ID NO: 50           moltype = DNA  length = 19
FEATURE                 Location/Qualifiers
misc_feature            1..19
                        note = Synthetic sequence; gRNA Recognition Sequence
source                  1..19
                        mol_type = other DNA
                        organism = synthetic construct
SEQUENCE: 50
cctagattct taagcatta                                                 19

SEQ ID NO: 51           moltype = DNA  length = 19
FEATURE                 Location/Qualifiers
```

```
misc_feature               1..19
                           note = Synthetic sequence; gRNA Recognition Sequence
source                     1..19
                           mol_type = other DNA
                           organism = synthetic construct
SEQUENCE: 51
aagcctgtgt aattgtgta                                                         19

SEQ ID NO: 52              moltype = DNA   length = 19
FEATURE                    Location/Qualifiers
misc_feature               1..19
                           note = Synthetic sequence; gRNA Recognition Sequence
source                     1..19
                           mol_type = other DNA
                           organism = synthetic construct
SEQUENCE: 52
agagttcaga tcactgcaa                                                         19

SEQ ID NO: 53              moltype = DNA   length = 19
FEATURE                    Location/Qualifiers
misc_feature               1..19
                           note = Synthetic sequence; gRNA Recognition Sequence
source                     1..19
                           mol_type = other DNA
                           organism = synthetic construct
SEQUENCE: 53
aggagacgta acgcttaca                                                         19

SEQ ID NO: 54              moltype = DNA   length = 19
FEATURE                    Location/Qualifiers
misc_feature               1..19
                           note = Synthetic sequence; gRNA Recognition Sequence
source                     1..19
                           mol_type = other DNA
                           organism = synthetic construct
SEQUENCE: 54
tgtaagcact aatgtgttc                                                         19

SEQ ID NO: 55              moltype = DNA   length = 19
FEATURE                    Location/Qualifiers
misc_feature               1..19
                           note = Synthetic sequence; gRNA Recognition Sequence
source                     1..19
                           mol_type = other DNA
                           organism = synthetic construct
SEQUENCE: 55
tgcagaatat gctgagagg                                                         19

SEQ ID NO: 56              moltype = DNA   length = 19
FEATURE                    Location/Qualifiers
misc_feature               1..19
                           note = Synthetic sequence; gRNA Recognition Sequence
source                     1..19
                           mol_type = other DNA
                           organism = synthetic construct
SEQUENCE: 56
actaagaagt aagtgtaac                                                         19

SEQ ID NO: 57              moltype = DNA   length = 19
FEATURE                    Location/Qualifiers
misc_feature               1..19
                           note = Synthetic sequence; gRNA Recognition Sequence
source                     1..19
                           mol_type = other DNA
                           organism = synthetic construct
SEQUENCE: 57
tgcagaatat gctgagagg                                                         19

SEQ ID NO: 58              moltype = DNA   length = 19
FEATURE                    Location/Qualifiers
misc_feature               1..19
                           note = Synthetic sequence; gRNA Recognition Sequence
source                     1..19
                           mol_type = other DNA
                           organism = synthetic construct
SEQUENCE: 58
ttggagatgt tcttggtcc                                                         19
```

METHODS OF TREATING DECREASED BONE MINERAL DENSITY WITH CLUSTER OF DIFFERENTIATION 109 (CD109) INHIBITORS

REFERENCE TO SEQUENCE LISTING

This application includes a Sequence Listing filed electronically as an XML file named 381203554SEQ, created on Sep. 21, 2022, with a size of 356 kilobytes. The Sequence Listing is incorporated herein by reference.

FIELD

The present disclosure relates generally to the treatment of subjects having decreased bone mineral density with Cluster of Differentiation 109 (CD109) inhibitors, and methods of identifying subjects having an increased risk of developing decreased bone mineral density.

BACKGROUND

Degenerative conditions of the bone can make individuals susceptible to bone fractures, bone pain, and other complications. Two significant degenerative conditions of the bone are osteopenia and osteoporosis. Decreased bone mineral density (osteopenia) is a condition of the bone that is less severe than osteoporosis and is characterized by a reduction in bone mass due to the loss of bone at a rate greater than new bone growth. Osteopenia manifests in bone having a mineral density lower than normal peak bone mineral density, but not as low as found in osteoporosis. Osteopenia can arise from a decrease in muscle activity, which may occur as the result of a bone fracture, bed rest, fracture immobilization, joint reconstruction, arthritis, and the like. Osteoporosis is a disease characterized by a gradual bone weakening due to demineralization of the bone and/or problems with its architecture. Osteoporosis manifests in bones by making them more susceptible to breaking. Hormone deficiencies related to menopause in women, and hormone deficiencies due to aging in both sexes contribute to degenerative conditions of the bone. In addition, insufficient dietary uptake of minerals essential to bone growth and maintenance are potential causes of bone loss. Genetic influences on osteoporosis have also been reported (Morris et al., Nature Genet., 2019, 51, 258-266).

The effects of osteopenia can be slowed, stopped, and even reversed by reproducing some of the effects of muscle use on the bone. This typically involves some application or simulation of the effects of mechanical stress on the bone. Compounds for the treatment of osteopenia or osteoporosis include pharmaceutical preparations that induce bone growth or retard bone demineralization, or mineral complexes that supplement the diet in an effort to replenish lost bone minerals. Low levels of estrogen in women, and low levels of androgen in men are the primary hormonal deficiencies that cause osteoporosis in the respective sexes. Other hormones such as the thyroid hormones, progesterone, and testosterone contribute to bone health. As such, the aforementioned hormonal compounds have been developed synthetically, or extracted from non-mammalian sources, and compounded into therapies for treating osteoporosis. Mineral supplement preparations containing iodine, zinc, manganese, boron, strontium, vitamin D3, calcium, magnesium, vitamin K, phosphorous, and copper have also been used to supplement insufficient dietary uptake of such minerals. However, long-term hormonal therapies have undesirable side effects such as increased cancer risk. In addition, it is uncertain if many of the mineral and hormonal supplements proposed can actually reduce the risk of fracture. Moreover, therapies using many synthetic or non-mammalian hormones have additional undesirable side effects, such as an increased risk of cardiovascular disorders, neurological disorders, or the exacerbation of pre-existing conditions.

Cluster Of Differentiation 109 (CD109) is a member of alpha2-macroglobulin/complement (AMCOM) family of thioester containing proteins. This glycosyl phosphatidylinositol (GPI)-linked glycoprotein localizes to the surface of platelets, activated T-cells, and endothelial cells. In addition, CD109 is expressed in hematopoietic cell lineages and some epithelial cells. CD109 protein binds to and negatively regulates signaling by transforming growth factor beta (TGF-β) in keratinocytes, and also associates with TGF-βRI and TGF-βRII. Moreover, CR109 could function as protease inhibitors like most members of AMCOM family.

SUMMARY

The present disclosure provides methods of treating a subject having decreased bone mineral density or at risk of developing decreased bone mineral density, the methods comprising administering a CD109 inhibitor to the subject.

The present disclosure also provides methods of treating a subject having osteopenia or at risk of developing osteopenia, the methods comprising administering a CD109 inhibitor to the subject.

The present disclosure also provides methods of treating a subject having Type I osteoporosis or at risk of developing Type I osteoporosis, the methods comprising administering a CD109 inhibitor to the subject.

The present disclosure also provides methods of treating a subject having Type II osteoporosis or at risk of developing Type II osteoporosis, the methods comprising administering a CD109 to the subject.

The present disclosure also provides methods of treating a subject having secondary osteoporosis or at risk of developing secondary osteoporosis, the methods comprising administering a CD109 inhibitor to the subject.

The present disclosure also provides methods of treating a subject with a therapeutic agent that treats or inhibits decreased bone mineral density, wherein the subject has decreased bone mineral density or is at risk of developing decreased bone mineral density, the methods comprising the steps of: determining whether the subject has a CD109 missense variant nucleic acid molecule encoding a CD109 predicted loss-of-function polypeptide by: obtaining or having obtained a biological sample from the subject; and performing or having performed a sequence analysis on the biological sample to determine if the subject has a genotype comprising the CD109 missense variant nucleic acid molecule encoding a CD109 predicted loss-of-function polypeptide; and: i) administering or continuing to administer the therapeutic agent that treats or inhibits decreased bone mineral density in a standard dosage amount to a subject that is CD109 reference, and/or administering a CD109 inhibitor to the subject; ii) administering or continuing to administer the therapeutic agent that treats or inhibits decreased bone mineral density in an amount that is the same as or less than a standard dosage amount to a subject that is heterozygous for the CD109 missense variant nucleic acid molecule, and/or administering a CD109 inhibitor to the subject; or iii) administering or continuing to administer the therapeutic agent that treats or inhibits decreased bone mineral density in an amount that is the same as or less than a standard dosage amount to a subject that is homozygous for the CD109 missense variant nucleic acid molecule; wherein the presence of a genotype having the CD109 missense variant nucleic acid molecule encoding the CD109 predicted loss-of-function polypeptide indicates the subject has a decreased risk of developing decreased bone mineral density.

The present disclosure also provides methods of identifying a subject having an increased risk of developing decreased bone mineral density, the methods comprising: determining or having determined the presence or absence of a CD109 missense variant nucleic acid molecule encoding a CD109 predicted loss-of-function polypeptide in a biological sample obtained from the subject; when the subject is CD109 reference, then the subject has an increased risk of developing decreased bone mineral density; and when the subject is heterozygous or homozygous for the CD109 missense variant nucleic acid molecule encoding the CD109 predicted loss-of-function polypeptide, then the subject has a decreased risk of developing decreased bone mineral density.

The present disclosure also provides therapeutic agents that treat or inhibit decreased bone mineral density for use in the treatment of decreased bone mineral density in a subject having: a CD109 missense variant genomic nucleic acid molecule encoding a CD109 predicted loss-of-function polypeptide; a CD109 missense variant mRNA molecule encoding a CD109 predicted loss-of-function polypeptide; or a CD109 missense variant cDNA molecule encoding a CD109 predicted loss-of-function polypeptide.

The present disclosure also provides CD109 inhibitors for use in the treatment of decreased bone mineral density in a subject that: a) is reference for a CD109 genomic nucleic acid molecule, a CD109 mRNA molecule, or a CD109 cDNA molecule; or b) is heterozygous for: i) a CD109 missense variant genomic nucleic acid molecule encoding a CD109 predicted loss-of-function polypeptide; ii) a CD109 missense variant mRNA molecule encoding a CD109 predicted loss-of-function polypeptide; or iii) a CD109 missense variant cDNA molecule encoding a CD109 predicted loss-of-function polypeptide.

DESCRIPTION

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or Alternately phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human. In some embodiments, the human is a patient under the care of a physician.

It has been observed in accordance with the present disclosure that CD109 missense variant nucleic acid molecules encoding a CD109 predicted loss-of-function polypeptide (whether these variations are homozygous or heterozygous in a particular subject) associate with a decreased risk of developing decreased bone mineral density. The details or directionality of CD109's involvement in bone mineral density is unclear. The data presented herein is the first to show that rare, nonsynonymous/loss-of-unction variants in CD109 are associated with a decreased risk of developing decreased bone mineral density. Therefore, subjects that are CD109 reference or heterozygous for CD109 missense variant nucleic acid molecules encoding CD109 predicted loss-of-function polypeptides may be treated with a CD109 inhibitor such that decreased bone mineral density is inhibited, the symptoms thereof are reduced, and/or development of symptoms is repressed. It is also believed that such subjects having decreased bone mineral density may further be treated with therapeutic agents that treat or inhibit decreased bone mineral density.

For purposes of the present disclosure, any particular subject, such as a human, can be categorized as having one of three CD109 genotypes: i) CD109 reference; ii) heterozygous for a CD109 missense variant nucleic acid molecule encoding a CD109 predicted loss-of-function polypeptide; or iii) homozygous for a CD109 missense variant nucleic acid molecules encoding a CD109 predicted loss-of-function polypeptide. A subject is CD109 reference when the subject does not have a copy of a CD109 missense variant nucleic acid molecules encoding a CD109 predicted lossof-function polypeptide. A subject is heterozygous for a CD109 missense variant nucleic acid molecules encoding a CD109 predicted loss-of-function polypeptide when the subject has a single copy of a CD109 missense variant nucleic acid molecule encoding a CD109 predicted loss-of-function polypeptide. A CD109 missense variant nucleic acid molecule encoding a CD109 predicted loss-of-function polypeptide is any nucleic acid molecule (such as, a genomic nucleic acid molecule, an mRNA molecule, or a cDNA molecule) encoding a variant CD109 polypeptide having a partial loss-of-function, a complete loss-of-function, a predicted partial loss-of-function, or a predicted complete loss-of-function. A subject who has a CD109 polypeptide having a partial loss-of-function (or predicted partial loss-of-function) is hypomorphic for CD109. A subject is homozygous for a CD109 missense variant nucleic acid molecule encoding a CD109 predicted loss-of-function polypeptide when the subject has two copies (same or different) of a CD109 missense variant nucleic acid molecules encoding a CD109 predicted loss-of-function polypeptide.

For subjects that are genotyped or determined to be CD109 reference, such subjects have an increased risk of developing decreased bone mineral density, such as osteopenia, Type I osteoporosis, Type II osteoporosis, and/or secondary osteoporosis. For subjects that are genotyped or determined to be either CD109 reference or heterozygous for a CD109 missense variant nucleic acid molecules encoding a CD109 predicted loss-of-function polypeptide, such subjects or subjects can be treated with a CD109 inhibitor.

In any of the embodiments described herein, the CD109 missense variant nucleic acid molecules encoding a CD109 predicted loss-of-function polypeptide can be any nucleic acid molecule (such as, for example, genomic nucleic acid molecule, mRNA molecule, or cDNA molecule) encoding a CD109 variant polypeptide having a partial loss-of-function, a complete loss-of-function, a predicted partial loss-of-function, or a predicted complete loss-of-function. In some embodiments, the CD109 missense variant nucleic acid molecules encoding a CD109 predicted loss-of-function polypeptide is associated with a reduced in vitro response to CD109 ligands compared with reference CD109. In some embodiments, the CD109 missense variant nucleic acid molecules encoding a CD109 predicted loss-of-function polypeptide is a CD109 variant that results in or is predicted to result in a premature truncation of a CD109 polypeptide compared to the human reference genome sequence. In some embodiments, the CD109 missense variant nucleic acid molecules encoding a CD109 predicted loss-of-function polypeptide is a variant that is predicted to be damaging by in vitro prediction algorithms such as Polyphen, SIFT, or similar algorithms. In some embodiments, the CD109 missense variant nucleic acid molecules encoding a CD109 predicted loss-of-function polypeptide is a variant that causes or is predicted to cause a nonsynonymous amino-acid substitution in CD109 and whose allele frequency is less than 1/100 alleles in the population from which the subject is selected. In some embodiments, the CD109 missense variant nucleic acid molecules encoding a CD109 predicted loss-of-function polypeptide is any rare missense variant (allele frequency <0.1%; or 1 in 1,000 alleles), or any splice-site, stop-gain, start-loss, stop-loss, frameshift, or in-frame indel, or other frameshift CD109 variant.

In any of the embodiments described herein, the CD109 predicted loss-of-function polypeptide can be any CD109 polypeptide having a partial loss-of-function, a complete loss-of-function, a predicted partial loss-of-function, or a predicted complete loss-of-function.

In any of the embodiments described herein, the CD109 missense variant nucleic acid molecules encoding a CD109 predicted loss-of-function polypeptide can include variations at positions of chromosome 6 using the nucleotide sequence of the CD109 reference genomic nucleic acid molecule (SEQ ID NO:1; ENSG00000156535.15 chr6:73,695,785-73,828,316 in the GRCh38/hg38 human genome assembly) as a reference sequence.

Numerous genetic variants in CD109 exist which cause subsequent changes in the CD109 polypeptide sequence including, but not limited to: 6:73730573:A:G, 6:73823473:GA:G (p.Ser1394fs, p.Ser1317fs, p. Ser1377fs), 6:73763607:C:A (p.Phe343Leu, p. Phe266Leu, p. Phe343Leu), 6:73803256:G:T (p.Gly972Val, p. Gly895Val, p. Gly972Val), 6:73818486:T:C (p.Val1337Ala, p. Val1260Ala, p. Val1320A1a), 6:73787379:G:A (p.Gly828Glu, p. Gly751Glu, p. Gly828Glu), 6:73771510:A:G (p.Ile586Val, p.Ile509Val, p.Ile586Val), 6:73806987:A:T (p.His1035Leu, p. His958Leu, p. His1035Leu), 6:73758991:A:G (p.Met241Val, p. Met164Val, p. Met241Val), 6:73823456:A:G 6:73762778:A:C (p.Glu298Ala, p. Glu221Ala, p. Glu298A1a), 6:73763660:A:G (p.Lys361Arg, p. Lys284Arg, p. Lys361Arg), 6:73730573:A:G (p.Lys169Arg, p. Lys169Arg), 6:73806956:G:A (p.Gly1025Ser, p. Gly948Ser, p. Gly1025Ser), 6:73792628:G:C (p.Asp902His, p. Asp825His, p. Asp902His), 6:73806926:A:T (p.Thr1015Ser, p. Thr938Ser, p. Thr1015Ser), 6:73771576:G:A (p.Glu608Lys, p. Glu531Lys, p. Glu608Lys), 6:73815026:C:T (p.Arg1272*, p. Arg1195*, p. Arg1255*), 6:73765952:G:A (p.Gly377Asp, p. Gly300Asp, p. Gly377Asp).

Any one or more (i.e., any combination) of the CD109 missense variant nucleic acid molecules encoding a CD109 predicted loss-of-function polypeptide can be used within any of the methods described herein to determine whether a subject has an increased risk of developing decreased bone mineral density. The combinations of particular variants can form a mask used for statistical analysis of the particular correlation of CD109 and increased risk of developing decreased bone mineral density.

In any of the embodiments described herein, the decreased bone mineral density is osteopenia, Type I osteoporosis, Type II osteoporosis, and/or secondary osteoporosis. In some embodiments, the decreased bone mineral density is osteopenia. In some embodiments, the decreased bone mineral density is Type I osteoporosis. In some embodiments, the decreased bone mineral density is Type II osteoporosis. In some embodiments, the decreased bone mineral density is secondary osteoporosis.

Symptoms of a decreased bone mineral density include, but are not limited to, increased bone fragility (manifesting as bone fracture as a result of a mild to moderate trauma), reduced bone density, localized bone pain and weakness in an area of a broken bone, loss of height or change in posture, such as stooping over, high levels of serum calcium or alkaline phosphatase on a blood test, vitamin D deficiency, and joint or muscle aches, or any combination thereof.

The present disclosure provides methods of treating a subject having decreased bone mineral density or at risk of developing decreased bone mineral density, the methods comprising administering a CD109 inhibitor to the subject.

The present disclosure also provides methods of treating a subject having osteopenia or at risk of developing osteopenia, the methods comprising administering a CD109 inhibitor to the subject.

The present disclosure also provides methods of treating a subject having Type I osteoporosis or at risk of developing Type I osteoporosis, the methods comprising administering a CD109 inhibitor to the subject.

The present disclosure also provides methods of treating a subject having Type II osteoporosis or at risk of developing Type II osteoporosis, the methods comprising administering a CD109 to the subject.

The present disclosure also provides methods of treating a subject having secondary osteoporosis or at risk of developing secondary osteoporosis, the methods comprising administering a CD109 inhibitor to the subject.

In some embodiments, the CD109 inhibitor comprises an inhibitory nucleic acid molecule. Examples of inhibitory nucleic acid molecules include, but are not limited to, antisense nucleic acid molecules, small interfering RNAs (siRNAs), and short hairpin RNAs (shRNAs). Such inhibitory nucleic acid molecules can be designed to target any region of a CD109 nucleic acid molecule. In some embodiments, the antisense RNA, siRNA, or shRNA hybridizes to a sequence within a CD109 genomic nucleic acid molecule or mRNA molecule and decreases expression of the CD109 polypeptide in a cell in the subject. In some embodiments, the CD109 inhibitor comprises an antisense molecule that hybridizes to a CD109 genomic nucleic acid molecule or mRNA molecule and decreases expression of the CD109 polypeptide in a cell in the subject. In some embodiments, the CD109 inhibitor comprises an siRNA that hybridizes to a CD109 genomic nucleic acid molecule or mRNA molecule and decreases expression of the CD109 polypeptide in a cell in the subject. In some embodiments, the CD109 inhibitor comprises an shRNA that hybridizes to a CD109 genomic nucleic acid molecule or mRNA molecule and decreases expression of the CD109 polypeptide in a cell in the subject.

The inhibitory nucleic acid molecules can comprise RNA, DNA, or both RNA and DNA. The inhibitory nucleic acid molecules can also be linked or fused to a heterologous nucleic acid sequence, such as in a vector, or a heterologous label. For example, the inhibitory nucleic acid molecules can be within a vector or as an exogenous donor sequence comprising the inhibitory nucleic acid molecule and a heterologous nucleic acid sequence. The inhibitory nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The inhibitory nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The inhibitory nucleic acid molecules can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $-O[(CH_2)_nO]_mCH_3$, $-O(CH_2)_nOCH_3$, $-O(CH_2)_nNH_2$, $-O(CH_2)_nCH_3$, $-O(CH_2)_n-ONH_2$, and $-O(CH_2)_nON[(CH_2)_nCH_3)]_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as CH$_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

In some embodiments, the antisense nucleic acid molecules are gapmers, whereby the first one to seven nucleotides at the 5' and 3' ends each have 2'-methoxyethyl (2'-MOE) modifications. In some embodiments, the first five nucleotides at the 5' and 3' ends each have 2'-MOE modifications. In some embodiments, the first one to seven nucleotides at the 5' and 3' ends are RNA nucleotides. In some embodiments, the first five nucleotides at the 5' and 3' ends are RNA nucleotides. In some embodiments, each of the backbone linkages between the nucleotides is a phosphorothioate linkage.

In some embodiments, the siRNA molecules have termini modifications. In some embodiments, the 5' end of the antisense strand is phosphorylated. In some embodiments, 5'-phosphate analogs that cannot be hydrolyzed, such as 5'-(E)-vinyl-phosphonate are used.

In some embodiments, the siRNA molecules have backbone modifications. In some embodiments, the modified phosphodiester groups that link consecutive ribose nucleosides have been shown to enhance the stability and in vivo bioavailability of siRNAs The non-ester groups (—OH, =O) of the phosphodiester linkage can be replaced with sulfur, boron, or acetate to give phosphorothioate, boranophosphate, and phosphonoacetate linkages. In addition, substituting the phosphodiester group with a phosphotriester can facilitate cellular uptake of siRNAs and retention on serum components by eliminating their negative charge. In some embodiments, the siRNA molecules have sugar modifications. In some embodiments, the sugars are deprotonated (reaction catalyzed by exo- and endonucleases) whereby the 2'-hydroxyl can act as a nucleophile and attack the adjacent phosphorous in the phosphodiester bond. Such alternatives include 2'-O-methyl, 2'-O-methoxyethyl, and 2'-fluoro modifications.

In some embodiments, the siRNA molecules have base modifications. In some embodiments, the bases can be substituted with modified bases such as pseudouridine, 5'-methylcytidine, $N_6$-methyladenosine, inosine, and $N_7$-methylguanosine.

In some embodiments, the siRNA molecules are conjugated to lipids. Lipids can be conjugated to the 5' or 3' termini of siRNA to improve their in vivo bioavailability by allowing them to associate with serum lipoproteins. Representative lipids include, but are not limited to, cholesterol and vitamin E, and fatty acids, such as palmitate and tocopherol.

In some embodiments, a representative siRNA has the following formula:
Sense: mN*mN*/i2FN/mN/i2FN/mN/i2FN/mN/i2FN/mN/ i2FN/mN/i2FN/mN/i2FN/mN/i2FN/*mN*/32FN/
Antisense: /52FN/*/i2FN/*mN/i2FN/mN/i2FN/mN/i2FN/ mN/i2FN/mN/i2FN/mN/i2FN/mN/i2FN/mN/i2FN/ mN*N*N wherein: "N" is the base; "2F" is a 2'-F modification; "m" is a 2'-O-methyl modification, "I" is an internal base; and "*" is a phosphorothioate backbone linkage.

The present disclosure also provides vectors comprising any one or more of the inhibitory nucleic acid molecules. In some embodiments, the vectors comprise any one or more of the inhibitory nucleic acid molecules and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

The present disclosure also provides compositions comprising any one or more of the inhibitory nucleic acid molecules. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

In some embodiments, the CD109 inhibitor is or comprises LY294002, which is a PI3K inhibitor that suppresses CD109 expression.

In some embodiments, the CD109 inhibitor comprises a nuclease agent that induces one or more nicks or double-strand breaks at a recognition sequence(s) or a DNA-binding protein that binds to a recognition sequence within a CD109 genomic nucleic acid molecule. The recognition sequence can be located within a coding region of the CD109 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the CD109 gene. For example, the recognition sequence can be located about 10, about 20, about 30, about 40, about 50, about 100, about 200, about 300, about 400, about 500, or about 1,000 nucleotides from the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair, about 15-18 bp for each ZFN, about 36 bp for a TALE protein or TALEN, and about 20 bp for a CRISPR/Cas guide RNA.

In some embodiments, CRISPR/Cas systems can be used to modify a CD109 genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of CD109 nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in a CD109 genomic nucleic acid molecule or it can be a nickase that creates a single-strand break in a CD109 genomic nucleic acid molecule. Additional examples of Cas proteins include, but are not limited to, Cas1, Cas1B, Cast, Cas3, Cas4, Cas5, Cas5e (CasD), Casio, Cas6e, Cas6f, Cas7, Cas8a1, Cas8a2, Cas8b, Cas8c, Cas9 (Csn1 or Csx12), Cas10, Cas10d, CasF, CasG, CasH, Csyl, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of CD109 genomic nucleic acid molecules can be generated by contacting a cell with a Cas protein and one or more gRNAs that hybridize to one or more gRNA recognition sequences within a target genomic locus in the CD109 genomic nucleic acid molecule. For example, a gRNA recognition sequence can be located within a region of SEQ ID NO:1. The gRNA recognition sequence can include or be proximate to the start codon of a CD109 genomic nucleic acid molecule or the stop codon of a CD109 genomic nucleic acid molecule. For example, the gRNA recognition sequence can be located from about 10, from about 20, from about 30, from about 40, from about 50, from about 100, from about 200, from about 300, from about 400, from about 500, or from about 1,000 nucleotides of the start codon or the stop codon.

The gRNA recognition sequences within a target genomic locus in a CD109 genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within a CD109 genomic nucleic acid molecule. An exemplary gRNA is a gRNA effective to direct a Cas enzyme to bind to or cleave a CD109 genomic nucleic acid molecule, wherein the gRNA comprises a DNA-targeting segment that hybridizes to a gRNA recognition sequence within the CD109 genomic nucleic acid molecule. Exemplary gRNAs comprise a DNA-targeting segment that hybridizes to a gRNA recognition sequence present within a CD109 genomic nucleic acid molecule that includes or is proximate to the start codon or the stop codon. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the start codon or located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the human CD109 reference gene are set forth in Table 1 as SEQ ID NOs:37-58.

TABLE 1

Guide RNA Recognition Sequences Near CD109

| Strand | gRNA Recognition Sequence | SEQ ID NO: |
|---|---|---|
| + | GCCTCCAAGTCCTGTCTCAAT | 37 |
| + | GGTACCATCACGGCAAAGTAT | 38 |
| + | GTACCATCACGGCAAAGTATA | 39 |
| + | GCTACAGTTGAAGGCCTATTT | 40 |
| + | GATTGAAGGAGTTAAGCTATA | 41 |
| + | GGTCTTGGACTAACAACTACT | 42 |
| + | GAAAGATGCCACTGAGGTTAA | 43 |
| + | GCATCTACTCAGGATACCACT | 44 |
| + | GGTACAGCCAACGGCAGTTAA | 45 |
| + | GGCTCTTATGGAAGTTAACCT | 46 |
| + | GACAGGCGGTGAGAAGTTACA | 47 |
| + | GCCCAGTGGTCTCAGTAGATA | 48 |
| + | GCCGATCCTTACATAGATA | 49 |
| + | CCTAGATTCTTAAGCATTA | 50 |
| + | AAGCCTGTGTAATTGTGTA | 51 |
| + | AGAGTTCAGATCACTGCAA | 52 |
| + | AGGAGACGTAACGCTTACA | 53 |
| + | TGTAAGCACTAATGTGTTC | 54 |
| + | CTGTACCTGATTCTATCAC | 55 |
| + | ACTAAGAAGTAAGTGTAAC | 56 |
| + | TGCAGAATATGCTGAGAGG | 57 |
| = | TTGGAGATGTTCTTGGTCC | 58 |

The Cas protein and the gRNA form a complex, and the Cas protein cleaves the target CD109 genomic nucleic acid molecule. The Cas protein can cleave the nucleic acid molecule at a site within or outside of the nucleic acid sequence present in the target CD109 genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the CD109 genomic nucleic acid molecule to which a DNA-targeting segment of a gRNA will bind.

Such methods can result, for example, in a CD109 genomic nucleic acid molecule in which a region of SEQ ID NO:1 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the CD109 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the methods of treatment further comprise detecting the presence or absence of a CD109 missense variant nucleic acid molecule encoding a CD109 predicted loss-of-function polypeptide in a biological sample from the subject. As used throughout the present disclosure, a "CD109 missense variant nucleic acid molecule encoding a CD109 predicted loss-of-function polypeptide" is any CD109 nucleic acid molecule (such as, for example, genomic nucleic acid molecule, mRNA molecule, or cDNA molecule) encoding a CD109 polypeptide having a partial loss-of-function, a complete loss-of-function, a predicted partial loss-of-function, or a predicted complete loss-of-function.

The present disclosure also provides methods of treating a subject with a therapeutic agent that treats or inhibits decreased bone mineral density, wherein the subject has decreased bone mineral density or is at risk of developing decreased bone mineral density. In some embodiments, the subject has decreased bone mineral density. In some embodiments, the subject is at risk of developing decreased bone mineral density. In some embodiments, the methods comprise determining whether the subject has a CD109 missense variant nucleic acid molecule encoding a CD109 predicted loss-of-function polypeptide by obtaining or having obtained a biological sample from the subject, and performing or having performed a sequence analysis on the biological sample to determine if the subject has a genotype comprising the CD109 missense variant nucleic acid molecule encoding a CD109 predicted loss-of-function polypeptide. In some embodiments, the methods further comprise administering or continuing to administer the therapeutic agent that treats or inhibits decreased bone mineral density in a standard dosage amount to a subject that is CD109 reference, and/or administering a CD109 inhibitor to the subject. In some embodiments, the methods further comprise administering or continuing to administer the therapeutic agent that treats or inhibits decreased bone mineral density in an amount that is the same as or less than a standard dosage amount to a subject that is heterozygous for the CD109 missense variant nucleic acid molecule, and/or administering a CD109 inhibitor to the subject. In some embodiments, the methods further comprise administering or continuing to administer the therapeutic agent that treats or inhibits decreased bone mineral density in an amount that is the same as or less than a standard dosage amount to a subject that is homozygous for the CD109 missense variant nucleic acid molecule. The presence of a genotype having the CD109 missense variant nucleic acid molecule encoding the CD109 predicted loss-of-function polypeptide indicates the subject has a decreased risk of developing decreased bone mineral density. In some embodiments, the subject is CD109 reference. In some embodiments, the subject is heterozygous for a CD109 missense variant nucleic acid molecule encoding a CD109 predicted loss-of-function polypeptide.

For subjects that are genotyped or determined to be either CD109 reference or heterozygous for a CD109 missense variant nucleic acid molecule encoding a CD109 predicted loss-of-function polypeptide, such subjects can be treated with a CD109 inhibitor, as described herein.

Detecting the presence or absence of a CD109 missense variant nucleic acid molecule encoding a CD109 predicted loss-of-function polypeptide in a biological sample from a subject and/or determining whether a subject has a CD109 missense variant nucleic acid molecule encoding a CD109 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when the subject is CD109 reference, the subject is administered a therapeutic agent that treats or inhibits decreased bone mineral density in a standard dosage amount. In some embodiments, when the subject is heterozygous for a CD109 missense variant nucleic acid molecule encoding a CD109 predicted loss-of-function polypeptide, the subject is administered a therapeutic agent that treats or inhibits decreased bone mineral density in a dosage amount that is the same as or less than a standard dosage amount.

In some embodiments, the treatment methods further comprise detecting the presence or absence of a CD109 predicted loss-of-function polypeptide in a biological sample from the subject. In some embodiments, when the subject does not have a CD109 predicted loss-of-function polypeptide, the subject is administered a therapeutic agent that treats or inhibits decreased bone mineral density in a standard dosage amount. In some embodiments, when the subject has a CD109 predicted loss-of-function polypeptide, the subject is administered a therapeutic agent that treats or inhibits decreased bone mineral density in a dosage amount that is the same as or less than a standard dosage amount.

The present disclosure also provides methods of treating a subject with a therapeutic agent that treats or inhibits decreased bone mineral density, wherein the subject has decreased bone mineral density or is at risk of developing decreased bone mineral density. In some embodiments, the subject has decreased bone mineral density. In some embodiments, the subject is at risk of developing decreased bone mineral density. In some embodiments, the method comprises determining whether the subject has a CD109 predicted loss-of-function polypeptide by obtaining or having obtained a biological sample from the subject, and performing or having performed an assay on the biological sample to determine if the subject has a CD109 predicted loss-of-function polypeptide. When the subject does not have a CD109 predicted loss-of-function polypeptide, the therapeutic agent that treats or inhibits decreased bone mineral density is administered or continued to be administered to the subject in a standard dosage amount, and/or a CD109 inhibitor is administered to the subject. When the subject has a CD109 predicted loss-of-function polypeptide, the therapeutic agent that treats or inhibits decreased bone mineral density is administered or continued to be administered to the subject in an amount that is the same as or less than a standard dosage amount, and/or a CD109 inhibitor is administered to the subject. The presence of a CD109 predicted loss-of-function polypeptide indicates the subject has a decreased risk of developing decreased bone mineral density. In some embodiments, the subject has a CD109 predicted loss-of-function polypeptide. In some embodiments, the subject does not have a CD109 predicted loss-of-function polypeptide.

Detecting the presence or absence of a CD109 predicted loss-of-function polypeptide in a biological sample from a subject and/or determining whether a subject has a CD109 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

Examples of therapeutic agents that treat or inhibit decreased bone mineral density include, but are not limited to: calcium and vitamin D supplementation (vitamin D2, vitamin D3, and cholecalciferol), bisphosphonate medications, such as FOSAMAX®, (alendronate), BONIVA® (ibandronate), RECLAST® (zoledronate), ACTONEL® (risedronate), MIACALCIN®, FORTICAL®, and CALCIMAR® (calcitonin), FORTEO® (teriparatide), PROLIA® (denosumab), hormone replacement therapy with estrogen and progesterone as well as EVISTA® (raloxifene), and EVENITY® (romosozumab). In some embodiments, the therapeutic agent that treats or inhibits decreased bone mineral density is vitamin D2, vitamin D3, cholecalciferol, alendronate, ibandronate, zoledronate, risedronate, calcitonin, teriparatide, denosumab, or raloxifene. In some embodiments, the therapeutic agent that treats or inhibits decreased bone mineral density is vitamin D2. In some embodiments, the therapeutic agent that treats or inhibits decreased bone mineral density is vitamin D3. In some embodiments, the therapeutic agent that treats or inhibits decreased bone mineral density is cholecalciferol. In some embodiments, the therapeutic agent that treats or inhibits decreased bone mineral density is alendronate. In some embodiments, the therapeutic agent that treats or inhibits decreased bone mineral density is ibandronate. In some embodiments, the therapeutic agent that treats or inhibits decreased bone mineral density is zoledronate. In some embodiments, the therapeutic agent that treats or inhibits decreased bone mineral density is risedronate. In some embodiments, the therapeutic agent that treats or inhibits decreased bone mineral density is calcitonin. In some embodiments, the therapeutic agent that treats or inhibits decreased bone mineral density is teriparatide. In some embodiments, the therapeutic agent that treats or inhibits decreased bone mineral density is denosumab. In some embodiments, the therapeutic agent that treats or inhibits decreased bone mineral density is raloxifene.

In some embodiments, the dose of the therapeutic agents that treat or inhibit decreased bone mineral density can be decreased by about 10%, by about 20%, by about 30%, by about 40%, by about 50%, by about 60%, by about 70%, by about 80%, or by about 90% for subjects that are heterozygous for a CD109 missense variant nucleic acid molecule encoding a CD109 predicted loss-of-function polypeptide (i.e., a less than the standard dosage amount) compared to subjects that are CD109 reference (who may receive a standard dosage amount). In some embodiments, the dose of the therapeutic agents that treat or inhibit decreased bone mineral density can be decreased by about 10%, by about 20%, by about 30%, by about 40%, or by about 50%. In addition, the subjects that are heterozygous for a CD109 missense variant nucleic acid molecule encoding a CD109 predicted loss-of-function polypeptide can be administered less frequently compared to subjects that are CD109 reference.

In some embodiments, the dose of the therapeutic agents that treat or inhibit decreased bone mineral density can be decreased by about 10%, by about 20%, by about 30%, by about 40%, by about 50%, for subjects that are homozygous for a CD109 missense variant nucleic acid molecule encoding a CD109 predicted loss-of-function polypeptide compared to subjects that are heterozygous for a CD109 missense variant nucleic acid molecule encoding a CD109 predicted loss-of-function polypeptide. In some embodiments, the dose of the therapeutic agents that treat or inhibit decreased bone mineral density can be decreased by about 10%, by about 20%, by about 30%, by about 40%, or by about 50%. In addition, the dose of therapeutic agents that treat or inhibit decreased bone mineral density in subjects that are homozygous for a CD109 missense variant nucleic acid molecule encoding a CD109 predicted loss-of-function polypeptide can be administered less frequently compared to subjects that are heterozygous for a CD109 missense variant nucleic acid molecule encoding a CD109 predicted loss-of-function polypeptide.

Administration of the therapeutic agents that treat or inhibit decreased bone mineral density and/or CD109 inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit decreased bone mineral density and/or CD109 inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in decreased bone mineral density, a decrease/reduction in the severity of decreased bone mineral density (such as, for example, a reduction or inhibition of development of decreased bone mineral density), a decrease/reduction in symptoms and decreased bone mineral density-related effects, delaying the onset of symptoms and decreased bone mineral density-related effects, reducing the severity of symptoms of decreased bone mineral density-related effects, reducing the number of symptoms and decreased bone mineral density-related effects, reducing the latency of symptoms and decreased bone mineral density-related effects, an amelioration of symptoms and decreased bone mineral density-related effects, reducing secondary symptoms, reducing secondary infections, preventing relapse to decreased bone mineral density, decreasing the number or frequency of relapse episodes, increasing latency between symptomatic episodes, increasing time to sustained progression, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of decreased bone mineral density development/progression (such as, for example, a complete or partial avoidance/inhibition or a delay), and an increased survival time of the affected host animal, following administration of a therapeutic protocol. Treatment of decreased bone mineral density encompasses the treatment of a subject already diagnosed as having any form of decreased bone mineral density at any clinical stage or manifestation, the delay of the onset or evolution or aggravation or deterioration of the symptoms or signs of decreased bone mineral density, and/or preventing and/or reducing the severity of decreased bone mineral density.

The present disclosure also provides methods of identifying a subject having an increased risk of developing decreased bone mineral density. In some embodiments, the method comprises determining or having determined in a biological sample obtained from the subject the presence or absence of a CD109 missense variant nucleic acid molecule (such as a genomic nucleic acid molecule, mRNA molecule, and/or cDNA molecule) encoding a CD109 predicted loss-of-function polypeptide encoding a CD109 polypeptide. When the subject lacks a CD109 missense variant nucleic acid molecule encoding a CD109 predicted loss-of-function polypeptide (i.e., the subject is genotypically categorized as a CD109 reference), then the subject has an increased risk of developing decreased bone mineral density. When the subject has a CD109 missense variant nucleic acid molecule encoding a CD109 predicted loss-of-function polypeptide (i.e., the subject is heterozygous or homozygous for a CD109 missense variant nucleic acid molecule encoding a CD109 predicted loss-of-function polypeptide), then the subject has a decreased risk of developing decreased bone mineral density.

Having a single copy of a CD109 missense variant nucleic acid molecule encoding a CD109 predicted loss-of-function polypeptide is more protective of a subject from developing decreased bone mineral density than having no copies of a CD109 missense variant nucleic acid molecule encoding a CD109 predicted loss-of-function polypeptide. Without intending to be limited to any particular theory or mechanism of action, it is believed that a single copy of a CD109 missense variant nucleic acid molecule encoding a CD109 predicted loss-of-function polypeptide (i.e., heterozygous for a CD109 missense variant nucleic acid molecule encoding a CD109 predicted loss-of-function polypeptide) is protective of a subject from developing decreased bone mineral density, and it is also believed that having two copies of a CD109 missense variant nucleic acid molecule encoding a CD109 predicted loss-of-function polypeptide (i.e., homozygous for a CD109 missense variant nucleic acid molecule encoding a CD109 predicted loss-of-function polypeptide) may be more protective of a subject from developing decreased bone mineral density, relative to a subject with a single copy. Thus, in some embodiments, a single copy of a CD109 missense variant nucleic acid molecule encoding a CD109 predicted loss-of-function polypeptide may not be completely protective, but instead, may be partially or incompletely protective of a subject from developing decreased bone mineral density. While not desiring to be bound by any particular theory, there may be additional factors or molecules involved in the development of decreased bone mineral density that are still present in a subject having a single copy of a CD109 missense variant nucleic acid molecule encoding a CD109 predicted loss-offunction polypeptide, thus resulting in less than complete protection from the development of decreased bone mineral density.

Determining whether a subject has a CD109 missense variant nucleic acid molecule encoding a CD109 predicted loss-of-function polypeptide in a biological sample from a subject and/or determining whether a subject has a CD109 missense variant nucleic acid molecule encoding a CD109 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when a subject is identified as having an increased risk of developing decreased bone mineral density, the subject is treated with a therapeutic agent that treats or inhibits decreased bone mineral density, and/or a CD109 inhibitor, as described herein. For example, when the subject is CD109 reference, and therefore has an increased risk of developing decreased bone mineral density, the subject is administered a CD109 inhibitor. In some embodiments, such a subject is also administered a therapeutic agent that treats or inhibits decreased bone mineral density. In some embodiments, when the subject is heterozygous for a CD109 missense variant nucleic acid molecule encoding a CD109 predicted loss-of-function polypeptide, the subject is administered the therapeutic agent that treats or inhibits decreased bone mineral density in a dosage amount that is the same as or less than a standard dosage amount, and is also administered a CD109 inhibitor. In some embodiments, such a subject is also administered a therapeutic agent that treats or inhibits decreased bone mineral density. In some embodiments, when the subject is homozygous for a CD109 missense variant nucleic acid molecule encoding a CD109 predicted loss-of-function polypeptide, the subject is administered the therapeutic agent that treats or inhibits decreased bone mineral density in a dosage amount that is the same as or less than a standard dosage amount. In some embodiments, the subject is CD109 reference. In some embodiments, the subject is heterozygous for a CD109 missense variant nucleic acid molecule encoding a CD109 predicted loss-of-function polypeptide. In some embodiments, the subject is homozygous for a CD109 missense variant nucleic acid molecule encoding a CD109 predicted loss-of-function polypeptide.

In some embodiments, any of the methods described herein can further comprise determining the subject's gene burden of having a CD109 missense variant nucleic acid molecule encoding a CD109 predicted loss-of-function polypeptide, and/or a CD109 predicted loss-of-function variant polypeptide associated with a decreased risk of developing decreased bone mineral density. The gene burden is the aggregate of all variants in the CD109 gene, which can be carried out in an association analysis with decreased bone mineral density. In some embodiments, the subject is homozygous for one or more CD109 missense variant nucleic acid molecules encoding a CD109 predicted loss-of-function polypeptide associated with a decreased risk of developing decreased bone mineral density. In some embodiments, the subject is heterozygous for one or more CD109 missense variant nucleic acid molecules encoding a CD109 predicted loss-of-function polypeptide associated with a decreased risk of developing decreased bone mineral density. The result of the association analysis suggests that CD109 missense variant nucleic acid molecules encoding a CD109 predicted loss-of-function polypeptide are associated with decreased risk of developing decreased bone mineral density. When the subject has a lower gene burden, the subject is at a higher risk of developing decreased bone mineral density and the subject is administered or continued to be administered the therapeutic agent that treats or inhibits decreased bone mineral density in a standard dosage amount. When the subject has a greater gene burden, the subject is at a lower risk of developing decreased bone mineral density and the subject is administered or continued to be administered the therapeutic agent that treats or inhibits decreased bone mineral density in an amount that is the same as or less than the standard dosage amount. The greater the gene burden, the lower the risk of developing decreased bone mineral density.

The CD109 missense variant nucleic acid molecule encoding a CD109 predicted loss-of-function polypeptide, and/or a CD109 predicted loss-of-function variant polypeptide used for determining the subject's gene burden include, but are not limited to 6:73730573:A:G, 6:73823473:GA:G (p.Ser1394fs, p.Ser1317fs, p. Ser1377fs), 6:73763607:C:A (p.Phe343Leu, p. Phe266Leu, p. Phe343Leu), 6:73803256: G:T (p.Gly972Val, p. Gly895Val, p. Gly972Val), 6:73818486:T:C (p.Val1337Ala, p. Val1260Ala, p. Val1320A1a), 6:73787379:G:A (p.Gly828Glu, p. Gly751Glu, p. Gly828Glu), 6:73771510:A:G (p.Ile586Val, p. Ile509Val, p.Ile586Val), 6:73806987:A:T (p.His1035Leu, p. His958Leu, p. His1035Leu), 6:73758991:A:G (p.Met241Val, p. Met164Val, p. Met241Val), 6:73823456: A:G 6:73762778:A:C (p.Glu298Ala, p. Glu221Ala, p. Glu298A1a), 6:73763660:A:G (p.Lys361Arg, p. Lys284Arg, p. Lys361Arg), 6:73730573:A:G (p.Lys169Arg, p. Lys169Arg), 6:73806956:G:A (p.Gly1025Ser, p. Gly948Ser, p. Gly1025Ser), 6:73792628:G:C (p.Asp902His, p. Asp825His, p. Asp902His), 6:73806926: A:T (p.Thr1015Ser, p. Thr938Ser, p. Thr1015Ser), 6:73771576:G:A (p.Glu608Lys, p. Glu531Lys, p. Glu608Lys), 6:73815026:C:T (p.Arg1272*, p. Arg1195*, p. Arg1255*), 6:73765952:G:A (p.Gly377Asp, p. Gly300Asp, p. Gly377Asp).

In some embodiments, the subject's gene burden of having any one or more CD109 missense variant nucleic acid molecules encoding a CD109 predicted loss-of-function polypeptide represents a weighted sum of a plurality of any of the CD109 missense variant nucleic acid molecules encoding a CD109 predicted loss-of-function polypeptide. In some embodiments, the gene burden is calculated using at least about 2, at least about 3, at least about 4, at least about 5, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, at least about 1,000, at least about 10,000, at least about 100,000, or at least about or more than 1,000,000 genetic variants present in or around (up to 10 Mb) the CD109 gene where the genetic burden is the number of alleles multiplied by the association estimate with decreased bone mineral density or related outcome for each allele (e.g., a weighted burden score). This can include any genetic variants, regardless of their genomic annotation, in proximity to the CD109 gene (up to 10 Mb around the gene) that show a non-zero association with decreased bone mineral density-related traits in a genetic association analysis. In some embodiments, when the subject has a gene burden above a desired threshold score, the subject has a decreased risk of developing decreased bone mineral density. In some embodiments, when the subject has an gene burden below a desired threshold score, the subject has an increased risk of developing decreased bone mineral density.

In some embodiments, the gene burden may be divided into quintiles, e.g., top quintile, intermediate quintile, and bottom quintile, wherein the top quintile of gene burden corresponds to the lowest risk group and the bottom quintile of gene burden corresponds to the highest risk group. In some embodiments, a subject having a greater gene burden comprises the highest weighted gene burdens, including, but not limited to the top 10%, top 20%, top 30%, top 40%, or top 50% of gene burdens from a subject population. In some embodiments, the genetic variants comprise the genetic variants having association with decreased bone mineral density in the top 10%, top 20%, top 30%, top 40%, or top 50% of p-value range for the association. In some embodiments, each of the identified genetic variants comprise the genetic variants having association with decreased bone mineral density with p-value of no more than about $10^{-2}$, about $10^{-3}$, about $10^{-4}$, about $10^{-5}$, about $10^{-6}$, about $10^{-7}$, about $10^{-8}$, about $10^{-9}$, about $10^{-10}$, about $10^{-11}$, about $10^{-12}$, about $10^{-13}$, about $10^{-14}$, about or $10^{-15}$. In some embodiments, the identified genetic variants comprise genetic variants having association with decreased bone mineral density with p-value of less than $5 \times 10^{-8}$. In some embodiments, the identified genetic variants comprise genetic variants having association with decreased bone mineral density in high-risk subjects as compared to the rest of the reference population with odds ratio (OR) about 1.5 or greater, about 1.75 or greater, about 2.0 or greater, or about 2.25 or greater for the top 20% of the distribution; or about 1.5 or greater, about 1.75 or greater, about 2.0 or greater, about 2.25 or greater, about 2.5 or greater, or about 2.75 or greater. In some embodiments, the odds ratio (OR) may range from about 1.0 to about 1.5, from about 1.5 to about 2.0, from about 2.0 to about 2.5, from about 2.5 to about 3.0, from about 3.0 to about 3.5, from about 3.5 to about 4.0, from about 4.0 to about 4.5, from about 4.5 to about 5.0, from about 5.0 to about 5.5, from about 5.5 to about 6.0, from about 6.0 to about 6.5, from about 6.5 to about 7.0, or greater than 7.0. In some embodiments, high-risk subjects comprise subjects having gene burdens in the bottom decile, quintile, or tertile in a reference population. The threshold of the gene burden is determined on the basis of the nature of the intended practical application and the risk difference that would be considered meaningful for that practical application.

In some embodiments, when a subject is identified as having an increased risk of developing decreased bone mineral density, the subject is treated with a therapeutic agent that treats or inhibits decreased bone mineral density, and/or a CD109 inhibitor, as described herein. For example, when the subject is CD109 reference, and therefore has an increased risk of developing decreased bone mineral density, the subject is administered a CD109 inhibitor. In some embodiments, such a subject is administered a therapeutic agent that treats or inhibits decreased bone mineral density. In some embodiments, when the subject is heterozygous for a CD109 missense variant nucleic acid molecule encoding a CD109 predicted loss-of-function polypeptide, the subject is administered the therapeutic agent that treats or inhibits decreased bone mineral density in a dosage amount that is the same as or less than a standard dosage amount, and is also administered a CD109 inhibitor. In some embodiments, the subject is CD109 reference. In some embodiments, the subject is heterozygous for a CD109 missense variant nucleic acid molecule encoding a CD109 predicted loss-of-function polypeptide. Furthermore, when the subject has a lower gene burden for having a CD109 missense variant nucleic acid molecule encoding a CD109 predicted loss-of-function polypeptide, and therefore has an increased risk of developing decreased bone mineral density, the subject is administered a therapeutic agent that treats or inhibits decreased bone mineral density. In some embodiments, when the subject has a lower gene burden for having a CD109 missense variant nucleic acid molecule encoding a CD109 predicted loss-of-function polypeptide, the subject is administered the therapeutic agent that treats or inhibits decreased bone mineral density in a dosage amount that is the same as or greater than the standard dosage amount administered to a subject who has a greater gene burden for having a CD109 missense variant nucleic acid molecule encoding a CD109 predicted loss-of-function polypeptide.

CD109 variants that can be used in the gene burden analysis include any one or more, or any combination, of the following (the Variant column indicates the chromosome, physical genomic position in base pairs, reference allele, and alternative allele for each variant, according to build 38 of the Human Genome sequence by the Human Genome Reference Consortium; coding DNA and protein changes are provided according to the Human Genome Variation Society nomenclature, and refer to three CD109 transcripts annotated in the in the Ensembl database (URL: world wide at "useast.ensembl.org/index.html"); annotations on these three transcripts are reported in the table in the following order: EN5100000287097:EN5100000422508: EN5100000437994):

| Variant | Coding DNA change | Protein change |
|---|---|---|
| 6:73696217:T:C | c.2T > C:c.2T > C:c.2T > C | p.Met1?:p.Met1?:p.Met1? |
| 6:73696249:C:T | c.34C > T:c.34C > T:c.34C > T | p.Leu12Phe:p.Leu12Phe:p.Leu12Phe |
| 6:73696250:T:G | c.35T > G:c.35T > G:c.35T > G | p.Leu12Arg:p.Leu12Arg:p.Leu12Arg |
| 6:73696250:TC:T | c.37delC:c.37delC:c.37delC | p.Leu13fs:p.Leu13fs:p.Leu13fs |
| 6:73697404:C:CG | c.81dupG:c.81dupG:c.81dupG | p.Phe28fs:p.Phe28fs:p.Phe28fs |
| 6:73697413:G:GT | c.89dupT:c.89dupT:c.89dupT | p.Thr31fs:p.Thr31fs:p.Thr31fs |
| 6:73697434:A:G | c.109A > G:c.109A > G:c.109A > G | p.Arg37Gly:p.Arg37Gly:p.Arg37Gly |
| 6:73697459:G:T | c.134G > T:c.134G > T:c.134G > T | p.Gly45Val:p.Gly45Val:p.Gly45Val |
| 6:73697504:C:T | c.179C > T:c.179C > T:c.179C > T | p.Ala60Val:p.Ala60Val:p.Ala60Val |
| 6:73697506:G:T | c.181G > T:c.181G > T:c.181G > T | p.Glu61*:p.Glu61*:p.Glu61* |
| 6:73697515:A:T | c.190A > T:c.190A > T:c.190A > T | p.Lys64*:p.Lys64*:p.Lys64* |
| 6:73697534:CTG:C | c.211_212delGT:c.211_212delGT:c.211_212delGT | p.Val71fs:p.Val71fs:p.Val71fs |
| 6:73723265:C:T | c.262C > T:c.262C > T:c.262C > T | p.Leu88Phe:p.Leu88Phe:p.Leu88Phe |
| 6:73723278:C:G | c.275C > G:c.275C > G:c.275C > G | p.Ser92*:p.Ser92*:p.Ser92* |
| 6:73730377:C:G | c.310C > G:c.310C > G | p.Leu104Val:p.Leu104Val |
| 6:73730398:C:T | c.331C > T:c.331C > T | p.Gln111*:p.Gln111* |
| 6:73730430:CT:C | c.365delT:c.365delT | p.Leu122fs:p.Leu122fs |

-continued

| Variant | Coding DNA change | Protein change |
| --- | --- | --- |
| 6:73730456:C:CT | c.390dupT:c.390dupT | p.Val131fs:p.Val131fs |
| 6:73730474:A:G | c.407A > G:c.407A > G | p.Asp136Gly:p.Asp136Gly |
| 6:73730475:C:G | c.408C > G:c.408C > G | p.Asp136Glu:p.Asp136Glu |
| 6:73730512:C:T | c.445C > T:c.445C > T | p.Arg149Cys:p.Arg149Cys |
| 6:73730513:G:A | c.446G > A:c.446G > A | p.Arg149His:p.Arg149His |
| 6:73730513:G:T | c.446G > T:c.446G > T | p.Arg149Leu:p.Arg149Leu |
| 6:73730528:T:TA | c.461_462insA:c.461_462insA | p.Phe154fs:p.Phe154fs |
| 6:73736444:C:G | c.569C > G:c.338C > G:c.569C > G | p.Ser190Cys:p.Ser113Cys:p.Ser190Cys |
| 6:73736450:CT:C | c.579delT:c.348delT:c.579delT | p.Gln194fs:p.Gln117fs:p.Gln194fs |
| 6:73736460:A:AT | c.586dupT:c.355dupT:c.586dupT | p.Ser196fs:p.Ser119fs:p.Ser196fs |
| 6:73736462:C:G | c.587C > G:c.356C > G:c.587C > G | p.Ser196Cys:p.Ser119Cys:p.Ser196Cys |
| 6:73736471:C:T | c.596C > T:c.365C > T:c.596C > T | p.Pro199Leu:p.Pro122Leu:p.Pro199Leu |
| 6:73736491:A:G | c.616A > G:c.385A > G:c.616A > G | p.Ile206Val:p.Ile129Val:p.Ile206Val |
| 6:73756670:G:A | c.661G > A:c.430G > A:c.661G > A | p.Val221Ile:p.Val144Ile:p.Val221Ile |
| 6:73756683:G:T | c.673 + 1G > T:c.442 + 1G > T:c.673 + 1G > T | |
| 6:73758949:C:T | c.679C > T:c.448C > T:c.679C > T | p.Pro227Ser:p.Pro150Ser:p.Pro227Ser |
| 6:73758966:T:TTG | c.697_698insGT:c.466_467insGT:c.697_698insGT | p.Leu233fs:p.Leu156fs:p.Leu233fs |
| 6:73759007:TA:T | c.740delA:c.509delA:c.740delA | p.Asn247fs:p.Asn170fs:p.Asn247fs |
| 6:73759013:G:A | c.743G > A:c.512G > A:c.743G > A | p.Gly248Asp:p.Gly171Asp:p.Gly248Asp |
| 6:73759024:C:T | c.754G > T:c.523G > T:c.754G > T | p.Ala252Ser:p.Ala175Ser:p.Ala252Ser |
| 6:73759025:C:A | c.755C > A:c.524C > A:c.755C > A | p.Ala252Glu:p.Ala175Glu:p.Ala252Glu |
| 6:73759026:AAAGT:A | c.757_758 + 2delAAGT:c.526_527 + 2delAAGT:c.757_758 + 2delAAGT | p.Lys253fs:p.Lys176fs:p.Lys253fs |
| 6:73759029:G:T | c.758 + 1G > T:c.527 + 1G > T:c.758 + 1G > T | |
| 6:73762393:TG:T | c.771delG:c.540delG:c.771delG | p.Lys258fs:p.Lys181fs:p.Lys258fs |
| 6:73762396:GA:G | c.773delA:c.542delA:c.773delA | p.Lys258fs:p.Lys181fs:p.Lys258fs |
| 6:73762400:C:T | c.775C > T:c.544C > T:c.775C > T | p.Pro259Ser:p.Pro182Ser:p.Pro259Ser |
| 6:73762403 :G:A | c.778G > A:c.547G > A:c.778G > A | p.Val260Met:p.Val183Met:p.Val260Met |
| 6:73762409:G:A | c.784G > A:c.553G > A:c.784G > A | p.Gly262Arg:p.Gly185Arg:p.Gly262Arg |
| 6:73762479:AG:A | c.844delG:c.613delG:c.844delG | p.Thr283fs:p.Thr206fs:p.Thr283fs |
| 6:73762481:G:A | c.855 + 1G > A:c.624 + 1G > A:c.855 + 1G > A | |
| 6:73762796:AT:A | c.913delT:c.682delT:c.913delT | p.Ser305fs:p.Ser228fs:p.Ser305fs |
| 6:73762870:GA:G | c.987delA:c.756delA:c.987delA | p.Glu329fs:p.Glu252fs:p.Glu329fs |
| 6:73762882:G:A | c.997G > A:c.766G > A:c.997G > A | p.Gly333Ser:p.Gly256Ser:p.Gly333Ser |
| 6:73762882:G:T | c.997G > T:c.766G > T:c.997G > T | p.Gly333Cys:p.Gly256Cys:p.Gly333Cys |
| 6:73763574:AG:A | c.998-1delG:c.767-1delG:c.998-1delG | |
| 6:73763575:G:A | c.998-1G > A:c.767-1G > A:c.998-1G > A | |
| 6:73763575:G:C | c.998-1G > C:c.767-1G > C:c.998-1G > C | |
| 6:73763576:G:A | c.998G > A:c.767G > A:c.998G > A | p.Gly333Asp:p.Gly256Asp:p.Gly333Asp |
| 6:73763624:A:T | c.1046A > T:c.815A > T:c.1046A > T | p.Tyr349Phe:p.Tyr272Phe:p.Tyr349Phe |
| 6:73763629:A:AT | c.1053dupT:c.822dupT:c.1053dupT | p.Glu352fs:p.Glu275fs:p.Glu352fs |
| 6:73763662:C:A | c.1084C > A:c.853C > A:c.1084C > A | p.Pro362Thr:p.Pro285Thr:p.Pro362Thr |
| 6:73763664:ATC:A | c.1091_1092delTC:c.860_861delTC:c.1091_1092delTC | p.Leu364fs:p.Leu287fs:p.Leu364fs |
| 6:73763666:C:A | c.1088C > A:c.857C > A:c.1088C > A | p.Ser363Tyr:p.Ser286Tyr:p.Ser363Tyr |
| 6:73765929:G:T | c.1108-1G > T:c.877-1G > T:c.1108-1G > T | |
| 6:73765949:A:G | c.1127A > G:c.896A > G:c.1127A > G | p.Asp376Gly:p.Asp299Gly:p.Asp376Gly |
| 6:73765957:C:T | c.1135C > T:c.904C > T:c.1135C > T | p.Gln379*:p.Gln302*:p.Gln379* |
| 6:73765969:G:T | c.1147G > T:c.916G > T:c.1147G > T | p.Glu383*:p.Glu306*:p.Glu383* |
| 6:73766146:C:T | c.1324C > T:c.1093C > T:c.1324C > T | p.Gln442*:p.Gln365*:p.Gln442* |
| 6:73766155:G:A | c.1332 + 1G > A:c.1101 + 1G > A:c.1332 + 1G > A | |
| 6:73766825:T:C | c.1399T > C:c.1168T > C:c.1399T > C | p.Tyr467His:p.Tyr390His:p.Tyr467His |
| 6:73766830:C:G | c.1404C > G:c.1173C > G:c.1404C > G | p.Ile468Met:p.Ile391Met:p.Ile468Met |
| 6:73766841:CAA:C | c.1416_1417delAA:c.1185_1186delAA:c.1416_1417delAA | p.Asp474fs:p.Asp397fs:p.Asp474fs |
| 6:73766861:G:A | c.1434 + 1G > A:c.1203 + 1G > A:c.1434 + 1G > A | |
| 6:73766946:A:G | c.1435-2A > G:c.1204-2A > G:c.1435-2A > G | |
| 6:73766951:G:A | c.1438G > A:c.1207G > A:c.1438G > A | p.Gly480Arg:p.Gly403Arg:p.Gly480Arg |
| 6:73766987:C:T | c.1474C > T:c.1243C > T:c.1474C > T | p.Arg492*:p.Arg415*:p.Arg492* |
| 6:73767006:A:C | c.1493A > C:c.1262A > C:c.1493A > C | p.Tyr498Ser:p.Tyr421Ser:p.Tyr498Ser |
| 6:73767006:A:G | c.1493A > G:c.1262A > G:c.1493A > G | p.Tyr498Cys:p.Tyr421Cys:p.Tyr498Cys |
| 6:73767012:T:C | c.1497 + 2T > C:c.1266 + 2T > C:c.1497 + 2T > C | |
| 6:73768070:C:T | c.1513C > T:c.1282C > T:c.1513C > T | p.Gln505*:p.Gln428*:p.Gln505* |
| 6:73768071:A:C | c.1514A > C:c.1283A > C:c.1514A > C | p.Gln505Pro:p.Gln428Pro:p.Gln505Pro |
| 6:73768110:C:CT | c.1556dupT:c.1325dupT:c.1556dupT | p.Leu519fs:p.Leu442fs:p.Leu519fs |
| 6:73768136:C:T | c.1579C > T:c.1348C > T:c.1579C > T | p.Pro527Ser:p.Pro450Ser:p.Pro527Ser |
| 6:73768137:C:T | c.1580C > T:c.1349C > T:c.1580C > T | p.Pro527Leu:p.Pro450Leu:p.Pro527Leu |
| 6:73768146:G:A | c.1589G > A:c.1358G > A:c.1589G > A | p.Cys530Tyr:p.Cys453Tyr:p.Cys530Tyr |
| 6:73768176:G:C | c.1619G > C:c.1388G > C:c.1619G > C | p.Gly540Ala:p.Gly463Ala:p.Gly540Ala |
| 6:73768176:G:T | c.1619G > T:c.1388G > T:c.1619G > T | p.Gly540Val:p.Gly463Val:p.Gly540Val |
| 6:73768178:G:A | c.1621G > A:c.1390G > A:c.1621G > A | p.Glu541Lys:p.Glu464Lys:p.Glu541Lys |
| 6:73768190:G:A | c.1633G > A:c.1402G > A:c.1633G > A | p.Asp545Asn:p.Asp468Asn:p.Asp545Asn |
| 6:73768197:T:TA | c.1645dupA:c.1414dupA:c.1645dupA | p.Ile549fs:p.Ile472fs:p.Ile549fs |
| 6:73768206:C:G | c.1649G > Gx.1418C > G:c.1649C > G | p.Pro550Arg:p.Pro473Arg:p.Pro550Arg |
| 6:73768232:G:C | c.1674 + 1G > C:c.1443 + 1G > C:c.1674 + 1G > C | |
| 6:73771427:A:G | c.1675-2A > G:c.1444-2A > G:c.1675-2A > G | |
| 6:73771428:G:T | c.1675-1G > T:c.1444-1G > T:c.1675-1G > T | |
| 6:73771463:C:T | c.1709C > T:c.1478C > T:c.1709C > T | p.Pro570Leu:p.Pro493Leu:p.Pro570Leu |

-continued

| Variant | Coding DNA change | Protein change |
| --- | --- | --- |
| 6:73771481:T:C | c.1727T > C:c.1496T > C:c.1727T > C | p.Leu576Pro:p.Leu499Pro:p.Leu576Pro |
| 6:73771502:C:T | c.1748C > T:c.1517C > T:c.1748C > T | p.Pro583Leu:p.Pro506Leu:p.Pro583Leu |
| 6:73771508:C:T | c.1754C > T:c.1523C > T:c.1754C > T | p.Ser585Phe:p.Ser508Phe:p.Ser585Phe |
| 6:73771526:C:G | c.1772C > G:c.1541C > G:c.1772C > G | p.Ala591Gly:p.Ala514Gly:p.Ala591Gly |
| 6:73771538:G:A | c.1784G > A:c.1553G > A:c.1784G > A | p.Ser595Asn:p.Ser518Asn: p.Ser595Asn |
| 6:73771564:G:T | c.1810G > T:c.1579G > T:c.1810G > T | p.Asp604Tyr:p.Asp527Tyr:p.Asp604Tyr |
| 6:73780421:TA:T | c.1828-2delA:c.1597-2delA:c.1828-2delA | |
| 6:73780423:G:T | c.1828-1G > T:c.1597-1G > T:c.1828-1G > T | |
| 6:73780425:TG:T | c.1831delG:c.1600delG:c.1831delG | p.Val611fs:p.Val534fs:p.Val611fs |
| 6:73780447:TA:T | c.1853delA:c.1622delA:c.1853delA | p.Asn618fs:p.Asn541fs:p.Asn618fs |
| 6:73780458:ATTAT:A | c.1866__1869delTTTA:c.1635__1638delTTTA:c.1866__1869delTTTA | p.Tyr622fs:p.Tyr545fs:p.Tyr622fs |
| 6:73780492:C:CT | c.1899dupT:c.1668dupT:c.1899dupT | p.Gln634fs:p.Gln557fs:p.Gln634fs |
| 6:73781262:T:C | c.1906T > C:c.1675T > C:c.1906T > C | p.Cys636Arg:p.Cys559Arg:p.Cys636Arg |
| 6:73781268:C:T | c.1912C > T:c.1681C > T:c.1912C > T | p.Leu638Phe:p.Leu561Phe:p.Leu638Phe |
| 6:73781269:T:A | c.1913T > A:c.1682T > A:c.1913T > A | p.Leu638His:p.Leu561His:p.Leu638His |
| 6:73781273:G:A | c.1917G > A:c.1686G > A:c.1917G > A | p.Trp639*:p.Trp562*:p.Trp639* |
| 6:73781320:G:A | c.1963 + 1G > A:c.1732 + 1G > A:c.1963 + 1G > A | |
| 6:73781320:GT:G | c.1963 + 2delT:c.1732 + 2delT:c.1963 + 2delT | |
| 6:73782612:A:C | c.1964-2A > C:c.1733-2A > C:c.1964-2A > C | |
| 6:73782612:AG:A | c.1964-1delG:c.1733-1delG:c.1964-1delG | |
| 6:73782618:CAA:C | c.1969__1970delAA:c.1738__1739delAA:c.1969__1970delAA | p.Asn657fs:p.Asn580fs:p.Asn657fs |
| 6:73782625:G:T | c.1975G > T:c.1744G > T:c.1975G > T | p.Glu659*:p.Glu582*:p.Glu659* |
| 6:73782696:C:CA | c.2047dupA:c.1816dupA:c.2047dupA | p.Ser683fs:p.Ser606fs:p.Ser683fs |
| 6:73782709:C:G | c.2059C > G:c.1828C > G:c.2059C > G | p.Arg687Gly:p.Arg610Gly:p.Arg687Gly |
| 6:73782709:C:T | c.2059C > T:c.1828C > T:c.2059C > T | p.Arg687*:p.Arg610*:p.Arg687* |
| 6:73782716:A:AT | c.2070dupT:c.1839dupT:c.2070dupT | p.Pro691fs:p.Pro614fs:p.Pro691fs |
| 6:73782718:T:C | c.2068T > C:c.1837T > C:c.2068T > C | p.Phe690Leu:p.Phe613Leu:p.Phe690Leu |
| 6:73783720:C:T | c.2119C > T:c.1888C > T:c.2119C > T | p.Gln707*:p.Gln630*:p.Gln707* |
| 6:73783723:G:T | c.2122G > T:c.1891G > T:c.2122G > T | p.Glu708*:p.Glu631*:p.Glu708* |
| 6:73783760:G:A | c.2159G > A:c.1928G > A:c.2159G > A | p.Trp720*:p.Trp643*:p.Trp720* |
| 6:73783761:G:C | c.2160G > C:c.1929G > C:c.2160G > C | p.Trp720Cys:p.Trp643Cys:p.Trp720Cys |
| 6:73783761:G:T | c.2160G > T:c.1929G > T:c.2160G > T | p.Trp720Cys:p.Trp643Cys:p.Trp720Cys |
| 6:73783765:G:T | c.2164G > T:c.1933G > T:c.2164G > T | p.Ala722Ser:p.Ala645Ser:p.Ala722Ser |
| 6:73783771:G:T | c.2170G > T:c.1939G > T:c.2170G > T | p.Gly724Cys:p.Gly647Cys:p.Gly724Cys |
| 6:73783772:GT:G | c.2175delT:c.1944delT:c.2175delT | p.Phe725fs:p.Phe648fs:p.Phe725fs |
| 6:73783783:T:C | c.2182T > C:c.1951T > C:c.2182T > C | p.Ser728Pro:p.Ser651Pro:p.Ser728Pro |
| 6:73783784:C:CT | c.2184dupT:c.1953dupT:c.2184dupT | p.Glu729fs:p.Glu652fs:p.Glu729fs |
| 6:73783795:6:C | c.2194G > C:c.1963G > C:c.2194G > C | p.Gly732Arg:p.Gly655Arg:p.Gly732Arg |
| 6:73783796:G:A | c.2195G > A:c.1964G > A:c.2195G > A | p.Gly732Asp:p.Gly655Asp:p.Gly732Asp |
| 6:73783810:AC:A | c.2210delC:c.1979delC:c.2210delC | p.Thr737fs:p.Thr660fs:p.Thr737fs |
| 6:73783817:C:T | c.2216C > T:c.1985C > T:c.2216C > T | p.Pro739Leu:p.Pro662Leu:p.Pro739Leu |
| 6:73785363:G:A | c.2224-1G > A:c.1993-1G > A:c.2224-1G > A | |
| 6:73785364:C:A | c.2224C > A:c.1993C > A:c.2224C > A | p.Leu742Ile:p.Leu665Ile:p.Leu742Ile |
| 6:73785364:CT:C | c.2225delT:c.1994delT:c.2225delT | p.Leu742fs:p.Leu665fs:p.Leu742fs |
| 6:73785365:T:C | c.2225T > C:c.1994T > C:c.2225T > C | p.Leu742Pro:p.Leu665Pro:p.Leu742Pro |
| 6:73785382:T:C | c.2242T > C:c.2011T > C:c.2242T > C | p.Phe748Leu:p.Phe671Leu:p.Phe748Leu |
| 6:73785385:T:C | c.2245T > C:c.2014T > C:c.2245T > C | p.Phe749Leu:p.Phe672Leu:p.Phe749Leu |
| 6:73785408:C:A | c.2268C > A:c.2037C > A:c.2268C > A | p.Tyr756*:p.Tyr679*:p.Tyr756* |
| 6:73785408:C:G | c.2268C > G:c.2037C > G:c.2268C > G | p.Tyr756*:p.Tyr679*:p.Tyr756* |
| 6:73785410:C:G | c.2270C > G:c.2039C > G:c.2270C > G | p.Ser757Cys:p.Ser680Cys:p.Ser757Cys |
| 6:73785419:G:A | c.2279G > A:c.2048G > A:c.2279G > A | p.Arg760Lys:p.Arg683Lys:p.Arg760Lys |
| 6:73785454:A:T | c.2314A > T:c.2083A > T:c.2314A > T | p.Asn772Tyr:p.Asn695Tyr:p.Asn772Tyr |
| 6:73785458:A:G | c.2318A > G:c.2087A > G:c.2318A > G | p.Tyr773Cys:p.Tyr696Cys:p.Tyr773Cys |
| 6:73787237:A:T | c.2341A > T:c.2110A > T:c.2341A > T | p.Lys781*:p.Lys704*:p.Lys781* |
| 6:73787241:T:A | c.2345T > A:c.2114T > A:c.2345T > A | p.Val782Glu:p.Val705Glu:p.Val782Glu |
| 6:73787264:T:G | c.2368T > G:c.2137T > G:c.2368T > G | p.Phe790Val:p.Phe713Val:p.Phe790Val |
| 6:73787271:T:G | c.2375T > G:c.2144T > G:c.2375T > G | p.Ile792Ser:p.Ile715Ser:p.Ile792Ser |
| 6:73787330:A:T | c.2434A > T:c.2203A > T:c.2434A > T | p.Ser812Cys:p.Ser735Cys:p.Ser812Cys |
| 6:73787338:TG:T | c.2446delG:c.2215delG:c.2446delG | p.Ala816fs:p.Ala739fs:p.Ala816fs |
| 6:73787366:C:T | c.2470C > T:c.2239C > T:c.2470C > T | p.Pro824Ser:p.Pro747Ser:p.Pro824Ser |
| 6:73787378:G:T | c.2482G > T:c.2251G > T:c.2482G > T | p.Gly828*:p.Gly751*:p.Gly828* |
| 6:73787379:G:A | c.2483G > A:c.2252G > A:c.2483G > A | p.Gly828Glu:p.Gly751Glu:p.Gly828Glu |
| 6:73787394:C:T | c.2498C > T:c.2267C > T:c.2498C > T | p.Thr833Ile:p.Thr756Ile:p.Thr833Ile |
| 6:73787447:G:A | c.2551G > A:c.2320G > A:c.2551G > A | p.Val851Ile:p.Val774Ile:p.Val851Ile |
| 6:73787448:T:TA | c.2555dupA:c.2324dupA:c.2555dupA | p.Ala853fs:p.Ala776fs:p.Ala853fs |
| 6:73787452:G:T | c.2556G > T:c.2325G > T:c.2556G > T | p.Lys852Asn:p.Lys775Asn:p.Lys852Asn |
| 6:73788469:C:G | c.2558C > G:c.2327C > G:c.2558C > G | p.Ala853Gly:p.Ala776Gly:p.Ala853Gly |
| 6:73788503:CT:C | c.2594delT:c.2363delT:c.2594delT | p.Leu865fs:p.Leu788fs:p.Leu865fs |
| 6:73788564:C:T | c.2653C > T:c.2422C > T:c.2653C > T | p.Pro885Ser:p.Pro808Ser:p.Pro885Ser |
| 6:73788565:C:T | c.2654C > T:c.2423C > T:c.2654C > T | p.Pro885Leu:p.Pro808Leu:p.Pro885Leu |
| 6:73788582:G:A | c.2671G > A:c.2440G > A:c.2671G > A | p.Gly891Ser:p.Gly814Ser:p.Gly891Ser |
| 6:73788588:G:T | c.2677G > T:c.2446G > T:c.2677G > T | p.Glu893*:p.Glu816*:p.Glu893* |
| 6:73788601:T:TC | c.2691dupC:c.2460dupC:c.2691dupC | p.Thr898fs:p.Thr821fs:p.Thr898fs |
| 6:73792622:CCAGGAG:C | c.2702-3__2704delCAGGAG:c.2471-3__2473delCAGGAG:c.2702-3__2704delCAGGAG | p.Gly901del:p.Gly824del:p.Gly901del |

-continued

| Variant | Coding DNA change | Protein change |
| --- | --- | --- |
| 6:73792628:G:C | c.2704G > C:c.2473G > C:c.2704G > C | p.Asp902His:p.Asp825His:p.Asp902His |
| 6:73792629:A:T | c.2705A > T:c.2474A > T:c.2705A > T | p.Asp902Val:p.Asp825Val:p.Asp902Val |
| 6:73792637:G:T | c.2713G > T:c.2482G > T:c.2713G > T | p.Gly905Cys:p.Gly828Cys:p.Gly905Cys |
| 6:73792686:G:T | c.2762G > T:c.2531G > T:c.2762G > T | p.Cys921Phe:p.Cys844Phe:p.Cys921Phe |
| 6:73792688:G:A | c.2764G > A:c.2533G > A:c.2764G > A | p.Gly922Ser:p.Gly845Ser:p.Gly922Ser |
| 6:73792703:A:C | c.2779A > C:c.2548A > C:c.2779A > C | p.Ile927Leu:p.Ile850Leu:p.Ile927Leu |
| 6:73792712:G:T | c.2788G > T:c.2557G > T:c.2788G > T | p.Ala930Ser:p.Ala853Ser:p.Ala930Ser |
| 6:73792718:A:G | c.2794A > G:c.2563A > G:c.2794A > G | p.Asn932Asp:p.Asn855Asp:p.Asn932Asp |
| 6:73792736:T:A | c.2812T > A:c.2581T > A:c.2812T > A | p.Tyr938Asn:p.Tyr861Asn:p.Tyr938Asn |
| 6:73792754:C:T | c.2830C > T:c.2599C > T:c.2830C > T | p.Gln944*:p.Gln867*:p.Gln944* |
| 6:73792775:G:GA | c.2856dupA:c.2625dupA:c.2856dupA | p.Ala953fs:p.Ala876fs:p.Ala953fs |
| 6:73792780:A:C | c.2856A > C:c.2625A > C:c.2856A > C | p.Lys952Asn:p.Lys875Asn:p.Lys952Asn |
| 6:73792782:C:A | c.2858C > A:c.2627C > A:c.2858C > A | p.Ala953Asp:p.Ala876Asp:p.Ala953Asp |
| 6:73792784:C:CT | c.2863dupT:c.2632dupT:c.2863dupT | p.Ser955fs:p.Ser878fs:p.Ser955fs |
| 6:73792799:C:T | c.2875C > T:c.2644C > T:c.2875C > T | p.Gln959*:p.Gln882*:p.Gln959* |
| 6:73792802:G:A | c.2878G > A:c.2647G > A:c.2878G > A | p.Gly960Ser:p.Gly883Ser:p.Gly960Ser |
| 6:73803231:G:A | c.2890G > A:c.2659G > A:c.2890G > A | p.Glu964Lys:p.Glu887Lys:p.Glu964Lys |
| 6:73803253:A:G | c.2912A > G:c.2681A > G:c.2912A > G | p.Asp971Gly:p.Asp894Gly:p.Asp971Gly |
| 6:73803256:G:A | c.2915G > A:c.2684G > A:c.2915G > A | p.Gly972Asp:p.Gly895Asp:p.Gly972Asp |
| 6:73803256:G:T | c.2915G > T:c.2684G > T:c.2915G > T | p.Gly972Val:p.Gly895Val:p.Gly972Val |
| 6:73803264:A:G | c.2923A > G:c.2692A > G:c.2923A > G | p.Ser975Gly:p.Ser898Gly:p.Ser975Gly |
| 6:73803298:C:T | c.2957C > T:c.2726C > T:c.2957C > T | p.Thr986Ile:p.Thr909Ile:p.Thr986Ile |
| 6:73803301:G:A | c.2960G > A:c.2729G > A:c.2960G > A | p.Trp987*:p.Trp910*:p.Trp987* |
| 6:73806844:G:T | c.2961G > T:c.2730G > T:c.2961G > T | p.Trp987Cys:p.Trp910Cys:p.Trp987Cys |
| 6:73806855:T:C | c.2972T > C:c.2741T > C:c.2972T > C | p.Phe991Ser:p.Phe914Ser:p.Phe991Ser |
| 6:73806870:T:G | c.2987T > G:c.2756T > G:c.2987T > G | p.Phe996Cys:p.Phe919Cys:p.Phe996Cys |
| 6:73806897:T:C | c.3014T > C:c.2783T > C:c.3014T > C | p.Ile1005Thr:p.Ile928Thr:p.Ile1005Thr |
| 6:73806902:C:T | c.3019C > T:c.2788C > T:c.3019C > T | p.Gln1007*:p.Gln930*:p.Gln1007* |
| 6:73806908:G:A | c.3025G > A:c.2794G > A:c.3025G > A | p.Val1009Met:p.Val932Met:p.Val1009Met |
| 6:73806921:C:CAT | c.3040_3041dupTA:c.2809_2810dupTA:c.3040_3041dupTA | p.Trp1016fs:p.Trp939fs:p.Trp1016fs |
| 6:73806956:G:A | c.3073G > A:c.2842G > A:c.3073G > A | p.Gly1025Ser:p.Gly948Ser:p.Gly1025Ser |
| 6:73806956:G:C | c.3073G > C:c.2842G > C:c.3073G > C | p.Gly1025Arg:p.Gly948Arg:p.Gly1025Arg |
| 6:73806981:T:A | c.3098T > A:c.2867T > A:c.3098T > A | p.Val1033Glu:p.Val956Glu:p.Val1033Glu |
| 6:73806984:T:G | c.3101T > G:c.2870T > G:c.3101T > G | p.Ile1034Ser:p.Ile957Ser:p.Ile1034Ser |
| 6:73806987:A:T | c.3104A > T:c.2873A > T:c.3104A > T | p.His1035Leu:p.His958Leu:p.His1035Leu |
| 6:73807002:G:A | c.3119G > A:c.2888G > A:c.3119G > A | p.Gly1040Asp:p.Gly963Asp:p.Gly1040Asp |
| 6:73807005:G:A | c.3122G > A:c.2891G > A:c.3122G > A | p.Gly1041Asp:p.Gly964Asp:p.Gly1041Asp |
| 6:73807029:C:G | c.3146C > G:c.2915C > G:c.3146C > G | p.Thr1049Arg:p.Thr972Arg:p.Thr1049Arg |
| 6:73807034:T:A | c.3151T > A:c.2920T > A:c.3151T > A | p.Tyr1051Asn:p.Tyr974Asn:p.Tyr1051Asn |
| 6:73807035:A:G | c.3152A > G:c.2921A > G:c.3152A > G | p.Tyr1051Cys:p.Tyr974Cys:p.Tyr1051Cys |
| 6:73807035:A:T | c.3152A > T:c.2921A > T:c.3152A > T | p.Tyr1051Phe:p.Tyr974Phe:p.Tyr1051Phe |
| 6:73808113:T:G | c.3220T > G:c.2989T > G:c.3220T > G | p.Phe1074Val:p.Phe997Val:p.Phe1074Val |
| 6:73808146:G:A | c.3253G > A:c.3022G > A:c.3253G > A | p.Asp1085Asn:p.Asp1008Asn:p.Asp1085Asn |
| 6:73808153:A:T | c.3260A > T:c.3029A > T:c.3260A > T | p.Tyr1087Phe:p.Tyr1010Phe:p.Tyr1087Phe |
| 6:73808156:C:T | c.3263C > T:c.3032C > T:c.3263C > T | p.Thr1088Ile:p.Thr1011Ile:p.Thr1088Ile |
| 6:73808159:T:C | c.3266T > C:c.3035T > C:c.3266T > C | p.Leu1089Pro:p.Leu1012Pro:p.Leu1089Pro |
| 6:73808176:G:T | c.3283G > T:c.3052G > T:c.3283G > T | p.Ala1095Ser:p.Ala1018Ser:p.Ala1095Ser |
| 6:73808244:AGAAGGTAAT:A | c.3352_3355 + 5delGAAGGTAAT:c.3121_3124 + 5delGAAGGTAAT:c.3352_3355 + 5delGAAGGTAAT | p.Glu1118fs:p.Glu1041fs:p.Glu1118fs |
| 6:73808245:GA:G | c.3354delA:c.3123delA:c.3354delA | p.Gly1119fs:p.Gly1042fs:p.Gly1119fs |
| 6:73809981:CA:C | c.3356-2delA:c.3125-2delA:c.3356-2delA | |
| 6:73809992:C:T | c.3364C > T:c.3133C > T:c.3364C > T | p.Gln112*:p.Gln1045*:p.Gln1122* |
| 6:73809995:T:A | c.3367T > A:c.3136T > A:c.3367T > A | p.Phe1123Ile:p.Phe1046Ile:p.Phe1123Ile |
| 6:73810034:C:A | c.3406C > A:c.3175C > A:c.3406C > A | p.Gln1136Lys:p.Gln1059Lys:p.Gln1136Lys |
| 6:73810044:C:T | c.3416C > T:c.3185C > T:c.3416C > T | p.Ser1139Phe:p.Ser1062Phe:p.Ser1139Phe |
| 6:73810054:T:G | c.3426T > G:c.3195T > G:c.3426T > G | p.Ile1142Met:p.Ile1065Met:p.Ile1142Met |
| 6:73810089:T:TA | c.3462dupA:c.3231dupA:c.3462dupA | p.Gln1155fs:p.Gln1078fs:p.Gln1155fs |
| 6:73810106:G:A | c.3478G > A:c.3247G > A:c.3478G > A | p.Glu1160Lys:p.Glu1083Lys:p.Glu1160Lys |
| 6:73810143:G:T | c.3515G > T:c.3284G > T:c.3515G > T | p.Arg1172Ile:p.Arg1095Ile:p.Arg1172Ile |
| 6:73810154:G:A | c.3526G > A:c.3295G > A:c.3526G > A | p.Gly1176Ser:p.Gly1099Ser:p.Gly1176Ser |
| 6:73810155:G:A | c.3527G > A:c.3296G > A:c.3527G > A | p.Gly1176Asp:p.Gly1099Asp:p.Gly1176Asp |
| 6:73810155:G:C | c.3527G > C:c.3296G > C:c.3527G > C | p.Gly1176Ala:p.Gly1099Ala:p.Gly1176Ala |
| 6:73810155:G:T | c.3527G > T:c.3296G > T:c.3527G > T | p.Gly1176Val:p.Gly1099Val:p.Gly1176Val |
| 6:73810157:G:T | c.3529G > T:c.3298G > T:c.3529G > T | p.Gly1177Cys:p.Gly1100Cys:p.Gly1177Cys |
| 6:73810158:G:A | c.3530G > A:c.3299G > A:c.3530G > A | p.Gly1177Asp:p.Gly1100Asp:p.Gly1177Asp |
| 6:73810172:C:T | c.3544C > T:c.3313C > T:c.3544C > T | p.Gln1182*:p.Gln1105*:p.Gln1182* |
| 6:73810990:A:G | c.3547-2A > G:c.3316-2A > G:c.3547-2A > G | |
| 6:73810993:A:C | c.3548A > C:c.3317A > C:c.3548A > C | p.Asp1183Ala:p.Asp1106Ala:p.Asp1183Ala |
| 6:73811013:G:C | c.3568G > C:c.3337G > C:c.3568G > C | p.Ala1190Pro:p.Ala1113Pro:p.Ala1190Pro |
| 6:73811013:G:T | c.3568G > T:c.3337G > T:c.3568G > T | p.Ala1190Ser:p.Ala1113Ser:p.Ala1190Ser |
| 6:73811029:C:A | c.3584C > A:c.3353C > A:c.3584C > A | p.Ala1195Glu:p.Ala1118Glu:p.Ala1195Glu |
| 6:73811051:GA:G | c.3607delA:c.3376delA:c.3607delA | p.Thr1203fs:p.Thr1126fs:p.Thr1203fs |
| 6:73811110:T:C | c.3665T > C:c.3434T > C | p.Ile1222Thr:p.Ile1145Thr |
| 6:73811120:CA:C | c.3677delA:c.3446delA | p.Asn1226fs:p.Asn1149fs |
| 6:73811121:A:T | c.3676A > T:c.3445A > T | p.Asn1226Tyr:p.Asn1149Tyr |
| 6:73812271:G:A | c.3768 + 1G > A:c.3537 + 1G > A:c.3717 + 1G > A | |
| 6:73812271:G:C | c.3768 + 1G > C:c.3537 + 1G > C:c.3717 + 1G > C | |

-continued

| Variant | Coding DNA change | Protein change |
| --- | --- | --- |
| 6:73812271:G:T | c.3768 + 1G > T:c.3537 + 1G > T:c.3717 + 1G > T | |
| 6:73812272:T:A | c.3768 + 2T > A:c.3537 + 2T > A:c.3717 + 2T > A | |
| 6:73814990:GTA:G | c.3783__3784delTA:c.3552__3553delTA:c.3732__3733delTA | p.Tyr1261fs:p.Tyr1184fs:p.Tyr1244fs |
| 6:73814994:A:G | c.3782A > G:c.3551A > G:c.3731A > G | p.Tyr1261Cys:p.Tyr1184Cys:p.Tyr1244Cys |
| 6:73815026:C:T | c.3814C > T:c.3583C > T:c.3763C > T | p.Arg1272*:p.Arg1195*:p.Arg1255* |
| 6:73815098:CAT:C | c.3887__3888delAT:c.3656__3657delAT:c.3836__3837delAT | p.His1296fs:p.His1219fs:p.His1279fs |
| 6:73815113:G:A | c.3901G > A:c.3670G > A:c.3850G > A | p.Val1301Met:p.Val1224Met:p.Val1284Met |
| 6:73815117:G:A | c.3905G > A:c.3674G > A:c.3854G > A | p.Cys1302Tyr:p.Cys1225Tyr:p.Cys1285Tyr |
| 6:73818386:A:G | c.3912-2A > G:c.3681-2A > G:c.3861-2A > G | |
| 6:73818413:A:G | c.3937A > G:c.3706A > G:c.3886A > G | p.Met1313Val:p.Met1236Val:p.Met1296Val |
| 6:73818415:G:C | c.3939G > C:c.3708G > C:c.3888G > C | p.Met1313Ile:p.Met1236Ile:p.Met1296Ile |
| 6:73818417:C:A | c.3941C > A:c.3710C > A:c.3890C > A | p.Ala1314Asp:p.Ala1237Asp:p.Ala1297Asp |
| 6:73818423:T:G | c.3947T > G:c.3716T > G:c.3896T > G | p.Met1316Arg:p.Met1239Arg:p.Met1299Arg |
| 6:73818425:G:A | c.3949G > A:c.3718G > A:c.3898G > A | p.Glu1317Lys:p.Glu1240Lys:p.Glu1300Lys |
| 6:73818443:G:T | c.3967G > T:c.3736G > T:c.3916G > T | p.Gly1323Cys:p.Gly1246Cys:p.Gly1306Cys |
| 6:73818450:TG:T | c.3976delG:c.3745delG:c.3925delG | p.Val1326fs:p.Val1249fs:p.Val1309fs |
| 6:73818456:CT:C | c.3982delT:c.3751delT:c.3931delT | p.Ser1328fs:p.Ser1251fs:p.Ser1311fs |
| 6:73818479:G:T | c.4003G > T:c.3772G > T:c.3952G > T | p.Glu1335*:p.Glu1258*:p.Glu1318* |
| 6:73820459:A:G | c.4060-2A > G:c.3829-2A > G:c.4009-2A > G | |
| 6:73820480:G:C | c.4079G > C:c.3848G > C:c.4028G > C | p.Cys1360Ser:p.Cys1283Ser:p.Cys1343Ser |
| 6:73820528:A:T | c.4127A > T:c.3896A > T:c.4076A > T | p.Asp1376Val:p.Asp1299Val:p.Asp1359Val |
| 6:73820537:T:C | c.4136T > C:c.3905T > C:c.4085T > C | p.Val1379Ala:p.Val1302Ala:p.Val1362Ala |
| 6:73820549:A:C | c.4148A > C:c.3917A > C:c.4097A > C | p.Asp1383Ala:p.Asp1306Ala:p.Asp1366Ala |
| 6:73820549:A:G | c.4148A > G:c.3917A > G:c.4097A > G | p.Asp1383Gly:p.Asp1306Gly:p.Asp1366Gly |
| 6:73820549:AT:A | c.4150delT:c.3919delT:c.4099delT | p.Tyr1384fs:p.Tyr1307fs:p.Tyr1367fs |
| 6:73823456:A:G | c.4163-2A > G:c.3932-2A > G:c.4112-2A > G | |
| 6:73823473:GA:G | c.4180delA:c.3949delA:c.4129delA | p.Ser1394fs:p.Ser1317fs:p.Ser1377fs |
| 6:73823481:A:G | c.4186A > G:c.3955A > G:c.4135A > G | p.Asn1396Asp:p.Asn1319Asp:p.Asn1379Asp |
| 6:73823485:C:G | c.4190C > G:c.3959C > G:c.4139C > G | p.Ser1397Cys:p.Ser1320Cys:p.Ser1380Cys |
| 6:73823530:GC:G | c.4236delC:c.4005delC:c.4185delC | p.Cys1413fs:p.Cys1336fs:p.Cys1396fs |
| 6:73823534:C:A | c.4239C > A:c.4008C > A:c.4188C > A | p.Cys1413*:p.Cys1336*:p.Cys1396* |
| 6:73823583:A:AT | c.4293dupT:c.4062dupT:c.4242dupT | p.Ile1432fs:p.Ile1355fs:p.Ile1415fs |
| 6:73823592:TTC:T | c.4299__4300delCT:c.4068__4069delCT:c.4248__4249delCT | p.Phe1433fs:p.Phe1356fs:p.Phe1416fs |
| 6:73823612:C:A | c.4317C > A:c.4086C > A:c.4266C > A | p.Tyr1439*:p.Tyr1362*:p.Tyr1422* |

The present disclosure also provides methods of detecting the presence or absence of a CD109 missense variant nucleic acid molecule (i.e., a genomic nucleic acid molecule, an mRNA molecule, or a cDNA molecule produced from an mRNA molecule) encoding a CD109 predicted loss-of-function polypeptide in a biological sample from a subject. It is understood that gene sequences within a population and mRNA molecules encoded by such genes can vary due to polymorphisms such as single-nucleotide polymorphisms. The sequences provided herein for the CD109 variant genomic nucleic acid molecule, CD109 variant mRNA molecule, and CD109 variant cDNA molecule are only exemplary sequences. Other sequences for the CD109 variant genomic nucleic acid molecule, variant mRNA molecule, and variant cDNA molecule are also possible.

The biological sample can be derived from any cell, tissue, or biological fluid from the subject. The biological sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any CD109 missense variant nucleic acid molecule encoding a CD109 predicted loss-of-function polypeptide, preliminary processing designed to isolate or enrich the biological sample for the genomic DNA can be employed. A variety of techniques may be used for this purpose. When detecting the level of any CD109 variant mRNA molecule, different techniques can be used enrich the biological sample with mRNA molecules. Various methods to detect the presence or level of an mRNA molecule or the presence of a particular variant genomic DNA locus can be used.

In some embodiments, detecting a CD109 missense variant nucleic acid molecule encoding a CD109 predicted loss-of-function polypeptide in a subject comprises performing a sequence analysis on a biological sample obtained from the subject to determine whether a CD109 genomic nucleic acid molecule in the biological sample, and/or a CD109 mRNA molecule in the biological sample, and/or a CD109 cDNA molecule produced from an mRNA molecule in the biological sample, comprises one or more variations that cause a loss-of-function (partial or complete) or are predicted to cause a loss-of-function (partial or complete).

In some embodiments, the methods of detecting the presence or absence of a CD109 missense variant nucleic acid molecule encoding a CD109 predicted loss-of-function polypeptide (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence.

In some embodiments, the biological sample comprises a cell or cell lysate. Such methods can further comprise, for example, obtaining a biological sample from the subject comprising a CD109 genomic nucleic acid molecule or mRNA molecule, and if mRNA, optionally reverse transcribing the mRNA into cDNA. Such assays can comprise, for example determining the identity of these positions of the particular CD109 nucleic acid molecule. In some embodiments, the method is an in vitro method.

In some embodiments, the determining step, detecting step, or sequence analysis comprises sequencing at least a portion of the nucleotide sequence of the CD109 genomic nucleic acid molecule, the CD109 mRNA molecule, or the CD109 cDNA molecule in the biological sample, wherein the sequenced portion comprises one or more variations that cause a loss-of-function (partial or complete) or are predicted to cause a loss-of-function (partial or complete).

In some embodiments, the assay comprises sequencing the entire nucleic acid molecule. In some embodiments, only a CD109 genomic nucleic acid molecule is analyzed. In some embodiments, only a CD109 mRNA is analyzed. In some embodiments, only a CD109 cDNA obtained from CD109 mRNA is analyzed.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay comprises contacting the biological sample with a primer or probe, such as an alteration-specific primer or alteration-specific probe, that specifically hybridizes to a CD109 variant genomic sequence, variant mRNA sequence, or variant cDNA sequence and not the corresponding CD109 reference sequence under stringent conditions, and determining whether hybridization has occurred.

In some embodiments, the determining step, detecting step, or sequence analysis comprises: a) amplifying at least a portion of the nucleic acid molecule that encodes the CD109 polypeptide; b) labeling the amplified nucleic acid molecule with a detectable label; c) contacting the labeled nucleic acid molecule with a support comprising an alteration-specific probe; and d) detecting the detectable label.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a CD109 variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneously with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to CD109 missense variant nucleic acid molecules (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to CD109 missense variant genomic nucleic acid molecules, CD109 missense variant mRNA molecules, and/or CD109 missense variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the CD109 variant missense genomic nucleic acid molecules, CD109 missense variant mRNA molecules, and/or CD109 missense variant cDNA molecules disclosed herein. The primers described herein can be used to amplify CD109 missense variant genomic nucleic acid molecules, CD109 missense variant mRNA molecules, or CD109 missense variant cDNA molecules, or a fragment thereof.

In the context of the disclosure "specifically hybridizes" means that the probe or primer (such as, for example, the alteration-specific probe or alteration-specific primer) does not hybridize to a nucleic acid sequence encoding a CD109 reference genomic nucleic acid molecule, a CD109 reference mRNA molecule, and/or a CD109 reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The nucleotide sequence of a CD109 reference genomic nucleic acid molecule is set forth in SEQ ID NO:1 (ENSG00000156535.15 chr6:73,695,785-73,828,316 in the GRCh38/hg38 human genome assembly).

The nucleotide sequence of a CD109 reference mRNA molecule is set forth in SEQ ID NO:2. The nucleotide sequence of another CD109 reference mRNA molecule is set forth in SEQ ID NO:3. The nucleotide sequence of another CD109 reference mRNA molecule is set forth in SEQ ID NO:4. The nucleotide sequence of another CD109 reference mRNA molecule is set forth in SEQ ID NO:5. The nucleotide sequence of another CD109 reference mRNA molecule is set forth in SEQ ID NO:6. The nucleotide sequence of another CD109 reference mRNA molecule is set forth in SEQ ID NO:7. The nucleotide sequence of another CD109 reference mRNA molecule is set forth in SEQ ID NO:8. The nucleotide sequence of another CD109 reference mRNA molecule is set forth in SEQ ID NO:9. The nucleotide sequence of another CD109 reference mRNA molecule is set forth in SEQ ID NO:10. The nucleotide sequence of another CD109 reference mRNA molecule is set forth in SEQ ID NO:11. The nucleotide sequence of another CD109 reference mRNA molecule is set forth in SEQ ID NO:12. The nucleotide sequence of another CD109 reference mRNA molecule is set forth in SEQ ID NO:13. The nucleotide sequence of another CD109 reference mRNA molecule is set forth in SEQ ID NO:14. The nucleotide sequence of another CD109 reference mRNA molecule is set forth in SEQ ID NO:15. The nucleotide sequence of another CD109 reference mRNA molecule is set forth in SEQ ID NO:16.

The nucleotide sequence of a CD109 reference cDNA molecule is set forth in SEQ ID NO:17. The nucleotide sequence of another CD109 reference cDNA molecule is set forth in SEQ ID NO:18. The nucleotide sequence of another CD109 reference cDNA molecule is set forth in SEQ ID NO:19. The nucleotide sequence of another CD109 reference cDNA molecule is set forth in SEQ ID NO:20. The nucleotide sequence of another CD109 reference cDNA molecule is set forth in SEQ ID NO:21. The nucleotide sequence of another CD109 reference cDNA molecule is set forth in SEQ ID NO:22. The nucleotide sequence of another CD109 reference cDNA molecule is set forth in SEQ ID NO:23. The nucleotide sequence of another CD109 reference cDNA molecule is set forth in SEQ ID NO:24. The nucleotide sequence of another CD109 reference cDNA molecule is set forth in SEQ ID NO:25. The nucleotide sequence of another CD109 reference cDNA molecule is set forth in SEQ ID NO:26. The nucleotide sequence of another CD109 reference cDNA molecule is set forth in SEQ ID NO:27. The nucleotide sequence of another CD109 reference cDNA molecule is set forth in SEQ ID NO:28. The nucleotide sequence of another CD109 reference cDNA molecule is set forth in SEQ ID NO:29.

The amino acid sequence of a CD109 reference polypeptide is set forth in SEQ ID NO:30, and is 1,428 amino acids in length. The nucleotide sequence of another CD109 reference polypeptide is set forth in SEQ ID NO:31, and is 1,368 amino acids in length. The nucleotide sequence of another CD109 reference polypeptide is set forth in SEQ ID NO:32, and is 1,445 amino acids in length. The nucleotide sequence of another CD109 reference polypeptide is set forth in SEQ ID NO:33, and is 665 amino acids in length. The nucleotide sequence of another CD109 reference polypeptide is set forth in SEQ ID NO:34, and is 1,374 amino acids in length. The nucleotide sequence of another CD109 reference polypeptide is set forth in SEQ ID NO:35, and is 854 amino acids in length. The nucleotide sequence of another CD109 reference polypeptide is set forth in SEQ ID NO:36, and is 847 amino acids in length.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×his or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

The present disclosure also provides therapeutic agents that treat or inhibit decreased bone mineral density for use in the treatment of decreased bone mineral density in a subject having: a CD109 missense variant genomic nucleic acid molecule encoding a CD109 predicted loss-of-function polypeptide; a CD109 missense variant mRNA molecule encoding a CD109 predicted loss-of-function polypeptide; or a CD109 missense variant cDNA molecule encoding a CD109 predicted loss-of-function polypeptide. Any of the therapeutic agents that treat or inhibit decreased bone mineral density described herein can be used in these methods. The subject can have or have a risk of developing decreased bone mineral density, osteopenia, Type I osteoporosis, Type II osteoporosis, or secondary osteoporosis.

The present disclosure also provides uses of therapeutic agents that treat or inhibit decreased bone mineral density for use in the preparation of a medicament for treating decreased bone mineral density in a subject having: a CD109 missense variant genomic nucleic acid molecule encoding a CD109 predicted loss-of-function polypeptide; a CD109 missense variant mRNA molecule encoding a CD109 predicted loss-of-function polypeptide; or a CD109 missense variant cDNA molecule encoding a CD109 predicted loss-of-function polypeptide. Any of the therapeutic agents that treat or inhibit decreased bone mineral density described herein can be used in these methods. The subject can have or have a risk of developing decreased bone mineral density, osteopenia, Type I osteoporosis, Type II osteoporosis, or secondary osteoporosis.

The present disclosure also provides CD109 inhibitors for use in the treatment of decreased bone mineral density in a subject that: a) is reference for a CD109 genomic nucleic acid molecule, a CD109 mRNA molecule, or a CD109 cDNA molecule; or b) is heterozygous for: i) a CD109 missense variant genomic nucleic acid molecule encoding a CD109 predicted loss-of-function polypeptide; ii) a CD109 missense variant mRNA molecule encoding a CD109 predicted loss-of-function polypeptide; or iii) a CD109 missense variant cDNA molecule encoding a CD109 predicted loss-of-function polypeptide. Any of the CD109 inhibitors described herein can be used in these methods. The subject can have or have a risk of developing decreased bone mineral density, osteopenia, Type I osteoporosis, Type II osteoporosis, or secondary osteoporosis.

The present disclosure also provides uses of CD109 inhibitors in the preparation of a medicament for treating decreased bone mineral density in a subject that: a) is reference for a CD109 genomic nucleic acid molecule, a CD109 mRNA molecule, or a CD109 cDNA molecule; or b) is heterozygous for: i) a CD109 missense variant genomic nucleic acid molecule encoding a CD109 predicted loss-of-function polypeptide; ii) a CD109 missense variant mRNA molecule encoding a CD109 predicted loss-of-function polypeptide; or iii) a CD109 missense variant cDNA molecule encoding a CD109 predicted loss-of-function polypeptide. Any of the CD109 inhibitors described herein can be used in these methods. The subject can have or have a risk of developing decreased bone mineral density, osteopenia, Type I osteoporosis, Type II osteoporosis, or secondary osteoporosis.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

General Methodology
UK Biobank Cohort Description

Genetic associations were examined in the United Kingdom (UK) Biobank (UKB). The UKB is a population-based cohort of individuals aged between 40 to 69 years and recruited via 22 testing centers in the UK between 2006-2010. Genetic and phenotypic information from close to 300,000 European-ancestry participants in UKB were used.

Phenotype Definition

Data pertaining to quantitative ultrasound of the heel were extracted from UKB. eBMD trait values (in $g/cm^2$) were derived using a combination of speed of sound (SOS) and bone ultrasound attenuation (BUA; eBMD=0.002592× (BUA+SOS)−3.687). Sex-specific quality control measures were implemented for SOS (Subjects were excluded if SOS≤1,450 or ≥1,700 m/s for men, ≤1,455 or ≥1,700 m/s for women), BUA (exclude if BUA≤27 or ≥138 dB/MHz for men, ≤22 or ≥138 dB/MHz for women), and eBMD (exclude if ≤0.18 or ≥1.06 $g/cm^2$ for men, ≤0.12 or ≥1.025 $g/cm^2$ for women). Phenotypic values for eBMD were first transformed using rank-based inverse normal transformation, applied within each ancestry group and separately in men and women, and adjusted for fine-mapped common genetic variants associated with eBMD.

Genotype Data

High coverage whole exome sequencing was performed as previously described (Dewey et al., Science, 2016, 354, aaf6814; and Van Hout et al., Nature, 2020, 586, 749-756) and as summarized below. A modified version of the xGen design available from Integrated DNA Technologies (IDT) was used for target sequence capture of the exome. A unique 10 bp barcode (IDT) was added to each DNA fragment during library preparation to facilitate multiplexed exome capture and sequencing. Equal amounts of sample were pooled prior to exome capture. Sequencing was performed using 75 bp paired-end reads on Illumina NovaSeq instruments. Sequencing had a coverage depth (i.e., number of sequence-reads covering each nucleotide in the target areas of the genome) sufficient to provide greater than 20× coverage over 90% of targeted bases in 99% of IDT samples. Data processing steps included sample de-multiplexing using Illumina software, alignment to the GRCh38 Human Genome reference sequence including generation of binary alignment and mapping files (BAM), processing of BAM files (e.g., marking of duplicate reads and other read mapping evaluations). Variant calling was performed using the GLNexus system (Lin et al., 2018, bioRxiv: 343970). Variant mapping and annotation were based on the GRCh38 Human Genome reference sequence and Ensembl v85 gene definitions using the snpEff software. The snpEff predictions that involve protein-coding transcripts with an annotated start and stop were then combined into a single functional impact prediction by selecting the most deleterious functional effect class for each gene. The hierarchy (from most to least deleterious) for these annotations was frameshift, stop-gain, stop-loss, splice acceptor, splice donor, stop-lost, in-frame indel, missense, other annotations. Predicted LoF genetic variants included: a) insertions or deletions resulting in a frameshift, b) insertions, deletions or single nucleotide variants resulting in the introduction of a premature stop codon or in the loss of the transcription start site or stop site, and c) variants in donor or acceptor splice sites. Missense variants were classified for likely functional impact according to the number of in silico prediction algorithms that predicted deleteriousness using SIFT (Vaser et al., Nature Protocols, 2016, 11, 1-9), Polyphen2_HDIV and Polyphen2_HVAR (Adzhubei et al., Nat. Methods, 2010, 7, 248-249), LRT (Chun et al., Genome Res., 2009, 19, 1553-1561) and MutationTaster (Schwarz et al., Nat. Methods, 2010, 7, 575-576). For each gene, the alternative allele frequency (AAF) and functional annotation of each variant determined inclusion into 7 gene burden exposures: 1) pLOF variants with AAF<1%; 2) pLOF or missense variants predicted deleterious by 5/5 algorithms with AAF<1%; 3) pLOF or missense variants predicted deleterious by 5/5 algorithms with AAF<0.1%; 4) pLOF or missense variants predicted deleterious by at least 1/5 algorithms with AAF<1%; 5) pLOF or missense variants predicted deleterious by at least 1/5 algorithms with AAF<0.1%; 6) pLOF or any missense with AAF<1%; 7) pLOF or any missense variants with AAF<0.1%. Association analysis of gene burden of rare pLOF and missense variation in CD109

Association between the burden of rare predicted loss-of-function or missense variants in CD109 and eBMD was examined by fitting a linear regression model, including adjustment for a polygenic score that approximates a genomic kinship matrix, using REGENIE v1.0 (Mbatchou et al., Nature Genetics, 2021). Analyses were adjusted for age, $age^2$, sex, age-by-sex and $age^2$-by-sex interaction terms, experimental batch-related covariates, ten common variant-derived principal components, and twenty rare variant-derived principal components. Association analyses were performed using single variants, and using gene burden tests. In gene burden tests, all individuals are labelled as heterozygotes if they carry one or more qualifying rare variant (as described above based on frequency and functional annotation) and as homozygotes if they carry any qualifying variant in the homozygous state. This "composite genotype" is then used to test for association.

Effector Index for eBMD Causal Genes

Effector Index, a novel machine-learning algorithm, has been described elsewhere in the literature (Forgetta et al., bioRxiv: 2021, 2020.2006.2028.171561). Training data were generated by performing GWAS analysis for eleven diseases and traits (type 2 diabetes, low density lipoprotein cholesterol level, adult height, calcium level, hypothyroidism, triglyceride level, glucose level, red blood cell count systolic blood pressure, diastolic blood pressure and direct bilirubin level). Fine-mapping was performed for each GWAS dataset, and genomic annotations were used as features to predict positive control genes at fine-mapped GWAS loci, using a gradient boosted trees algorithm (XGBoost). This trained algorithm was then tested on fine-mapped and annotated eBMD associations data at the CD109 locus to test the probability that the CD109 gene is the gene at this locus that influences eBMD.

Mendelian Randomization Analysis of Circulating CD109

Two-sample Mendelian randomization (MR) was used to examine the association between genetically-predicted circulating CD109 and eBMD. This approach uses common genetic variants associated with CD109 protein concentration (termed protein quantitative trait loci, or pQTLs) as instrumental variables. The lead CD109 cis-pQTL was identified in two previously published studies performed in the INTERVAL (N=3,301) and AGES (N=3,200) cohorts (Sun et al., Nature, 2018, 558, 73-79; and Emilsson et al., Science, 2018, eaaq1327). The pQTL-outcome associations for this analysis were extracted from a previously published GWAS of eBMD in UKB, and the TwoSampleMR R package was used to perform MR analysis using the Wald ratio method. Colocalization analyses were performed to interrogate the influence of confounding by linkage disequilibrium. This entailed assessing the whether the genetic association signal for CD109 protein concentration is likely to share the same causal variant with the eBMD genetic association signal at CD109. These colocalization analyses were implemented using two previously published algorithms, Coloc (Giambartolomei et al., PLOS Genetics, 2014, 10, e1004383) and eCAVIAR (Hormozdiari et al., Am. J. Hum. Genet., 2016, 99, 1245-1260).

Example 1: Loss-of-Function of CD109 is Associated with Higher Estimated Bone Mineral Density Whole exome sequencing of 278,807 European-ancestry individuals in the UK Biobank (UKB) was performed to identify predicted loss-of-function (pLoF) and missense genetic variants in each gene in the genome. The association of each sequenced gene and genetic variant in UKB with estimated bone mineral density (eBMD, measured using ultrasound of the heel) was examined. eBMD is a commonly-used biomarker of bone density and strength, and is highly correlated with bone mineral density as measured using dual-energy X-ray absorptiometry (DXA) technology. Lower levels of bone density are strongly associated with a higher risk of osteoporotic fractures.

The exome-wide analysis in UKB found that the burden of rare (alternative allele frequency [AAF]<1%) pLoF variants in the CD109 gene is associated with 0.18 standard deviation units higher eBMD (P-value=$1.20 \times 10^{-09}$, meeting a Bonferroni-corrected, exome-wide statistical significance threshold of $P<3.6 \times 10^{-7}$ (corrected for 20,000 genes and seven variant aggregation models)) (Table 2; estimates of association pertain to the burden of CD109 pLoF variants with AAF<1%, and were derived in UKB).

TABLE 2

Association of rare pLOF variants in CD109 with higher eBMD.

| Beta, per allele, SD units of eBMD (95% CI) | Beta, per allele, $g/cm^2$ units of eBMD (95% CI) | P-value | Genotype counts, RR\|RA\|AA genotypes | AAF |
|---|---|---|---|---|
| 0.18 (0.12, 0.24) | 0.022 (0.015, 0.029) | $1.20 \times 10^{-09}$ | 277945\|862\|0 | 0.0015 |

Genotype counts indicates the number of individuals in each of three genotype categories: RR indicates individuals carrying no rare pLoF variants in CD109; RA indicates individuals carrying a rare pLoF variant in a single CD109 allele; AA indicates individuals carrying rare pLoF variants in both CD109 alleles. AAF indicates the alternative allele frequency of pLoF variants included in this analysis. $g/cm^2$, grams per centimeter squared; SD, standard deviation; CI, confidence interval.

The association of CD109 variants with higher eBMD was also significant when examining the gene burden of rare pLoF or predicted-damaging missense variants in CD109 (Table 3; estimates of association pertain to the burden of CD109 pLoF or predicted-damaging missense variants with AAF<1% or <0.1% and were derived in UKB (see Genotype Data below for description of in silico algorithms used to identify predicted damaging missense variants)). These genetic data suggest that loss-of-function of CD109 leads to a higher eBMD in humans.

TABLE 3

Association of rare pLOF or missense variants in CD109 with higher eBMD

| Genetic exposure | Beta, per allele, SD units of eBMD (95% CI) | Beta, per allele, g/cm² units of eBMD (95% CI) | P-value | Genotype counts, RR\|RA\|AA genotypes | AAF |
|---|---|---|---|---|---|
| pLoF or damaging missense variants, AAF <1% | 0.07 (0.04, 0.09) | 0.008 (0.005, 0.011) | $7.0 \times 10^{-08}$ | 273953\|4846\|8 | 0.0087 |
| pLoF or damaging missense variants, AAF <0.1% | 0.11 (0.08, 0.15) | 0.014 (0.009, 0.018) | $3.2 \times 10^{-09}$ | 276693\|2114\|0 | 0.0038 |

Genotype counts indicates the number of individuals in each of three genotype categories: RR indicates individuals carrying no rare pLoF variants in CD109; RA indicates individuals carrying a rare pLoF or damaging missense variant in a single CD109 allele; AA indicates individuals carrying rare pLoF variants or damaging missense variants in both CD109 alleles. AAF, alternative allele frequency of variants included in this analysis. g/cm², grams per centimeter squared; SD, standard deviation; CI, confidence interval.

Example 2: Variants Associated with Lower CD109 Protein Concentration in Blood are Also Associated with Higher eBMD Using Mendelian randomization, it was discovered that lower circulating CD109 protein (encoded by the CD109 gene) due to common genetic variants in the CD109 locus was associated with higher eBMD (Table 4; the lead cis protein quantitative trait locus (pQTL) for CD109 was obtained in two independent cohorts: INTERVAL and AGES. A two-sample Mendelian randomization analysis was performed using eBMD GWAS data from UKB as the outcome dataset). This relationship was further supported by a colocalization analysis, performed using two distinct algorithms (Coloc and eCAVIAR; Coloc posterior probability of H3=0.042, Coloc posterior probability of H4=0.958; eCAVIAR CLPP C1=0.024, CLPP C2=0.002). These results provide complementary evidence for the results reported in Table 2, which showed that loss-of-function of CD109 is associated with a higher eBMD. Several individual rare pLoF and missense variants in CD109 showed nominal evidence of association with eBMD in UKB (P-value for association <0.05; Table 4).

TABLE 4

Mendelian randomization analysis supports a causal influence of circulating CD109 concentration on eBMD

| pQTL source | PQTL | Effect on eBMD, in SD units, per SD unit decrease in circulating CD109 concentration | P-value |
|---|---|---|---|
| INTERVAL | rs6903575 | 0.056 (SE = 0.004) | $6.4 \times 10^{-37}$ |
| AGES | rs6909201 | 0.043 (SE = 0.003) | $3.2 \times 10^{-09}$ | pQTL, protein quantitative trait locus; SD, standard deviation; SE, standard error.

Example 3: Machine-Learning Algorithm Applied to Common Genetic Variation at CD109 Identifies Further Evidence Implicating CD109 as the Causal Gene Mediating the Association with eBMD A machine-learning algorithm (Effector Index) was applied to eBMD genome-wide association data and strong evidence was observed to suggest that CD109 is the causal gene mediating the eBMD GWAS association in this genomic region (Effector index=0.96, which indicates that the probability that CD109 is the causal gene at this locus is high).

What is claimed is:

1. A method of treating a subject having decreased bone mineral density or at risk of developing decreased bone mineral density, the method comprising administering a Cluster of Differentiation 109 (CD109) inhibitor to the subject, wherein the CD109 inhibitor comprises an inhibitory nucleic acid molecule that hybridizes to a CD109 nucleic acid molecule.

2. The method of claim 1, wherein the decreased bone mineral density is an osteopenia, Type I osteoporosis, Type II osteoporosis, or secondary osteoporosis.

3. The method according to claim 1, wherein the inhibitory nucleic acid molecule comprises an anti sense nucleic acid molecule, a small interfering RNA (siRNA), or a short hairpin RNA (shRNA).

4. The method according to claim 1, further comprising detecting the presence or absence of a CD109 missense variant nucleic acid molecule encoding a CD109 predicted loss-of-function polypeptide in a biological sample from the subject.

5. The method according to claim 4, further comprising administering a therapeutic agent that treats or inhibits decreased bone mineral density in a standard dosage amount to a subject wherein the CD109 missense variant nucleic acid molecule is absent from the biological sample.

6. The method according to claim 4, further comprising administering a therapeutic agent that treats or inhibits decreased bone mineral density in a dosage amount that is the same as or less than a standard dosage amount to a subject that is heterozygous for the CD109 missense variant nucleic acid molecule.

7. The method according to claim 4, wherein the CD109 predicted missense variant nucleic acid molecule is a splice-site variant, a stop-gain variant, a start-loss variant, a stop-loss variant, a frameshift variant, or an in-frame indel variant, or a variant that encodes a truncated CD109 predicted loss-of-function polypeptide.

8. The method according to claim 4, wherein the CD109 predicted loss-of-function variant nucleic acid molecule is 6:73730573:A:G, 6:73823473:GA:G, 6:73763607:C:A, 6:73803256:G:T, 6:73818486:T:C, 6:73787379:G:A, 6:73771510:A:G, 6:73806987:A:T, 6:73758991:A:G, 6:73823456:A:G 6:73762778:A:C, 6:73763660:A:G, 6:73730573:A:G, 6:73806956:G:A, 6:73792628:G:C, 6:73806926:A:T, 6:73771576:G:A, 6:73815026:C:T, 6:73765952:G:A, or an mRNA molecule produced therefrom, or a cDNA molecule produced from the mRNA molecule.

9. The method according to claim 7, wherein the CD109 missense variant nucleic acid molecule encodes a truncated CD109 predicted loss-of-function polypeptide.

10. A method of treating a subject with a therapeutic agent that treats or inhibits decreased bone mineral density, wherein the subject has decreased bone mineral density or is at risk of developing decreased bone mineral density, the method comprising the steps of:
   determining whether the subject has a Cluster of Differentiation 109 (CD109) missense variant nucleic acid molecule encoding a CD109 predicted loss-of-function polypeptide by:
      obtaining or having obtained a biological sample from the subject; and
      performing or having performed a sequence analysis on the biological sample to determine if the subject has a genotype comprising the CD109 missense variant nucleic acid molecule; and
   administering or continuing to administer the therapeutic agent that treats or inhibits decreased bone mineral density in a standard dosage amount to a subject that is CD109 reference, and/or administering a CD109 inhibitor to the subject, wherein the CD109 inhibitor comprises an inhibitory nucleic acid molecule that hybridizes to a CD109 nucleic acid molecule;
   administering or continuing to administer the therapeutic agent that treats or inhibits decreased bone mineral density in an amount that is the same as or less than a standard dosage amount to a subject that is heterozygous for the CD109 missense variant nucleic acid molecule, and/or administering a CD109 inhibitor to the subject, wherein the CD109 inhibitor comprises an inhibitory nucleic acid molecule that hybridizes to a CD109 nucleic acid molecule; or
   administering or continuing to administer the therapeutic agent that treats or inhibits decreased bone mineral density in an amount that is the same as or less than a standard dosage amount to a subject that is homozygous for the CD109 missense variant nucleic acid molecule;
   wherein the presence of a genotype having the CD109 missense variant nucleic acid molecule encoding the CD109 predicted loss-of-function polypeptide indicates the subject has a decreased risk of developing decreased bone mineral density.

11. The method according to claim 10, wherein the subject is CD109 reference, and the subject is administered or continued to be administered the therapeutic agent that treats or inhibits decreased bone mineral density in a standard dosage amount, and is administered a CD109 inhibitor.

12. The method according to claim 10, wherein the subject is heterozygous for a CD109 missense variant nucleic acid molecule, and the subject is administered or continued to be administered the therapeutic agent that treats or inhibits decreased bone mineral density in an amount that is the same as or less than a standard dosage amount, and is administered a CD109 inhibitor.

13. The method according to claim 10, wherein the CD109 missense variant nucleic acid molecule is a splice-site variant, a stop-gain variant, a start-loss variant, a stop-loss variant, a frameshift variant, or an in-frame indel variant, or a variant that encodes a truncated CD109 predicted loss-of-function polypeptide.

14. The method according to claim 10, wherein the CD109 predicted loss-of-function variant nucleic acid molecule is 6:73730573:A:G, 6:73823473:GA:G, 6:73763607:C:A, 6:73803256:G:T, 6:73818486:T:C, 6:73787379:G:A, 6:73771510:A:G, 6:73806987:A:T, 6:73758991:A:G, 6:73823456:A:G 6:73762778:A:C, 6:73763660:A:G, 6:73730573:A:G, 6:73806956:G:A, 6:73792628:G:C, 6:73806926:A:T, 6:73771576:G:A, 6:73815026:C:T, 6:73765952:G:A, or an mRNA molecule produced therefrom, or a cDNA molecule produced from the mRNA molecule.

15. The method according to claim 10, wherein the CD109 missense variant nucleic acid molecule encodes a truncated CD109 predicted loss-of-function polypeptide.

16. The method according to claim 10, wherein the inhibitory nucleic acid molecule comprises an anti sense nucleic acid molecule, a small interfering RNA (siRNA), or a short hairpin RNA (shRNA).

17. The method according to claim 10, wherein the decreased bone mineral density is an osteopenia, Type I osteoporosis, Type II osteoporosis, or secondary osteoporosis.

18. The method according to claim 10, wherein the therapeutic agent is chosen from alendronate, ibandronate, zoledronate, risedronate, calcitonin, teriparatide, denosumab, estrogen and progesterone, raloxifene, or any combination thereof.

\* \* \* \* \*